United States Patent
Shilatifard et al.

(10) Patent No.: US 11,453,640 B2
(45) Date of Patent: Sep. 27, 2022

(54) SMALL MOLECULES FOR DISRUPTING THE SUPER ELONGATION COMPLEX AND INHIBITING TRANSCRIPTION ELONGATION FOR CANCER THERAPY

(71) Applicant: NORTHWESTERN UNIVERSITY, Evanston, IL (US)

(72) Inventors: Ali Shilatifard, Chicago, IL (US); Kaiwei Liang, Chicago, IL (US); Edwin R. Smith, Chicago, IL (US); Gary E. Schiltz, Naperville, IL (US); Rama K. Mishra, Chicago, IL (US); Kristen Stoltz, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/981,654

(22) PCT Filed: Mar. 21, 2019

(86) PCT No.: PCT/US2019/023397
§ 371 (c)(1),
(2) Date: Sep. 16, 2020

(87) PCT Pub. No.: WO2019/183373
PCT Pub. Date: Sep. 26, 2019

(65) Prior Publication Data
US 2021/0094907 A1    Apr. 1, 2021

Related U.S. Application Data

(60) Provisional application No. 62/645,890, filed on Mar. 21, 2018, provisional application No. 62/744,950, filed on Oct. 12, 2018.

(51) Int. Cl.
| | |
|---|---|
| C07C 235/74 | (2006.01) |
| A61P 35/00 | (2006.01) |
| C07C 235/78 | (2006.01) |
| C07D 213/40 | (2006.01) |
| C07D 213/75 | (2006.01) |
| C07D 231/14 | (2006.01) |
| C07D 239/36 | (2006.01) |
| C07D 239/42 | (2006.01) |
| C07D 241/20 | (2006.01) |
| C07D 257/06 | (2006.01) |
| C07D 261/18 | (2006.01) |
| C07D 271/07 | (2006.01) |
| C07D 277/46 | (2006.01) |

(52) U.S. Cl.
CPC ............ *C07C 235/74* (2013.01); *A61P 35/00* (2018.01); *C07C 235/78* (2013.01); *C07D 213/40* (2013.01); *C07D 213/75* (2013.01); *C07D 231/14* (2013.01); *C07D 239/36* (2013.01); *C07D 239/42* (2013.01); *C07D 241/20* (2013.01); *C07D 257/06* (2013.01); *C07D 261/18* (2013.01); *C07D 271/07* (2013.01); *C07D 277/46* (2013.01); *C07C 2601/08* (2017.05)

(58) Field of Classification Search
CPC ..................................................... C07C 235/74
See application file for complete search history.

(56) References Cited

FOREIGN PATENT DOCUMENTS

| RU | 2342364 C1 | 12/2008 |
|---|---|---|
| RU | 2364591 C1 | 8/2009 |
| SU | 686308 A1 * | 10/1981 |
| WO | 2011014299 A2 | 2/2011 |
| WO | 2014139014 A1 | 9/2014 |

OTHER PUBLICATIONS

Online: "http://web.archive.org/web/20070406205858/http://www.aurorafinechemicals.com/english/order.html" dated Apr. 6, 2007, accessed Feb. 19, 2015.*
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
"Exploiting Chemical Diversity for Drug Discovery" Edited by Paul A Bartlett and Michael Entzeroth, The Royal Society of Chemistry, 2006, pp. 113-118.*
Nie Z, et al. (2012). c-Myc is a universal amplifier of expressed genes in lymphocytes and embryonic stem cells. Cell 151, 68-79.
Peterlin BM, et al. (2006). Controlling the elongation phase of transcription with PTEFb. Mol Cell 23, 297-305.
Piunti, A., et al. (2017). Therapeutic targeting of polycomb and BET bromodomain proteins in diffuse intrinsic pontine gliomas. Nat Med 23, 493-500.
Price, D.H. (2000). P-TEFb, a cyclin-dependent kinase controlling elongation by RNA polymerase II. Mol Cell Biol 20, 2629-2634.
Rahl PB, et al. (2010). c-Myc regulates transcriptional pause release. Cell 141, 432-445.
Sabo A, et al. (2014). Selective transcriptional regulation by Myc in cellular growth control and lymphomagenesis. Nature 511, 488-492.

(Continued)

*Primary Examiner* — David K O'Dell
(74) *Attorney, Agent, or Firm* — Quarles & Brady LLP

(57) ABSTRACT

Disclosed are compounds which may be utilized to inhibit transcription by RNA Polymerase II (Pol II), and in particular to disrupt the Super Elongation Complex (SEC). The compounds may be utilized in pharmaceutical compositions and methods for treating diseases and disorders associated with the biological activity of SEC, and in particular, diseases and disorders that are associated with high levels of expression of genes whose expression is SEC-dependent and that promote, support, or otherwise are required for the disease or disorder such as cancers.

5 Claims, 94 Drawing Sheets

(56) References Cited

OTHER PUBLICATIONS

Saldanha AJ (2004). Java Treeview—extensible visualization of microarray data. Bioinfomnatics 20, 3246-3248.
Schulze-Gahmen U, et al. (2013). The AFF4 scaffold binds human P-TEFb adjacent to HIV Tat. Elife 2, e00327.
Shilatifard A, et al. (1997). ELL2, a new member of an ELL family of RNA polymerase II elongation factors. Proc Natl Acad Sci U S A 94, 3639-3643.
Shilatifard A., et al. (1996). An RNA polymerase II elongation factor encoded by the human ELL gene. Science 271, 1873-1876.
Smith E, et al. (2011). The super elongation complex (SEC) and MLL in development and disease. Genes Dev 25, 561-672.
Sobhian B, et al. (2010). HIV-1 Tat assembles a multifunctional transcription elongation complex and stably associates with the 7SK snRNP. Mol Cell 38, 439-451.
Takahashi H, et al. (2011). Human mediator subunit MED26 functions as a docking site for transcription elongation factors. Cell 146, 92-104.
Tripathi S, et al. (2015). Meta- and Orthogonal Integration of Influenza "OMICs" Data Defines a Role for UBR4 in Virus Budding. Cell Host Microbe 18, 723-735.
Walz S, et al. (2014). Activation and repression by oncogenic MYC shape tumour-specific gene expression profiles. Nature 511, 483-487.
Wan L, et al. (2017). ENL links histone acetylation to oncogenic gene expression in acute myeloid leukaemia. Nature 543, 265-269.
Wang L, et al. (2017). A cytoplasmic COMPASS is necessary for cell survival and triple-negative breast cancer pathogenesis by regulating metabolism. Genes Dev 31, 2056-2066.
Winter GE, et al. (2015). Phthalimide conjugation as a strategy for in vivo target protein degradation. Science 348, 1376-1381.
Winter GE, et al. (2017). BET Bromodomain Proteins Function as Master Transcription Elongation Factors Independent of CDK9 Recruitment. Mol Cell 67, 5-18e19.
Yang Z, et al. (2005). Recruitment of P-TEFb for stimulation of transcriptional elongation by the bromodomain protein Brd4. Mol Cell 19, 535-545.
Yokoyama A, et al. (2010). A higher-order complex containing AF4 and ENL family proteins with P-TEFb facilitates oncogenic and physiologic MLL-dependent transcription. Cancer Cell 17, 198-212.
Zeller KI, et al. (2003). An integrated database of genes responsive to the Myc oncogenic transcription factor: identification of direct genomic targets. Genome Biol 4, R69.
Zhang Y, et al. (2008). Model-based analysis of ChIP-Seq (MACS). Genome Biol 9, R137.
Zhou Q, et al. (2012). RNA polymerase II elongation control. Annu Rev Biochem 81, 119-143.
Andreichikov, Yu S., et al. "Synthesis and biological activity of aroylpyruvoylaminobenzonitriles and 3-phenacylidene-6 (7)-cyano-3, 4-dihydro-2-quinoxalones." Pharmaceutical Chemistry Journal 23.8 (1989): 665-668.
Baell JB, et al. (2010). New substructure filters for removal of pan assay interference compounds (PAINS) from screening libraries and for their exclusion in bioassays. J Med Chem 53, 2719-2740.
Belyaev, A. O., et al. "Substituted Amides and Hydrazides of Acylpyruvic Acids. Part 10. Synthesis, Antimicrobial and Analgesic Activity of 4-Aryl-2-arylamino-4-oxo-2-butenoic Acid Arylamides." Pharmaceutical Chemistry Journal 38.7 (2004): 364-367.
Bezzi M, et al. (2013). Regulation of constitutive and alternative splicing by PRMT5 reveals a role for Mdm4 pre-mRNA in sensing defects in the spliceosomal machinery. Genes Dev 27, 1903-1916.
Bolger AM, et al. (2014). Trimmomatic: a flexible trimmer for Illumina sequence data. Bioinfomnatics 30, 2114-2120.
Bradner JE, et al. (2017) Transcriptional Addiction in Cancer. Cell 168, 629-643.
Chao SH, et al. (2001). Flavopiridol inactivates P-TEFb and blocks most RNA polymerase II transcription in vivo. J Biol Chem 276, 31793-31799.

Chen FX, et al. (2018). Born to run: control of transcription elongation by RNA polymerase II. Nat Rev Mol Cell Biol 19, 464-478.
Danko CG, et al. (2013). Signaling pathways differentially affect RNA polymerase II initiation, pausing, and elongation rate in cells. Mol Cell 50, 212-222.
Dawson MA, et al. (2011). Inhibition of BET recruitment to chromatin as an effective treatment for MLL-fusion leukaemia. Nature 478, 529-533.
Delmore JE, et al. (2011). BET bromodomain inhibition as a therapeutic strategy to target c-Myc. Cell 146, 904-917.
Erb MA, et al. (2017). Transcription control by the ENL YEATS domain in acute leukaemia. Nature 543, 270-274.
Filippakopoulos P, et al. (2010). Selective inhibition of BET bromodomains. Nature 468, 1067-1073.
Fong N, et al. (2014). Pre-mRNA splicing is facilitated by an optimal RNA polymerase II elongation rate. Genes Dev 28, 2663-2676.
Fong N, et al. (2015). Effects of Transcription Elongation Rate and Xm2 Exonuclease Activity on RNA Polymerase II Termination Suggest Widespread Kinetic Competition. Mol Cell 60, 256-267.
Fong N, et al. (2017). RNA Pol II Dynamics Modulate Co-transcriptional Chromatin Modification, CTD Phosphorylation, and Transcriptional Direction. Mol Cell 66, 546-557 e543.
Fuchs G, et al. (2014). 4sUDRB-seq: measuring genomewide transcriptional elongation rates and initiation frequencies within cells. Genome Biol 15, R69.
Galbraith MD, et al. (2013). HIF1A employs CDK8-mediator to stimulate RNAPII elongation in response to hypoxia. Cell 153, 1327-1339.
Gu J, et al. (2014). Crystal structure of HIV-1 Tat complexed with human P-TEFb and AFF4. Cell Cycle 13, 1788-1797.
He N, et al. (2010). HIV-1 Tat and host AFF4 recruit two transcription elongation factors into a bifunctional complex for coordinated activation of HIV-1 transcription. Mol Cell 38, 428-438.
Hsu TY, et al. (2015). The spliceosome is a therapeutic vulnerability in MYC-driven cancer. Nature 525, 384-388.
Hu D, et al. (2013). The little elongation complex functions at initiation and elongation phases of snRNA gene transcription. Mol Cell 51, 493-505.
International Searching Authority. International Search Report and Written Opinion for application PCT/US2019/023397. dated Jun. 13, 2019. 9 pages.
Izumi K, et al. (2015). Germline gain-of-function mutations in AFF4 cause a developmental syndrome functionally linking the super elongation complex and cohesin. Nat Genet 47, 338-344.
Jang, M.K., et al. (2005). The bromodomain protein Brd4 is a positive regulatory component of P-TEFb and stimulates RNA polymerase II-dependent transcription. Mol Cell 19, 523-534.
Ji X, et al. (2013). SR proteins collaborate with 7SK and promoter-associated nascent RNA to release paused polymerase. Cell 153, 855-868.
Jonkers I, et al. (2015). Getting up to speed with transcription elongation by RNA polymerase II. Nat Rev Mol Cell Biol 16, 167-177.
Jordan A, et al. (2003). HIV reproducibly establishes a latent infection after acute infection of T cells in vitro. EMBO J 22, 1868-1877.
Kataev, S. S., et al. "N-(2-pyridyl) amides of 2,4-dioxobutyric acids in reactions with diazoalkanes." Chemistry of Heterocyclic Compounds 39.10 (2003): 1326-1331.
Koh CM, et al. (2015). MYC regulates the core pre-mRNA splicing machinery as an essential step in lymphomagenesis. Nature 523, 96-100.
Koz'Minykh, V. O., et al. "Acylpyruvic acid amides and hydrazides: XII. Reaction of 4-Aryl-2-hydroxy-4-oxo-2-butenic acids arylamides with tripheny/phosphoranylideneacetic acid esters." Russian journal of general chemistry 76.7 (2006): 1041-1047.
Kwak H, et al. (2013). Precise maps of RNA polymerase reveal how promoters direct initiation and pausing. Science 339, 950-953.
Langmead B, et al. (2009). Ultrafast and memory-efficient alignment of short DNA sequences to the human genome. Genome Biol 10, R25.

(56) References Cited

OTHER PUBLICATIONS

Lee SC, et al. (2016). Therapeutic targeting of splicing in cancer. Nat Med 22, 976-986.

Liang K, et al. (2015). Mitotic Transcriptional Activation: Clearance of Actively Engaged Pol II via Transcriptional Elongation Control in Mitosis. Mol Cell 60, 435-445.

Liang K, et al. (2017). Therapeutic Targeting of MLL Degradation Pathways in MLL-Rearranged Leukemia. Cell 168, 59-72 e13.

Liang, K., et al. "Targeting processive transcription elongation via SEC disruption for MYC-induced cancer therapy." Cell 175.3 (2018): 766-779.

Lin C, et al. (2010). AFF4, a component of the ELL/P-TEFb elongation complex and a shared subunit of MLL chimeras, can link transcription elongation to leukemia. Mol Cell 37, 429-437.

Lin C, et al. (2011). Dynamic transcriptional events in embryonic stem cells mediated by the super elongation complex (SEC). Genes Dev 25, 1486-1498.

Lin CY, et al. (2012). Transcriptional amplification in tumor cells with elevated c-Myc. Cell 151, 56-67.

Lu J, et al. (2015). Hijacking the E3 Ubiquitin Ligase Cereblon to Efficiently Target BRD4. Chem Biol 22, 755-763.

Lu, H., et al. (2015). Gene target specificity of the Super Elongation Complex (SEC) family: how HIV-1 Tat employs selected SEC members to activate viral transcription. Nucleic Acids Res 43, 5868-5879.

Luo Z, et al. (2012). The super elongation complex family of RNA polymerase II elongation factors: gene target specificity and transcriptional output. Mol Cell Biol 32, 2608-2617.

Luo Z, et al. (2012). The super elongation complex (SEC) family in transcriptional control. Nat Rev Mol Cell Biol 13, 543-547.

Mahat DB, et al. (2016). Base-pair-resolution genome-wide mapping of active RNA polymerases using precision nuclear run-on (PRO-seq). Nat Protoc 11, 1455-1476.

Mahat DB, et al. (2016). Mammalian Heat Shock Response and Mechanisms Underlying Its Genome-wide Transcriptional Regulation. Mol Cell 62, 63-78.

Martin M (2011). Cutadapt Removes Adapter Sequences From High-Throughput Sequencing Reads. EMBnetjournal 17, 10-12.

McNamara RP, et al. (2016). Transcription elongation control by the 7SK snRNP complex: Releasing the pause. Cell Cycle 15, 2115-2123.

Mohan M, et al. (2010). Licensed to elongate: a molecular mechanism for MLL-based leukaemogenesis. Nat Rev Cancer 10, 721-728.

Neklesa TK, et al. (2017). Targeted protein degradation by PROTACs. Pharmacol Ther 174, 138-144.

\* cited by examiner

A Gene ontology analysis of downregulated genes by KL-1 and KL-2

| Term | Description | Log(q-value) |
|---|---|---|
| R-HSA-8953854 | Metabolism of RNA | -83.036879 |
| GO:0022613 | ribonucleoprotein complex biogenesis | -50.864174 |
| GO:1903311 | regulation of mRNA metabolic process | -20.365638 |
| GO:0022618 | ribonucleoprotein complex assembly | -20.156044 |
| GO:0006403 | RNA localization | -19.364994 |
| hsa03013 | RNA transport | -13.496347 |
| M5926 | HALLMARK MYC TARGETS V1 | -50.143922 |
| M5901 | HALLMARK G2M CHECKPOINT | -29.676502 |
| R-HSA-1640170 | Cell Cycle | -24.40832 |
| GO:0051301 | cell division | -17.819457 |
| GO:0010564 | regulation of cell cycle process | -16.187298 |
| GO:0033044 | regulation of chromosome organization | -16.201624 |
| GO:0006325 | chromatin organization | -15.713772 |

Gene ontology analysis of upregulated genes by KL-1 and KL-2

| Term | Description | Log(q-value) |
|---|---|---|
| GO:0034620 | cellular response to unfolded protein | -15.818596 |
| GO:0006281 | DNA repair | -6.9658101 |
| GO:0045786 | negative regulation of cell cycle | -6.9625896 |
| GO:0097193 | intrinsic apoptotic signaling pathway | -6.4829808 |

C

Gene ontology analysis of downregulated genes by both SEC inhibitors and SEC depletion      N=1226

| Term | Description | Log(q-value) |
|---|---|---|
| GO:0022613 | Ribonucleoprotein Complex Biogenesis | -35.848642 |
| M5926 | HALLMARK MYC TARGETS V1 | -30.059716 |
| GO:0000398 | mRNA Splicing, via Spliceosome | -15.949607 |
| M5928 | HALLMARK MYC TARGETS V2 | -14.255887 |

Figure 13 (continued)

SMALL MOLECULES FOR DISRUPTING THE SUPER ELONGATION COMPLEX AND INHIBITING TRANSCRIPTION ELONGATION FOR CANCER THERAPY

CROSS REFERENCE TO RELATED APPLICATIONS

The present application is a national stage entry under 35 U.S.C. 371 of International Application No. PCT/US2019/023397, filed Mar. 21, 2019, which claims the benefit of priority under 35 U.S.C. 119(e) to U.S. Provisional Application No. 62/744,950, filed on Oct. 12, 2018 and to U.S. Provisional Application No. 62/645,890 filed on Mar. 21, 2018, the contents of which are incorporated herein by reference in their entireties.

STATEMENT REGARDING FEDERALLY SPONSORED RESEARCH OR DEVELOPMENT

This invention was made with government support under CA214035 and CA211428 awarded by the National Institutes of Health. The government has certain rights in the invention.

BACKGROUND

The field of the invention relates to small molecules which may be utilized to inhibit transcription by RNA Polymerase II (Pol II). In particular, the field of the invention relates to small molecules that may be utilized to disrupt the Super Elongation Complex (SEC) utilized in transcription regulation by Pol II which is misregulated in a large number of cancers. Therefore, the disclosed small molecules may be utilized in cancer therapy for cancers that are characterized by misregulation of SEC.

The Super Elongation Complex (SEC) is a multiprotein complex that promotes productive transcription elongation by RNA Polymerase II (Pol II). SEC is an essential cofactor in multiple forms of cancer, including cancers driven by high levels of Myc expression and mixed lineage leukemia (MLL) chimeras in acute myeloid leukemia (AML) and acute lymphoid leukemia (ALL). SEC is also an essential cofactor of human immunodeficiency virus (HIV) Tat protein, which is required for HIV replication due to its role in the expression of the provirus.

The protein referred to as "AF4/FMR2 family, member 4" (AFF4) is the scaffold for SEC, bringing together the Pol II c-terminal domain (CTD) kinase (P-TEFb) via an interaction with the Cyclin T subunit of P-TEFb, and the transcription elongation factor (ELL2), among other proteins. We have developed peptidomimetics of AFF4 that disrupt the interaction of AFF4 with the Cyclin T subunit of P-TEFb. This results in the destabilization of SEC. In turn, the destabilization of SEC results in the subsequent decreased expression of Myc and Myc target genes, and the subsequent decreased expression of MLL chimera target genes, as well as attenuated Tat-dependent transcriptional activation. Because Myc has previously been proven to be an undruggable target, disrupting Myc's cofactor SEC provides an important unmet need in Myc-driven cancers. In addition, leukemias with MLL translocations are particularly aggressive with poor prognosis, for which there have been no effective targeted therapies. Leukemias with MLL translocations depend on the cofactor SEC and inhibition of SEC provides a therapeutic target for MLL leukemias. Finally, inhibition of Tat-dependent HIV transcription through targeting SEC provides a novel specific approach to targeting HIV.

The only known inhibitors of transcription elongation inhibit expression of all Pol II transcribed genes equally. Inhibitors that specifically disrupt SEC and regulate the elongation stage of transcription are desirable for specifically inhibiting expression of genes that exhibit high levels of transcription, such as Myc, MLL-fusion proteins, and HIV Tat target genes. Such inhibitors can be instrumental and very useful for disease therapeutics.

SUMMARY

Disclosed are compounds which may be utilized to inhibit transcription by RNA Polymerase II (Pol II), and in particular to disrupt the Super Elongation Complex (SEC). The compounds may be utilized in pharmaceutical compositions and methods for treating diseases and disorders associated with the biological activity of SEC, and in particular, diseases and disorders that are associated with high levels of expression of genes whose expression is SEC-dependent and that promote, support, or otherwise are required for the disease or disorder.

The disclosed compounds may include compounds, tautomers thereof, and/or pharmaceutical salts thereof, where the compounds have a formula:

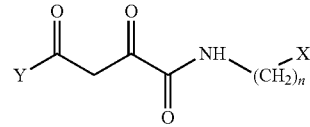

wherein n is 0-6;

X and Y are the same or different and are selected from carbocycles and heterocycles which are saturated or unsaturated at one or more bonds and which optionally are substituted with substituents selected from the group consisting of alkyl, alkoxy, halo, haloalkyl, hydroxyl, amino, cyano, and carboxyl;

and optionally with the proviso that the compound is not 2,4-dioxo-N,4-diphenylbutanamide and optionally with the proviso that the compound is not N-(5-chloro-2-methylphenyl)-4-hydroxy-4-(3-methoxyphenyl)-2-oxobut-3-enamide and optionally with the proviso that the compound is not N-(5-chloro-2-methylphenyl)-4-(4-fluorophenyl)-4-hydroxy-2-oxobut-3-enamide.

Preferably, the disclosed compounds disrupt an interaction between two or more components of the SEC. In particular, preferably the disclosed compounds disrupt the interaction between components of the SEC selected from an interaction between any of the following components: the protein referred to as "AF4/FMR2 family, member 4" (AFF4), the protein referred to as Pol II c-terminal domain (CTD) kinase (P-TEFb), and/or the protein referred to as transcription elongation factor (ELL2). In some embodiments, the disclosed compounds disrupt the interaction between AFF4 and P-TEFb, for example, the interaction between AFF4 and the Cyclin T subunit of P-TEFb.

The disclosed compounds may be formulated as pharmaceutical compositions comprising: (i) one or more of the disclosed compounds, a tautomer thereof, or a pharmaceutical salt thereof, and (ii) a suitable pharmaceutical carrier, excipient, or diluent. The disclosed compounds or pharmaceutical compositions comprising the disclosed compounds may be administered to a subject in need thereof, for example, to treat a disease or disorder associated with Super Elongation Complex (SEC) activity, where disruption of the SEC by the disclosed compounds treats the disease or disorder.

Diseases or disorders treated by the disclosed compounds, pharmaceutical compositions, and methods may include cell proliferative diseases or disorders, such as cancers, and in particular, cancers requiring and/or associated with relatively high levels of Myc expression. Cancers treated by the disclosed compounds, pharmaceutical compositions, and methods may include cancers associated with expression of a mixed lineage leukemia (MLL) chimera, such as acute myeloid leukemia (AML) or acute lymphoid leukemia (ALL). Diseases treated by the disclosed compounds, pharmaceutical compositions, and methods, may include human immunodeficiency virus (HIV) infection.

DETAILED DESCRIPTION

Figure 1:
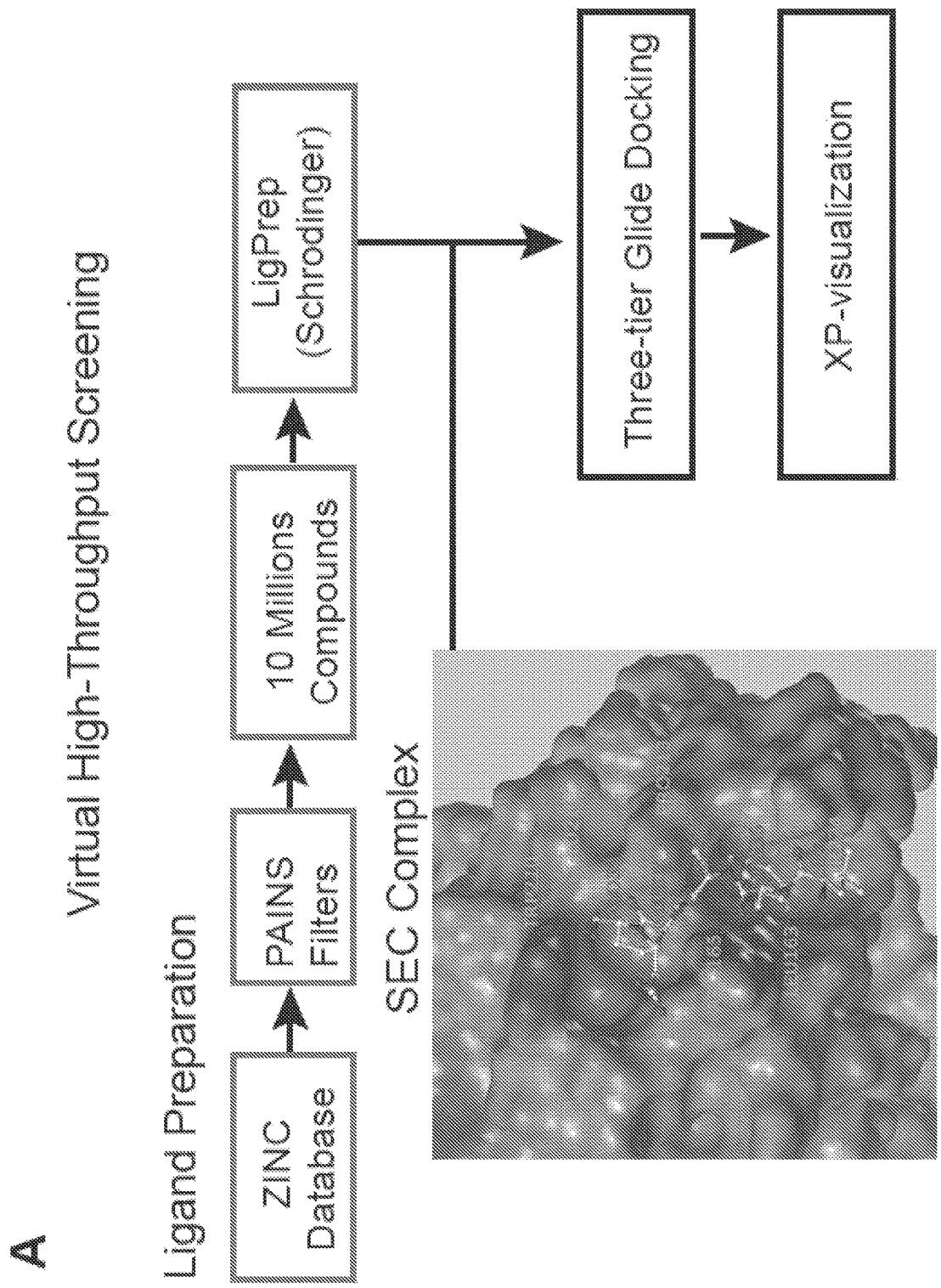
FIG. 1. Peptidomimetic identification of disruptors of the AFF4-CCNT1 interaction within the Super Elongation Complex. (A) Schematic for the identification of small molecule inhibitors of the AFF4-CCNT1 interaction using in silico high-throughput screening. Compounds from the ZINC database were docked with the AFF4-CCNT1 structure (4IMY) using a three-tier glide-docking algorithm, which led to 40 candidates. Residues forming the deep binding pocket of CCNT1 are labeled orange and residues of the AFF4 peptide are labeled red. (B) Validation screening identified KL-1 as a potential SEC disruptor using AlphaLISA screening. GST-CCNT1 (AA 1-300) and biotin-labeled AFF4 peptide (AA 32-67) were used to measure the AFF4-CCNT1 interaction with the AlphaLISA assay. (C) Similarity search for KL-1-like molecules identified KL-2. The peptidomimetic potential of KL-1 and KL-2 can be seen by overlaying them with the AFF4 peptide LFAEP structure. (D) Dose-dependent inhibition of KL-1 and KL-2 on AFF4-CCNT1 interaction. The $K_i$ constants of both compounds were measured with the AlphaLISA assays. (E) Treatment of HEK293T cells with KL-1 and KL-2 results in reduced protein levels of SEC components AFF1 and AFF4 but not CDK9 or CCNT1. HEK293T cells were treated with 20 µM of SEC inhibitors KL-1 or KL-2 for 6 hr. 5 µl, 10 and 20 µl cell lysates were loaded and the protein levels of AFF1, AFF4, CCNT1, CDK9 and Tubulin (load control) were determined by western blotting. (F–H) ChIP-seq analysis demonstrates that KL-1 and KL-2 treatment results in decreased occupancy of AFF1 and AFF4 on chromatin as seen at the HSPA8 gene (F) or by metaplot analysis at AFF1 (G) and AFF4 peak regions (H).
Figure 1:
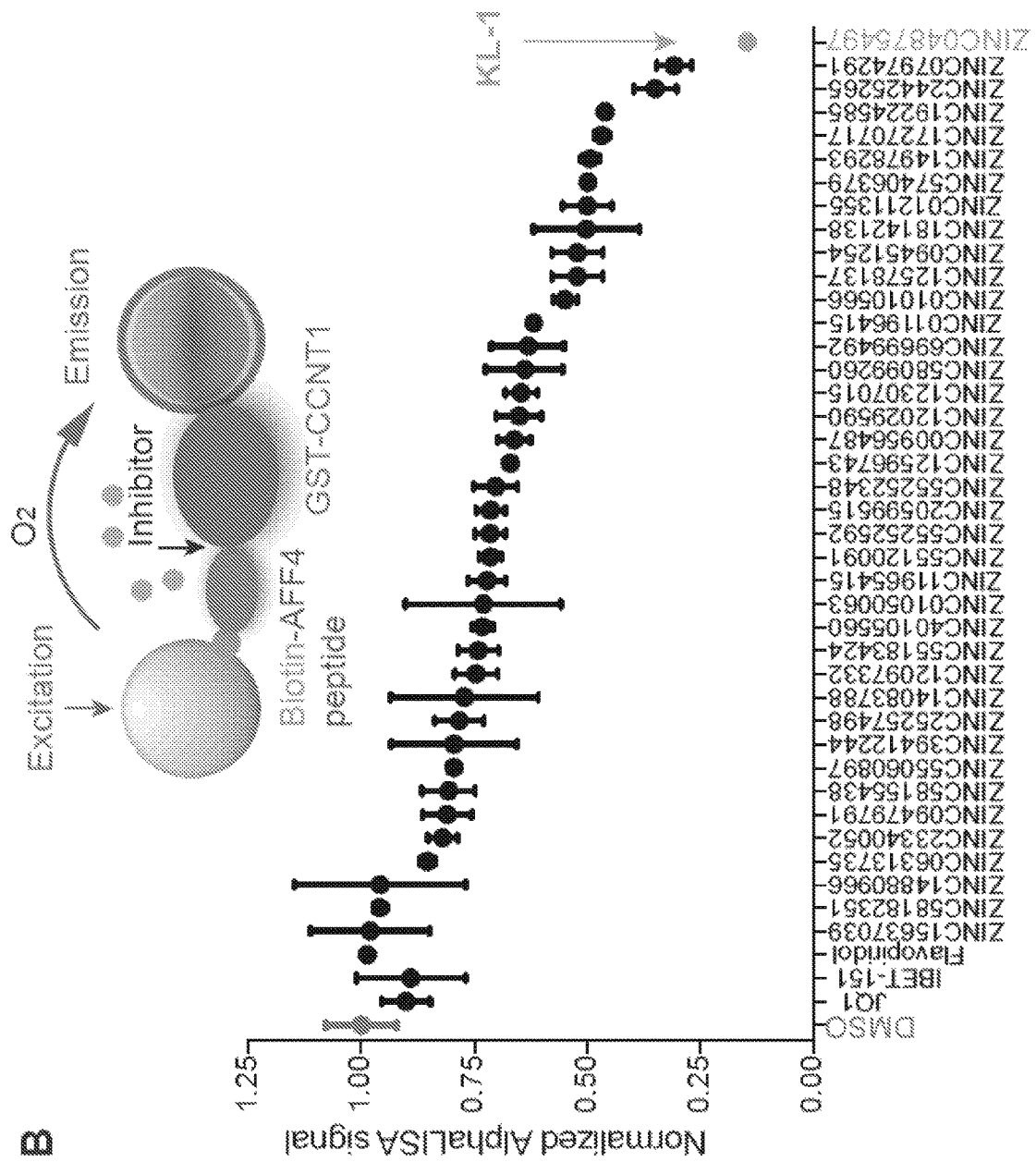
Figure 1:
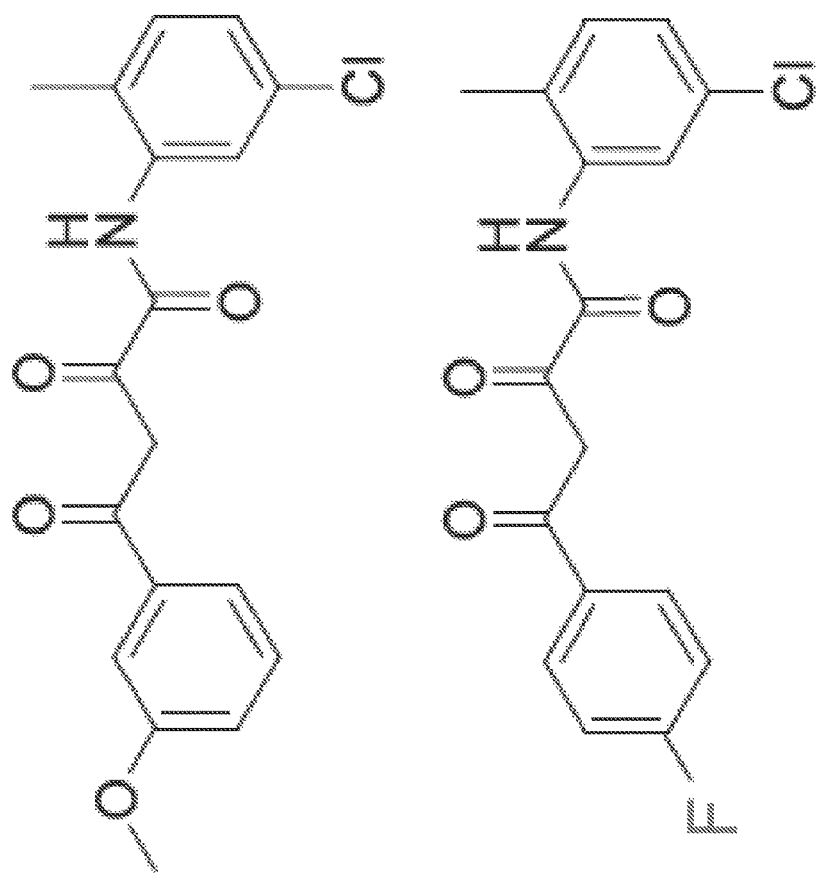
Figure 1:
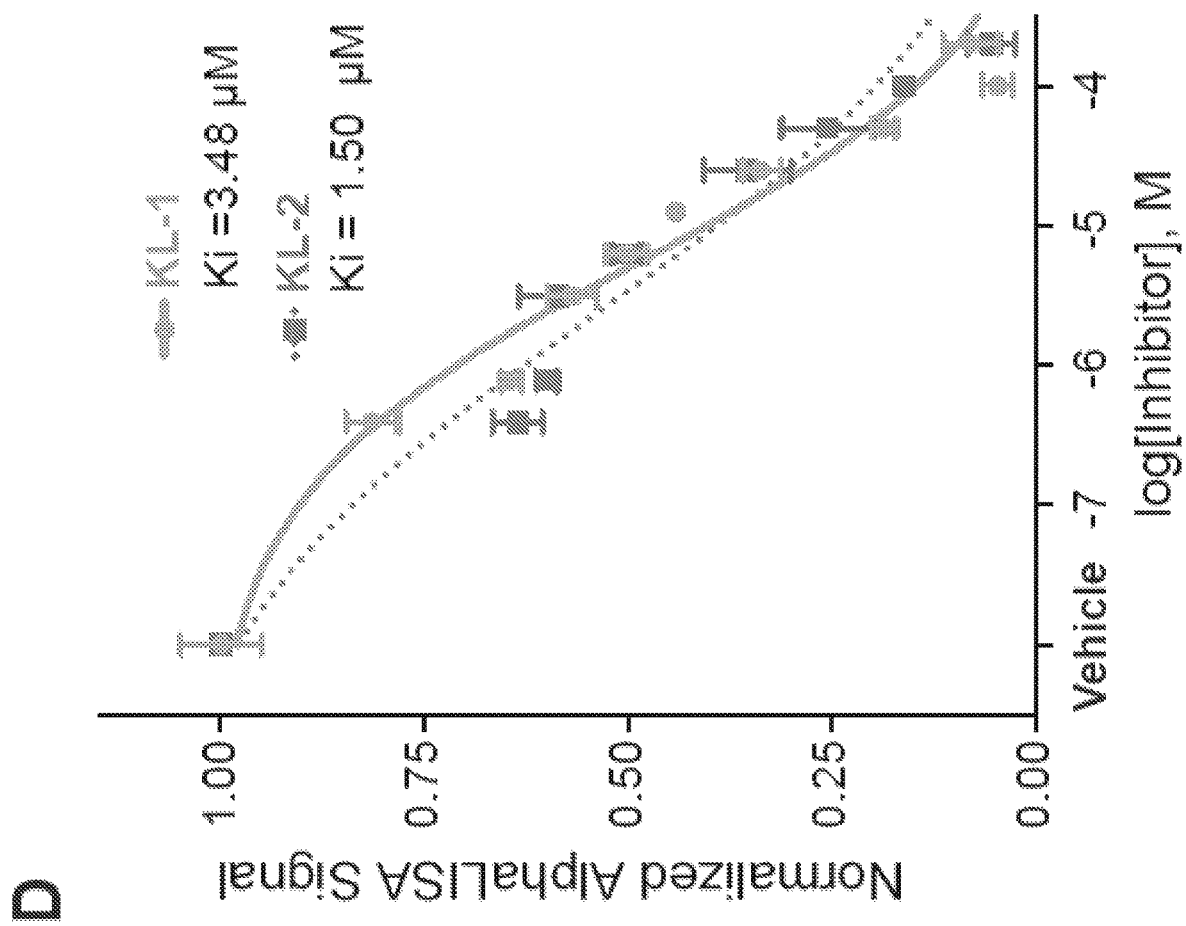
Figure 1:
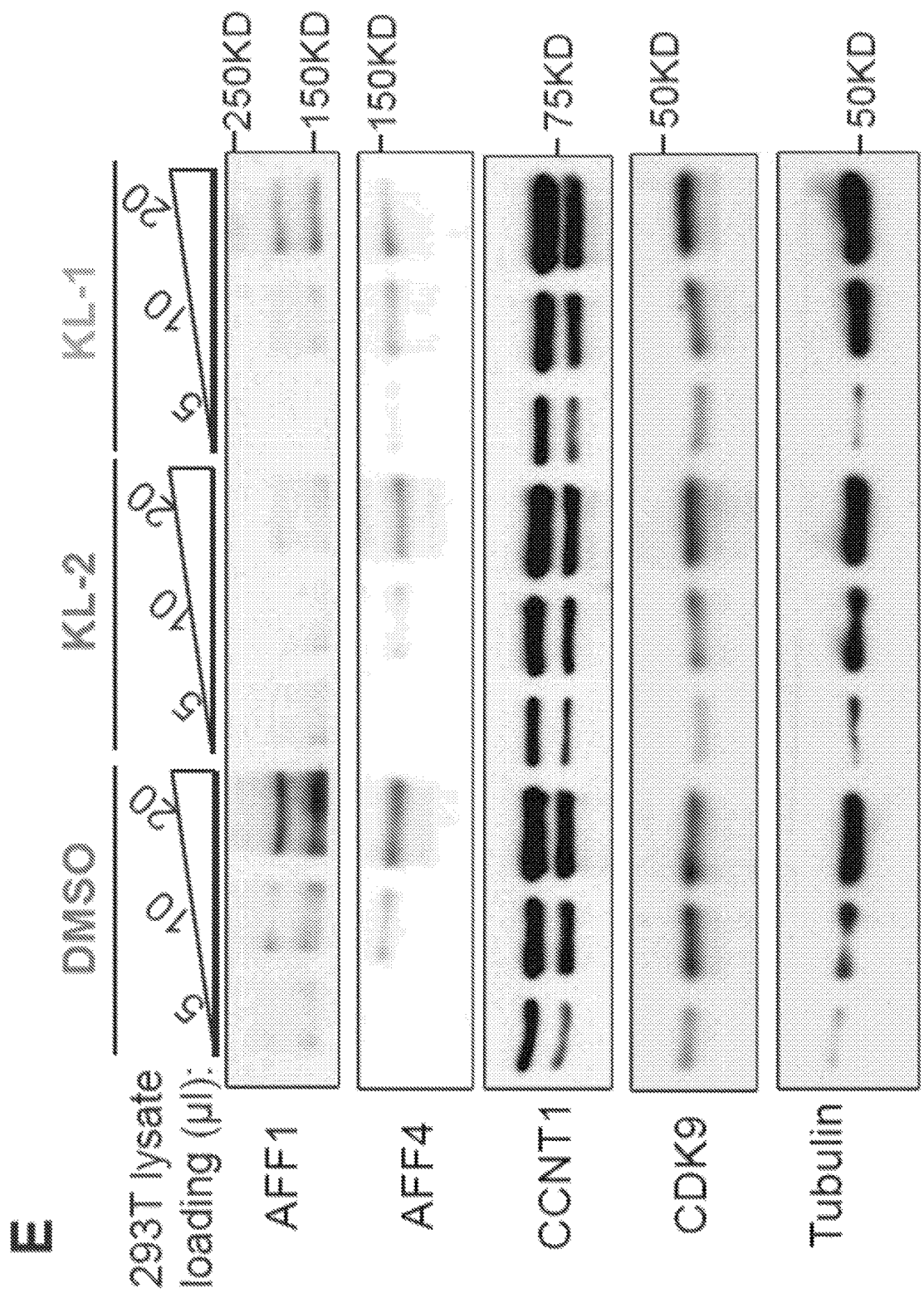
Figure 1:
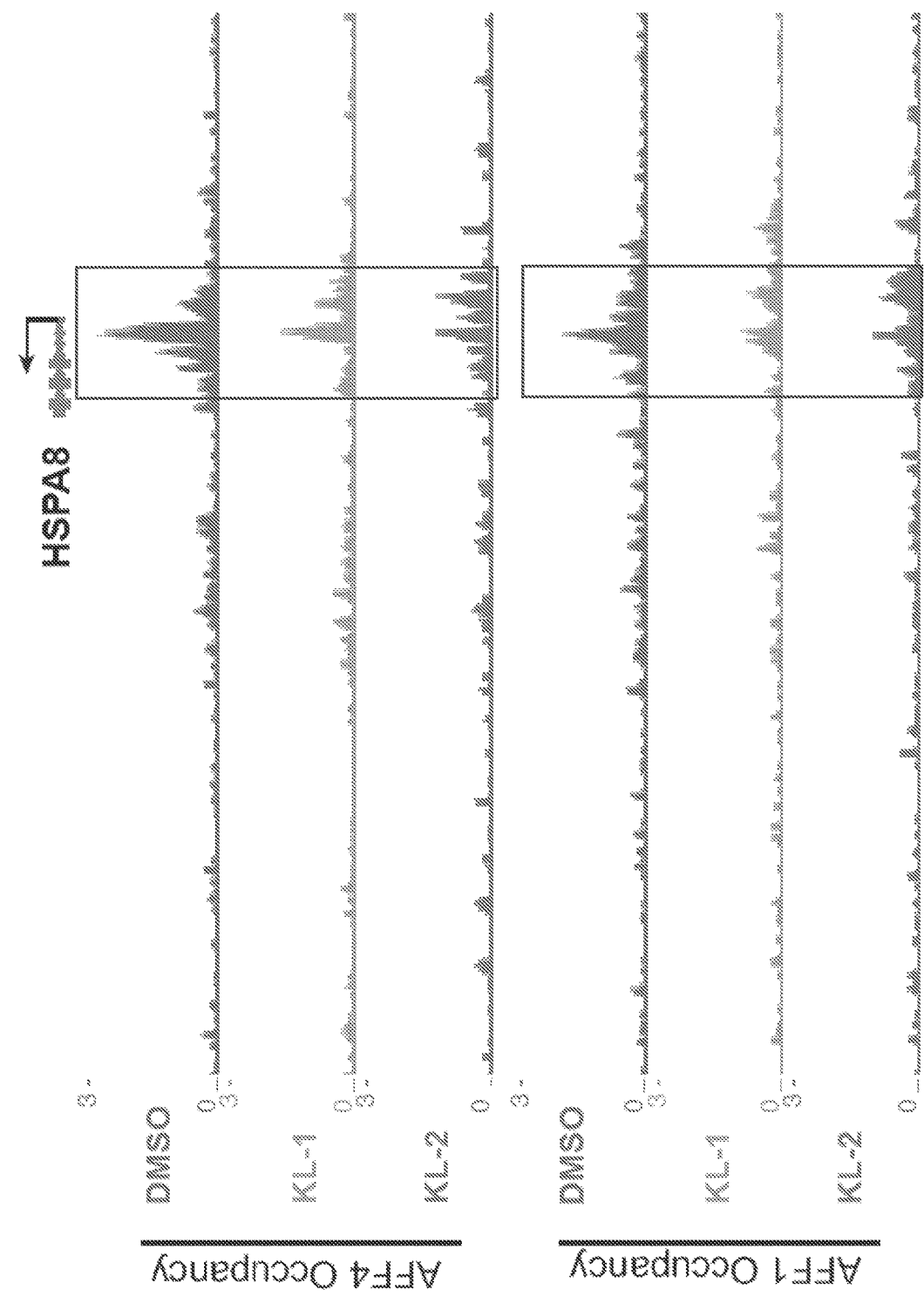
Figure 1:
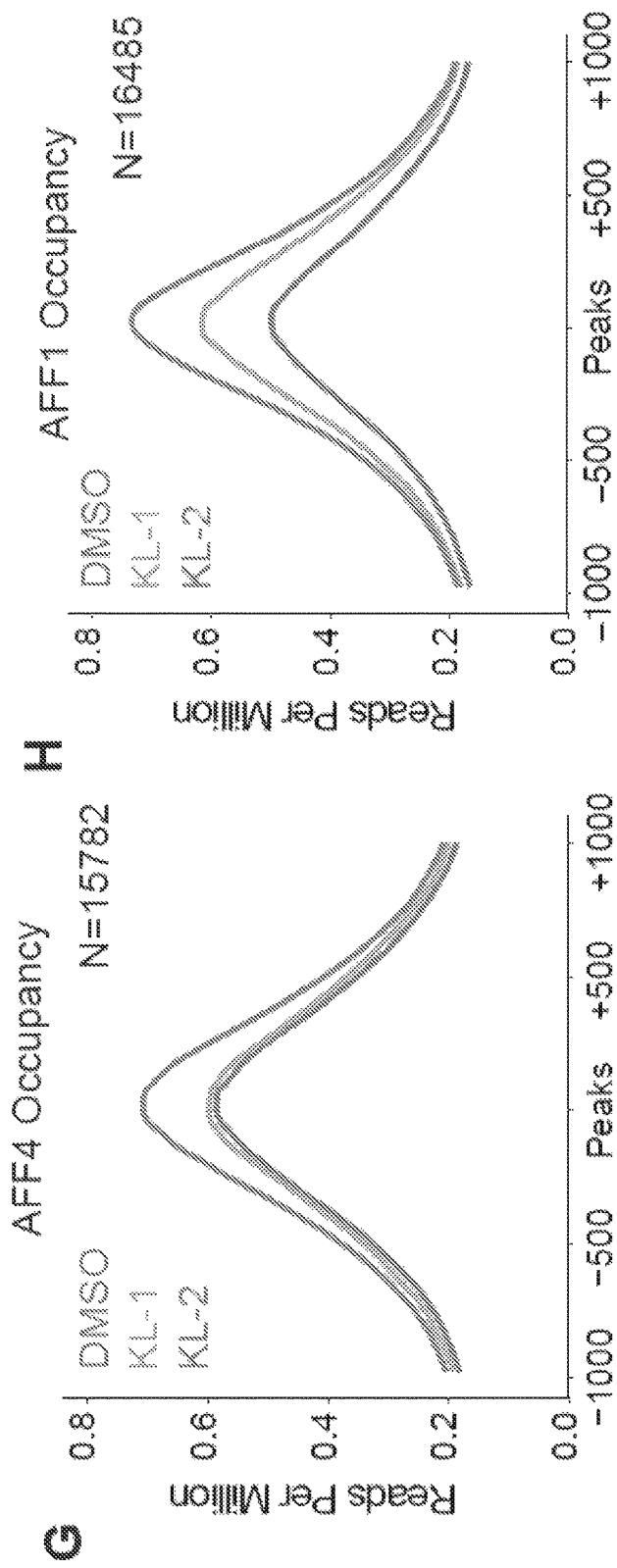

The present invention is described herein using several definitions, as set forth below and throughout the application.

Definitions

Unless otherwise specified or indicated by context, the terms "a", "an", and "the" mean "one or more." For example, "a compound" or "an inhibitor" should be interpreted to mean "one or more compounds" and "one or more inhibitors," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus <10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

Subject in Need Thereof

As used herein, a "subject" may be interchangeable with "patient" or "individual" and means an animal, which may be a human or non-human animal, in need of treatment, for example, treatment by include administering a therapeutic amount of one or more therapeutic agents that disrupt an interaction between two or more components of the Super Elongation Complex (SEC) or otherwise inhibit the biological activity of the SEC (e.g, where the therapeutic agents inhibit transcription elongation).

A "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need of treatment" may include a subject having a disease or disorder associated with expression of a mixed-lineage leukemia (MLL) chimera. A "subject in need of treatment" may include a subject having a cancer that is characterized by rearrangement in and expression of the mixed lineage leukemia gene (e.g., via translocation), which may be referred to as a "MLL-r cancer." The mixed-lineage leukemia 1 (MLL1) gene may otherwise be referred to as Lysine [K]-specific MethylTransferase 2A or KMT2A) on chromosome 11q23. MLL1 may exist in several isoforms (e.g., isoforms 1, 2, and 3). In particular, some leukemia such as acute lymphoblastic leukemia (ALL) or acute myelogenous leukemia (AML) have been shown to be characterized by MLL-r. A subject in need of treatment may include a subject having a disease or disorder associated with relatively high expression of a MLL chimera that is dependent on the SEC A "subject in need of treatment" may include a subject having a disease, disorder, or condition that is characterized by relatively high expression of one or more tumor promoters for example Myc (c-Myc) or mutant forms thereof. For example, a "subject in need of treatment" may include a subject having a cell proliferative disease, disorder, or condition such as cancer characterized by and/or associated with relatively high expression of Myc which is dependent upon the SEC. Such cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need of treatment" may include a subject infected with the human immunodeficiency virus (HIV) and HIV-1 in particular. A subject in need of treatment may include a subject having a HIV infection characterized by Tat-dependent, SEC-dependent transcription.

Therapeutic Agents

As used herein, a "therapeutic agent" may refer to any agent that is administering to a subject in thereof in order to treat the subject. A therapeutic agent may refer to an agent that modulates the biological activity of the Super Elongation Complex (SEC). For example, a therapeutic agent may disrupt the SEC. Therapeutic agents may include, but are not limited to, small molecules or compounds as disclosed herein. Therapeutic agents may include, but are not limited to, pharmaceutical compositions comprising small molecules or compounds as disclosed herein.

Chemical Entities

Chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., —($CH_2$)n—where n is an integer such as an integer between 1 and 20). An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen.

Accordingly, the substituent of an alkyl that renders that alkyl an ether is or resembles an alkoxyl, such as may be represented by one of —O—alkyl, —O—alkenyl, —O—alkynyl, and the like.

The term "carbonyl" as used herein refers to the radical—C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R'C(O)N(R$^2$)R$^3$—, —C(O)NR$^2$R$^3$, or —C(O)NH$_2$, wherein R', R$^2$ and R$^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof.

Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound). The compounds may have an undefined double stereo bond whose substituents may be present in either of the syn-conformation or the anti-conformation (or alternatively in the E-conformation or the Z-conformation).

Use of the Disclosed Compounds as Therapeutic Agents and Pharmaceutical Compositions The disclosed compounds may be formulated as therapeutics. In particular, the disclosed compounds may be formulated as anti-cancer therapeutics.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and pharmaceutical compositions comprising the disclosed compounds may be administered in methods of treating a subject in need thereof. For example, in the methods of treatment a subject in need thereof may include a subject having a cell proliferative disease, disorder, or condition such as cancer.

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenyl acetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

In addition, the methods disclosed herein may be practiced using solvate forms of the compounds disclosed herein. Solvate forms may include ethanol solvates, hydrates, and the like.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds are formulated as a composition for administration orally (e.g., in a solvent such as 5% DMSO in oil such as vegetable oil).

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Compounds and Uses Thereof for Disrupting and/or Inhibiting the Super Elongation Complex (SEC) and Pharmaceutical Compositions and Methods of Treatment Utilizing the Compounds for Treating SEC-Dependent Diseases and Disorders Disclosed herein are compounds having the following formula I or tautomers or pharmaceutical salts thereof:

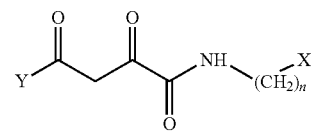

wherein n is 0-6, in particular where n is 0 or 1;

X and Y are the same or different and are selected from carbocycles and heterocycles which are saturated or unsaturated at one or more bonds and which optionally are substituted with substituents selected from the group consisting of alkyl, alkoxy, halo, haloalkyl, hydroxyl, amino, cyano, and carboxyl;

and optionally with the proviso that the compound is not 2,4-dioxo-N,4-diphenylbutanamide and optionally with the proviso that the compound is not N-(5-chloro-2-methylphenyl)-4-hydroxy-4-(3-methoxyphenyl)-2-oxobut-3-enamide and optionally with the proviso that the compound is not N-(5-chloro-2-methylphenyl)-4-(4-fluorophenyl)-4-hydroxy-2-oxobut-3-enamide.

Tautomers of the disclosed compounds may include, but are not limited to compounds having a formula Ia, Ib, or Ic:

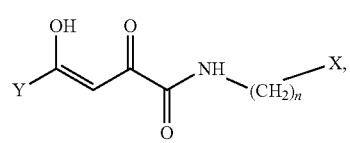

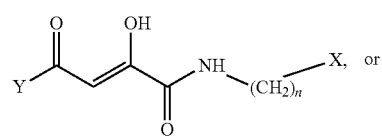

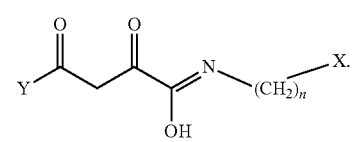

In the disclosed compounds, substituent Y is selected from carbocycles and heterocycles (e.g., carbocycles or heterocycles having 3-8 atoms, where heteroatoms may include, but are not limited to N, O, and S), which carbocycles and heterocycles are saturated or unsaturated at one or more bonds and which optionally are substituted with substituents selected from the group consisting of alkyl, alkyoxy, halo, haloalkyl, hydroxyl, amino, alkylamino, cyano, and carboxyl. In some embodiments, Y is unsubstituted or substituted phenyl (e.g., where Y is selected from 4-fluorophenyl, 4-chlorophenyl, 3-methyoxyphenyl, 4-ethoxyphenyl, 4-methylphenyl, and 2,5-dimethoxyphenyl).

In the disclosed compounds, substituent X is selected from carbocycles and heterocycles (e.g., carbocycles or heterocycles having 3-8 atoms, where heteroatoms may include, but are not limited to N, O, and S), which carbocycles and heterocycles are saturated or unsaturated at one or more bonds and which optionally are substituted with substituents selected from the group consisting of alkyl, alkyoxy, halo, haloalkyl, hydroxyl, amino, alkylamino, cyano, and carboxyl. In some embodiments, X is unsubstituted or substituted phenyl (e.g., where X is selected from 2-fluorophenyl, 2-chlorphenyl, 3-fluorophenyl, 3-chlorophenyl, 4-fluorophenyl, 4-chlorophenyl, 3,4-difluorophenyl, 3,4-dichlorophenyl, 2-methyl-3-methoxyphenyl, 3,5-dimethyoxyphenyl, 3-carboxyl-6-methylphenyl or 4-methylbenzo-3-yl, 5-chloro-2-methoxyphenyl, 3-methoxyphenyl, 5-methyl-2-methoxyphenyl, 3,4-dimethoxyphenyl, 5-chloro-2-methylphenyl, 2,6-dimethylphenyl, 2,4-dimethylphenyl, 3-chloro-2-methylphenyl, 2,3-dimethylphenyl, 4-fluoro-3-chlorophenyl, 4-ethoxyphenyl, 4-ethylphenyl, 4-bromophenyl, 4-methyl-3-chlorophenyl, 2-ethylphenyl, and 3-chloro-2-methylphenyl).

In some embodiments of the disclosed compounds, X is a heterocycle. For example, in some embodiments, X may be selected from the group consisting of unsubstituted or substituted pyridinyl (e.g., pyridin-3-yl, 5-fluoro-pyridin-3-yl, or pyridin-4-yl), unsubstituted or substituted pyrimidinyl (e.g., pyrimidin-5-yl or 4-methyl-pyrimidin-5-yl), unsubstituted or substituted pyrazinyl (e.g., pyrazin-2-yl or 3-methyl-pyrazin-2-yl), unsubstituted or substituted thiazol (e.g., thiaz-2-ol), unsubstituted or substituted tetrazolyl (e.g. 2H-tetrazol-5-yl), and unsubstituted or substituted oxadiazolyl (e.g., 1,2,4-oxadiazol-3-yl or 5-methyl-1,2,4-oxadiazol-3-yl).

In some embodiments of the disclosed compounds, X and Y are substituted or unsubstituted phenyl and the compounds have a formula:

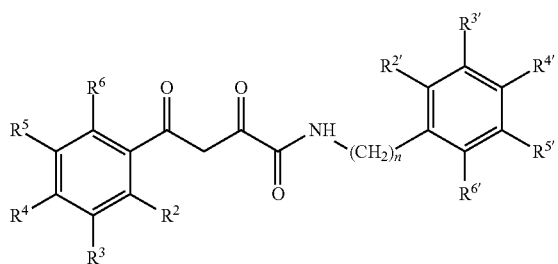

wherein $R^2$, $R^3$, $R^4$, $R^5$, $R^6$ and $R^{2'}$, $R^{3'}$, $R^{4'}$, $R^{5'}$, and $R^{6'}$ are selected from alkyl, alkyoxy, halo, haloalkyl, hydroxyl, amino, cyano, and carboxyl and optionally n is 0 or 1.

In particular, the disclosed compounds may have a formula:

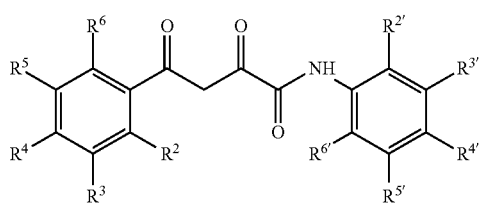

optionally wherein $R^4$ is fluoro,
optionally wherein $R^5$ is methoxy,
optionally wherein $R^{2'}$ is methyl, and
optionally wherein $R^{5'}$ is chloro.

As contemplated herein, the compound having the following formula or a tautomer thereof:

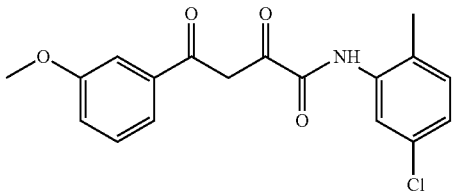 [SMILES: COc1cccc(C(=O)CC(=O)C(=O)Nc2cc(Cl)ccc2C)c1]

and named
N-(5-chloro-2-methylphenyl)-4-oxo-4-(3-methoxyphenyl)-2-oxobutanamide (or its tautomer N-(5-chloro-2-methylphenyl)-4-hydroxy-4-(3-methoxyphenyl)-2-oxobut-3-enamide) may alternatively be referred to as "KL-1."

As contemplated herein, the compound having the following formula or a tautomer thereof:

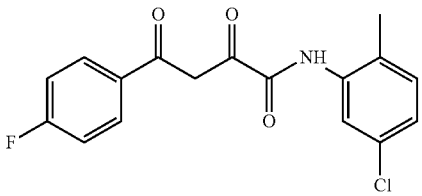 [SMILES: Cc1ccc(Cl)cc1NC(=O)C(=O)CC(=O)c1ccc(F)cc1]

and named N-(5-chloro-2-methylphenyl)-4-oxo-(4-fluorophenyl)-2-oxobutanamide (or its tautomer N-(5-chloro-2-methylphenyl)-4-hydroxy-(4-fluorophenyl)-2-oxobut-3-enamide) may alternatively be referred to as "KL-2."

Pharmaceutical compositions comprising the disclosed compounds also are contemplated herein. The disclosed pharmaceutical compositions may comprise one or more of the compounds disclosed herein or a tautomer or pharmaceutical salt thereof, together with a pharmaceutically suitable carrier or excipient. The disclosed pharmaceutical compositions in particular may comprise one or more of the compounds referred to herein as KL-1 and KL-2.

Methods of treatment also are disclosed herein. The disclosed methods may be practiced for treating a disease or disorder associated with Super Elongation Complex (SEC) activity in a subject in need thereof, where the methods include administering to the subject any of the compounds disclosed or contemplated herein or any of the pharmaceutical compositions disclosed or contemplated herein. The disclosed methods may be practiced in order to treat a subject having or at risk for developing a cell proliferative disease or disorder (e.g., cancer). The disclosed methods may be practiced in order to treat a subject having or at risk for developing a disease or disorder associated with high levels of Myc expression (e.g., a c-Myc dependent cancer). The disclosed methods may be practiced in order to treat a subject having or at risk for developing a mixed lineage leukemia (MLL) chimera. The disclosed methods may be practiced in order to treat a subject having or at risk for developing acute myeloid leukemia (AML) or acute lymphoid leukemia (ALL). The disclosed methods may be practiced in order to treat a subject having or at risk for developing an active infection by human immunodeficiency virus (HIV).

The compounds disclosed herein preferably modulate activity of the Super Elongation Complex (SEC). Modulation may include inhibiting the biological activity of the SEC, for example, inhibiting the biological activity of the SEC by disrupting an interaction between two or more components of the SEC. Preferably, the disclosed compounds disrupt an interaction between two or more components of the SEC selected from the protein referred to as "AF4/FMR2 family, member 4" (AFF4), the protein referred to as Pol II c-terminal domain (CTD) kinase (P-TEFb), and/or the protein referred to as transcription elongation factor (ELL2). Even more preferably, the disclosed compounds disrupt the interaction between AFF4 and the Cyclin T subunit of P-TEFb, for example by mimicking the molecule structure of the peptide LFGEP present in AFF4.

SEC activity may be assessed utilizing methods known in the art and the methods disclosed herein, including the methods disclosed in the Examples provided herein. In some embodiments, the compounds disrupt the SEC and/or decrease the biological activity of the SEC relative to a control (e.g., by at least about 10%, 20%, 30%, 40%, 50%, 60%, 70%, 80%, 90%, or more). In other embodiments, an $IC_{50}$ value for the compound in regard to disrupting the SEC and/or decreasing the biological activity of the SEC may be determined and preferably the compound has an $IC_{50}$ value of less than about 10 µM, 5 µM, or 1 µM, 0.5 µM, 0.1 µM, 0.05 µM, 0.01 µM, 0.005 µM, or 0.001 µM.

The compounds disclosed herein (e.g., compounds of Formula I) may exist in one or more tautomeric forms as known in the art (e.g., compounds of Formula Ia, Ib, and Ic). The disclosed compounds encompass tautomeric derivatives as would be known in the art. The compounds disclosed herein (e.g., compounds of Formula I) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.) As used herein, formulae which do not specify the orientation at one or more chiral centers are meant to encompass all orientations and mixtures thereof.

The compounds for use according to the methods of disclosed herein may be administered as a single compound or a combination of compounds. For example, a compound that disrupts the SEC or inhibits the biological activity of the SEC may be administered as a single compound or in combination with another compound that disrupts the SEC or inhibits the biological activity of the SEC or that has a different pharmacological activity.

Exemplary Compounds

Exemplary compounds disclosed herein optionally for use in the disclosed pharmaceutical compositions and methods disclosed may include, but are not limited to, the following compounds, tautomers thereof, or pharmaceutical salts thereof:

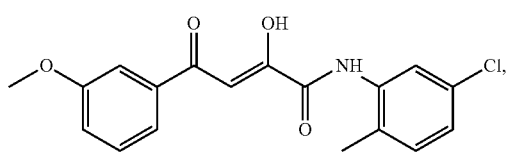

-continued

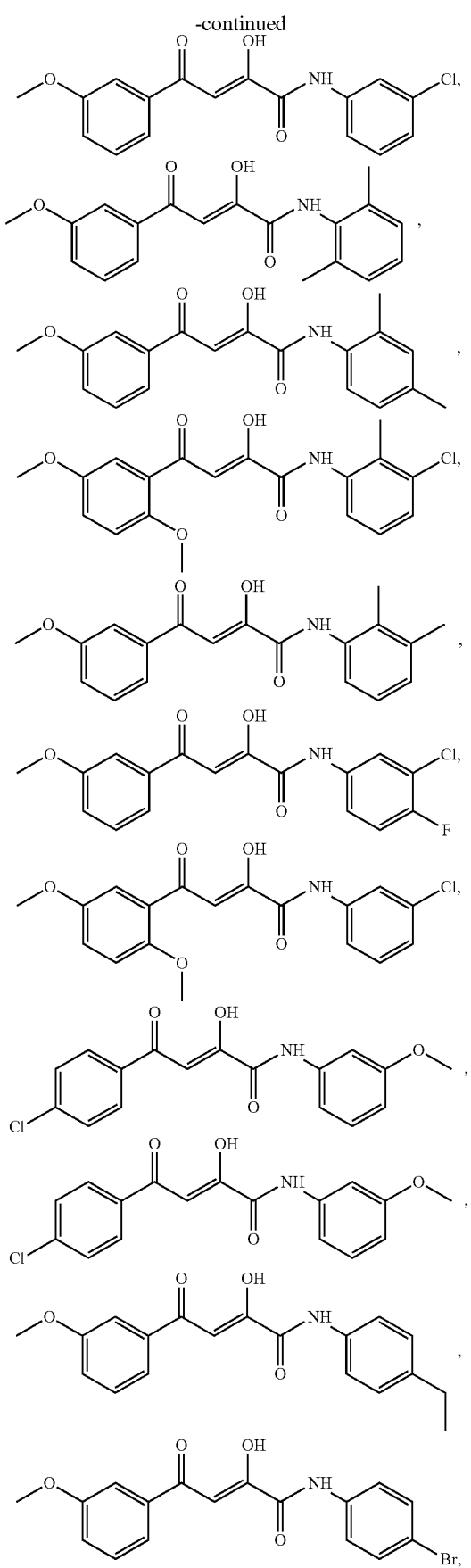

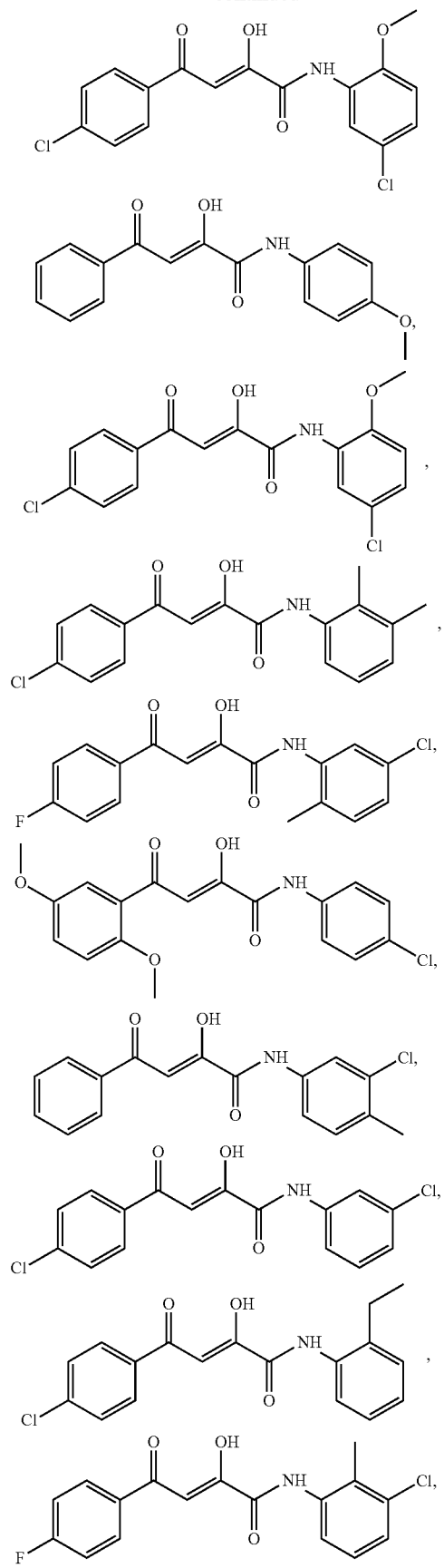
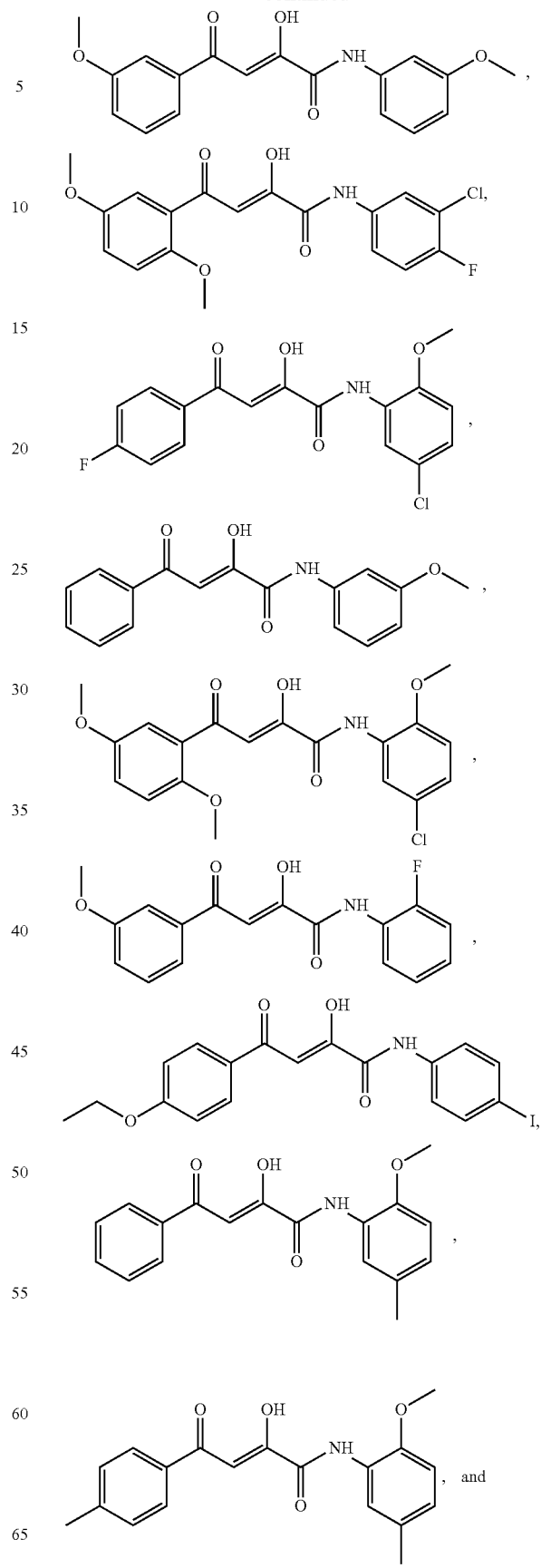

-continued

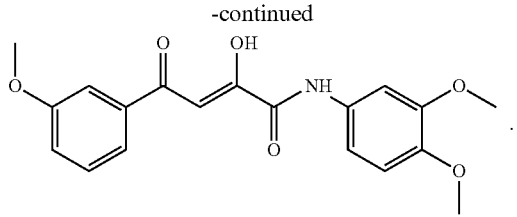

In other embodiments, exemplary compounds disclosed herein optionally for use in the disclosed pharmaceutical compositions and methods disclosed may include, but are not limited to, the following compounds, tautomers thereof, or pharmaceutical salts thereof:

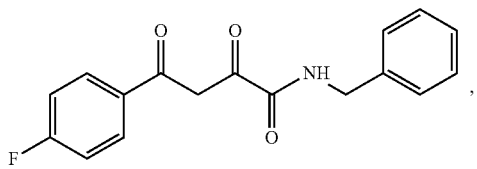

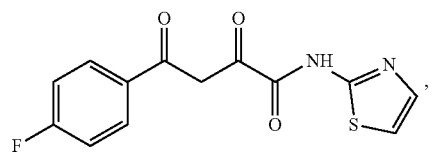

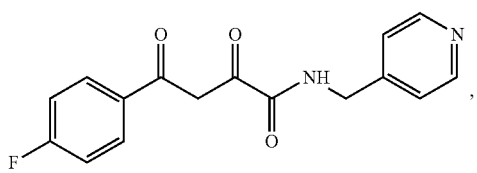

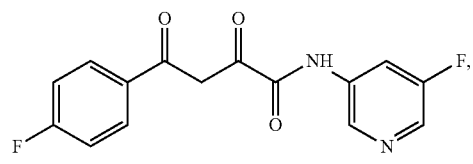

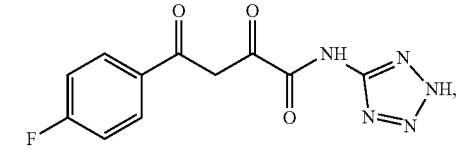

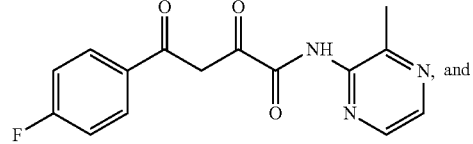

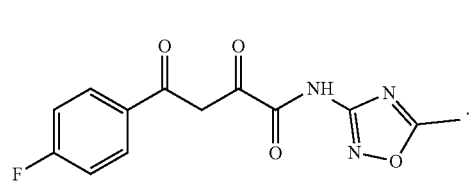

In other embodiments, exemplary compounds disclosed herein optionally for use in the disclosed pharmaceutical compositions and methods disclosed may include, but are not limited to, the following compounds, tautomers thereof, or pharmaceutical salts thereof:

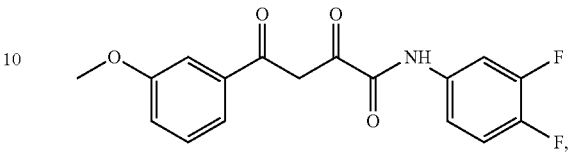

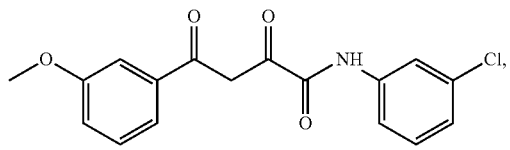

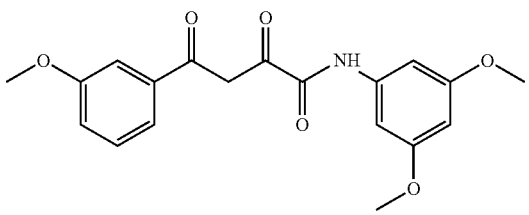

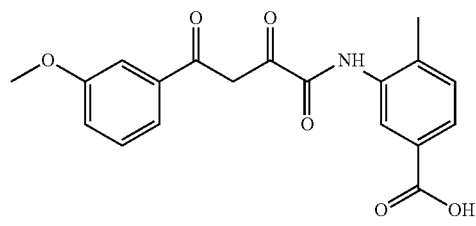

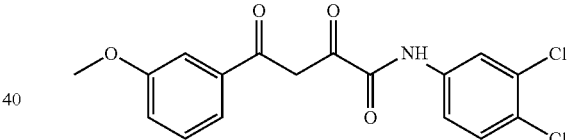

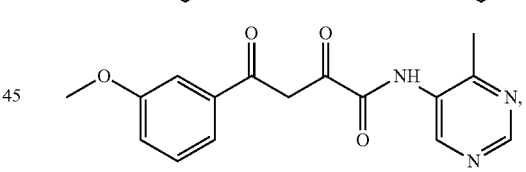

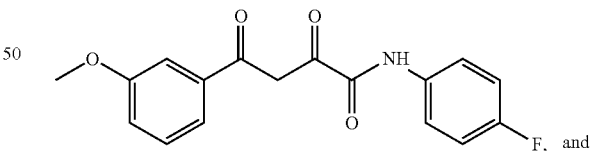

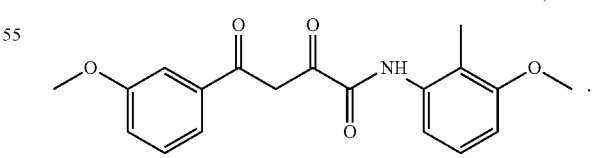

Additional Exemplary Compounds

In some embodiments of the disclosed compounds, X and Y are substituted or unsubstituted phenyl and the compounds have a formula:

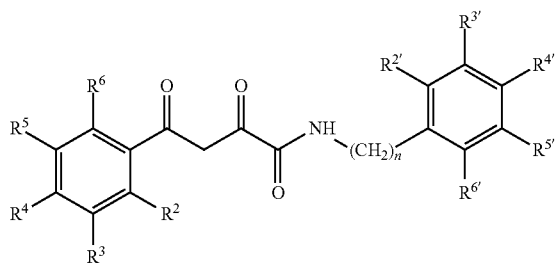

wherein:

n is 0-6

$R^2$, $R^3$, $R^4$, $R^5$, $R^6$ are selected from alkyl, alkyoxy, halo, haloalkyl, hydroxyl, amino, cyano, and carboxyl;

at least one of $R^{2'}$, $R^{3'}$, $R^{4'}$, $R^{5'}$, and $R^{6'}$ is

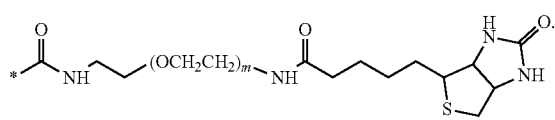

wherein m is 0=6; and the remainder of $R^{2'}$, $R^{3'}$, $R^{4'}$, $R^{5'}$, and $R^{6'}$ are selected from alkyl, alkyoxy, halo, haloalkyl, hydroxyl, amino, cyano, and carboxyl.

Exemplary Formulations

The following list of formulations is illustrative and should not be interpreted to limit the scope of the claimed subject matter. These illustrative formulations may be suitable for preparing pharmaceutical compositions that include the disclosed compounds as "active ingredients."

Formulation 1

Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3 An aerosol solution is prepared containing the following components:

|  | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to 30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8
An intravenous formulation containing 100 mg of medicament per 5 ml dose can be prepared as follows:

| | |
|---|---|
| Active Ingredient | 100 mg |
| Mannitol | 100 mg |
| 5N Sodium hydroxide | 200 ml |
| Purified water to total | 5 n |

ILLUSTRATIVE EMBODIMENTS

The following embodiments are illustrative and should not be interpreted to limit the scope of the claimed subject matter.

Embodiment 1. A compound, a tautomer, or a pharmaceutical salt thereof having a formula:

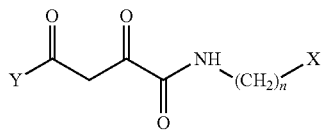

wherein n is 0-6;

X and Y are the same or different and are selected from carbocycles and heterocycles which are saturated or unsaturated at one or more bonds and which optionally are substituted with substituents selected from the group consisting of alkyl, alkoxy, halo, haloalkyl, hydroxyl, amino, cyano, and carboxyl;

and optionally with the proviso that the compound is not 2,4-dioxo-N,4-diphenylbutanamide and optionally with the proviso that the compound is not N-(5-chloro-2-methylphenyl)-4-oxo-4-(3-methoxyphenyl)-2-oxobutanamide and optionally with the proviso that the compound is not N-(5-chloro-2-methylphenyl)-4-oxo-(4-fluorophenyl)-2-oxobutanamide.

Embodiment 2. The compound of embodiment 1, wherein n is 0 or 1.

Embodiment 3. The compound of embodiment 1 or 2, wherein Y is unsubstituted or substituted phenyl (e.g., 4-fluorophenyl, 4-chlorophenyl, 3-methyoxyphenyl, 4-ethoxyphenyl, 4-methylphenyl, and 2,5-dimethoxyphenyl).

Embodiment 4. The compound of any of the foregoing embodiments wherein X is unsubstituted or substituted phenyl (e.g., 2-fluorophenyl, 4-fluorophenyl, 3,4-difluorophenyl, 3-chlorophenyl, 3,4-dichlorophenyl, 2-methyl-3-methoxyphenyl, 3,5-dimethyoxyphenyl, or 3-carboxyl-6-methylphenyl, 4-methylbenzo-3-yl, 5-chloro-2-methoxyphenyl, 3-methoxyphenyl, 5-methyl-2-methoxyphenyl, 3,4-dimethoxyphenyl, 5-chloro-2-methylphenyl, 2,6-dimethylphenyl, 2,4-dimethylphenyl, 3-chloro-2-methylphenyl, 2,3-dimethylphenyl, 4-fluoro-3-chlorophenyl, 4-ethoxyphenyl, 4-ethylphenyl, 4-bromophenyl, 4-methyl-3-chlorophenyl, 2-ethylphenyl, and 3-chloro-2-methylphenyl).

Embodiment 5. The compound of any of embodiments 1-3, wherein X is selected from the group consisting of unsubstituted or substituted pyridinyl (e.g., pyridin-3-yl, 5-fluoro-pyridin-3-yl, or pyridin-4-yl), unsubstituted or substituted pyrimidinyl (e.g., pyrimidin-5-yl or 4-methyl-pyrimidin-5-yl), unsubstituted or substituted pyrazinyl (e.g., pyrazin-2-yl or 3-methyl-pyrazin-2-yl), unsubstituted or substituted thiazol (e.g., thiaz-2-ol), unsubstituted or substituted tetrazolyl (e.g. 2H-tetrazol-5-yl), and unsubstituted or substituted oxadiazolyl (e.g, 1,2,4-oxadiazol-3-yl or 5-methyl-1,2,4-oxadiazol-3-yl).

Embodiment 6. The compound of any of the foregoing embodiments having a formula:

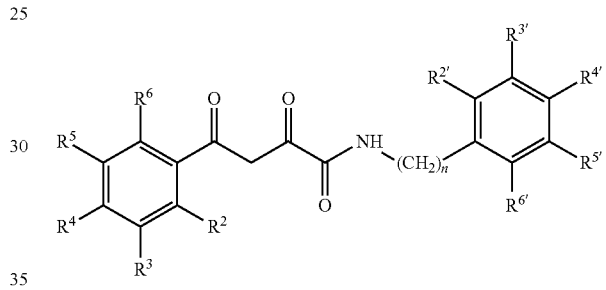

wherein $R^2$, $R^3$, $R^4$, $R^5$, $R^6$ and $R^{2'}$, $R^{3'}$, $R^{4'}$, $R^{5'}$, and $R^{6'}$ are selected from alkyl, alkyoxy, halo, haloalkyl, hydroxyl, amino, cyano, and carboxyl and optionally n is 0 or 1

Embodiment 7. The compound of any of the foregoing embodiments having a formula:

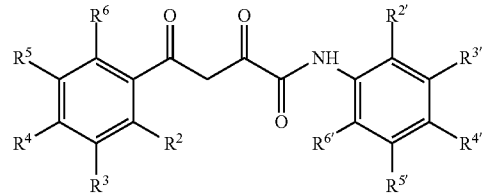

optionally wherein $R^4$ is fluoro,
optionally wherein $R^5$ is methoxy,
optionally wherein $R^{2'}$ is methyl, and
optionally wherein $R^{5'}$ is chloro.

Embodiment 8. A pharmaceutical composition comprising the following compound or a tautomer or pharmaceutical salt thereof and a pharmaceutically acceptable carrier:

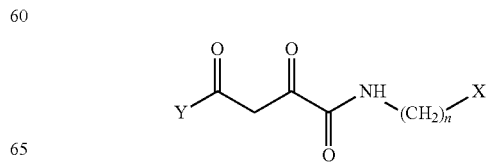

wherein n is 1-6;

and X and Y are the same or different and are selected from carbocycles and heterocycles which are saturated or unsaturated at one or more bonds and which optionally are substituted with substituents selected from the group consisting of alkyl, alkyoxy, halo, haloalkyl, hydroxyl, amino, cyano, and carboxyl.

Embodiment 9. The pharmaceutical composition of embodiment 8, wherein n is 0 or 1.

Embodiment 10. The pharmaceutical composition of embodiment 8 or 9, wherein Y is unsubstituted or substituted phenyl (e.g., 4-fluorophenyl, 4-chlorophenyl, 3-methyoxyphenyl, 4-ethoxyphenyl, 4-methylphenyl, 2,5-dimethoxyphenyl).

Embodiment 11. The pharmaceutical composition of any of embodiments 8-10, wherein X is unsubstituted or substituted phenyl (e.g., 2-fluorophenyl, 4-fluorophenyl, 3,4-difluorophenyl, 3-chlorophenyl, 3,4-dichlorophenyl, 2-methyl-3-methoxyphenyl, 3,5-dimethyoxyphenyl, or 3-carboxyl-6-methylphenyl, 4-methylbenzo-3-yl, 5-chloro-2-methoxyphenyl, 3-methoxyphenyl, 5-methyl-2-methoxyphenyl, 3,4-dimethoxyphenyl, 5-chloro-2-methylphenyl, 2,6-dimethylphenyl, 2,4-dimethylphenyl, 3-chloro-2-methylphenyl, 2,3-dimethylphenyl, 4-fluoro-3-chlorophenyl, 4-ethoxyphenyl, 4-ethylphenyl, 4-bromophenyl, 4-methyl-3-chlorophenyl, 2-ethylphenyl, 3-chloro-2-methylphenyl).

Embodiment 12. The pharmaceutical composition of any of embodiments 8-10, wherein X is selected from the group consisting of unsubstituted or substituted pyridinyl (e.g., pyridin-3-yl, 5-fluoro-pyridin-3-yl, or pyridin-4-yl), unsubstituted or substituted pyrimidinyl (e.g., pyrimidin-5-yl or 4-methyl-pyrimidin-5-yl), unsubstituted or substituted pyrazinyl (e.g., pyrazin-2-yl or 3-methyl-pyrazin-2-yl), unsubstituted or substituted thiazol (e.g., thiaz-2-ol), unsubstituted or substituted tetrazolyl (e.g. 2H-tetrazol-5-yl), and unsubstituted or substituted oxadiazolyl (e.g, 1,2,4-oxadiazol-3-yl or 5-methyl-1,2,4-oxadiazol-3-yl).

Embodiment 13. The pharmaceutical composition of any of embodiments 8-12, wherein the compound has the following formula or a tautomer thereof:

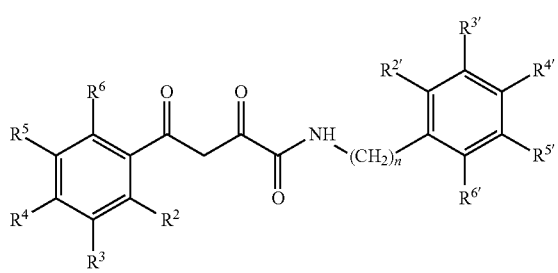

wherein $R^2$, $R^3$, $R^4$, $R^5$, $R^6$ and $R^{2'}$, $R^{3'}$, $R^{4'}$, $R^{5'}$, and $R^{6'}$ are selected from alkyl, alkyoxy, halo, haloalkyl, hydroxyl, amino, cyano, and carboxyl and optionally n is 0 or 1.

Embodiment 14. The pharmaceutical composition of any of embodiments 8-13, wherein the compound has the following formula or a tautomer thereof:

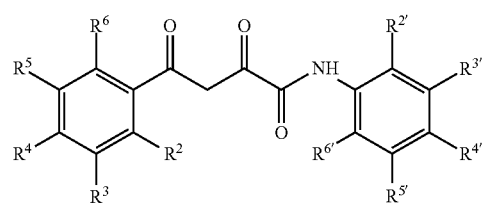

optionally wherein $R^4$ is fluoro, optionally wherein $R^5$ is methoxy, optionally wherein $R^{2'}$ is methyl, and optionally wherein $R^{5'}$ is chloro.

Embodiment 15. The pharmaceutical composition of any of embodiments 8-14, wherein the compound has the following formula or a tautomer thereof:

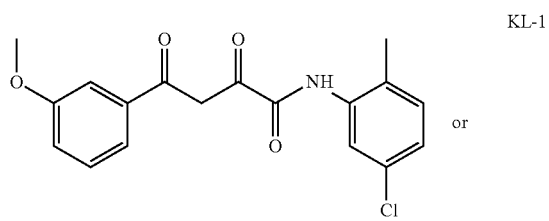

or

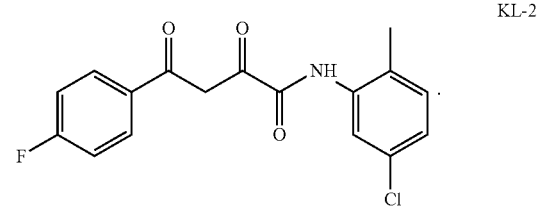

Embodiment 16. A method for treating a disease or disorder associated with Super Elongation Complex (SEC) activity in a subject in need thereof, the method comprising administering to the subject any of the compounds of embodiments 1-7 or any of the pharmaceutical compositions of embodiments 8-15.

Embodiment 17. The method of embodiment 16, wherein the disease or disorder is a cell proliferative disease or disorder (e.g., cancer).

Embodiment 18. The method of embodiment 16 or 17, wherein the disease or disorder is associated with relatively high levels of Myc expression.

Embodiment 19. The method of any of embodiments 16-18, wherein the disease or disorder is associated with expression of a mixed lineage leukemia (MLL) chimera.

Embodiment 20. The method of any of embodiments 16-19, wherein the disease or disorder is acute myeloid leukemia (AML) or acute lymphoid leukemia (ALL).

Embodiment 21. The method of any of embodiments 16-20, wherein the disease or disorder is an infection by human immunodeficiency virus (HIV).

Embodiment 22. A compound, a tautomer, or a pharmaceutical salt thereof having a formula:

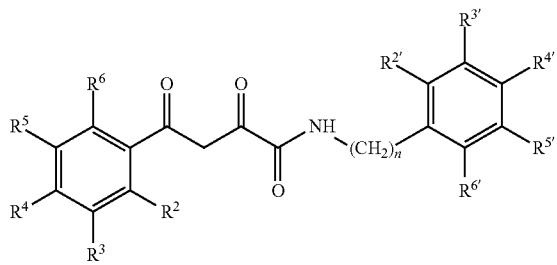

wherein:
n is 0-6
$R^2$, $R^3$, $R^4$, $R^5$, $R^6$ are selected from alkyl, alkyoxy, halo, haloalkyl, hydroxyl, amino, cyano, and carboxyl;
at least one of $R^{2'}$, $R^{3'}$, $R^{4'}$, $R^{5'}$, and $R^{6'}$ is

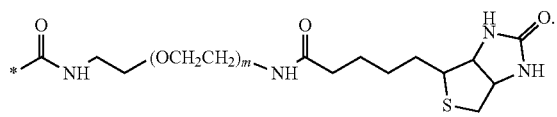

wherein m is 0-6; and
the remainder of $R^{2'}$, $R^{3'}$, $R^{4'}$, $R^{5'}$, and $R^{6'}$ are selected from alkyl, alkyoxy, halo, haloalkyl, hydroxyl, amino, cyano, and carboxyl.

Embodiment 23. A pharmaceutical composition comprising the compound of embodiment 22.

Embodiment 24. A method for treating a disease or disorder associated with Super Elongation Complex (SEC) activity in a subject in need thereof, the method comprising administering to the subject the compound of embodiment 22 or the pharmaceutical composition of embodiments 23.

Embodiment 25. The method of embodiment 24, wherein the disease or disorder is a cell proliferative disease or disorder (e.g., cancer).

Embodiment 26. The method of embodiment 24 or 25, wherein the disease or disorder is associated with relatively high levels of Myc expression.

Embodiment 27. The method of any of embodiments 24-26, wherein the disease or disorder is associated with expression of a mixed lineage leukemia (MLL) chimera.

Embodiment 28. The method of any of embodiments 24-27, wherein the disease or disorder is acute myeloid leukemia (AML) or acute lymphoid leukemia (ALL).

Embodiment 29. The method of any of embodiments 24-28, wherein the disease or disorder is an infection by human immunodeficiency virus (HIV).

EXAMPLES

The following Examples are illustrative and are not intended to limit the scope of the claimed subject matter.

Example 1

Reference is made to the manuscript Liang et al., "Targeting Processive Transcription Elongation through SEC Disruption for Myc-Induced Cancer Therapy," Oct. 18, 2018, Cell, 175:1-14, the content of which is incorporated herein by reference in its entirety.

SUMMARY

The Super Elongation Complex (SEC) is required for high levels of productive transcription through the release of RNA Polymerase II (Pol II) by its P-TEFb module and by promoting processivity with its ELL2 subunit. Malfunction of SEC contributes to multiple human diseases including cancer. Here, we identify peptidomimetic lead compounds, KL-1 and its structural homolog KL-2, which disrupt the interaction between the SEC scaffolding protein AFF4 and the P-TEFb module, result in impaired release of Pol II from promoter-proximal pausing and a reduced average rate of transcription elongation. SEC is required for induction of heat shock genes and treating cells with KL-1 and KL-2 attenuates the heat shock response. SEC inhibition downregulates MYC and MYC-dependent transcriptional programs in cells and delays tumor progression in a mouse xenograft model of MYC-driven cancer. These findings suggest that the direct disruption of SEC through inhibitors such as KL-1 and KL-2 could be used for targeting processive transcriptional elongation in targeted therapy of cancer.

INTRODUCTION

Transcription by RNA Polymerase II (Pol II) is highly regulated at different stages of the transcription cycle, including transcription initiation, release into productive elongation, and termination. In most metazoans, the vast majority of Pol II-transcribed genes are regulated at a step called promoter-proximal pausing (Chen et al., 2018; Jonkers and Lis, 2015). Release from pausing requires phosphorylation of the Pol II C-terminal domain (CTD) by cyclin-dependent kinase 9 (CDK9)-containing positive transcription elongation factor b (P-TEFb) (Peterlin and Price, 2006; Zhou et al., 2012). Proper regulation of this transcriptional checkpoint is vital for physiological responses in metazoan development and misregulation of this checkpoint has been found to contribute to human diseases, including cancer (Bradner et al., 2017; Shilatifard et al., 1996; Smith et al., 2011; Takahashi et al., 2011).

The majority of P-TEFb, comprised of CDK9 and its cyclin partner Cyclin T1 (CCNT1), is sequestered in an inactive form by RNA binding proteins HEXIM1 or HEXIM2 associating with 7SK snRNP (Luo et al., 2012a; Zhou et al., 2012). This inactive complex occupies promoter-proximal regions on chromatin (Ji et al., 2013; McNamara et al., 2016). P-TEFb can be released from the 7SK/HEXIM complex into active complexes such as BRD4/P-TEFb (Yang et al., 2005) and the Super Elongation Complex (SEC) (Luo et al., 2012b; Zhou et al., 2012). Inhibition of all P-TEFb activity can be achieved with CDK9 inhibitors such as flavopiridol (Chao and Price, 2001). The activity of the BRD4/P-TEFb complex activity can be inhibited with small molecules inhibiting its recruitment to chromatin (Dawson et al., 2011; Filippakopoulos et al., 2010) and phthalimides-conjugated compounds (Winter et al., 2015; Winter et al., 2017), which induce the rapid degradation of BRD4 protein. Blocking BRD4/P-TEFb with these compounds has been shown to inhibit release of paused Pol II into productive elongation during the early stage of transcription elongation with profound effects on MYC targets (Bradner et al., 2017; Delmore et al., 2011). However, mechanistic and functional studies of SEC in cells are limited due to the lack of convenient perturbation methods such as small molecular inhibitors for this Pol II elongation complex.

SEC is a large complex that in addition to P-TEFb contains AF4/FMR2 (AFF) family protein (AFF1-4), the YEATS domain protein family members ENL or AF9 (encoded by the MLLT1 and MLLT3 genes), the Pol II elongation factors eleven-nineteen lysine-rich leukemia (ELL) proteins, and ELL-associated factor 1 (EAF1) or EAF2

(Chen et al., 2018; Luo et al., 2012b). Within SEC, the AFF proteins function as scaffolds for the binding of the other subunits to allow the regulation of multiple steps of transcription elongation. The P-TEFb module is required for the phosphorylation of Pol II CTD on serine 2 (Ser2P) and transcription elongation factor SPT5 on its C-terminal region to promote release from the promoter-proximal transcription elongation checkpoint, while the ELL proteins have been demonstrated to enhance processivity of elongation by RNA Pol II using in vitro transcription assays (Shilatifard et al., 1997; Shilatifard et al., 1996) and in cells (Hu et al., 2013).

SEC plays important roles in physiological processes and development. SEC is required for rapid induction of transcription in response to cellular signals (Galbraith et al., 2013; Lin et al., 2011; Takahashi et al., 2011) and is hijacked by HIV Tat to activate proviral genome transcription (He et al., 2010; Sobhian et al., 2010). Mistargeting of SEC is essential for leukemogenesis driven by rearrangements of the mixed lineage leukemia (MLL) gene (Liang et al., 2017; Mohan et al., 2010; Yokoyama et al., 2010). Mutations that stabilize SEC have been identified as being causative for the developmental syndrome CHOPS (Izumi et al., 2015). Importantly, SEC is a regulatory factor of MYC (Erb et al., 2017; Luo et al., 2012a; Takahashi et al., 2011; Wan et al., 2017), which is a master regulator for cancer cell proliferation and contributes to the pathogenesis of a majority of human cancers by coordinated amplification of transcription (Lin et al., 2012; Nie et al., 2012; Sabo et al., 2014; Walz et al., 2014), and is particularly required for expression of cell division and pre-mRNA splicing factors (Hsu et al., 2015; Koh et al., 2015). Given the importance of transcription elongation control in cancer pathogenesis and the paradigm of BET domain inhibitors in targeting MYC expression and the transcriptional elongation misregulation in cancers (Bradner et al., 2017), development of inhibitors of SEC can serve as a tool for both mechanistic studies of SEC and for cancer therapeutics.

Results

Peptidomimetic identification of disruptors of the AFF4-CCNT1 interaction within the Super Elongation Complex. To identify small molecule disruptors of the Super Elongation Complex (SEC), we first examined the crystal structure (PDB: 4IMY) showing AFF4 bound to the Cyclin T1 (CCNT1) subunit of P-TEFb (Gu et al., 2014; Schulze-Gahmen et al., 2013). Five residues of the N-terminus of AFF4 (L34, F35, A36, E37 and P38) interacted with the binding groove of CCNT1, comprised of the residues W221, Y224, L163, V164, R165, Y175, F176, D169, W207, W210 and E211 (FIG. 1A). Mutation data of CCNT1 residues Y175, E211, D169, F176, R165, W210 and W207 demonstrated the importance of this pocket for interactions with AFF4 (Schulze-Gahmen et al., 2013). We therefore surmised that this region could be an ideal pocket for small molecule disruption of AFF4-CCNT1 interaction. A three-tiered grid-based ligand docking glide algorithm was employed to screen for potential compounds binding to the CCNT1 binding pocket (FIG. 1A).

Figure 8:
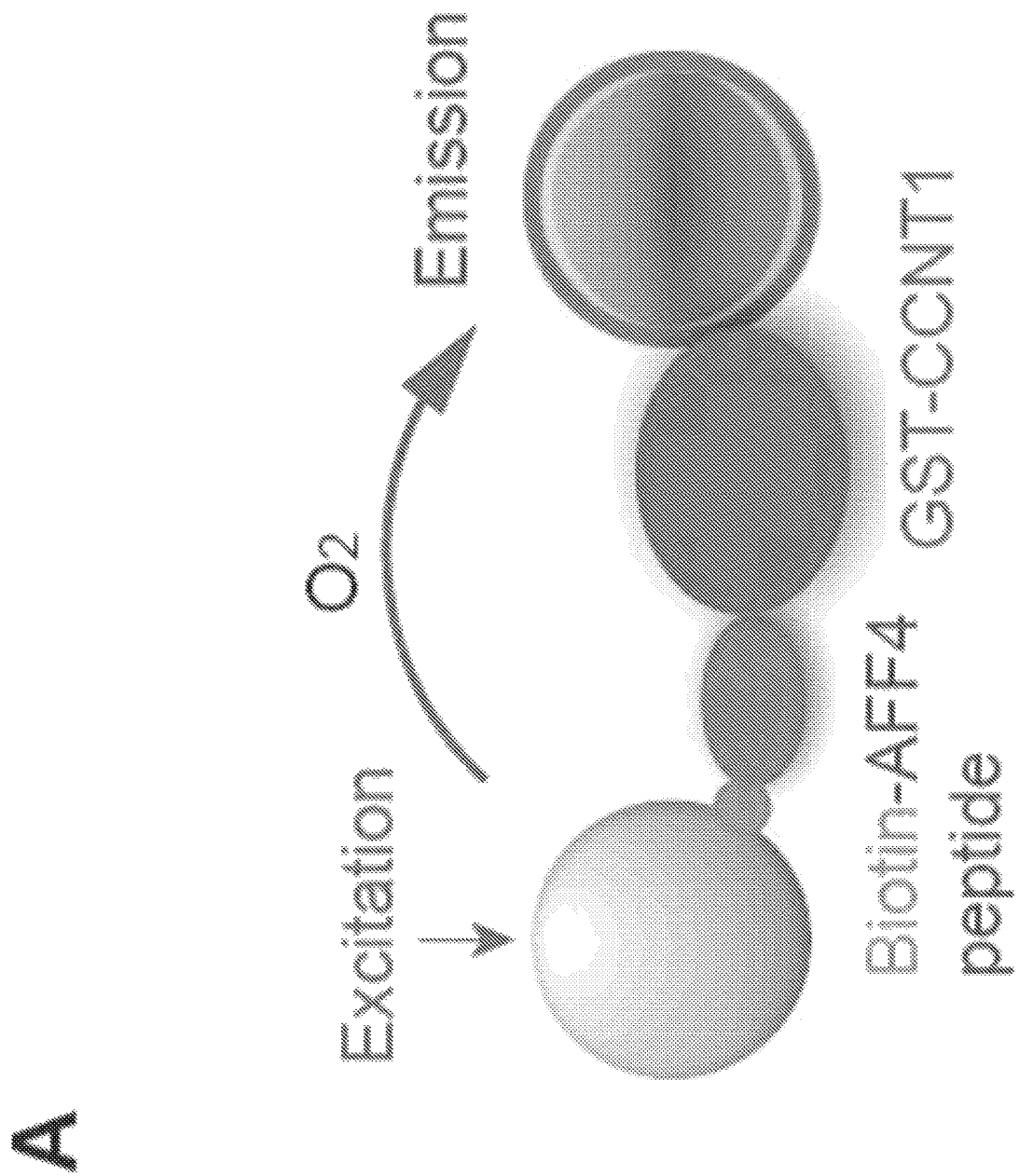
FIG. 8, related to FIG. 1. Peptidomimetic identification of disruptors of the AFF4-CCNT1 interaction within the Super Elongation Complex. (A) Schematic of AlphaLISA assay of the AFF4-CCNT1 interaction. Anti-GST AlphaLISA acceptor beads and AlphaScreen streptavidin donor beads (Perkin Elmer) were used to detect the interaction of GST-CCNT1 (AA1-300) and biotin-AFF4 (AA32-67). (B-C) Optimization of the AlphaLISA assay with various biotin-AFF4 peptide and GST-CCNT1 concentrations. No CCNT1 (B) and mutant AFF4 (C) were used as negative controls. Data are represented as Mean+/−SD. (D) Scheme for chemical synthesis of SEC inhibitors KL-1 and KL-2. Reagents and conditions: a. LDA, THF, −78° C., 15 min., then diethyl oxalate, −78° C. to room temperature. b. NaOH, THF/H$_2$O, room temperature, 15 min. c. EEDQ, 5-chloro-2-methylaniline, THF, room temperature, 24 hr. (E) 6 hr of treatment with KL-1 or KL-2 does not significantly reduce the protein levels of BRD2, BRD4, Pol II (RPB 1) and MYC in 293T cells. 293T cells were treated with 20 µM of KL-1 or KL-2 for 6 hr, and the protein levels of BRD2, BRD4, Pol II (RPB1), SPT5, MED26, MYC, HSP90 (load control) and Tubulin (load control) were measured by western blotting. (F) Treatment of HCT-116 cells with KL-1 and KL-2 reduced protein levels of SEC components AFF1 and AFF4 but not CDK9 or CCNT1. HCT-116 cells were treated with 20 µM of KL-1 or KL-2 for 6 hr, and the protein levels of AFF1, AFF4, CCNT1, CDK9 and Tubulin (load control) were determined by western blotting. (G-H) Treating cells with KL-1 and KL-2 results in reduced levels of AFF 1 and AFF4. FLAG-AFF1 (G) and FLAG-AFF4 (H) were expressed under the Tet-inducible promoter in HEK293T cells. Cells were treated with 20 µM of the indicated inhibitors for 6 hr for western blotting. (I) KL1 and KL-2 do not lead to reduced mRNA expression of SEC subunits AFF1, AFF4, ELL2, CCNT1 and CDK9 in HEK293T cells. RNA-seq was performed in HEK293T cells treated for 12 hr with 20 µM of the indicated inhibitors. The log$_2$CPM (counts per million) of the SEC subunits were calculated with HTseq. KL-1 and KL-2 had no significant effects on CCNT1, CDK9 and AFF1 expression, but modest increases in the mRNA levels of AFF4 and ELL2 were observed (n=3). Unpaired two-way ANOVA was used for the statistical testes. ,p<0.05, *,p<0.001.
Figure 8:
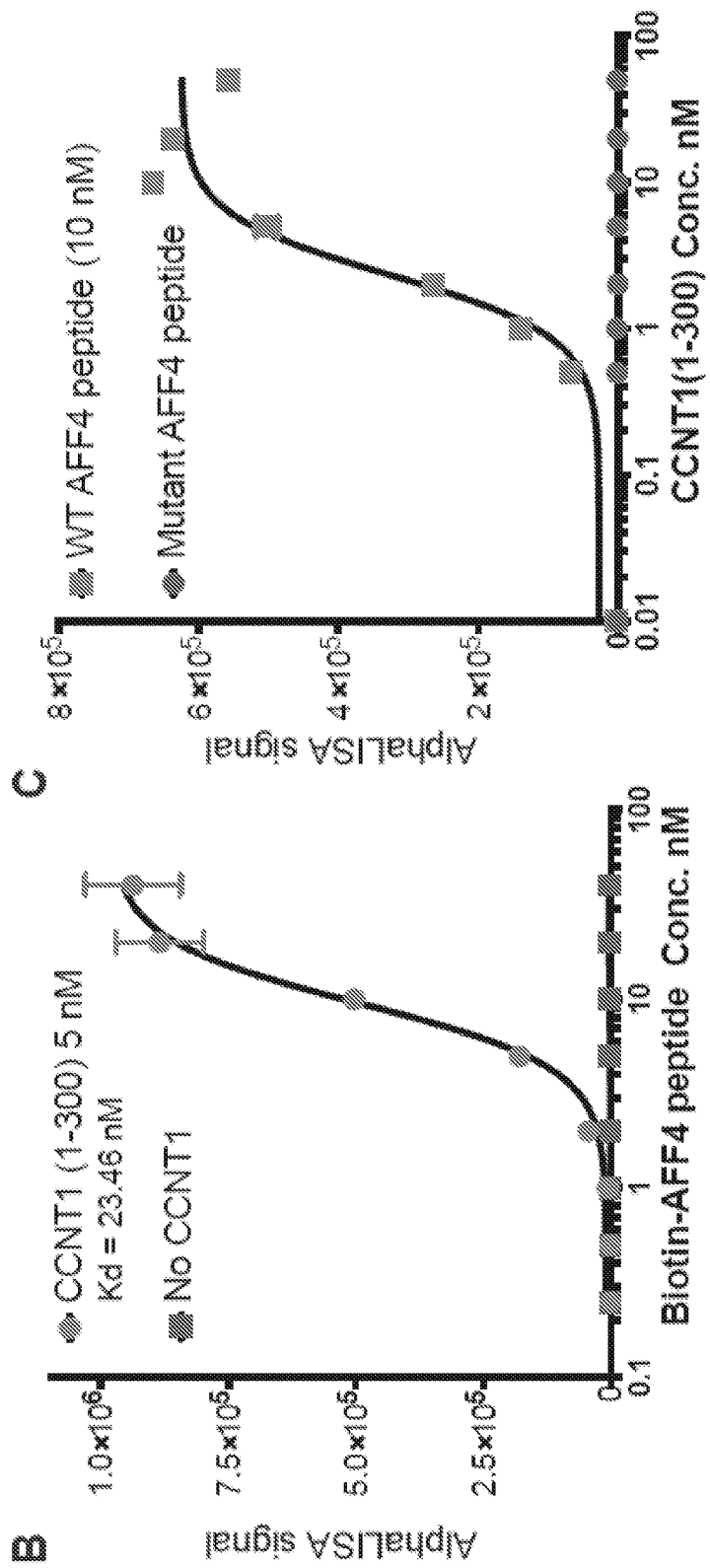
Figure 8:
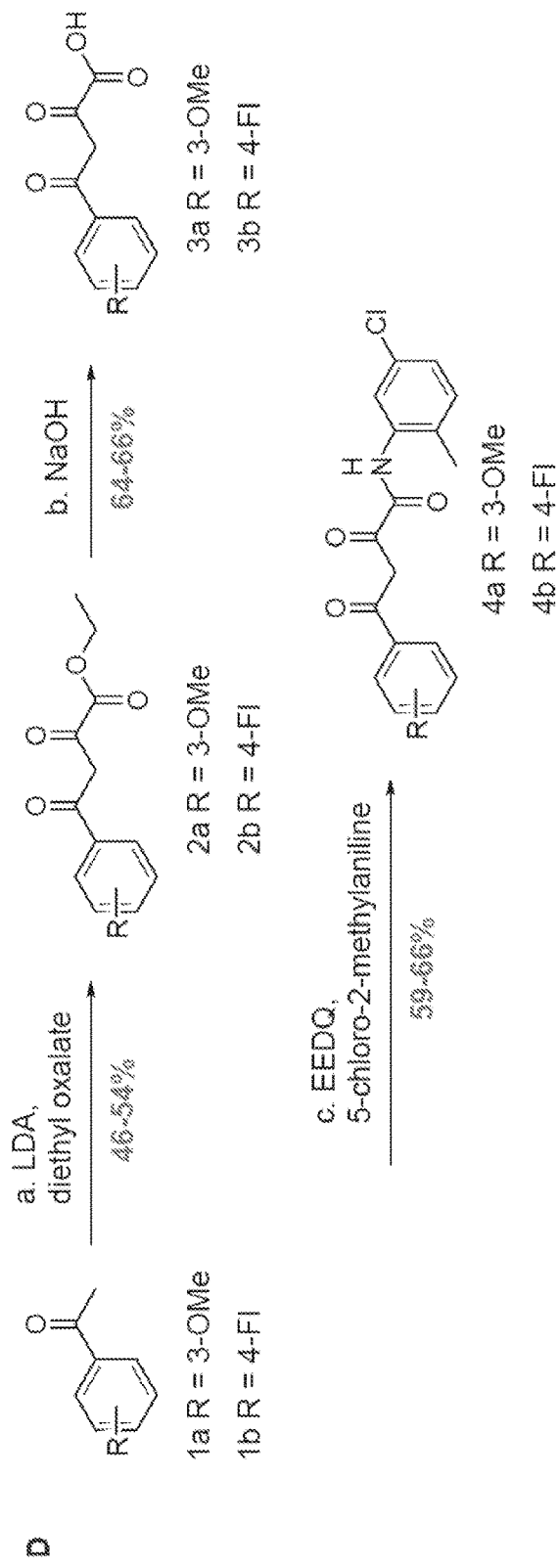
Figure 8:
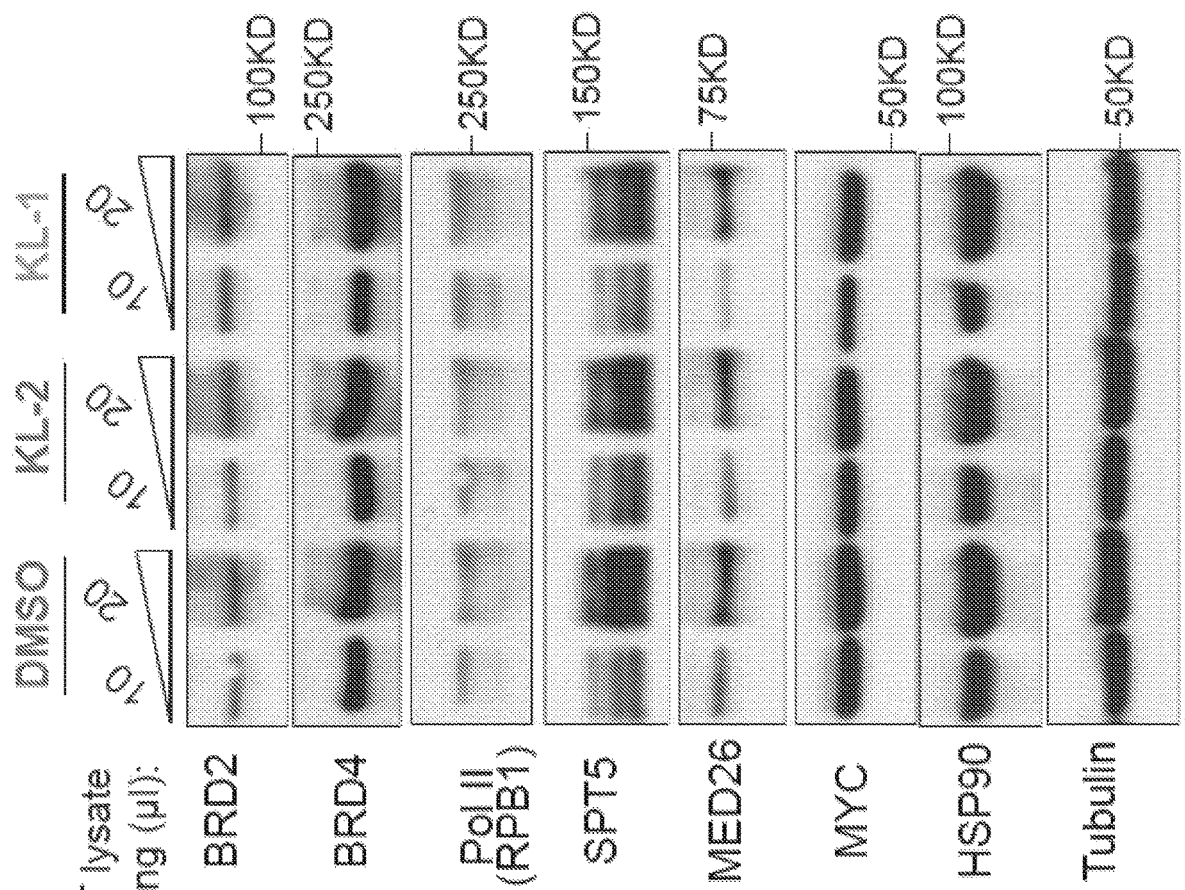
Figure 8:
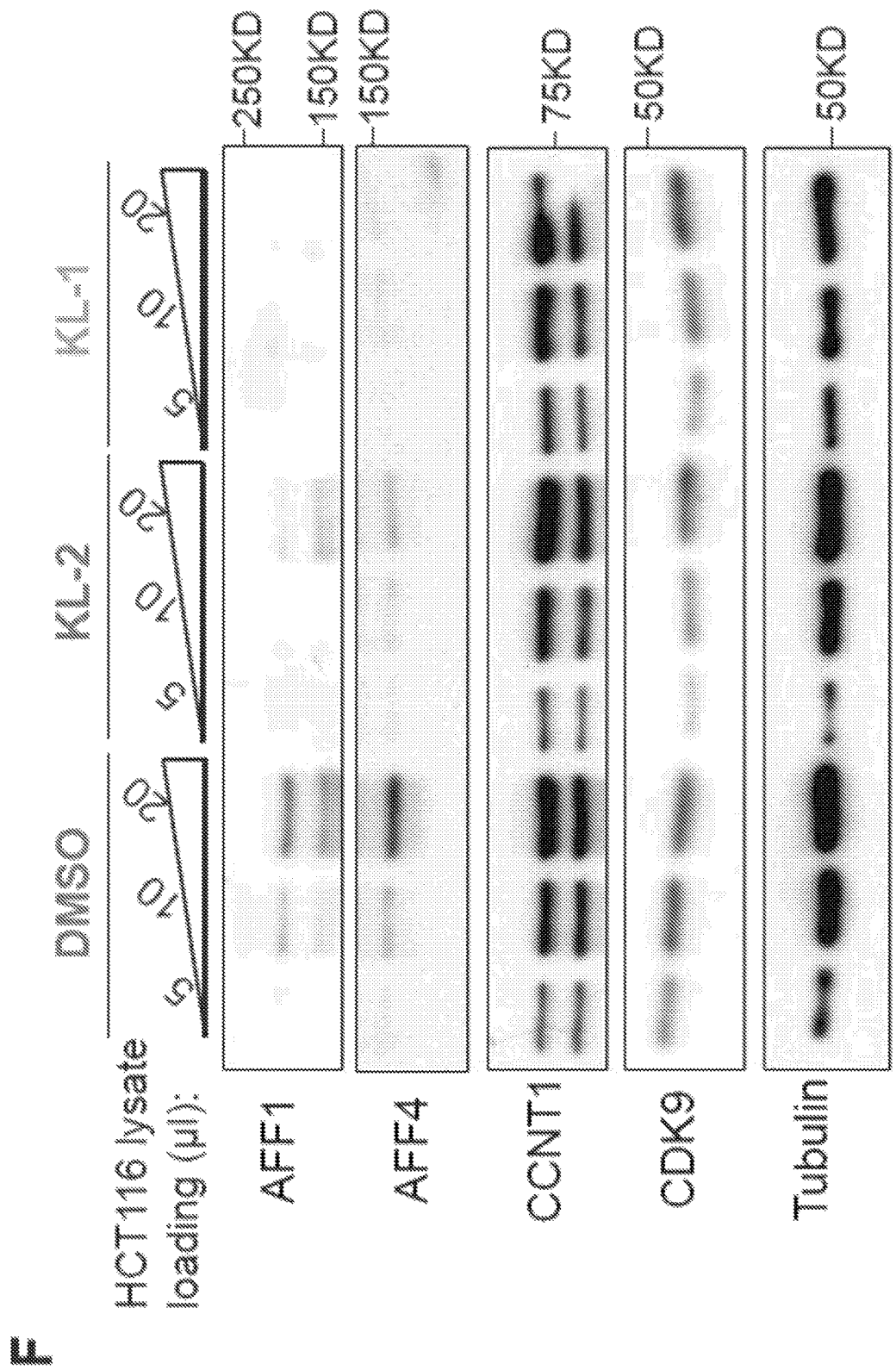
Figure 8:
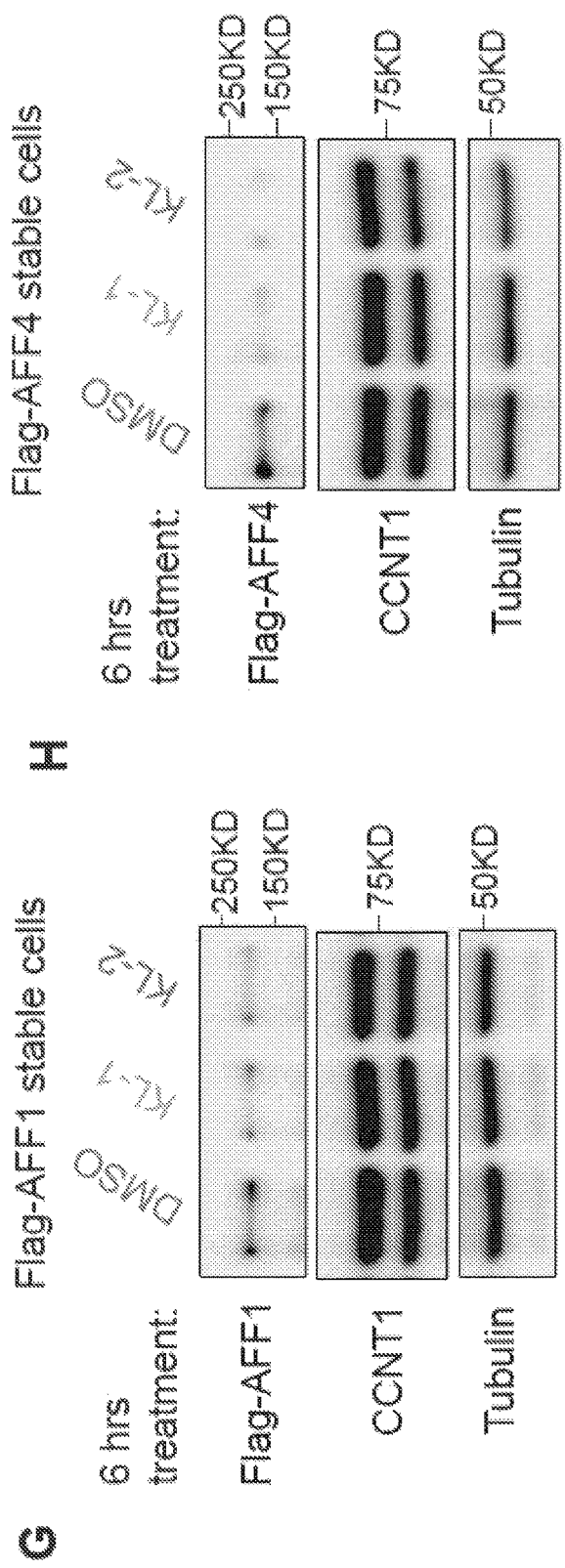
Figure 8:
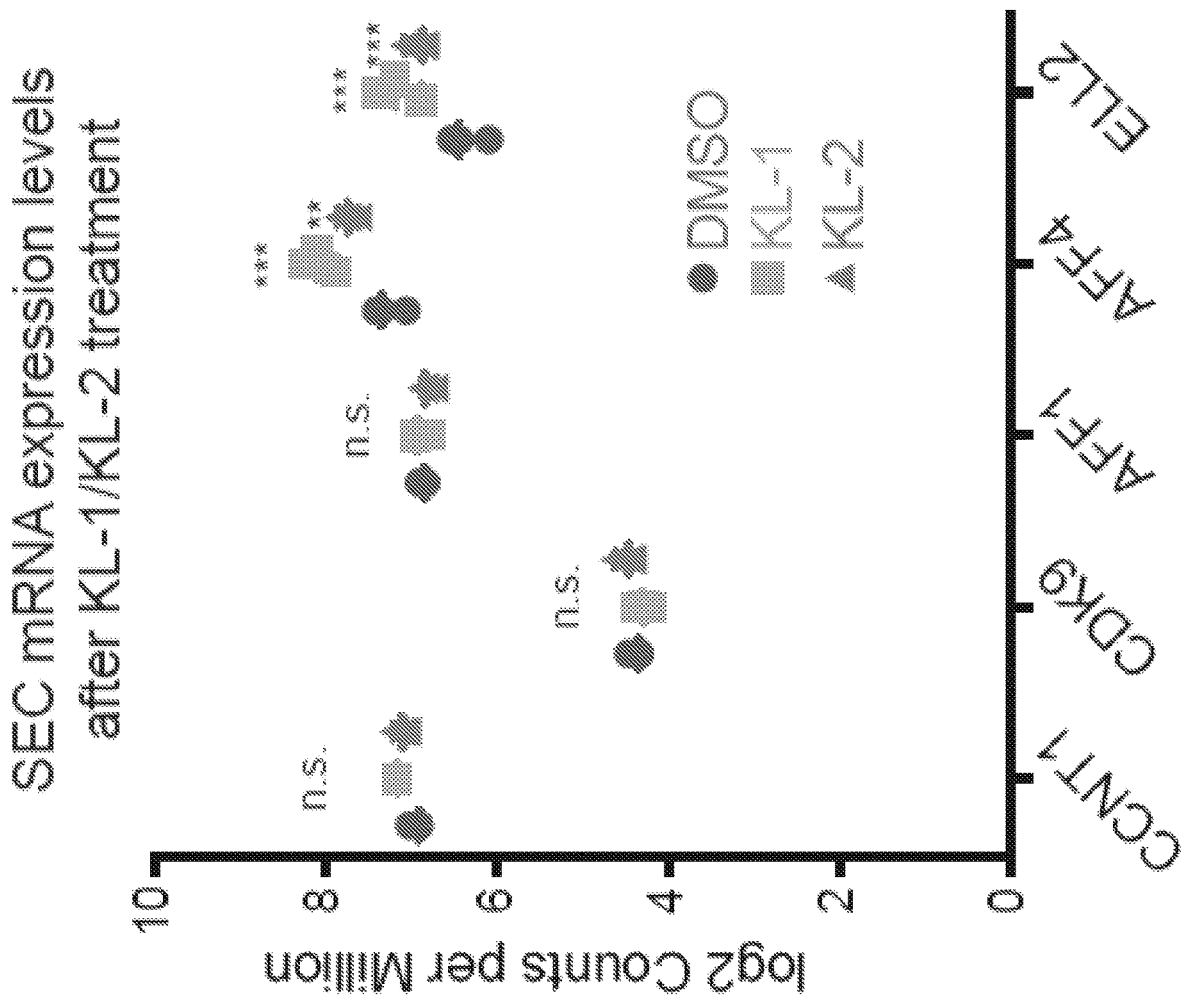

To test if candidate compounds can disrupt the AFF4-CCNT1 interaction in vitro, we established and optimized a bead-based AlphaLISA assay with recombinant CCNT1 (1-300) protein and synthesized Biotin-AFF4 peptides (AA 32-67) (FIGS. 8A, 8B and 8C). We tested the 40 compounds identified from the in silico screening at 20 µM with the AlphaLISA assay (FIG. 1B) and found that the compound (2Z)—N-(5-Chloro-2-methylphenyl)-2-hydroxy-4-(3-methoxyphenyl)-4-oxo-2-butenamide, referred to as "KL-1" (FIG. 1C), could inhibit the interaction of AFF4-CCNT1, while neither the pan-CDK9 kinase inhibitor flavopiridol nor the BET domain inhibitors disrupted the AFF4-CCNT1 interaction (FIG. 1B).

Based on the structure of KL-1 (FIG. 1C), we performed a KL-1 similarity search with ChemDiv compounds and tested the top 32 most similar compounds. The compound (2Z)-N-(5-Chloro-2-methylphenyl)-4-(4-fluorophenyl)-2-hydroxy-4-oxo-2-butenamide (referred to as "KL-2") shares the same scaffold as KL-1 and modeling of their structures reveals similar peptidomimetic potential for the AFF4 pentapeptide LFAEP (FIG. 1C). Furthermore, both compounds exhibited dose-dependent inhibitory effects on the AFF4-CCNT1 interaction with observed $K_i$ of 3.48 µM and 1.50 µM, respectively, for KL-1 and KL-2 (FIG. 1D), demonstrating the identification of a lead scaffold for compounds that can disrupt the AFF4-CCNT1 interaction. In order to study the functions of KL-1 and KL-2 in depth, we synthesized these compounds in house as shown in FIG. 8D.

Testing the potential of these compounds for disrupting the AFF4-CCNT1 interaction in cells, we found that both KL-1 and KL-2 led to depletion of SEC components AFF1 and AFF4 in both HEK293T and HCT-116 cells within 6 hr (FIG. 1E, FIGS. 8E and 8F), but no major effect on the protein levels of P-TEFb components CCNT1 and CDK9, or on Pol II, BRD2 and BRD4. We confirmed that treating cells with these two compounds results in decreased AFF1 and AFF4 protein using doxycycline-inducible Flag-AFF1 and Flag-AFF4 HEK293T cells (FIGS. 8G and 8H). KL-1 and KL-2 treatments do not result in decreased mRNA levels of SEC components (FIG. 8I). Together, these data demonstrate that KL-1 and KL-2 disrupt the interaction of CCNT1 and the SEC scaffolding AFF proteins, which results in reduced levels of cellular SEC. To investigate the consequences of AFF1 and AFF4 protein reduction on their association with chromatin, we performed ChIP-seq of AFF1 and AFF4 in HEK293T cells treated with KL-1 and KL-2 for 6 hr. Genome browser views of the HSPA8 gene demonstrate that both inhibitors lead to decreased occupancy of AFF1 and AFF4 (FIG. 1F) and reduced AFF1 and AFF4 chromatin occupancy is observed by genome-wide analysis (FIGS. 1G and 1H).

Figure 2:
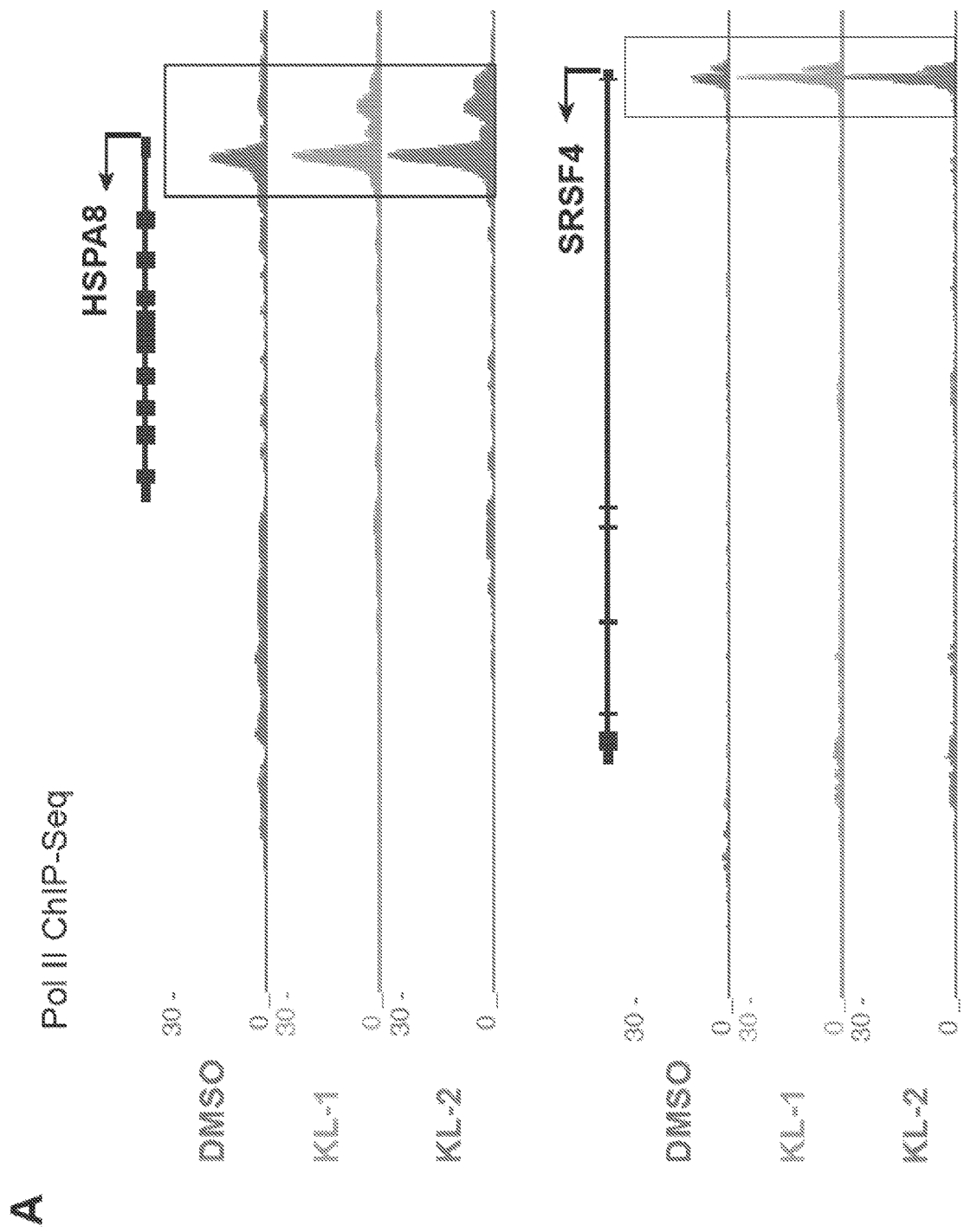
FIG. 2. Small molecule disruption of SEC increases promoter-proximal pausing. (A) SEC inhibitors increase Pol II occupancy near the transcription start sites (TSS) of the HSPA8 and SRSF4 genes. Pol II ChIP-seq was performed in HEK293T cells with 20 µM SEC inhibitors KL-1 and KL-2 for 6 hr. Coverage is in reads per million (rpm) and is displayed in the UCSC genome browser. (B) Heatmap analysis of Pol II occupancy at SEC-occupied genes in cells treated with KL-1 and KL-2. SEC inhibition results in increased Pol II occupancy at promoter-proximal regions of genes occupied by SEC. Rows are sorted by Pol II occupancy in the DMSO condition and metaplots of Pol II occupancy are shown at the bottom. Corresponding AFF1 and AFF4 occupancy (rpm) in the vehicle-treated condition is shown. (C-D) Scatter plots of the $log_2$ fold changes of Pol II occupancy versus the $log_2$ fold changes of AFF4 (left panels) or AFF1 in (right panels) in KL-1 (C) or KL-2 (D) treated cells. SEC inhibitor treatments result in increased Pol II occupancy and decreased AFF4 and AFF1 occupancy at most of the 6,119 expressed and SEC-occupied genes. (E) Illustration of the pausing index calculation. The pausing index is calculated based on the ratio of Pol II occupancy around the TSS to Pol II occupancy in the gene body. (F) Empirical cumulative density function (ECDF) plots of Pol II pausing index in vehicle and SEC inhibitors-treated cells. Increased Pol II pausing indexes are seen when considering the 6,840 expressing genes in 293T cells. (G-H) Knockdown of AFF1 and AFF4 by shRNA-mediated RNAi shows similar pausing index changes as SEC inhibitors. (G) Genome browser tracks of Pol II occupancy at the SRSF4 gene. (H) ECDF plot of Pol II pausing index in non-targeting (shGFP), AFF1 knockdown (shAFF1) and AFF4 knockdown (shAFF4).
Figure 2:
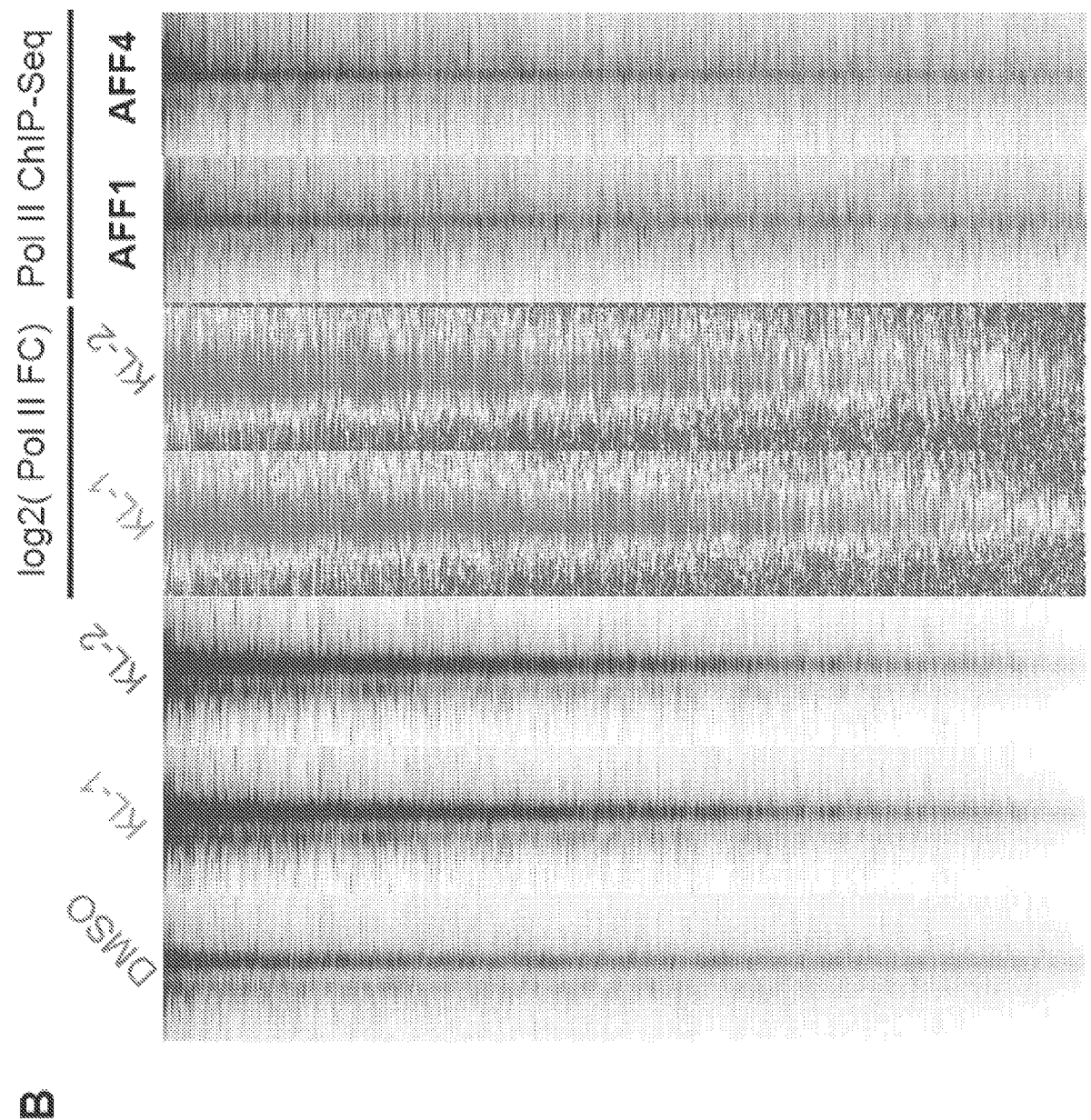
Figure 2:
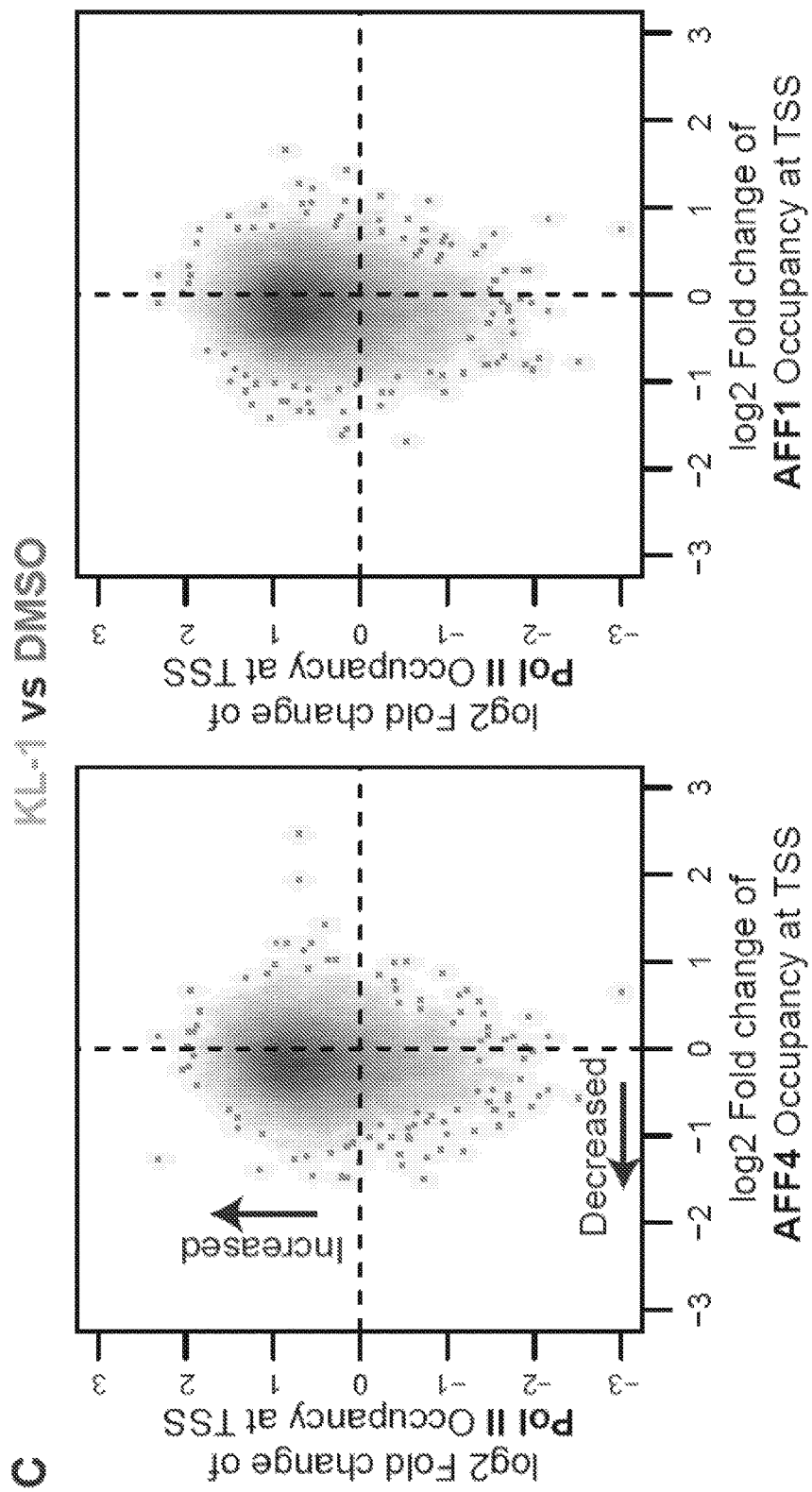
Figure 2:
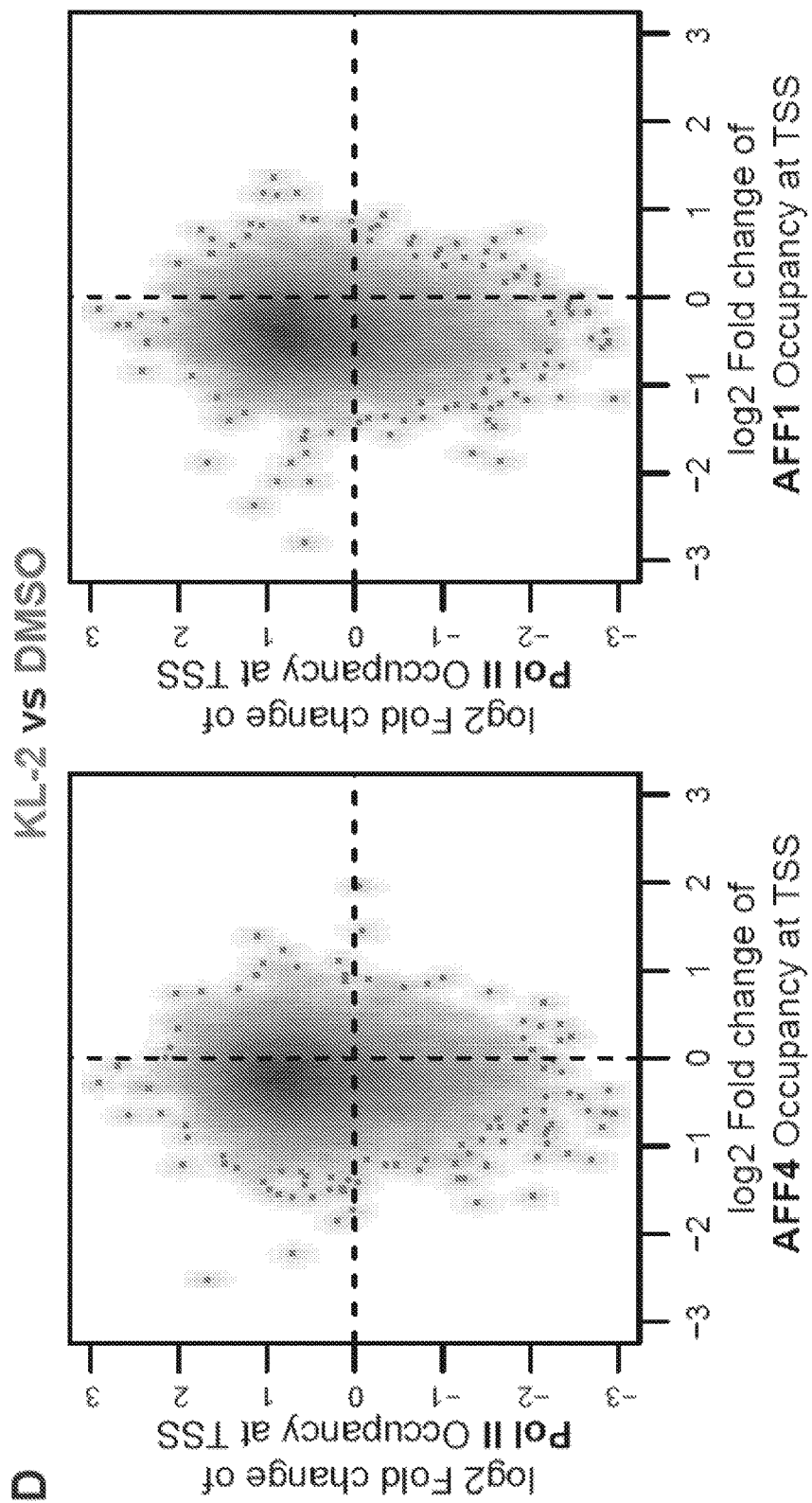
Figure 2:
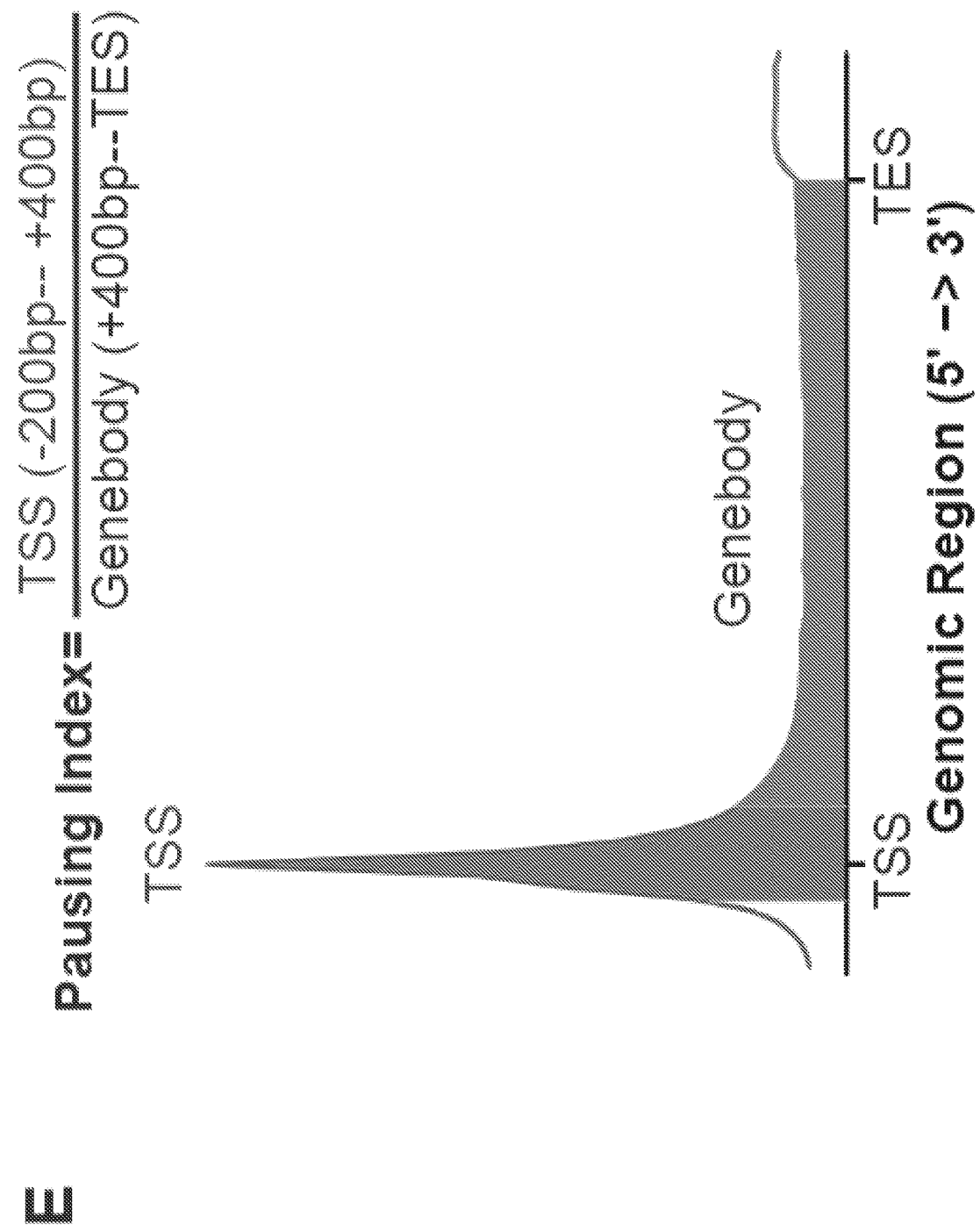
Figure 2:
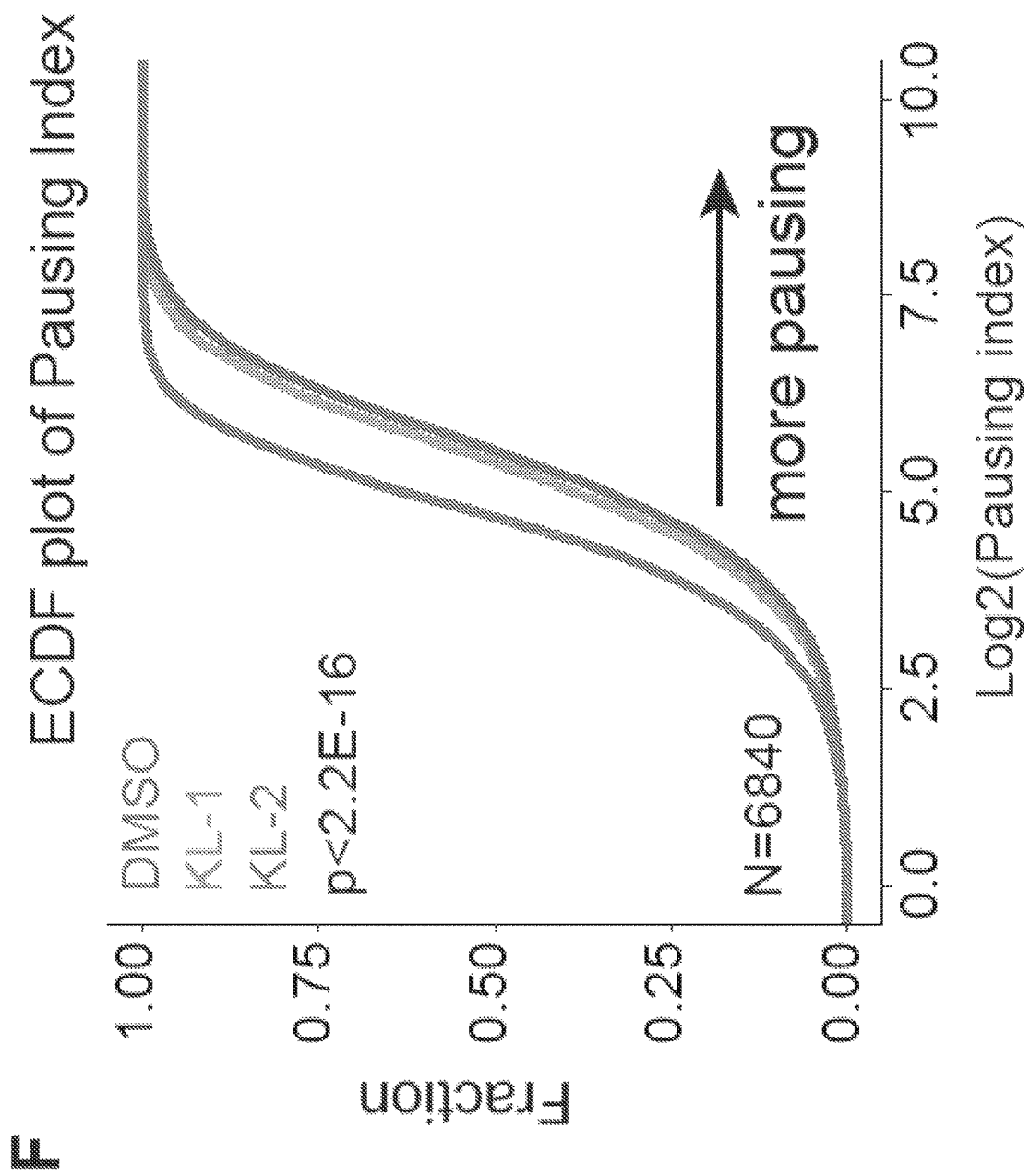
Figure 2:
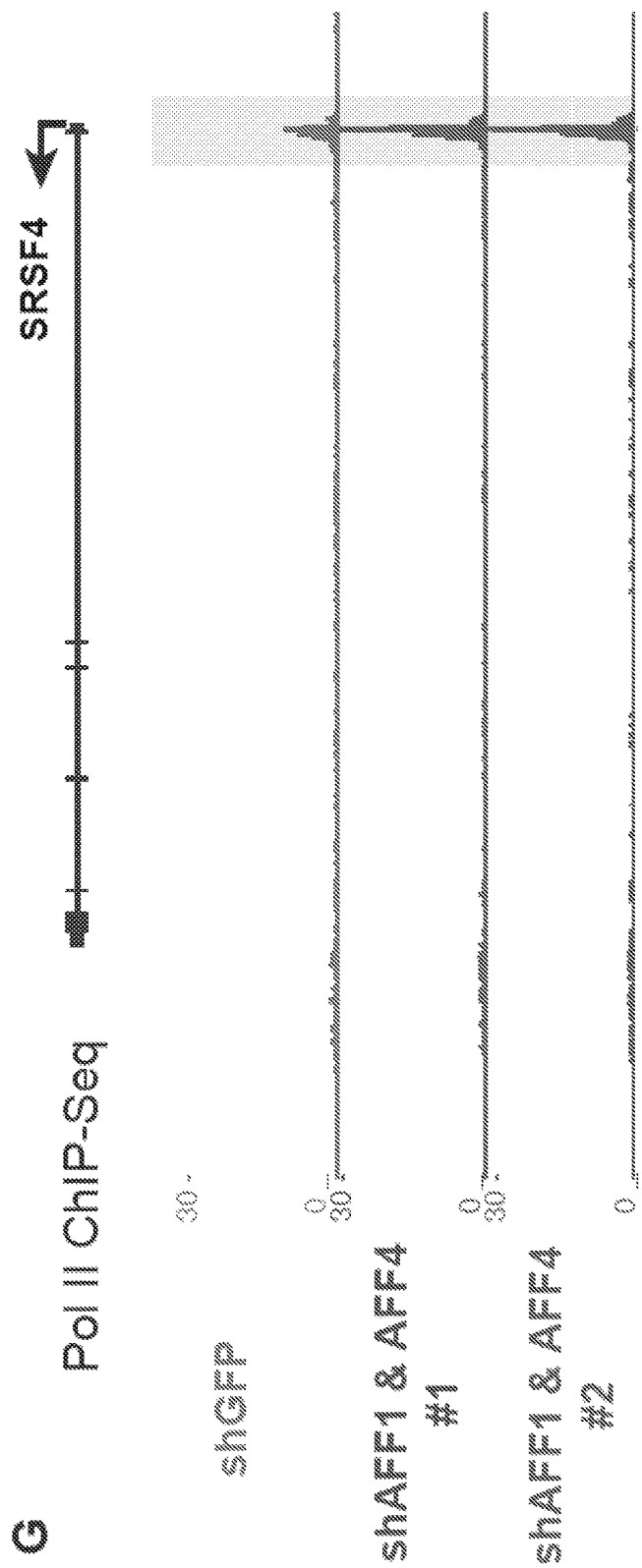
Figure 2:
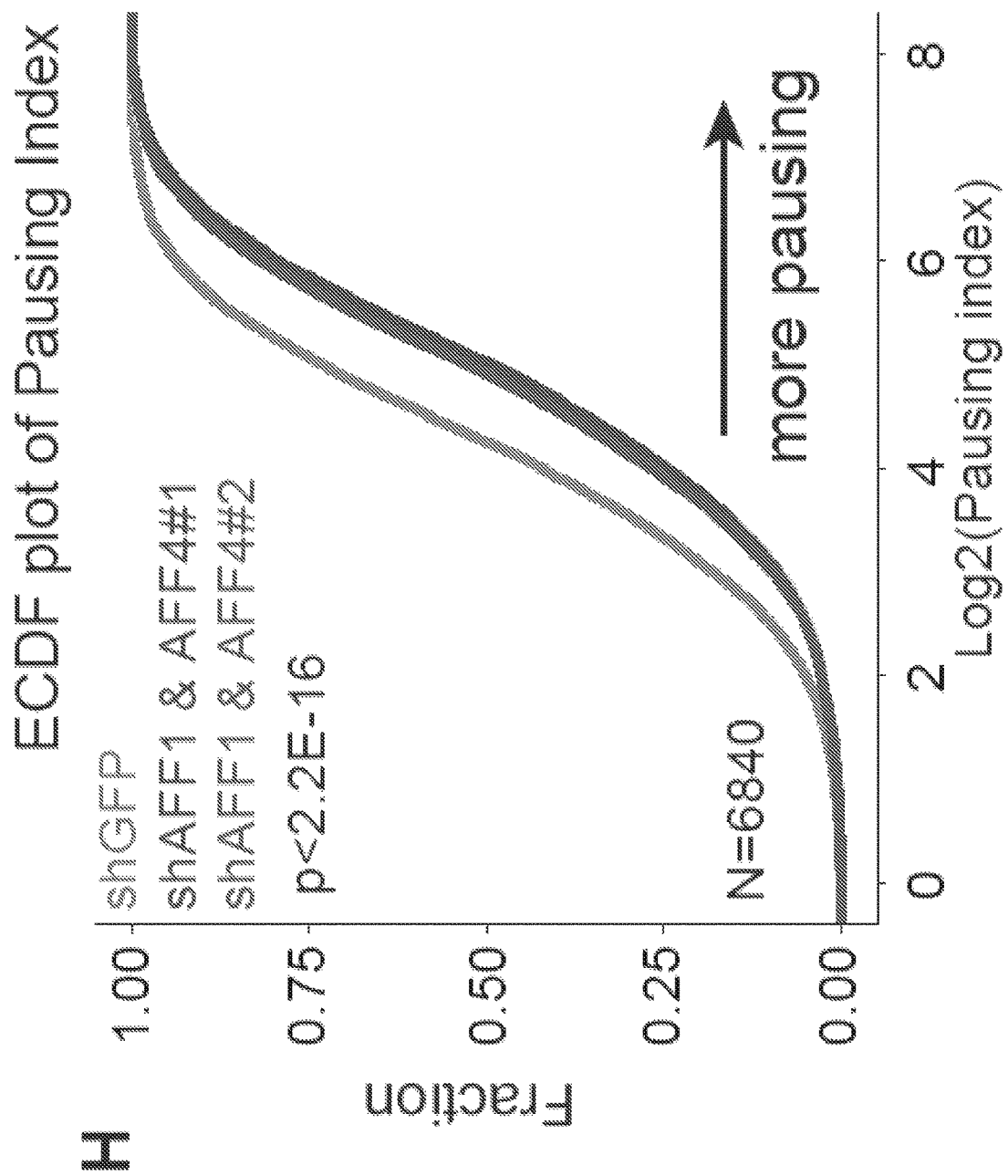
Figure 9:
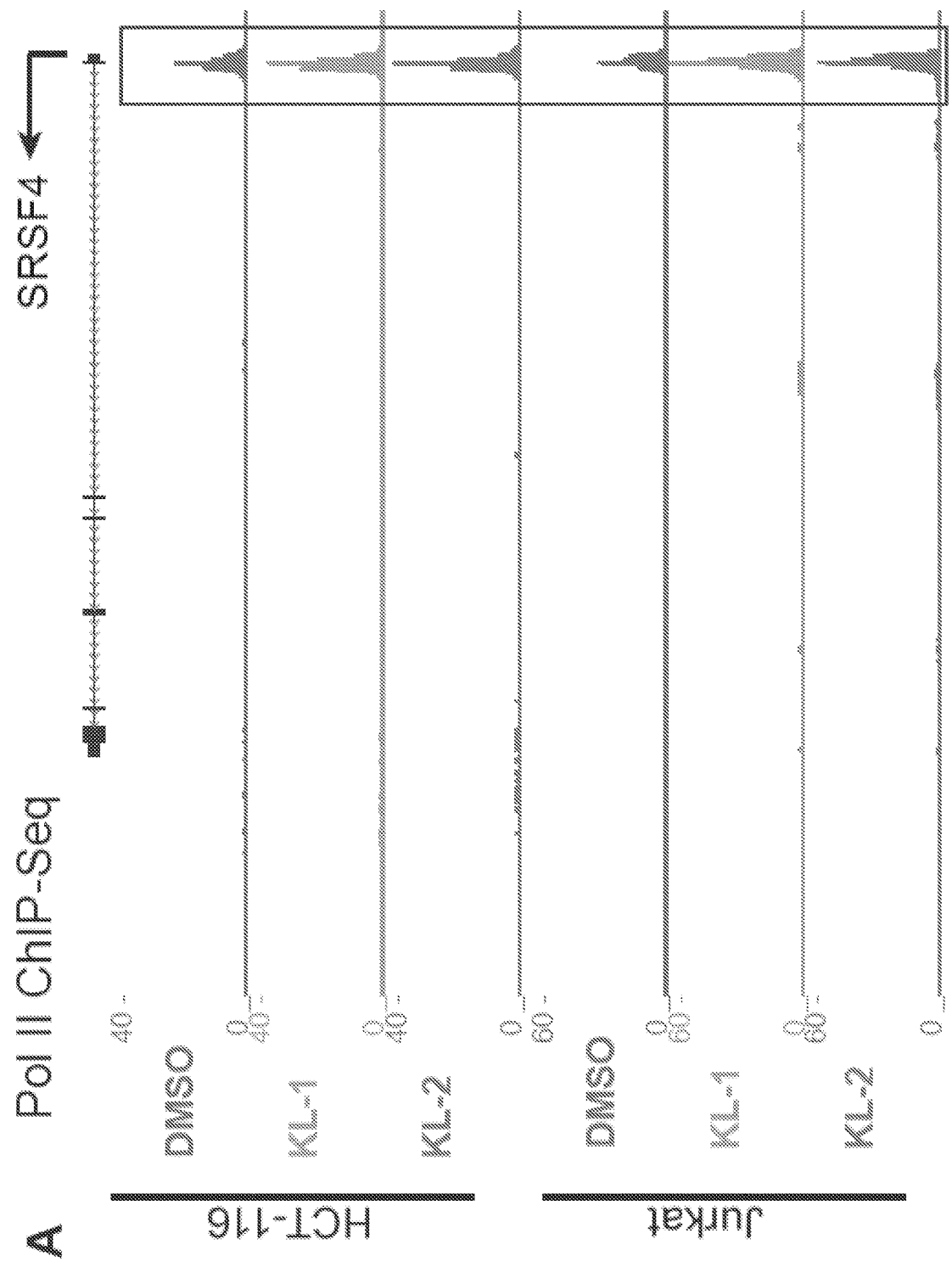
FIG. 9, related to FIG. 2. Small molecule disruption of SEC increases promoter-proximal pausing. (A) Genome browser tracks of Pol II occupancy at the SRSF4 gene in vehicle or SEC inhibitor-treated cells gene in HCT-116 (top panel) and Jurkat cells (bottom panel). (B-C) Metaplots of Pol II occupancy for all expressing genes with Pol II occupancy in HCT-116 (B) and Jurkat cells (C). SEC inhibitor treatments result in increased Pol II occupancy around the TSS. Pol II density is plotted in a −2 kb and +2 kb window around the TSS. (D) K-means 3 clustered heatmap of Pol II fold change of the 6,840 genes after SEC inhibitor treatments. The region around the TSS is shown. Group I genes are preferentially affected by the SEC inhibitors. (E-F) Boxplot analysis of AFF1 (E) and AFF4 (F) occupancy at the three clusters from (D). (G-H) ECDF plots of Pol II pausing indexes for all expressing genes in HCT-116 (G) and Jurkat cells (H) in the presence of vehicle or SEC inhibitors. (I-J) SEC inhibition results in a 5' shift of Pol II density near the Transcription End Site (TES) at the HSPA8 and SRSF4 genes. Pol II coverage in HEK293T cells is displayed in the UCSC genome browser.
Figure 9:
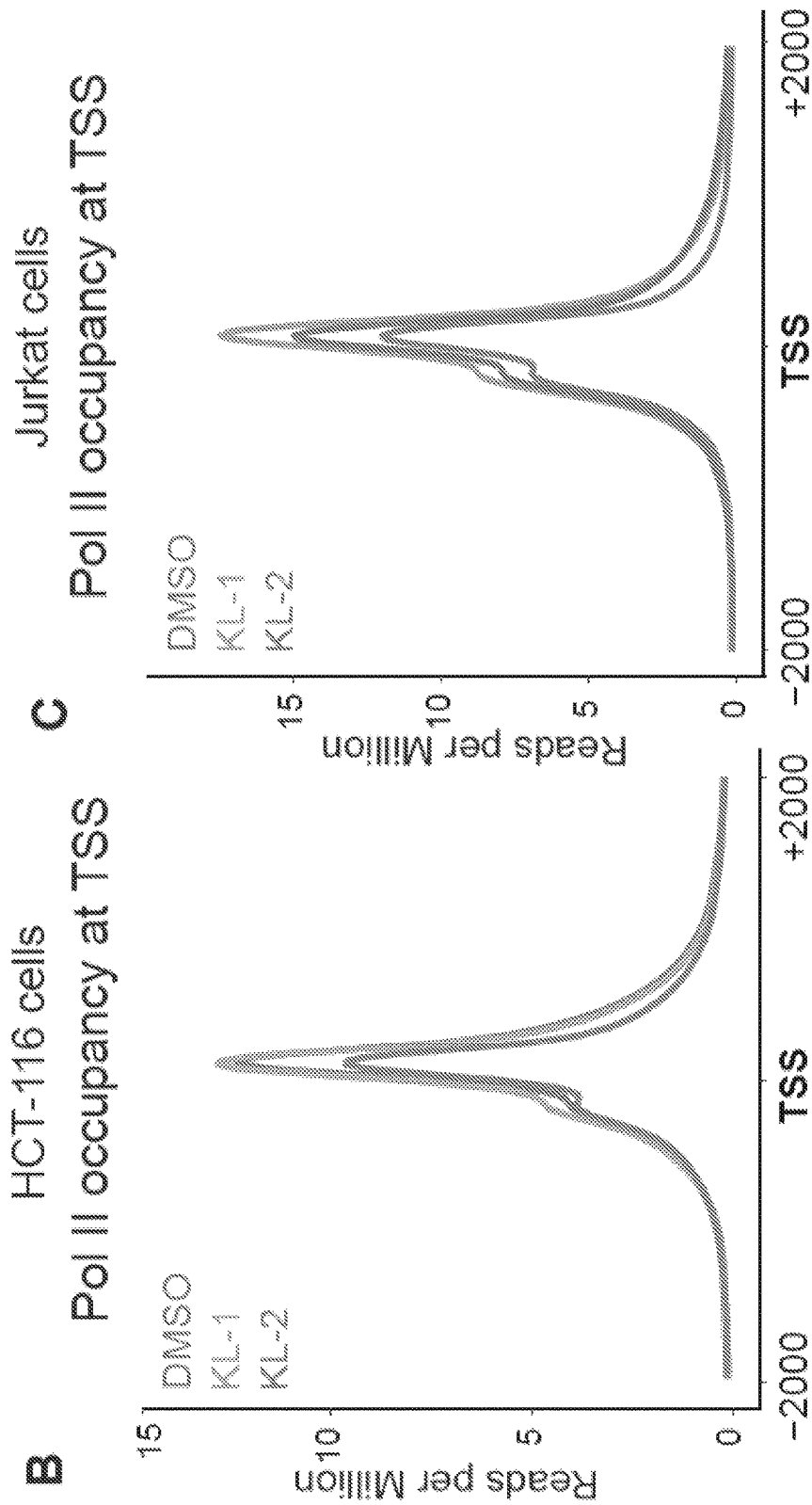
Figure 9:
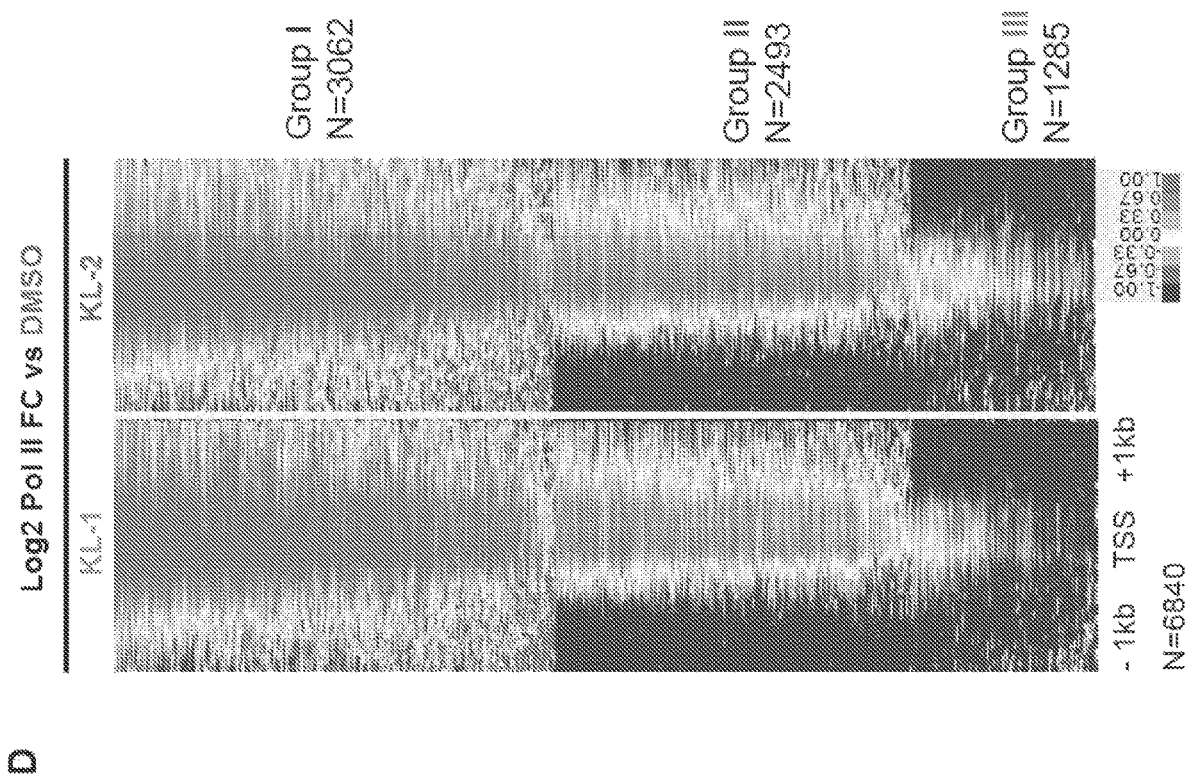
Figure 9:
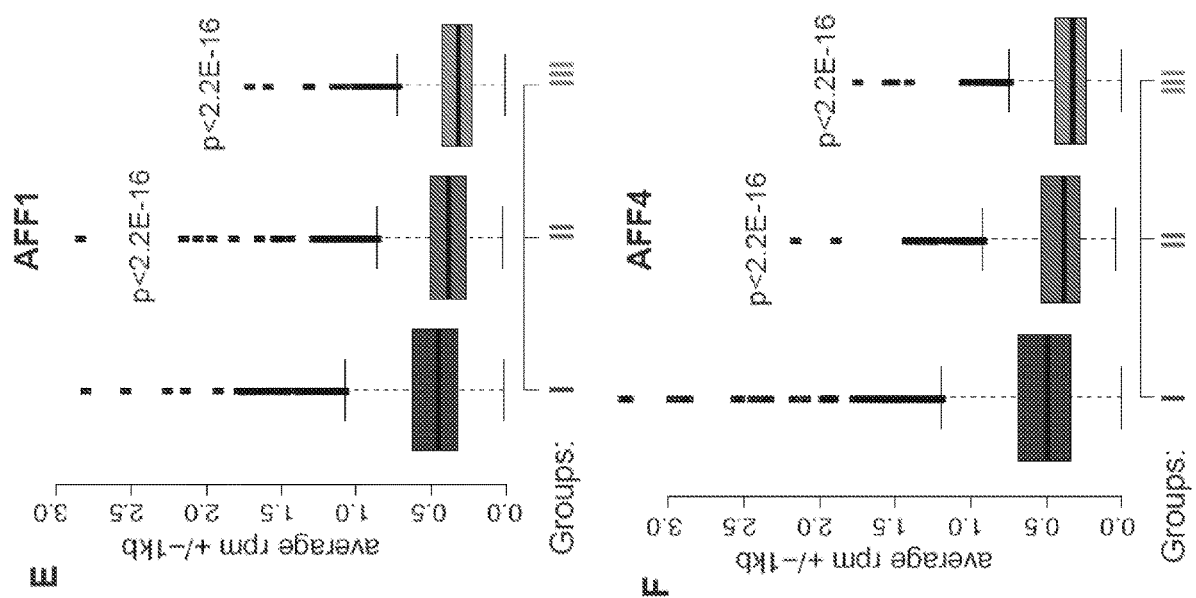
Figure 9:
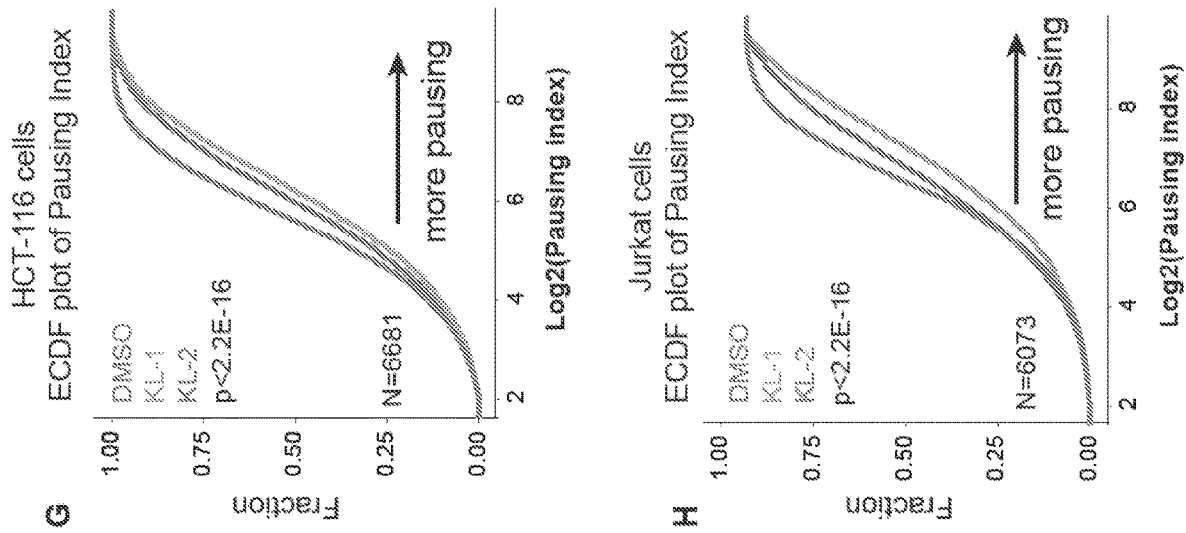
Figure 9:
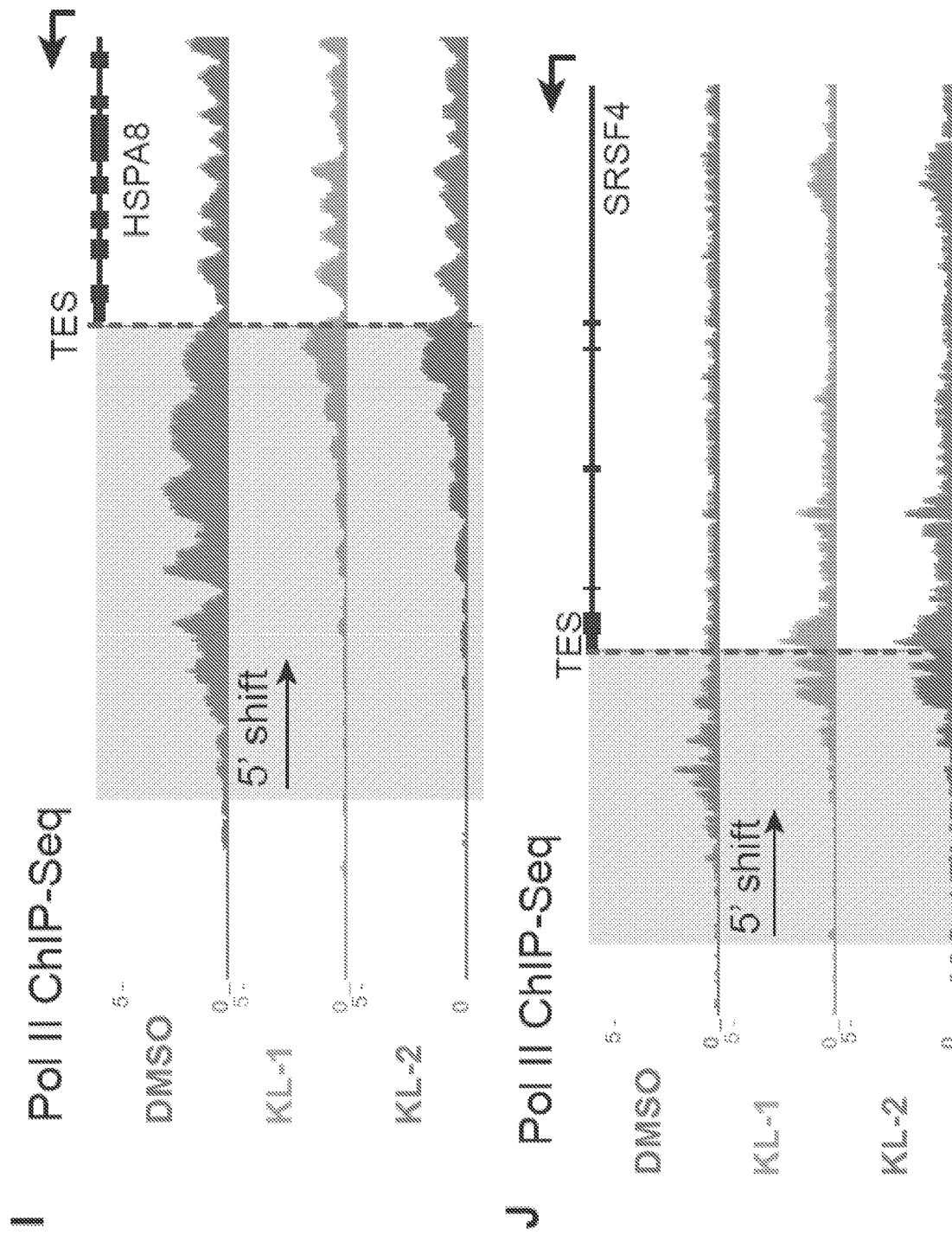

Small molecule disruption of SEC increases promoter-proximal pausing. Since P-TEFb is required for the release of Pol II from promoter-proximal pausing, and KL-1 and KL-2 disrupt SEC and reduce AFF1 and AFF4 chromatin occupancy, we tested the effect of these inhibitors on Pol II pausing in HEK293T cells. Both KL-1 and KL-2 resulted in increased Pol II occupancy at the promoter-proximal regions of HSPA8 and SRSF4 loci (FIG. 2A). Analysis of the 6,119 Pol II occupied genes in HEK293T cells that are also occupied by AFF1 or AFF4, showed that these genes have increased Pol II occupancy at the promoter-proximal regions when cells are treated with KL-1 and KL-2 (FIG. 2B). We also tested the SEC inhibitors in HCT-116 and Jurkat (J-Lat 6.3 clone) (Jordan et al., 2003) cells and observed similar increases of Pol II occupancy in promoter-proximal regions (FIGS. 9A, 9B and 9C).

To further investigate the relationship between Pol II and SEC occupancy changes due to SEC inhibitor treatments, we k-means clustered the 6,119 Pol II and SEC-occupied genes into three groups: Group I, II and III (FIG. 9D). Group I genes exhibited the highest fold-change increase in Pol II occupancy and have the highest AFF1 (FIG. 9E) and AFF4 (FIG. 9F) occupancy in the control condition, suggesting that the increased Pol II occupancy observed in the presence of KL-1 and KL-2 could be attributed to changes in SEC occupancy. Scatter plot analysis shows that KL-1 (FIG. 2C) and KL-2 (FIG. 2D) globally reduce AFF1 and AFF4 occupancy (leftward shift) and increases Pol II occupancy (upward shift) at co-occupied genes, suggesting that disruption of SEC by small molecules leads to increases in promoter-proximal Pol II occupancy.

We calculated levels of Pol II pausing based on the ratio of Pol II reads in the gene body and promoter (FIG. 2E). Analysis of pausing index in HEK293T cells revealed that SEC disruptors KL-1 and KL-2 could increase promoter-proximal pausing as shown by the Empirical Cumulative Distribution Function (ECDF) plot (FIG. 2F). ECDF analysis of pausing indexes in HCT-116 and Jurkat cells showed similar effects as seen in HEK293T (FIGS. 9G and 9H), demonstrating that SEC inhibition leads to increased promoter-proximal pausing. To further demonstrate that SEC inhibition through KL-1 and KL-2 increases pausing at the early stage of transcription elongation, we depleted AFF1 and AFF4 proteins in HEK293T cells with short hairpin RNAs (shRNA) and found that co-knockdown of AFF1 and AFF4 leads to increased Pol II occupancy in promoter-proximal regions, as can be seen at the SRSF4 gene (FIG. 2G) and by ECDF analysis (FIG. 2H) similar to the use of KL-1 and KL-2 (FIG. 2F).

Figure 3:
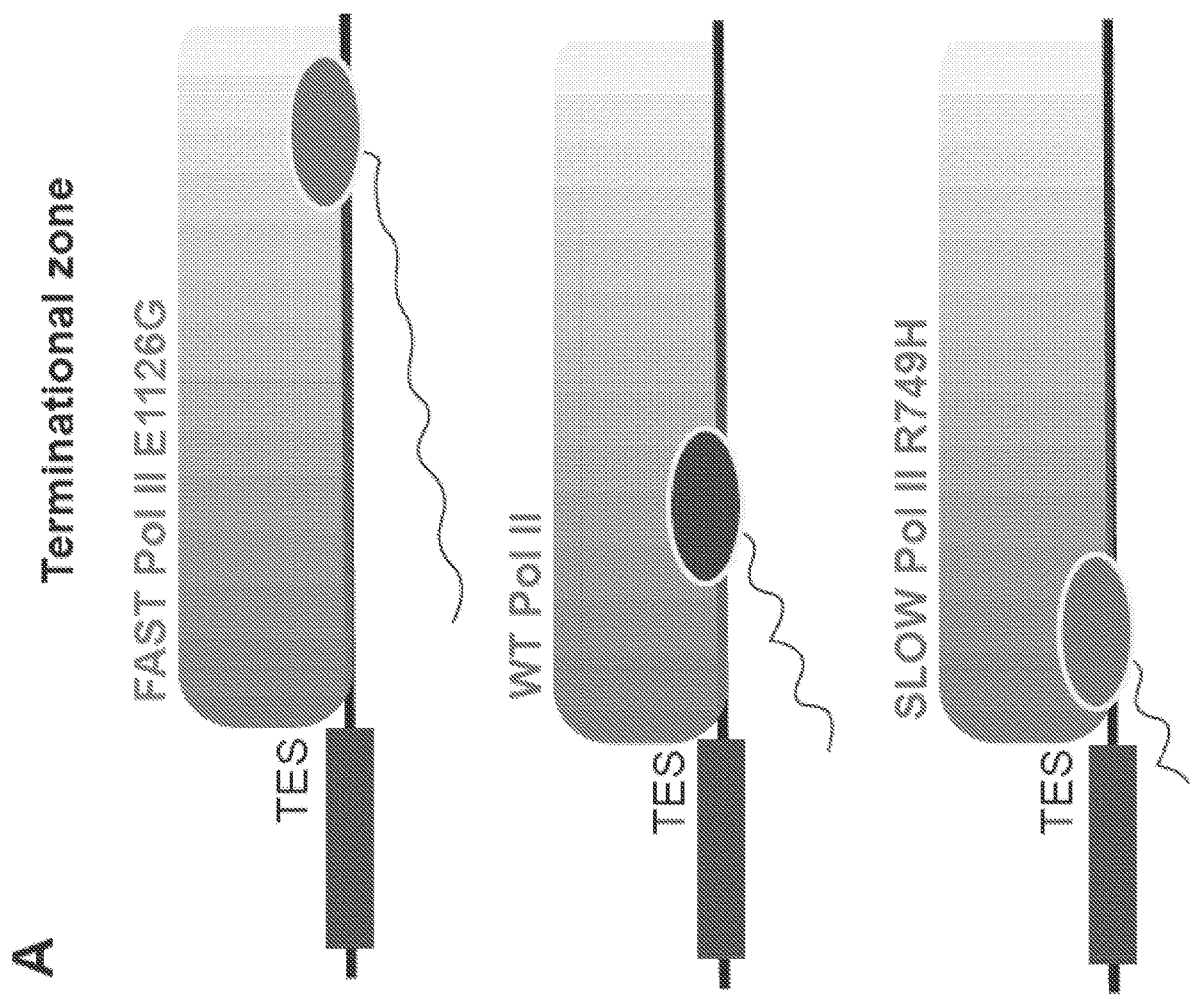
FIG. 3. Disruption of SEC phenocopies slow Pol II mutants and reduces Pol II processivity. (A) Schematic showing alpha-amanitin resistant (N792D) versions of Pol II that are otherwise wild-type (WT) or have a mutation in the trigger loop (E1126G) that results in faster Pol II or the funnel domain (R749H) that results in slower Pol II (Fong et al., 2014). Alpha-amanitin resistant Pol II is induced with doxycycline while alpha-amanitin is used to inhibit and cause the degradation of endogenous Pol II. (B-C) Genome browser tracks of Pol II ChIP-seq coverage at the ACTB (B) and PIM3 (C) genes in the fast, WT and slow Pol II mutant cells after both SEC inhibitors. Dotted line indicates the position of the annotated transcription end site (TES) site. (D) Metaplots of Pol II ChIP-seq coverage at the 3'-end of genes in the fast, WT and slow Pol II mutant cells. The region from TES to 7.5 kb downstream of the TES for the 1,057 genes with typical Pol II termination signals in HEK293T cells is plotted (FIG. 10A). Pol II appears to terminate earlier in the R749H slow Pol II mutant relative to WT Pol II cells, while the E1126G fast Pol II mutant appears to have a delayed termination with a less prominent peak of Pol II signal 3' of the TES. (E) Treatment of the fast Pol II mutant expressing cells with SEC inhibitors leads to a Pol II phenotype similar to slower Pol II mutant expressing cells as viewed at the 3'-end of genes. (F-H) PRO-seq analysis of transcribing Pol II in the presence or absence of SEC inhibitors. (F) HEK293T cells were treated for 6 hr with the indicated compounds before nuclear isolation and precision nuclear run-on sequencing (PRO-seq). (G) Genome browser tracks of PRO-seq signal at the SRSFJ gene in vehicle and SEC inhibitor-treated cells showing increased engaged Pol II in the promoter-proximal region and decreased engaged Pol II in the region surrounding the TES. (H) Metagene plot of PRO-seq signal from pausing sites to TES. (H) Heatmap of Pol II occupancy (rpm) and $log_2$ fold changes in vehicle or the indicated SEC inhibitors at single-nucleotide resolution. Rows represent genes and are sorted by gene length from shortest to longest and are shown from the predicted pausing site determined by PRO-seq to 50 kb downstream. (I-J) SEC inhibitors reduce the Pol II processivity at gene body, especially, the 3'-end of the gene body. Metagene plotting (I) and Metaplot analysis of PRO-seq signal in the 10 kb region surrounding the annotated TES (J) were performed with all of the expressing genes (N=6,840).
Figure 3:
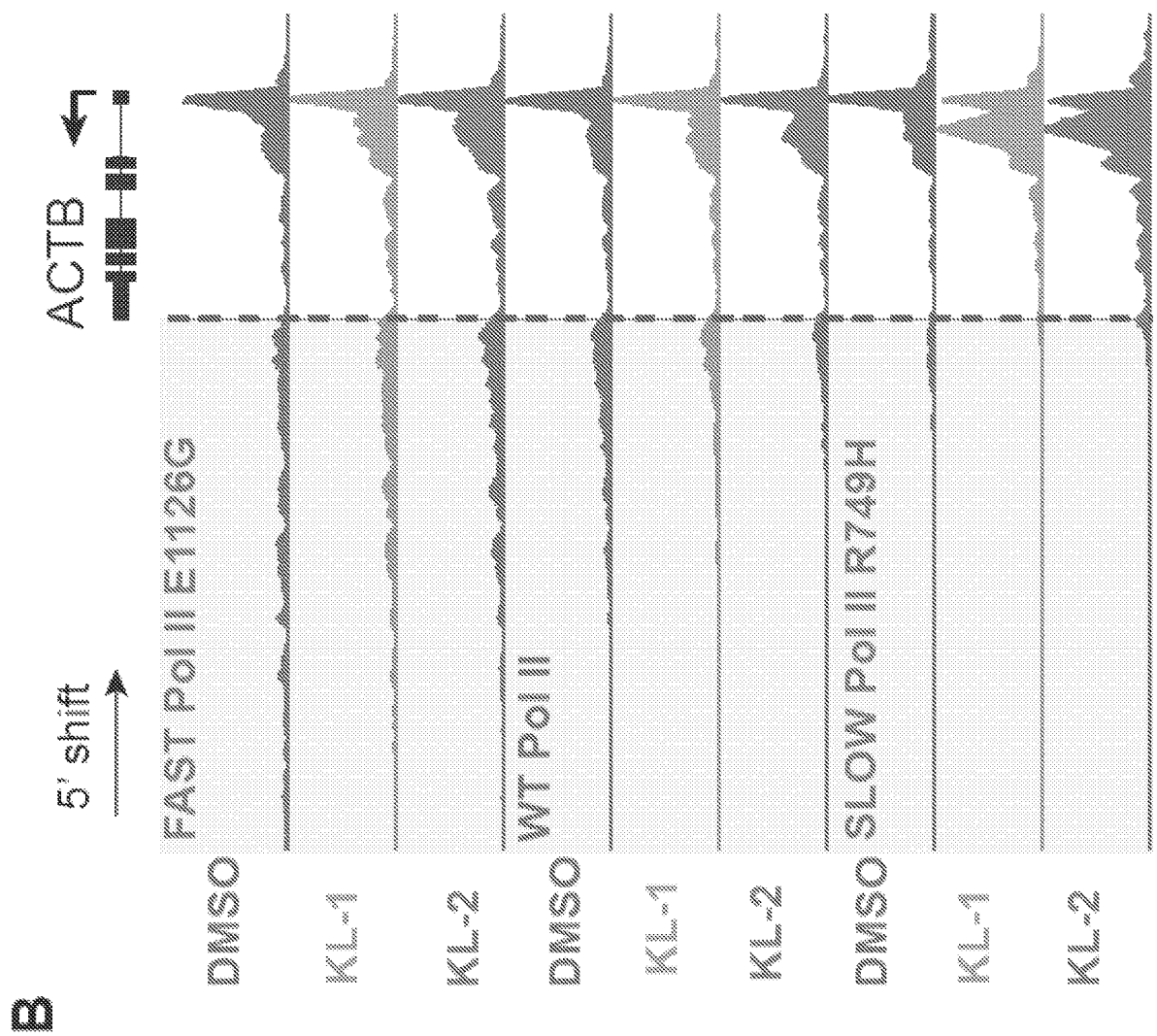
Figure 3:
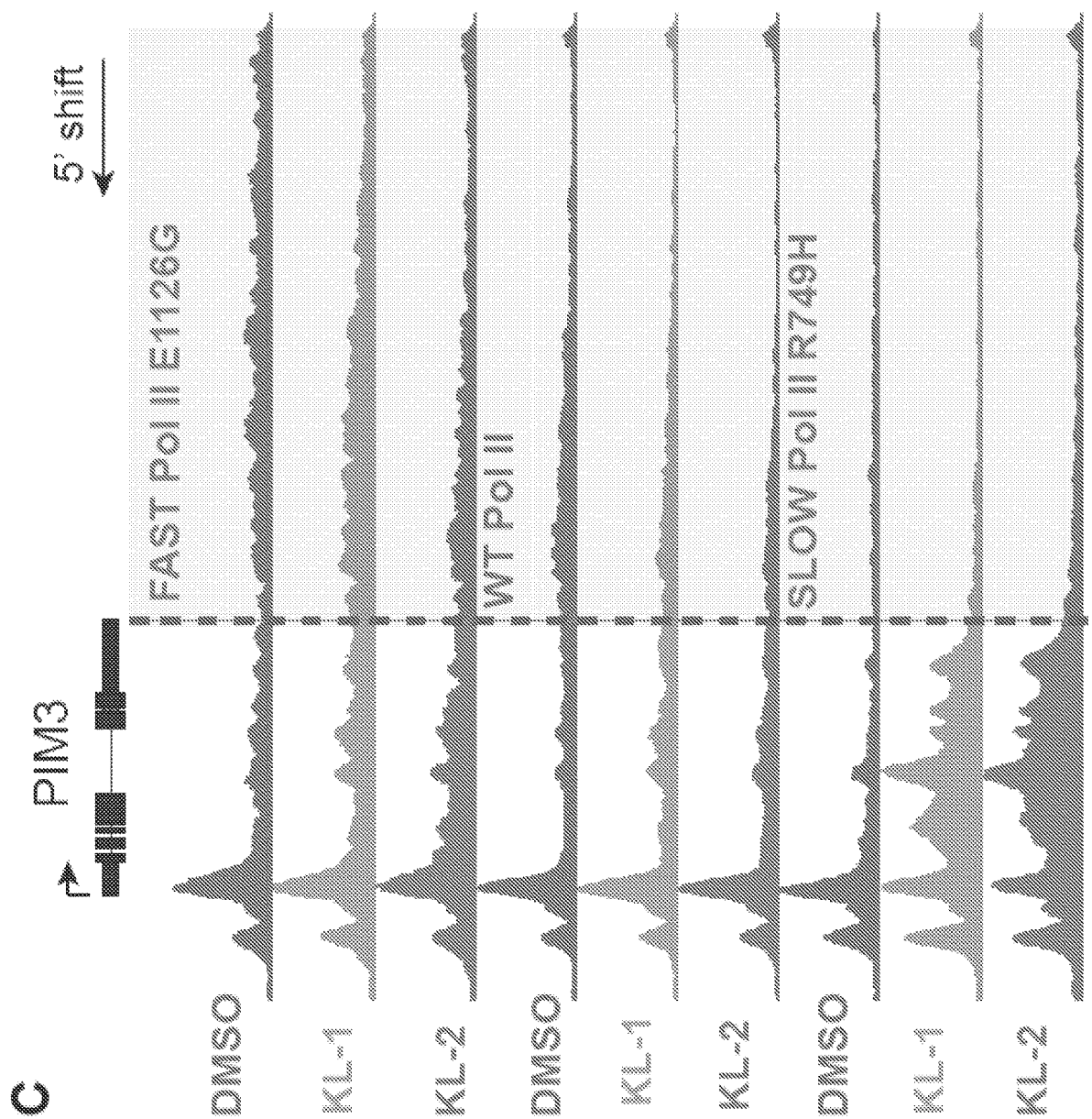
Figure 3:
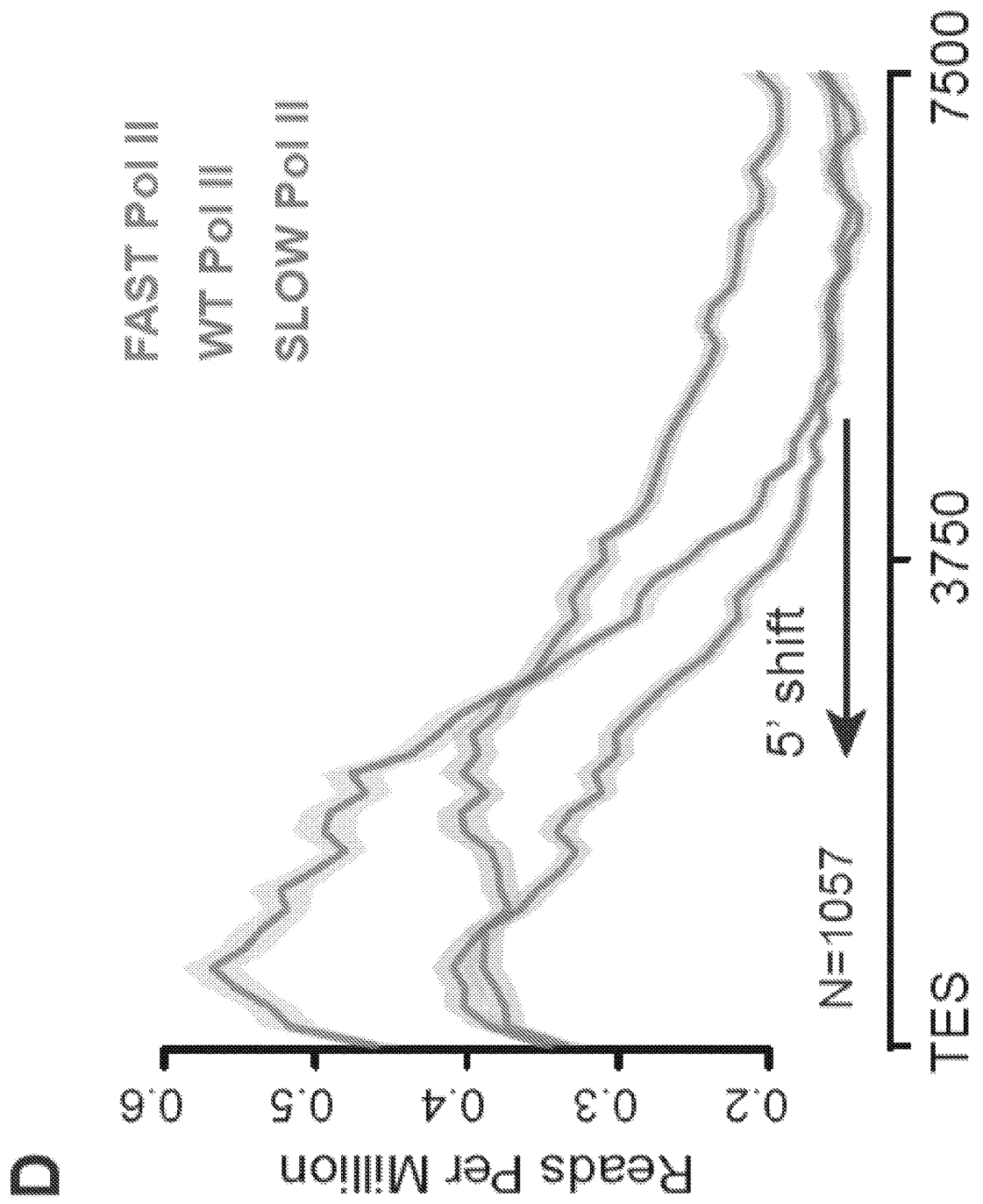
Figure 3:
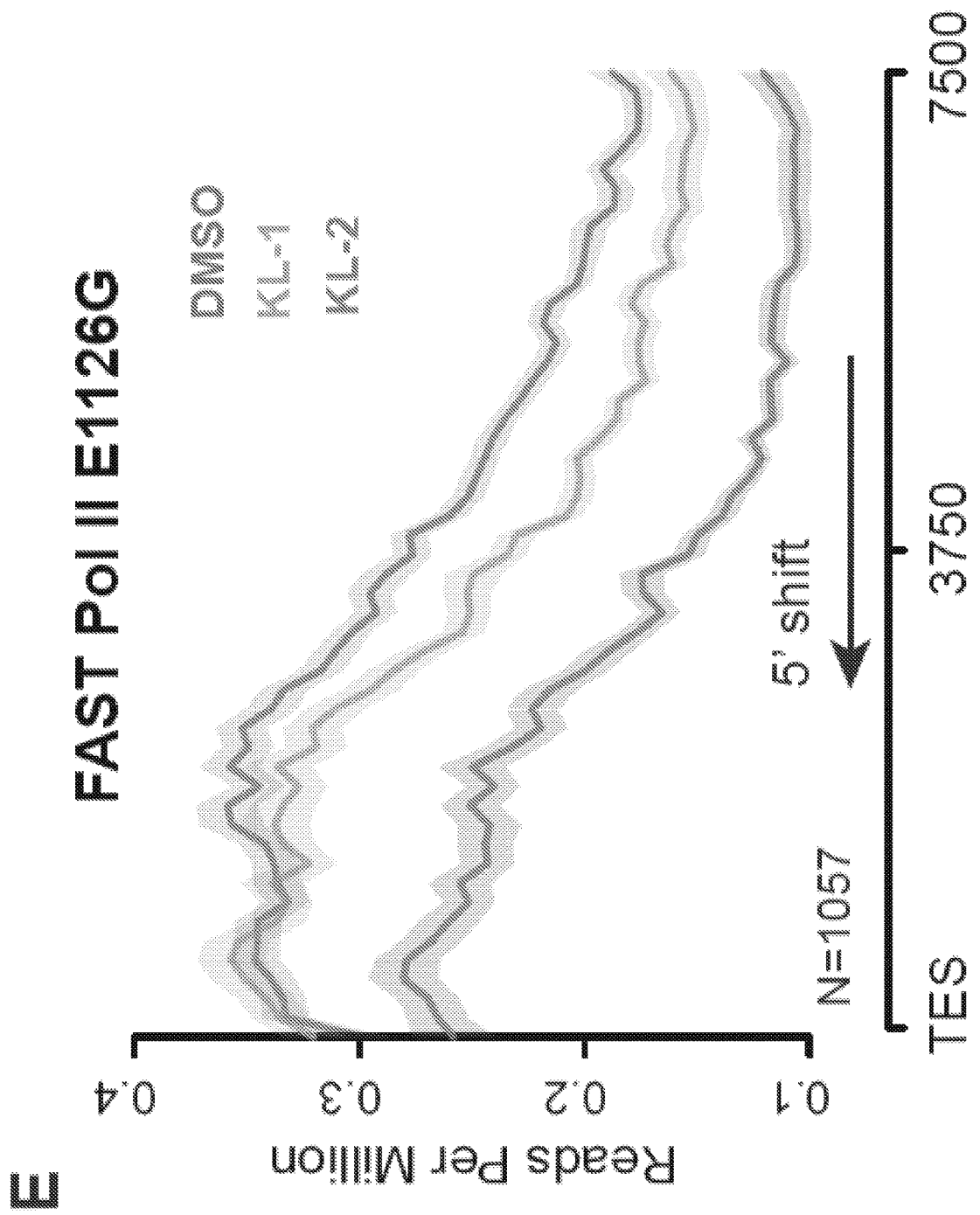
Figure 3:
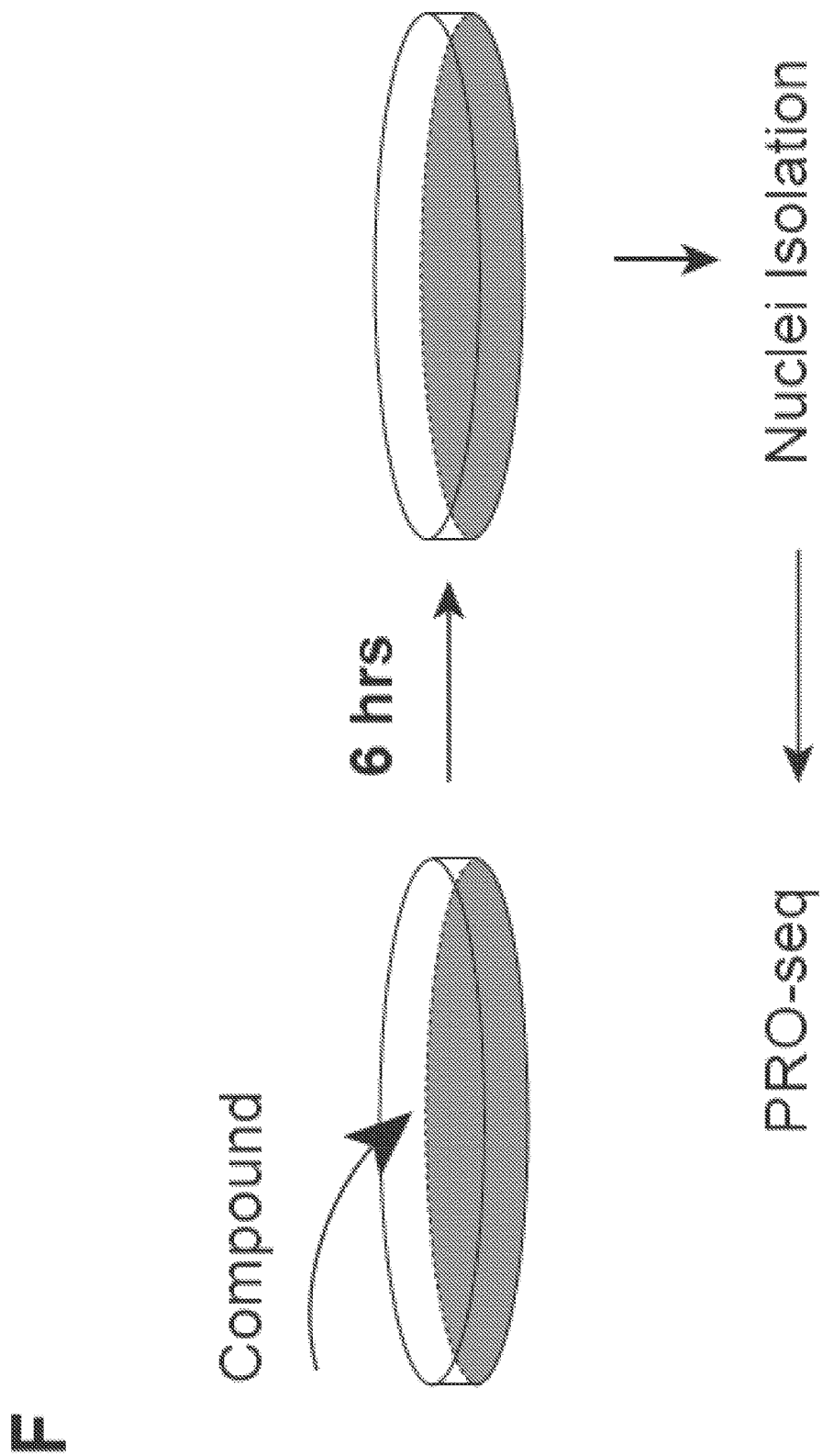
Figure 3:
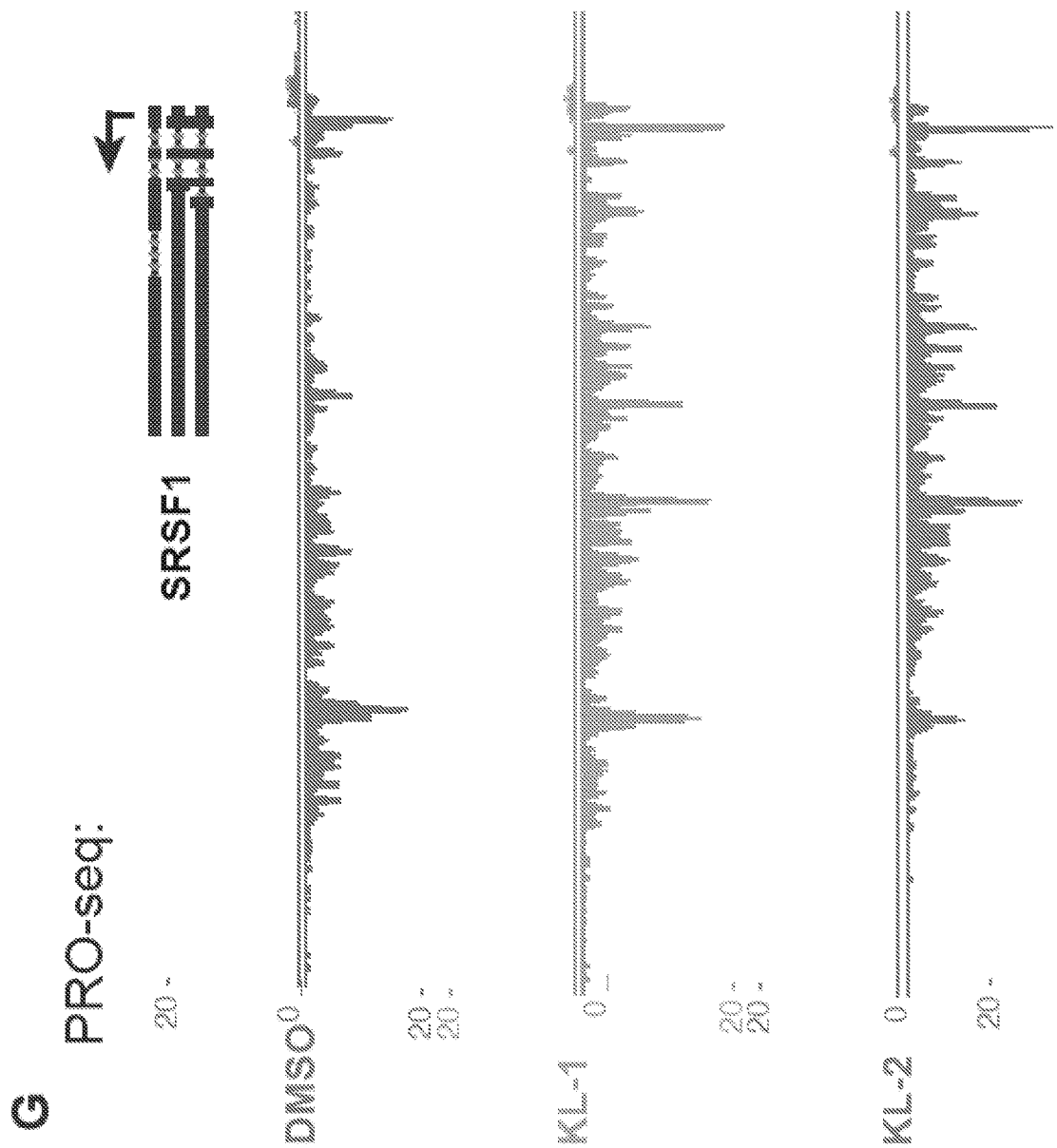
Figure 3:
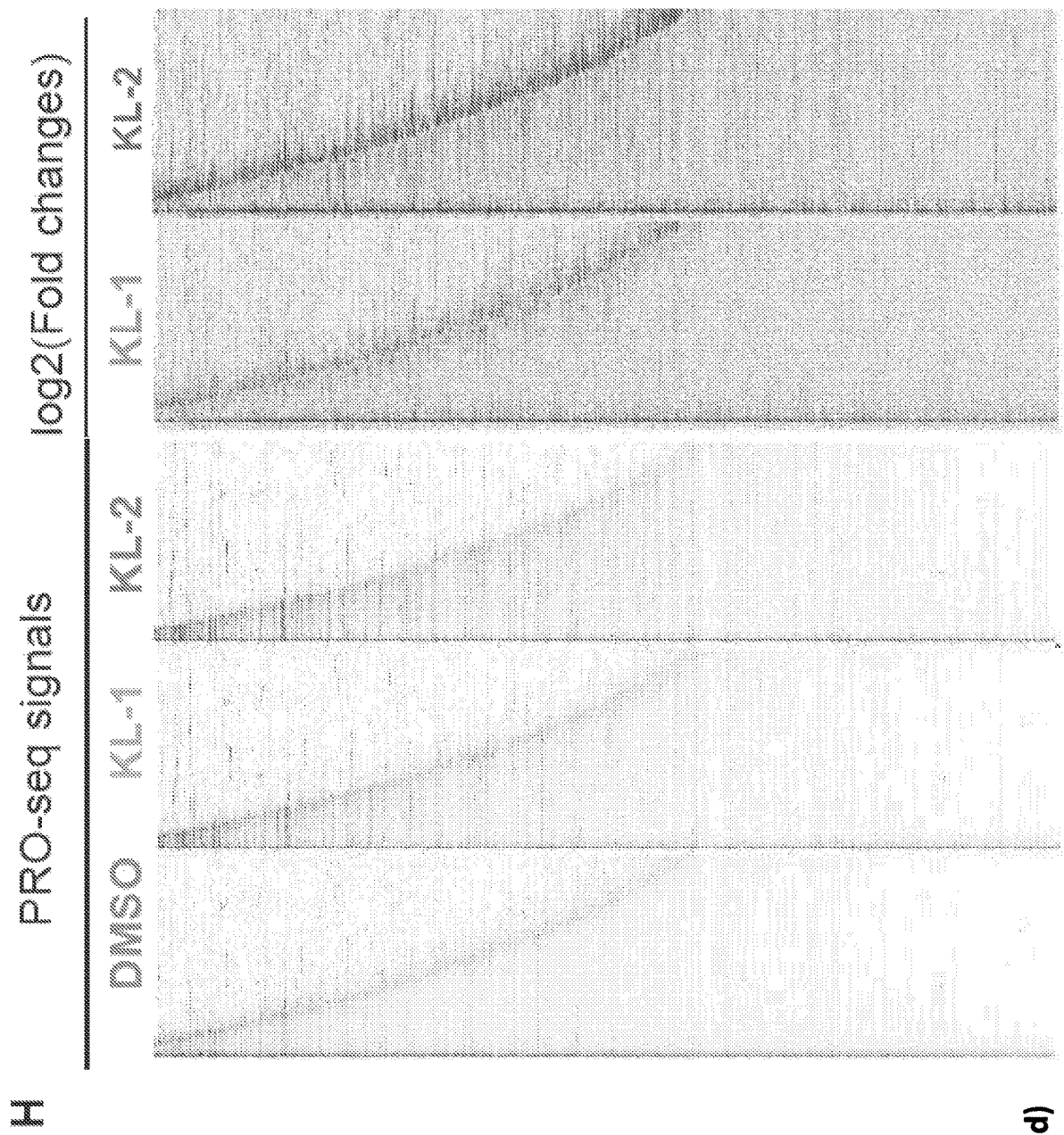
Figure 3:
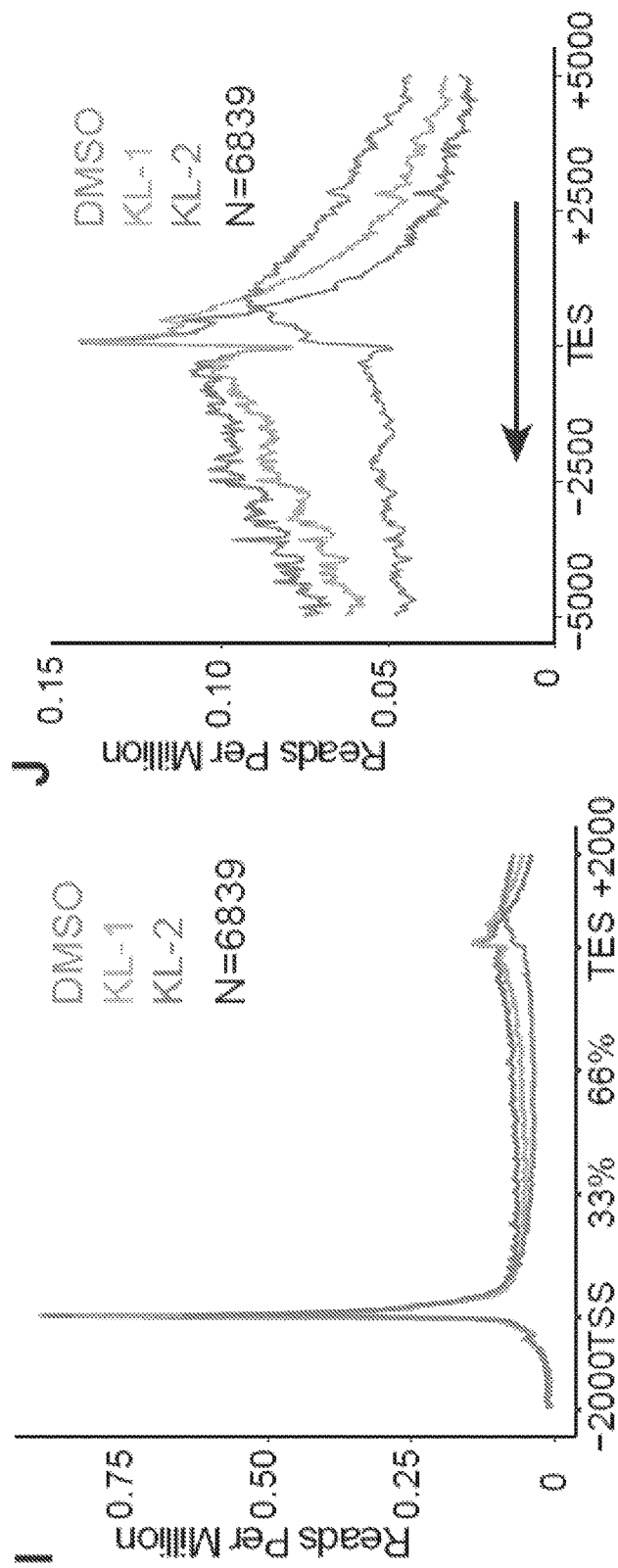
Figure 10:
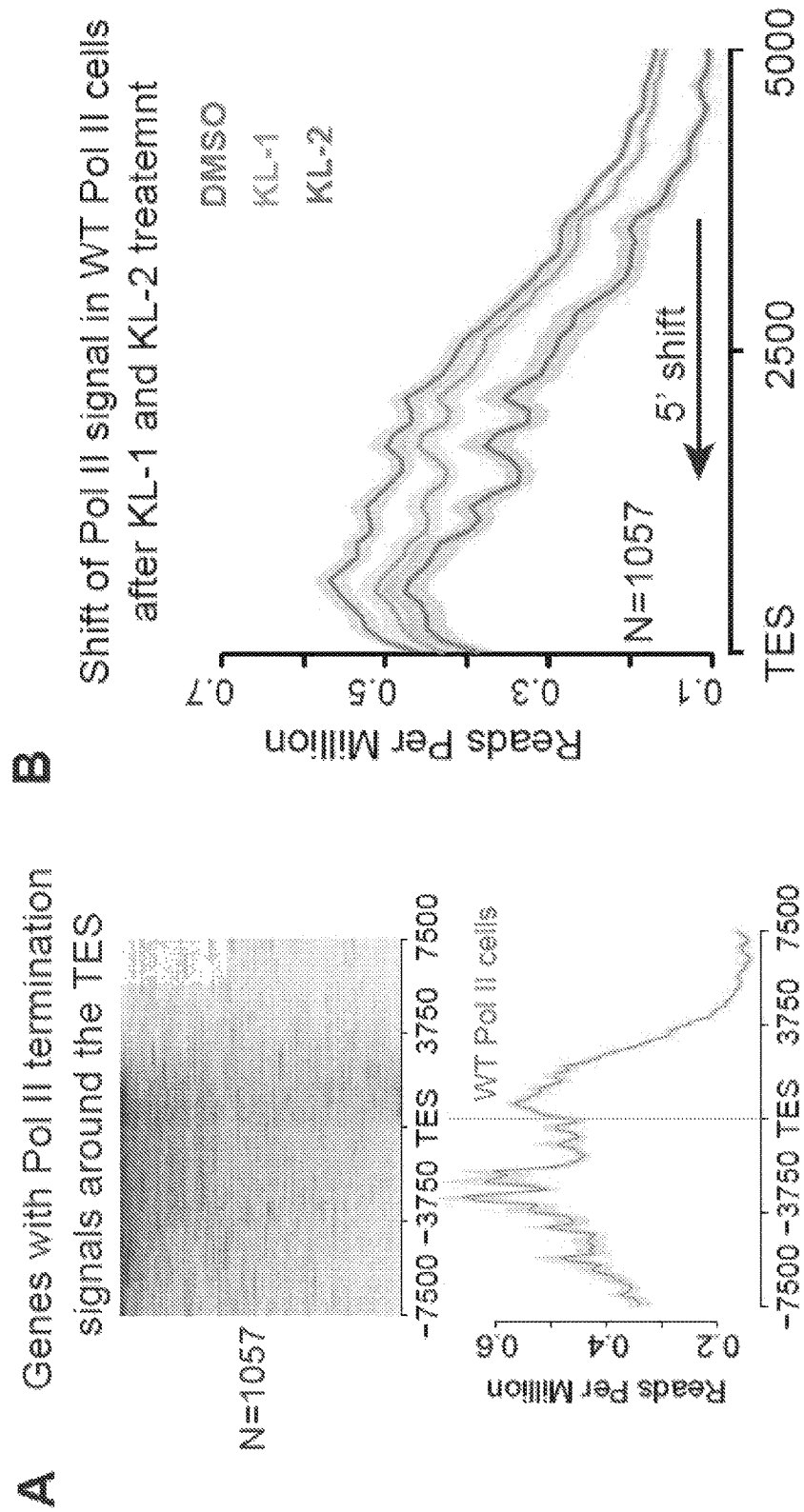
FIG. 10, related to FIG. 3. Disruption of SEC phenocopies slow Pol II mutants and reduces Pol II processivity. (A) Identification of the 1,057 genes with typical Pol II termination signals around the TES. Pol II signals from WT Pol II mutant expressing cells were K-means clustered into 5 groups with a window of 15 kb around the TES. The expressing genes from clusters with a typical Pol II termination signals were selected and plotted. (B) SEC inhibitor treatments of the WT Pol II mutant expressing cells lead to a Pol II phenotype similar to slower Pol II mutant expressing cells as viewed at the 3'-end of genes. (C-D) Time-dependent and dose-dependent shift of Pol II signals around the TES sites by KL-2 treatment (N=1,057). (E) Genome browser tracks of Serine 2 phosphorylated (Ser2P) Pol II at the SRSF1 gene in HEK293T cells treated with vehicle or SEC inhibitors. SEC inhibitor treatments result in increased Pol II occupancy at the promoter-proximal region and increased occupancy of Ser2P Pol II in the gene body. (F-G) Metagene plot of Pol II Ser2P occupancy (F) and log$_2$ Ser2P/total Pol II ratio (G) for 6,840 well-expressed genes after SEC inhibitor treatments, indicating that disruption of SEC leads to altered Pol II dynamics, with increased CTD Ser2 phosphorylation ratio near TSS sites and decreased Ser2P occupancy after the annotated TES sites. (H) SEC inhibition results in decreased protein levels of the SEC subunit ELL2. 293T cells were treated with 20 µM of the indicated inhibitors for 6 hr before harvesting cells for western blotting. (I-K) Depletion of ELL2 in HEK293T cells (I) results in apparent early termination of Pol II with reduced Pol II occupancy downstream of the PIM3 (J) and ACTB (K) annotated TES. (L) Metaplots of Pol II occupancy at TES regions for all of the 1,057 genes in FIG. 10A. ELL2 knockdown results in a 5' shift of Pol II in these regions. (M-N) Metaplot and heatmap analysis of PRO-seq signal in HEK293T cells treated with vehicle or SEC inhibitors for the region 500 bp upstream and 500 bp downstream of the empirical promoter-proximal pausing site identified in the control condition. Rows represent genes and are sorted according to total PRO-seq signal in the control condition (N). The right two panels display log$_2$ fold changes in PRO-seq signal with the indicated inhibitors. Increased Pol II occupancy in promoter-proximal regions is observed along with decreased occupancy in the region downstream.
Figure 10:
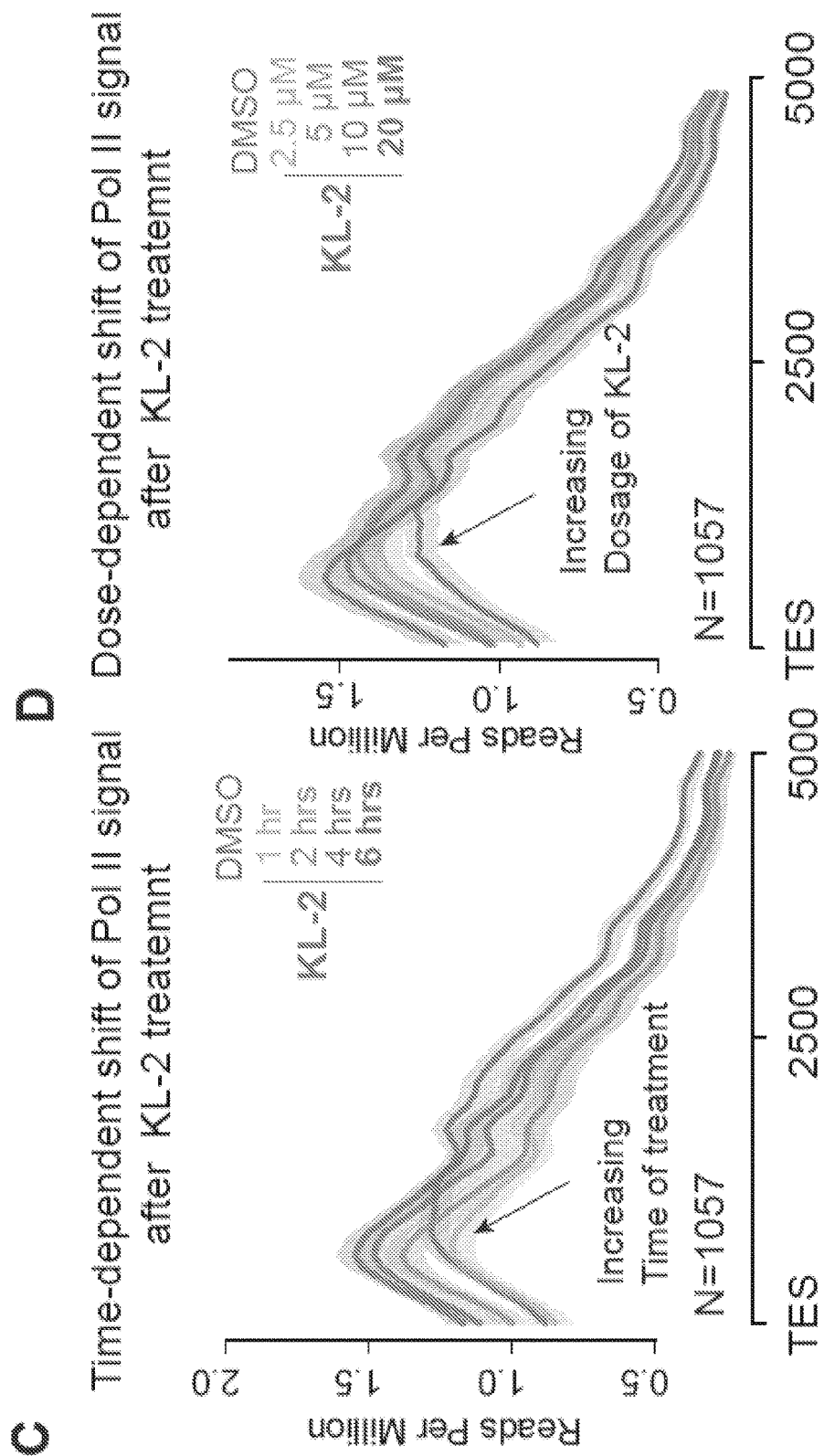
Figure 10:
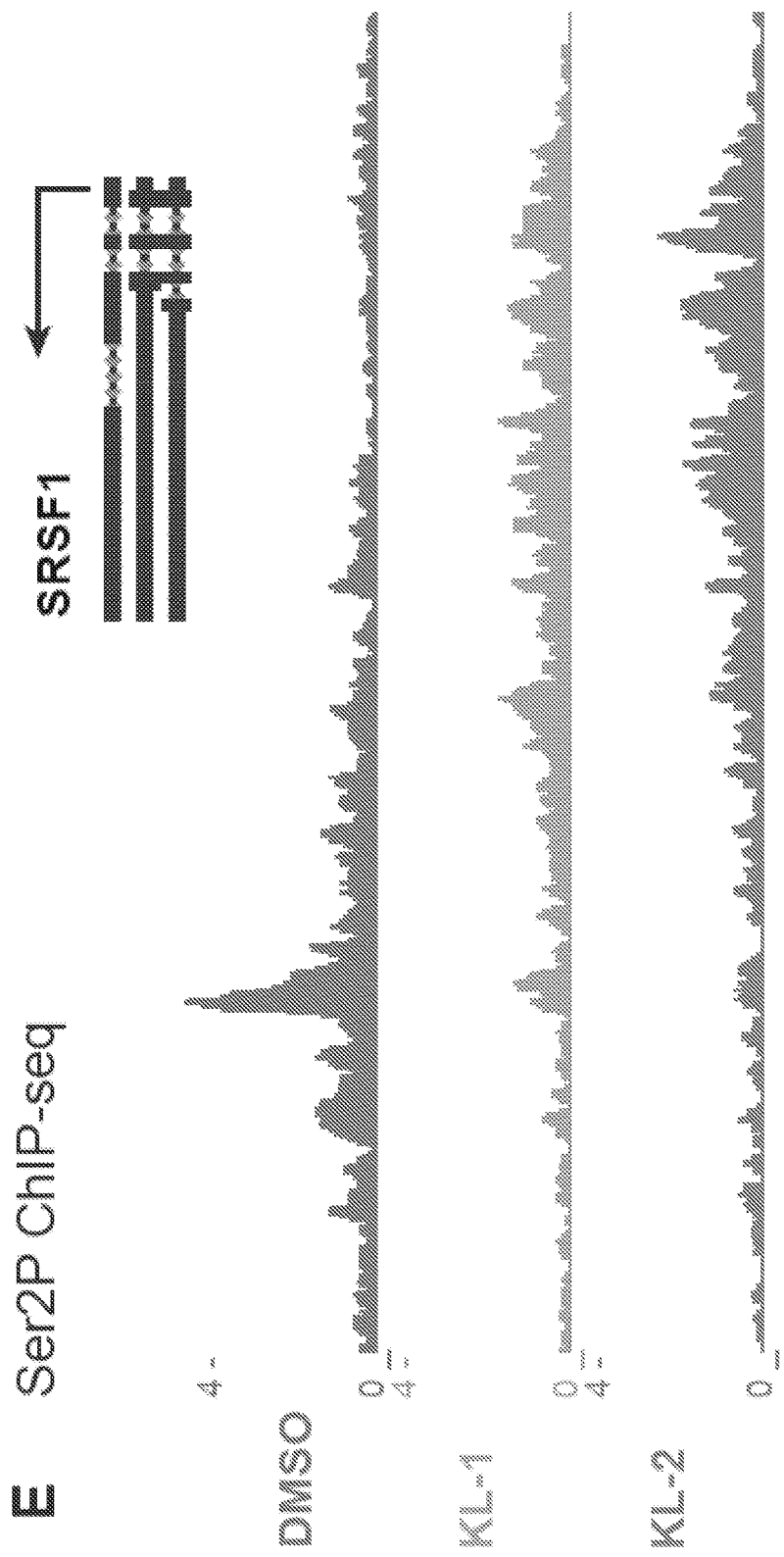
Figure 10:
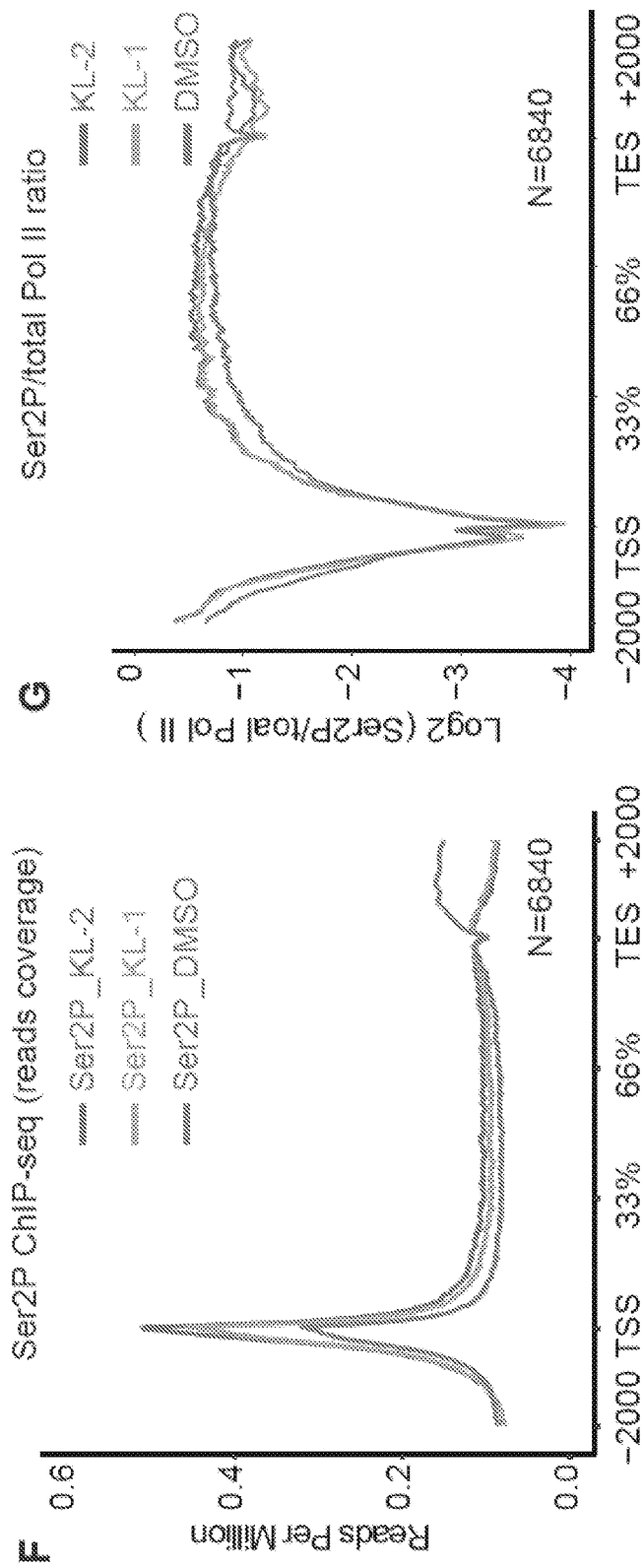
Figure 10:
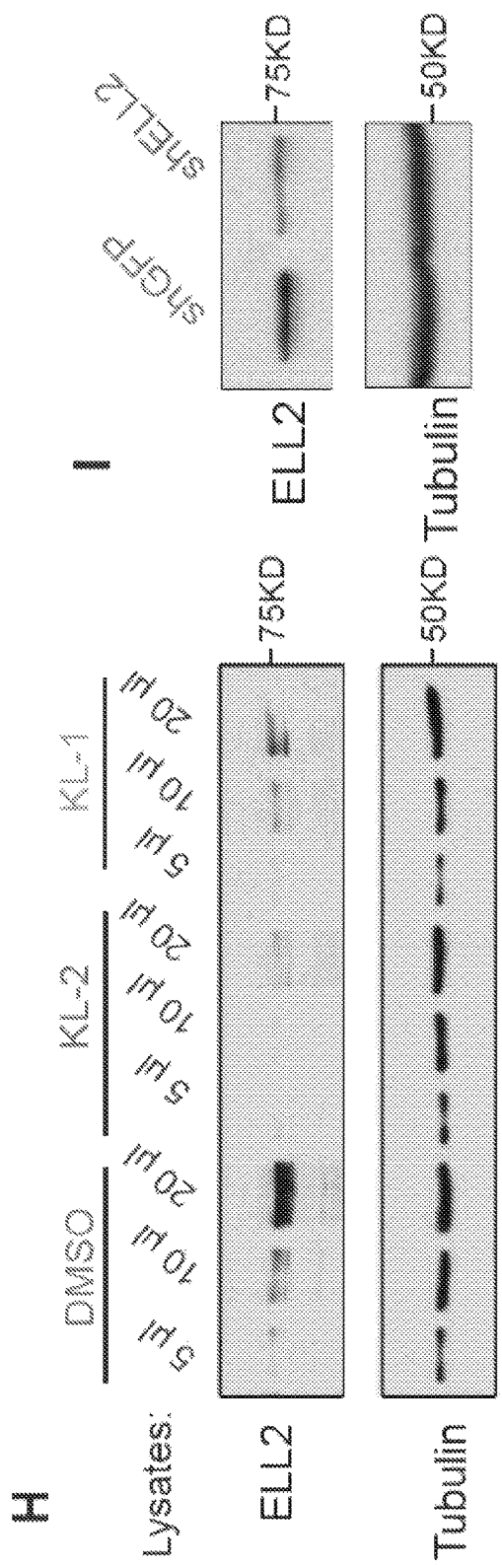
Figure 10:
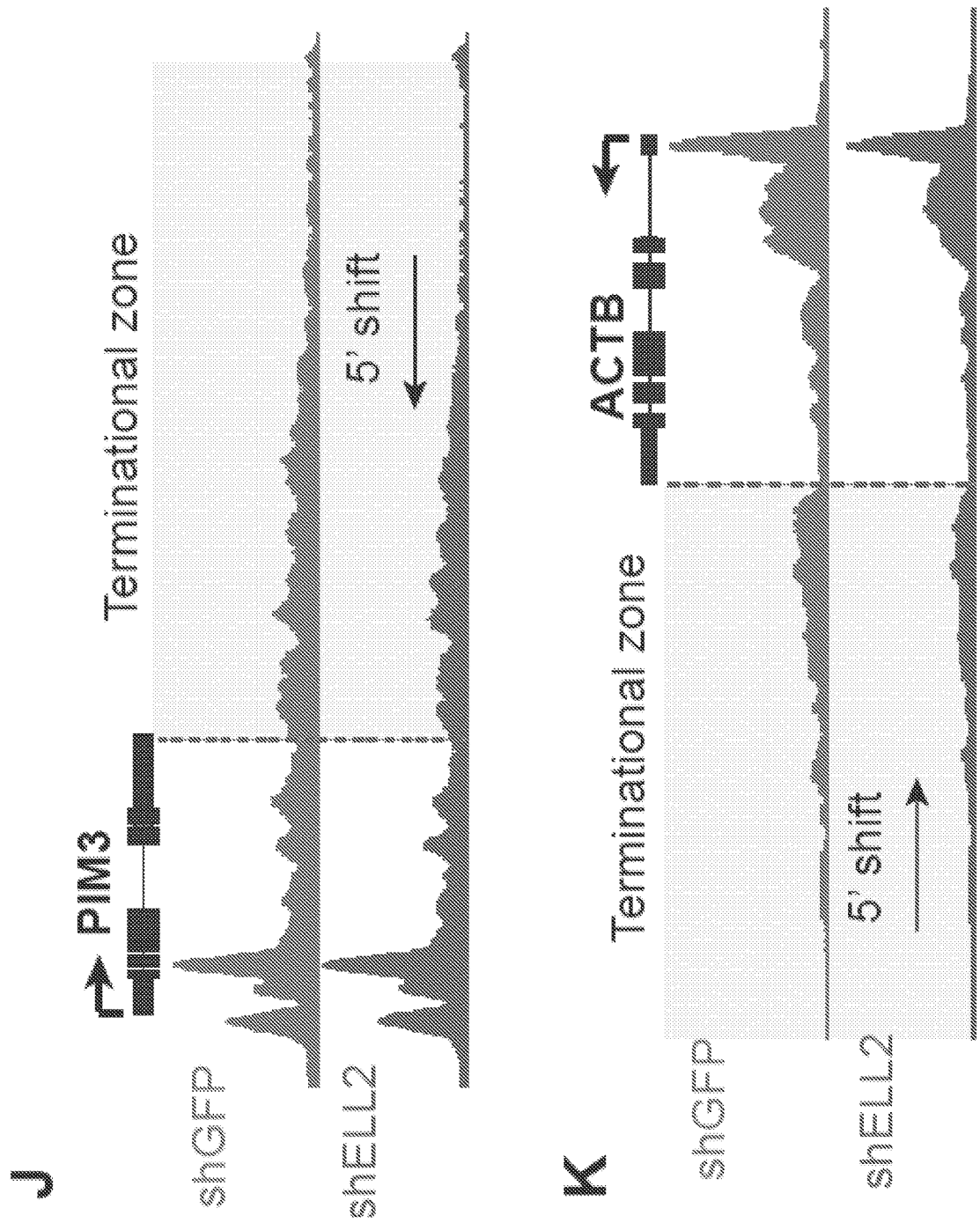
Figure 10:
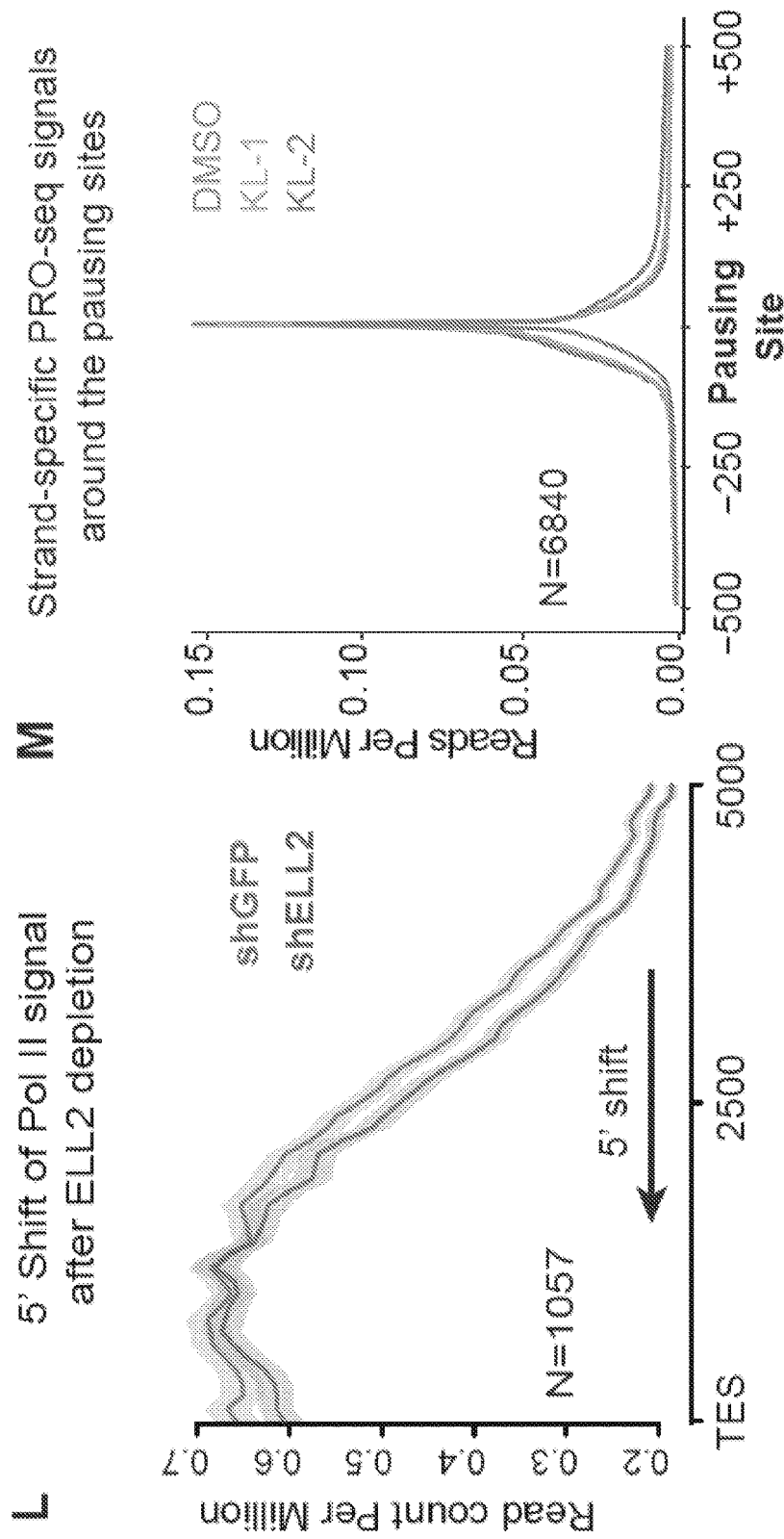
Figure 10:
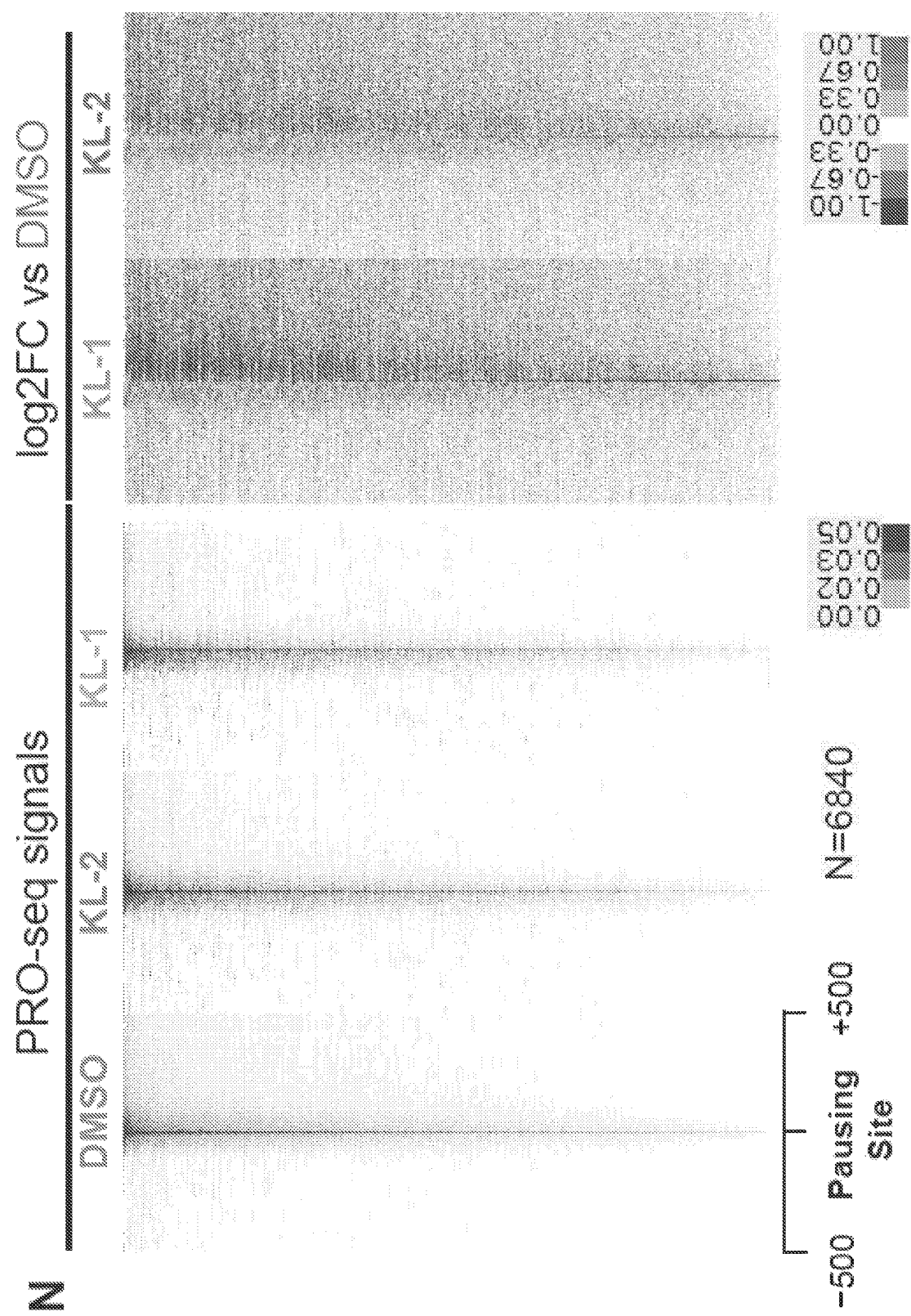

Disruption of SEC phenocopies slow Pol II mutants and reduces Pol II processivity. Examination of the Pol II changes at the 3'-end of genes, such as SRSF4 and HSPA8, revealed a 5'-end shift of Pol II from the normal transcription termination sites (FIGS. 9I and 9J), which is reminiscent of the recently published phenotype of slow Pol II mutants (FIG. 3A) (Fong et al., 2015). Therefore, we tested the effect of KL-1 and KL-2 treatments with the Pol II speed-mutant cells generously provided by the Bentley laboratory (University of Colorado). KL-1 and KL-2 treatments shift the Pol II profile downstream of the TES more 5' in the fast, wild-type (WT) and slow Pol II mutant cells at the ACTB and PIM3 gene (FIG. 3B and 3C). Performing genome-wide analysis of genes with Pol II termination signals around the TES sites (FIG. 10A), we observed similar Pol II profiles observed by Bentley and colleagues in the slow and fast Pol II cells (FIG. 3D) (Fong et al., 2015). Treatment of fast Pol II mutant cells with SEC inhibitors leads to a similar Pol II pattern as the slow Pol II mutant, with a 5' shift in read coverage at the 3'-end of genes (FIGS. 3D, 3E and 10B), indicating that disruption of SEC phenocopies slow Pol II mutants. To further verify these phenotypes, we performed time and dose-dependent treatment of KL-2 in the 293T cells and observed dose- and time-dependent 5' shifts of Pol II signal around TES sites (FIGS. 10C and 10D).

Since slow Pol II mutants exhibited hyperphosphorylation of the CTD on Ser2 at the 5'-end of genes due to higher "dwell-time" (Fong et al., 2017), we asked if SEC inhibitor treatments mimicked this phenotype as well. We performed ChIP-seq for the Ser2P form of Pol II in HEK293T cells after 6 hr of KL-1 and KL-2 treatments and observed that KL-1 or KL-2 elevates Pol II Ser2P levels around transcription start sites and their downstream regions, as can be seen at the SRSFJ gene (FIG. 10E) and by metagene analysis of Pol II Ser2P changes (FIGS. 10F and 10G), further suggesting that KL-1 and KL-2 treatments could slow down Pol II transcription elongation.

Since both ELL and the related factor ELL2 were originally biochemically and mechanistically identified to function as transcription elongation factors for processive transcription in vitro (Shilatifard et al., 1997; Shilatifard et al., 1996) and KL-1 and KL-2 treated cells exhibited phenotypes indicative of less processive Pol II, we first measured ELL2 protein levels after KL-1 and KL-2 treatments. We found that KL-1 and KL-2 led to reduced ELL2 protein levels in cells as seen by western blotting (FIG. 10H), suggesting that ELL2 reduction may account for the observed slow-down of Pol II (FIGS. 3E and 10B). To test this idea, we depleted ELL2 in HEK293T cells (FIG. 10I) and found that ELL2 knockdown results in a 5' shift of Pol II signal at TES sites (FIGS. 10J, 10K and 10L) similar to the KL-1 and KL-2 treatments or the slow Pol II mutant, albeit to a lesser extent. Together, these data suggest that ELL2 reduction contributes to the slow Pol II phenotypes resulting from KL-1 and KL-2 treatments.

To better delineate the changes in Pol II occupancy in response to KL-1 and KL-2, we performed precision nuclear run-on and sequencing (PRO-seq) (Kwak et al., 2013), which allows single-nucleotide resolution of polymerase position (FIGS. 3F and 3G). PRO-seq analysis confirmed that KL-1 and KL-2 treatments result in increased promoter-proximal pausing (FIGS. 10M and 10N). Analysis of the PRO-seq data reveals increased occupancy of engaged Pol II in the gene body, particularly at the 3'-end of genes as can be seen by metagene analysis (FIGS. 3H and 3I). Heatmap analysis of expressed genes ranked by gene length is consistent with KL-1 and KL-2 treatments reducing Pol II processivity, which in turn leads to premature termination due to slower transcription elongation of Pol II (FIG. 3H). Furthermore, PRO-seq analysis confirms a 3'-end transcriptional defect (FIGS. 3H and 3J), which is consistent with the Pol II profiles observed in the slow Pol II mutant cells.

Figure 4:
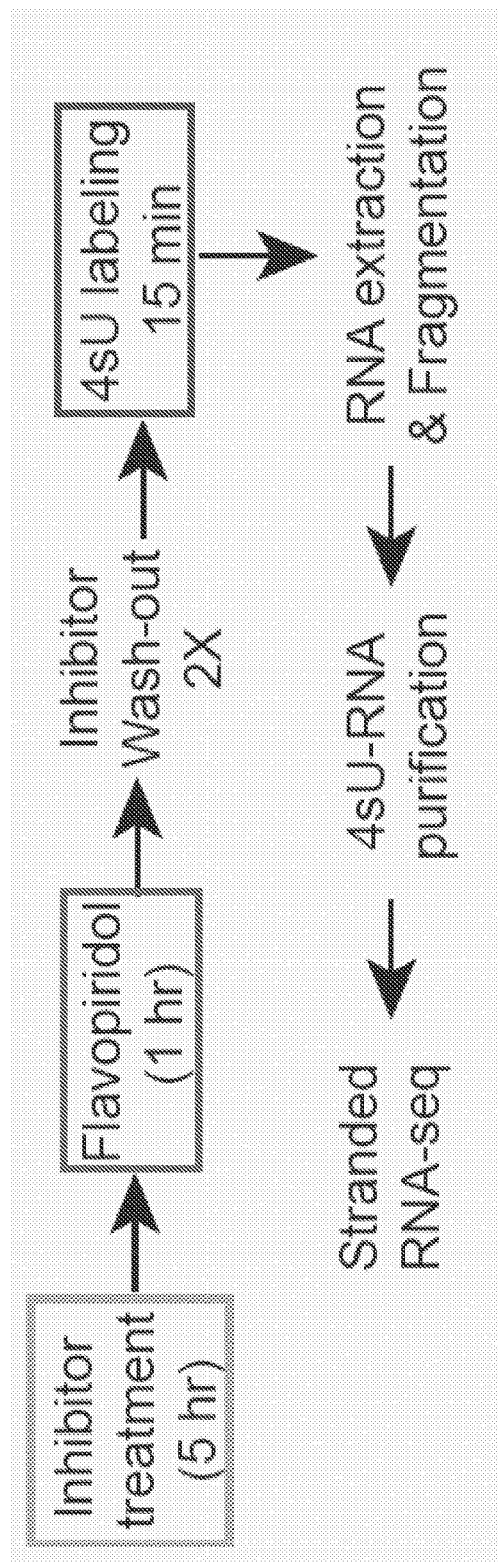
FIG. 4. Small molecule disruption of SEC slows Pol II elongation rates. (A) Workflow of 4sU-FP-seq based measurement of the transcription elongation rate of RNA Pol II. HEK293T cells were pretreated with vehicle or 20 µM SEC inhibitors for 5 hr before addition of the CDK9 inhibitor flavopiridol for 1 hr to arrest Pol II at the promoter-proximal pause site. Inhibitors are washed out with PBS before allowing transcription to proceed in the presence of with fresh medium containing 500 µM 4-Thiouridine (4sU) for 15 min. The 4sU-labeled RNA is then extracted and fragmented before purification, and followed with RNA-seq. (B) Genome browser tracks of 4sU-FP-seq for vehicle and SEC inhibitor-treated cells at the ACTN2 and MTR loci. SEC inhibitors reduce the distance Pol II travels following Pol II release, suggesting that SEC inhibition decrease the elongation rate of Pol II. (C) Heatmap analysis of 4sU-FP-seq in vehicle and the indicated SEC inhibitors in HEK293T cells. All genes longer than 50 kb (N=5,568) were plotted and ordered using the total 4sU-FP-seq signals in the vehicle-treated cells. (D) Metaplot of strand-specific 4sU-FP-seq signals in vehicle and SEC inhibitors-treated cells. (E) Hidden Markov Model (HMM) for elongation rates analysis. Raw changes in 4sU-FP-seq read counts in non-overlapping 50 bp windows used to infer elongation rates for the MTR gene. The boxes show the span of advancing wave inferred by a 3-state HMM analysis, demonstrating that SEC inhibitors decrease the elongation rates of Pol II on MTR gene. (F-G) Histograms (F) and boxplots (G) comparing the transcription elongation rates for 982 genes in HEK293T cells for which high confidence elongation rates could be determined. The statistical analysis was performed with the Wilcoxon test.
Figure 4:
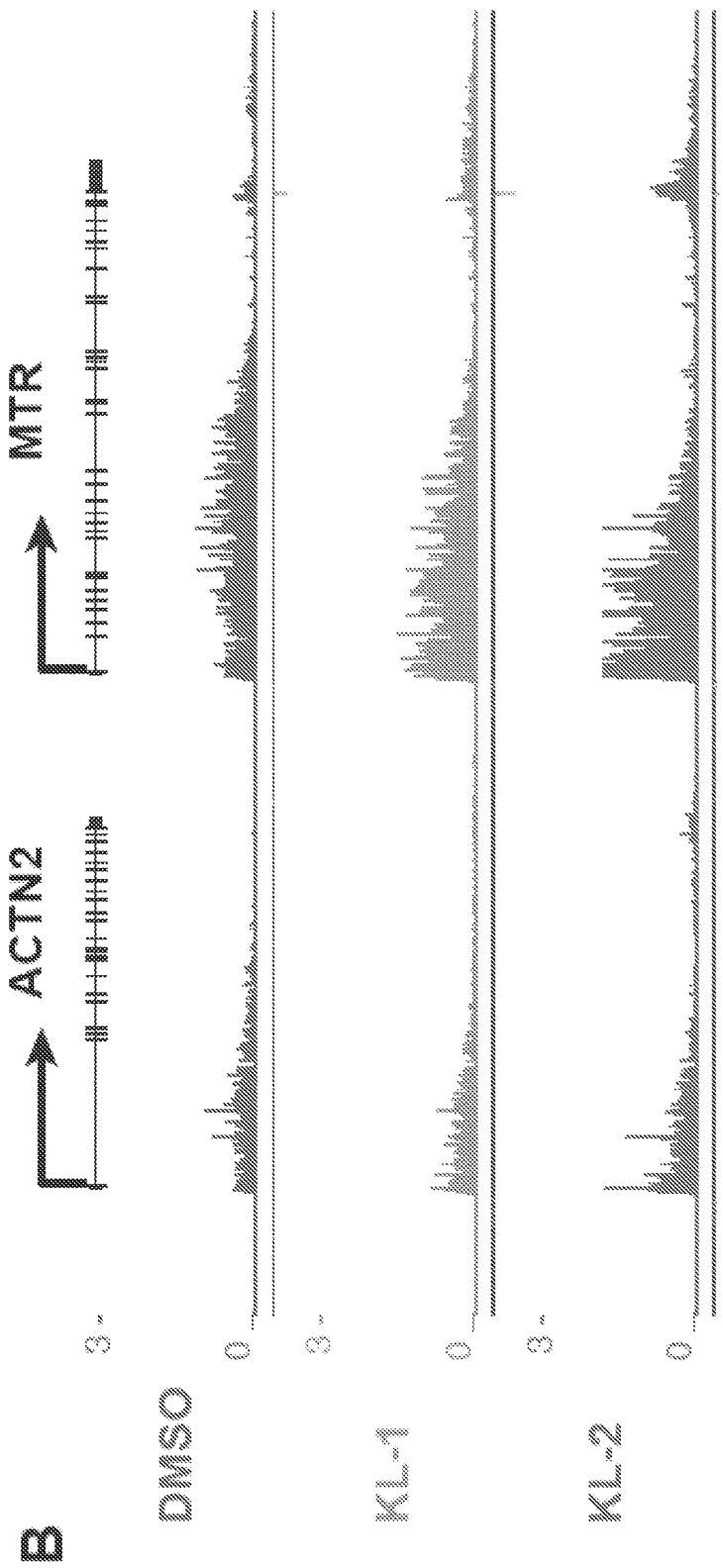
Figure 4:
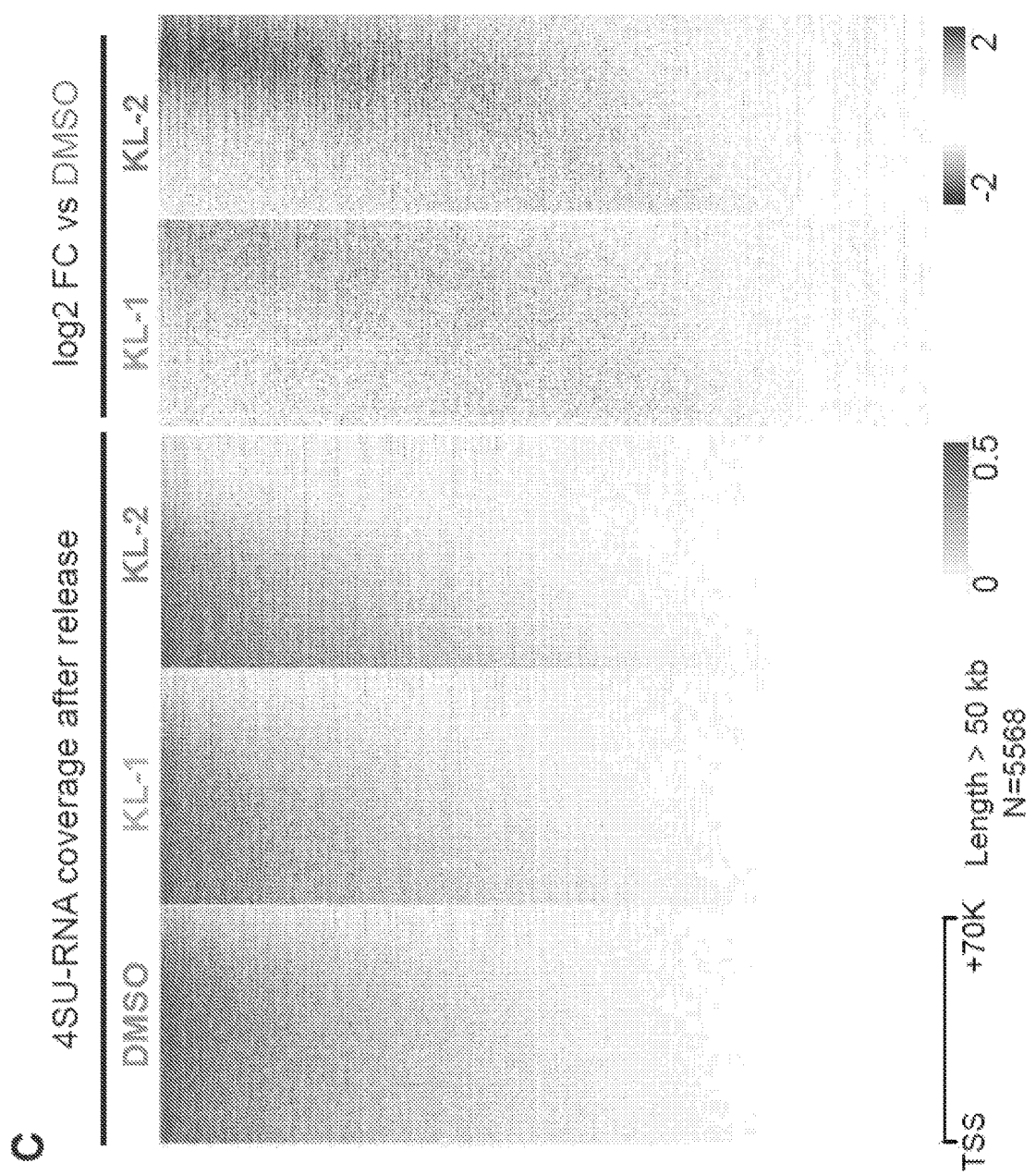
Figure 4:
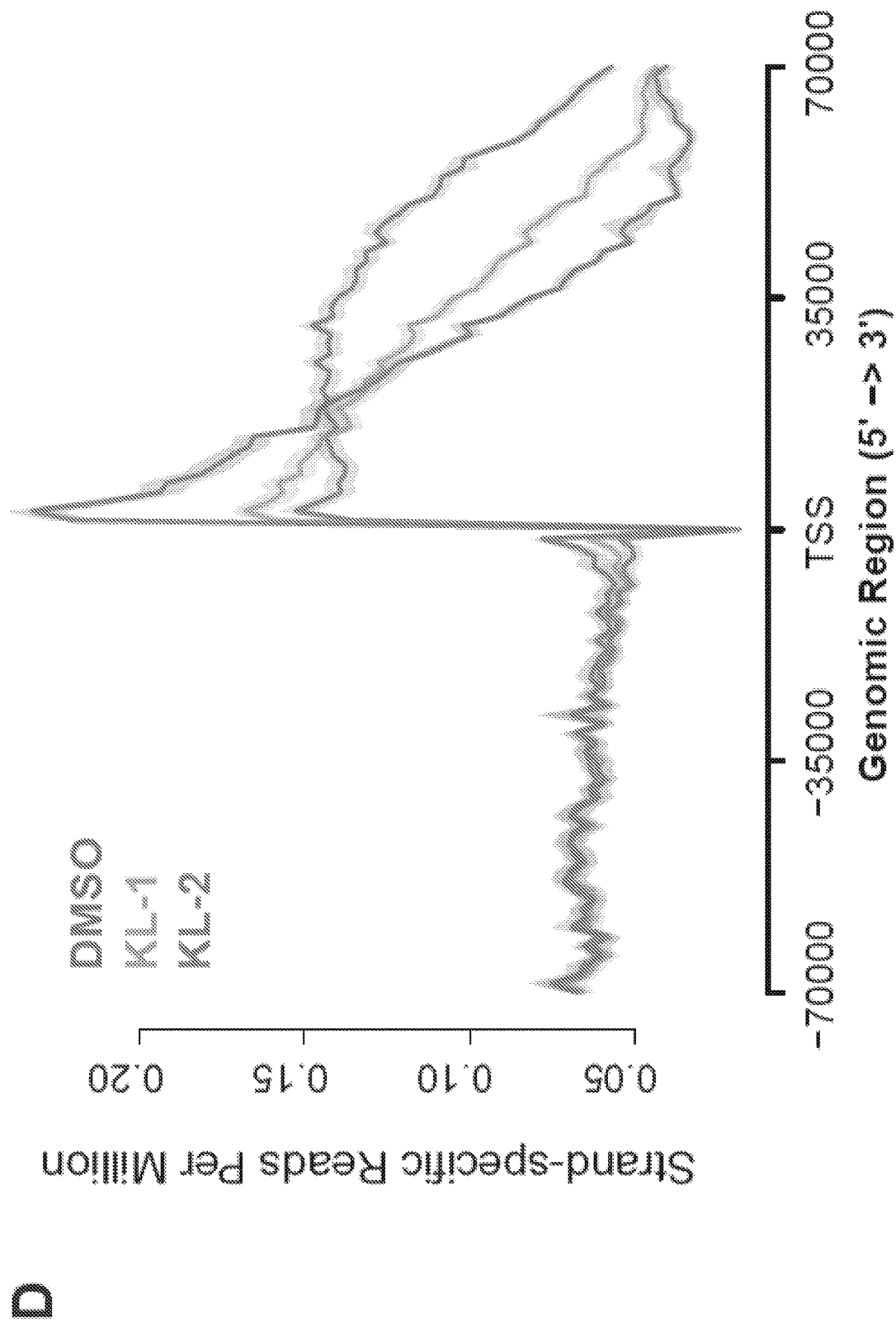
Figure 4:
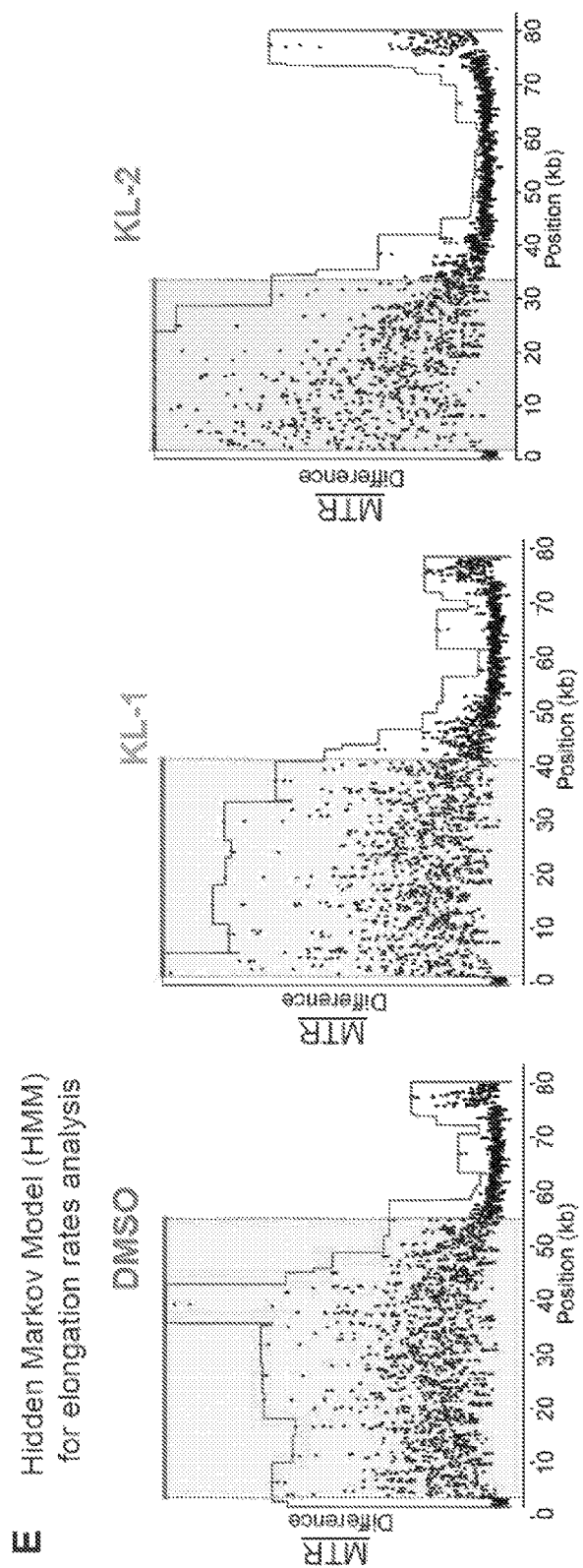
Figure 4:
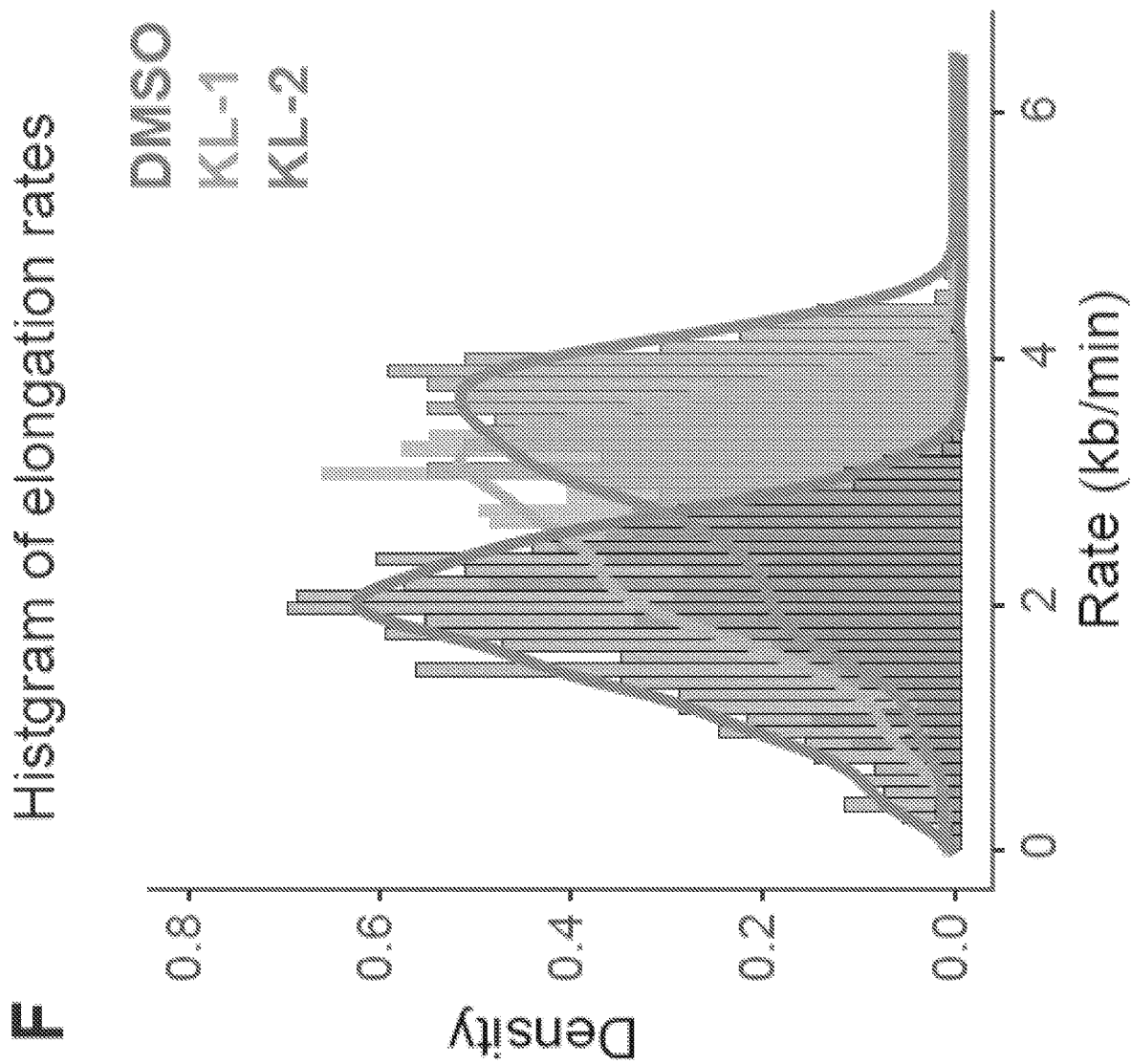
Figure 4:
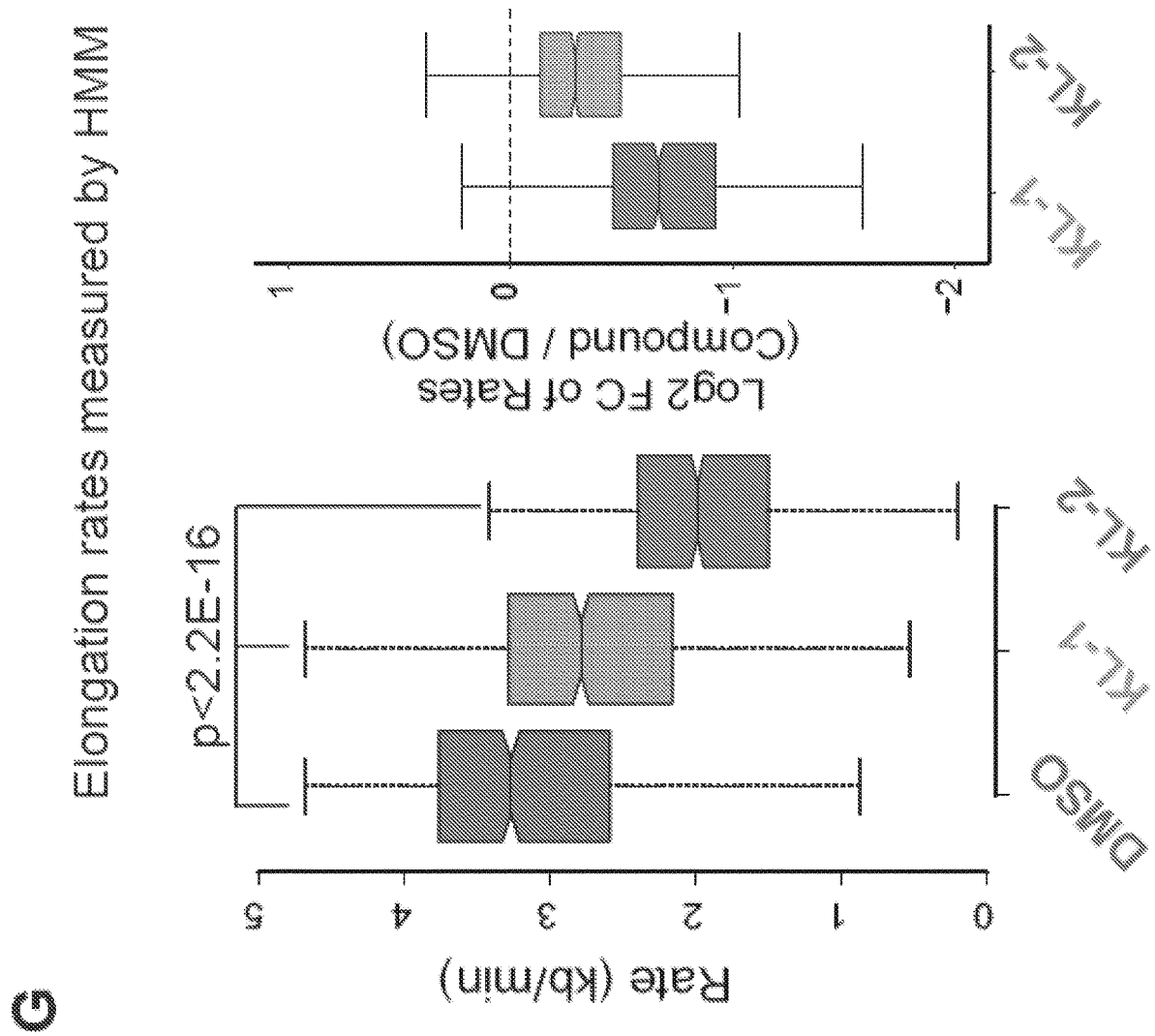

Small molecule disruption of SEC slows Pol II elongation rates. To measure the effects of SEC inhibition on transcription elongation rates, we used a 4sU-FP-seq strategy that employs flavopiridol (FP)-mediated Pol II pausing followed by release in the presence of 4sU labeling to measure nascent RNA production (Fuchs et al., 2014) (FIG. 4A). When cells are pretreated with KL-1 and KL-2, the distance that Pol II was able to travel after release from flavopiridol was markedly reduced, as seen by genome browser views of individual genes (FIG. 4B) and by heatmap analysis (FIG. 4C). Metaplot analysis of 4sU signal also demonstrates that KL-1 and KL-2 treatments resulted in decreased distance traveled by Pol II following release from flavopiridol (FIG. 4D).

Figure 11:
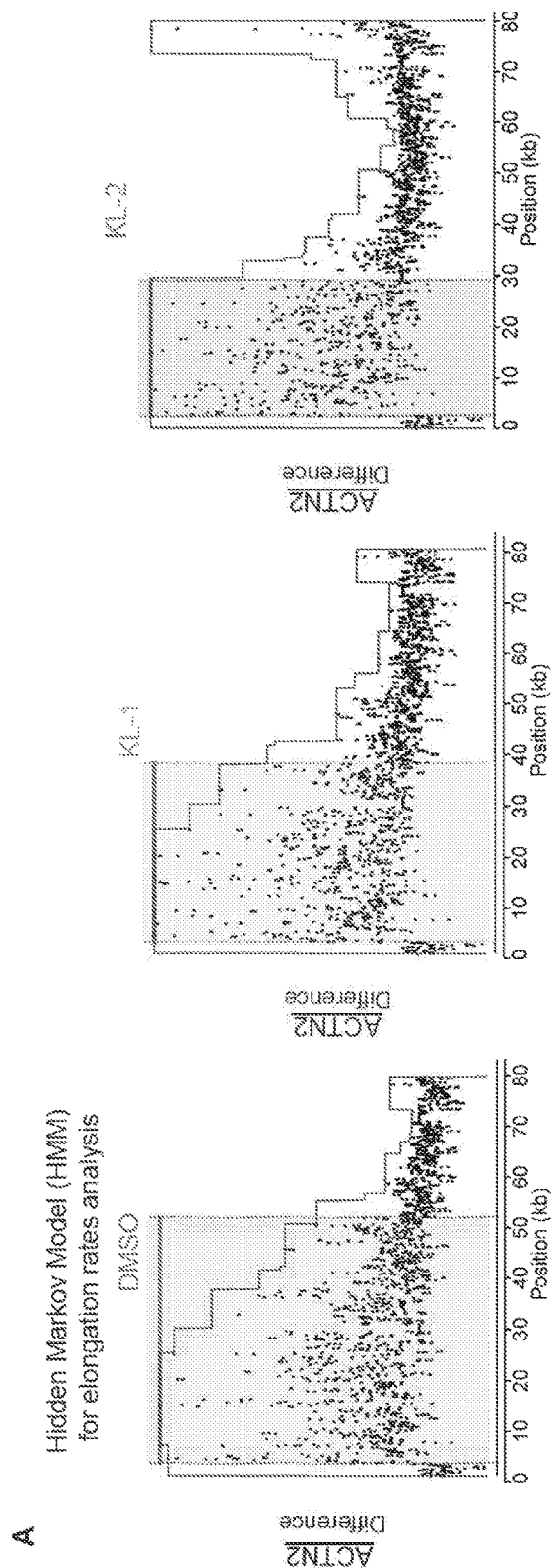
FIG. 11, related to FIG. 4. Small molecule disruption of SEC slows Pol II elongation rates. (A) Hidden Markov Model (HMM) for elongation rates analysis. Raw changes in 4sU-FP-seq read counts in non-overlapping 50 bp windows used to infer elongation rates for the ACTN2 gene. The boxes show the span of advancing wave inferred by a 3-state HMM analysis, demonstrating that SEC inhibitors decrease the elongation rates of Pol II elongation at the ACTN2 gene. (B) Calculation of Pol II elongation rate using the length of SICER-called peaks of 4sU-FP-seq data to measure distance traveled. Genome browser tracks of 4sU-FP-seq signals at the MIR gene in vehicle and SEC inhibitor-treated HEK293T cells. Black bars beneath the tracks indicate SICER-called peaks. Note that in the DMSO condition, Pol II has traveled further during the 15 minutes of release from flavopiridol resulting in a longer distance traveled. (C-D) Histograms of elongation rates (N=1,484) calculated form SICER data for DMSO (C-D) and SEC inhibitors KL-1 (C) and KL-2 (D). (E) Boxplot analysis of SICER-based elongation rates (N=1,484, left panel) and log$_2$ fold change of elongation rates (right panel) for the indicated treatments Wilcoxon test was used for the statistical analysis.
Figure 11:
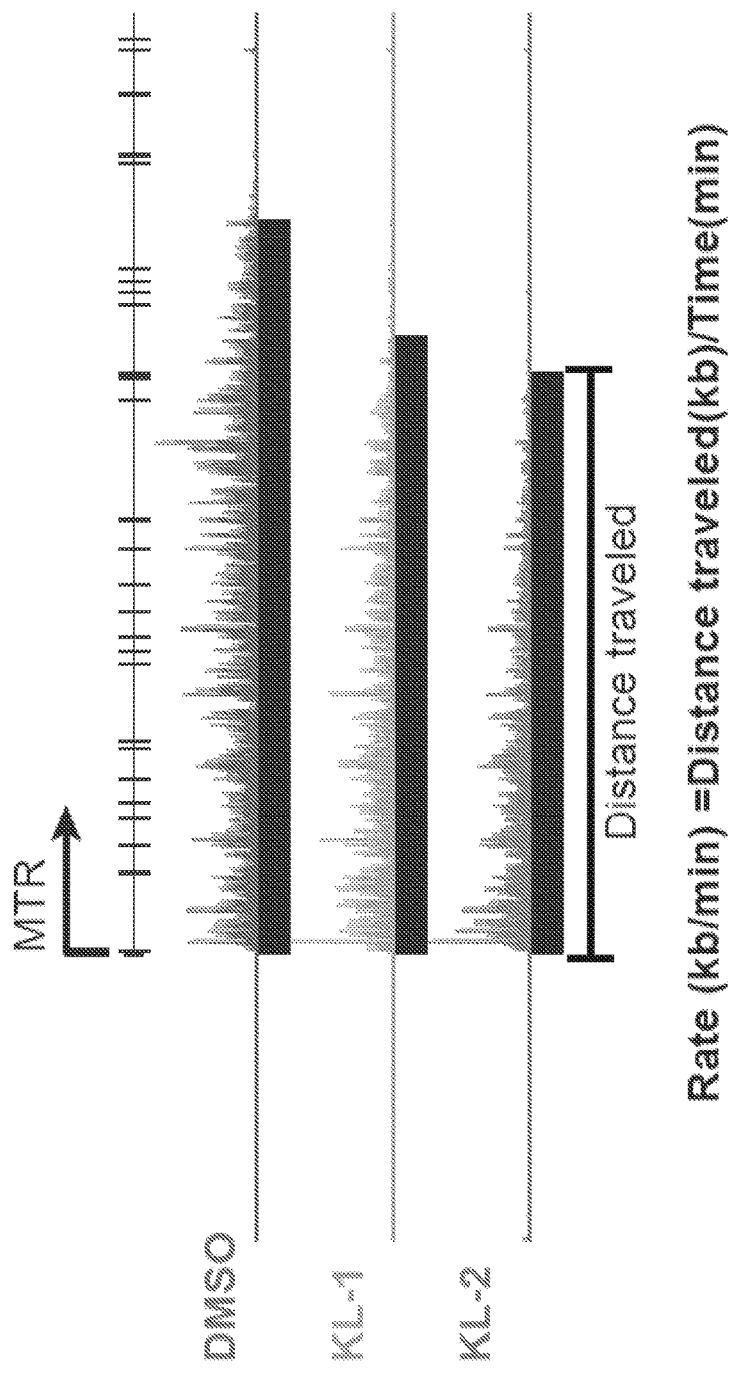
Figure 11:
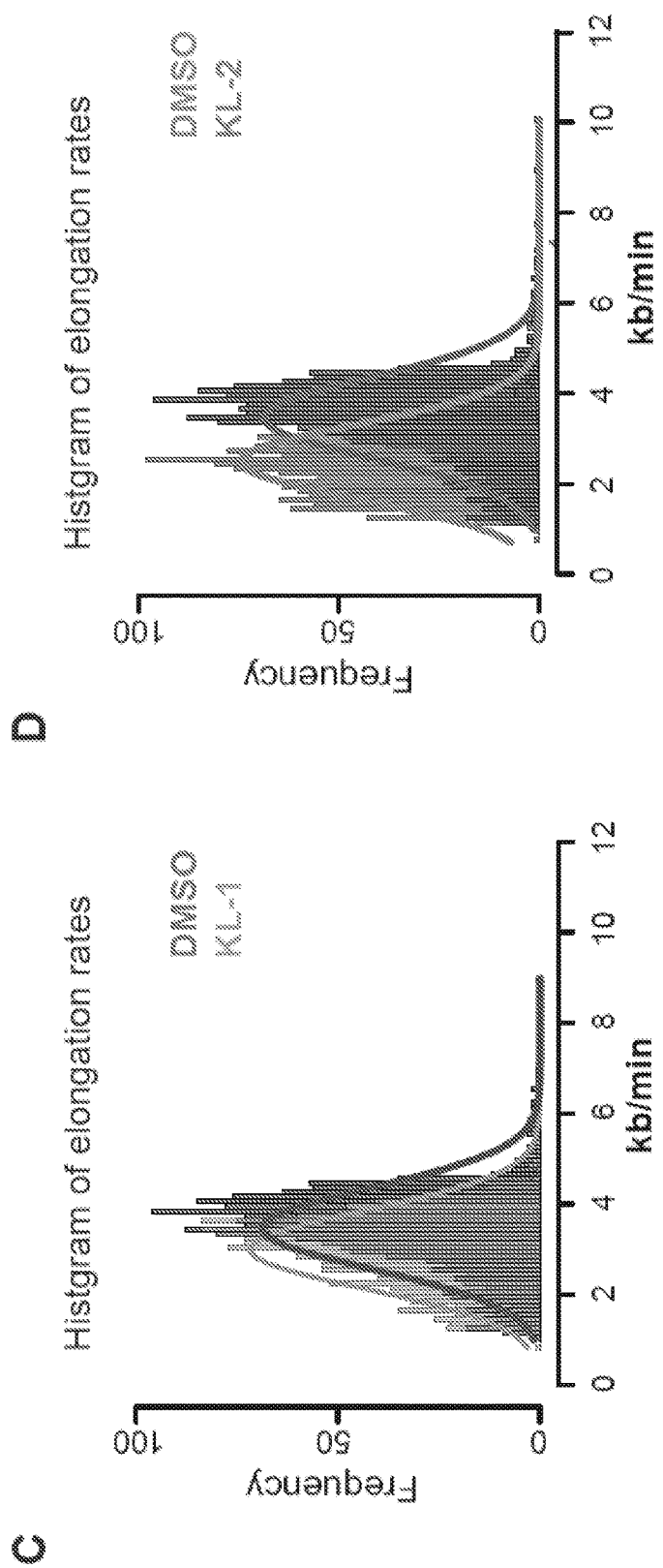
Figure 11:
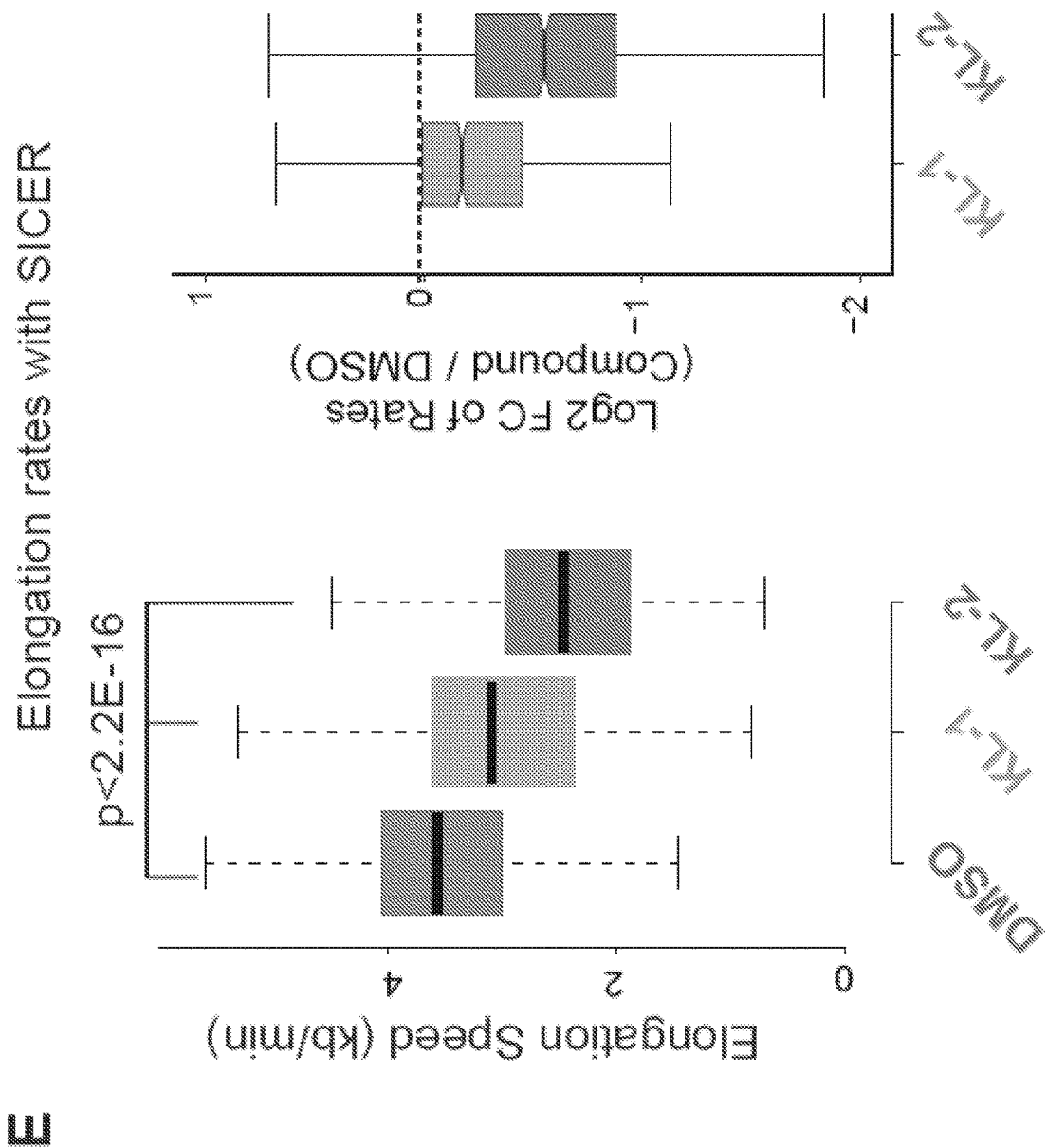

We used two different approaches to measure elongation rates in the 4sU-FP-seq experiments. First, we employed the previously published Hidden Markov Model (HMM) method for calculating elongation rates (Danko et al., 2013). Applying this model, we were able to measure elongation rates across all samples for 982 genes (the number of genes for which the model could detect a wave front of Pol II elongation). This analysis demonstrated that both KL-1 and KL-2 treatments decreased the elongation rate of Pol II at the ACTN2 and MTR genes (FIGS. 4E and 11A), and globally as can be seen by boxplot and histogram analyses of these 982 genes (FIGS. 4F and 4G). As an alternative, we used the island-based peak caller SICER to determine regions of 4sU signal coverage (FIG. 11B). In this method, the width of the peak overlapping TSS regions corresponds to the distance traveled. Consistent with the HMM analysis, we found that the SICER-based analysis demonstrated that KL-1 and KL-2 significantly reduced the transcription elongation rate of Pol II (FIGS. 11C, 11D and 11E). Together, these data suggest that small molecule disruption of SEC results in slower elongating Pol II.

SEC inhibitors block transcription elongation in SEC-dependent rapid response models. SEC has been shown to mediate transcription elongation in rapid response models such as heat shock induced gene expression (Lin et al., 2010; Takahashi et al., 2011) and Tat-induced HIV proviral transcription (He et al., 2010; Sobhian et al., 2010). Therefore, we tested if KL-1 and KL-2 could inhibit the function of SEC in these rapid-response models.

Figure 5:
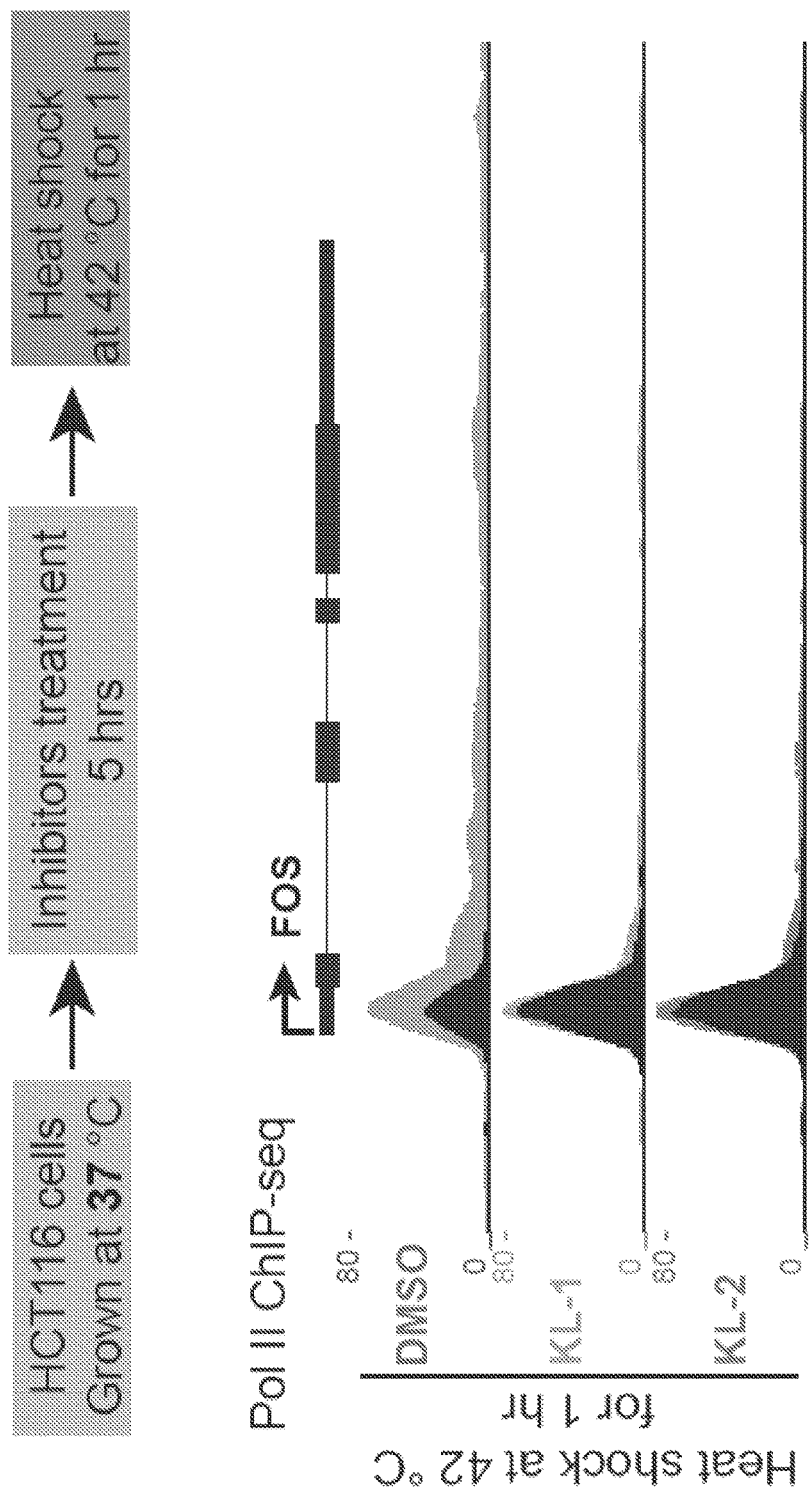
FIG. 5. SEC inhibitors block transcription elongation in SEC-dependent rapid response models. (A-B) Genome browser tracks of Pol II ChIP-seq at the FOS, HSPD1 and HSPE1 genes after 1 hr heat shock of HCT-116 cells treated with vehicle (DMSO) or the indicated SEC inhibitors. HCT-116 cells were pretreated with inhibitors for 5 hr at 37° C. before exchanging medium with conditioned 42° C. medium. Dark and light colors indicate the 37 and 42° C. conditions, respectively. (C) Genome-wide identification of heat shock-induced genes with fold change of reads per million in gene bodies and pausing index. Red dots are the 136 heat shock-induced genes according to Pol II signals (fold change of reads per million in gene bodies >1.5 and pausing index decreased >1.5-fold in the DMSO-treated condition). (D-E) Metagene plot of the 136 heat-shock induced genes shows that attenuated induction is seen in both inhibitors (D). Box plot analysis depicts the $\log_2$ fold changes of reads per million in gene bodies (E) (y axis) after heat shock with pretreatment of vehicle or SEC inhibitors. (F) Sequence alignment of the CCNT1 interacting region in human AFF family proteins and the *Drosophila* homolog Lilliputian indicates that the SEC inhibitors could disrupt the CCNT1 interaction for all of the human AFF proteins and *Drosophila* Lilliputian. (G) Genome-wide analysis demonstrates that SEC inhibitors attenuate the induction of heat shock genes in *Drosophila* S2 cells (N=215). S2 cells were heat shocked at 37° C. with and without 20 µM SEC inhibitors for 6 hr (left panel). The statistical analysis was performed with the Wilcoxon test.
Figure 5:
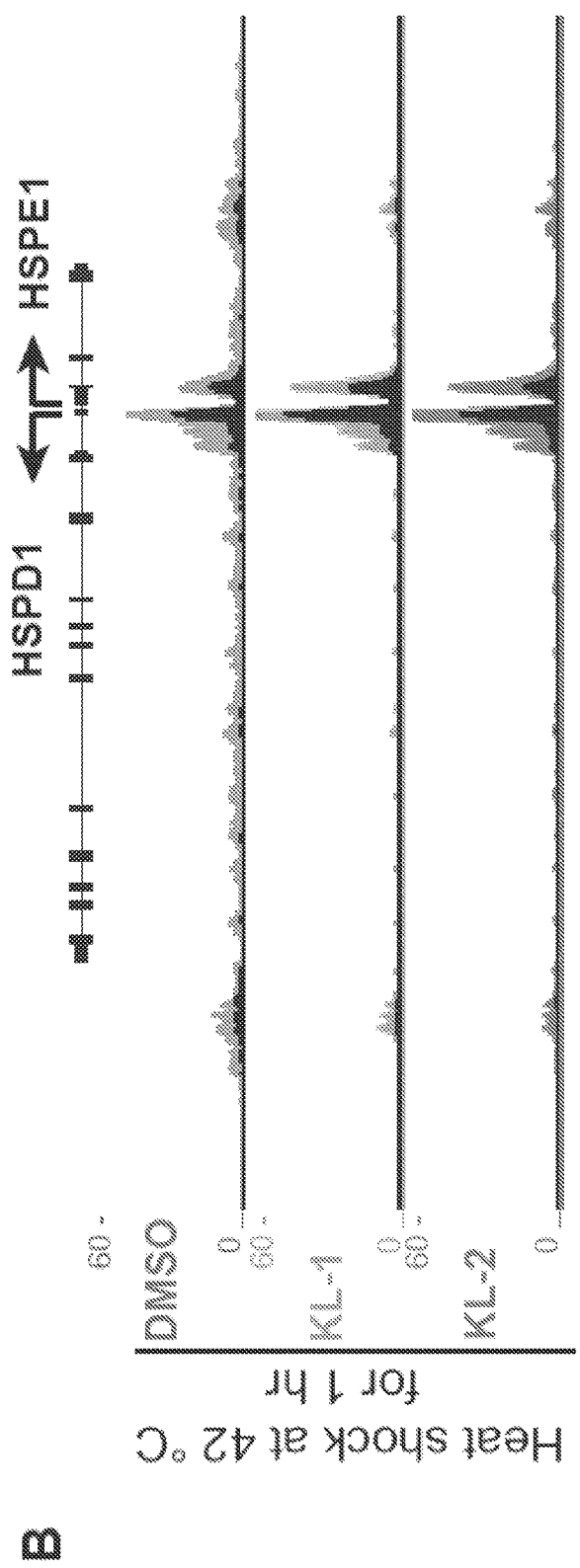
Figure 5:
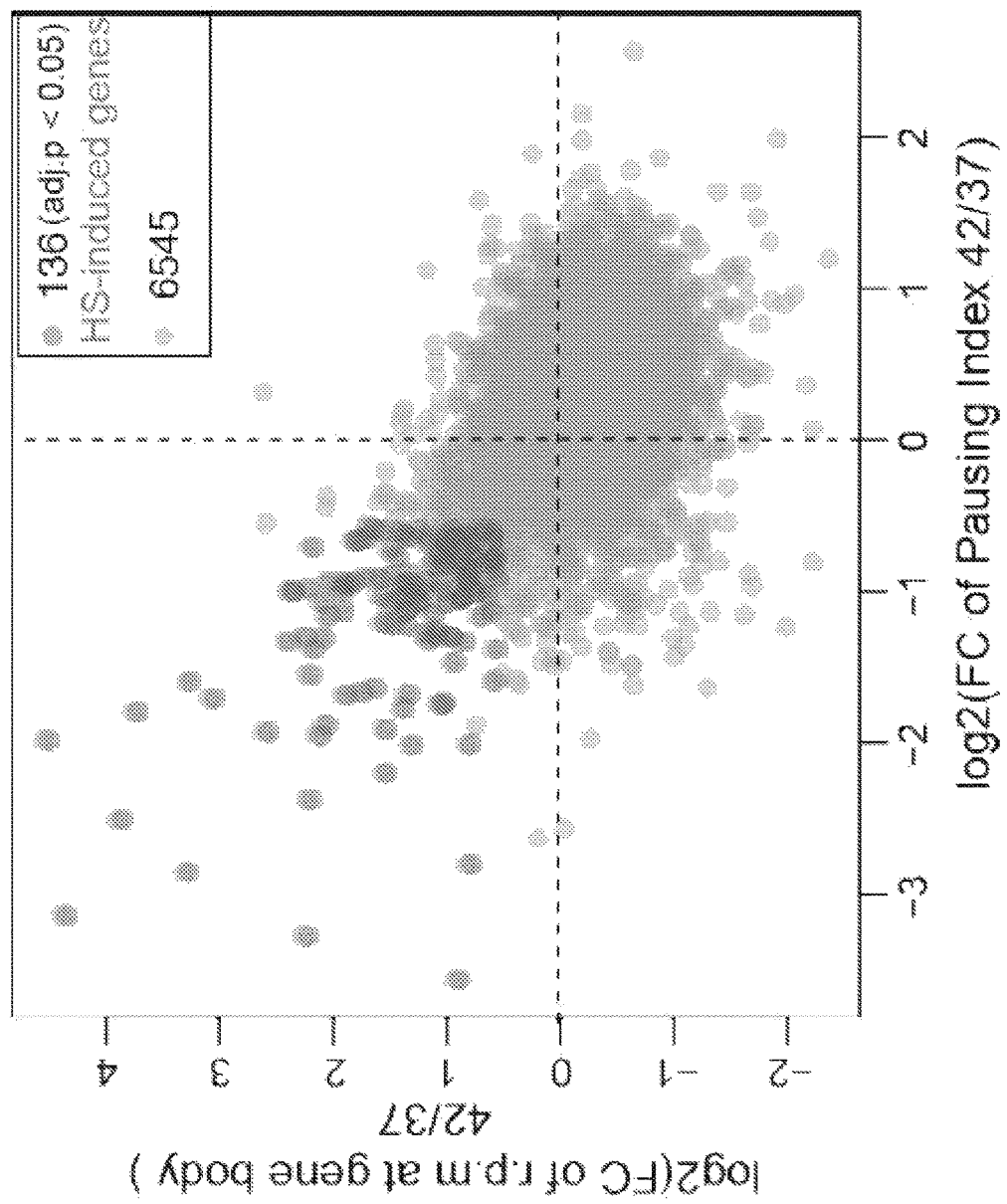
Figure 5:
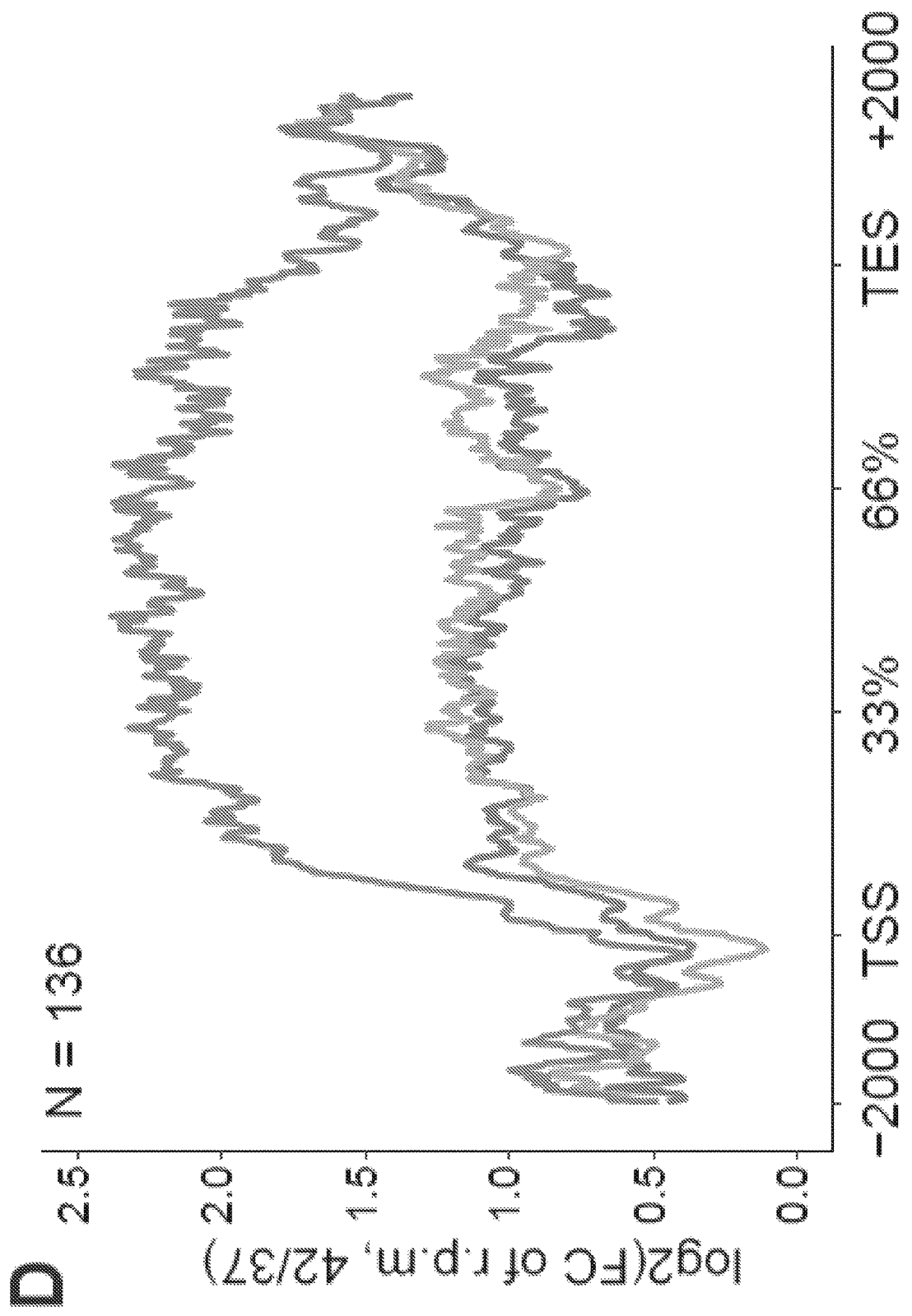
Figure 5:
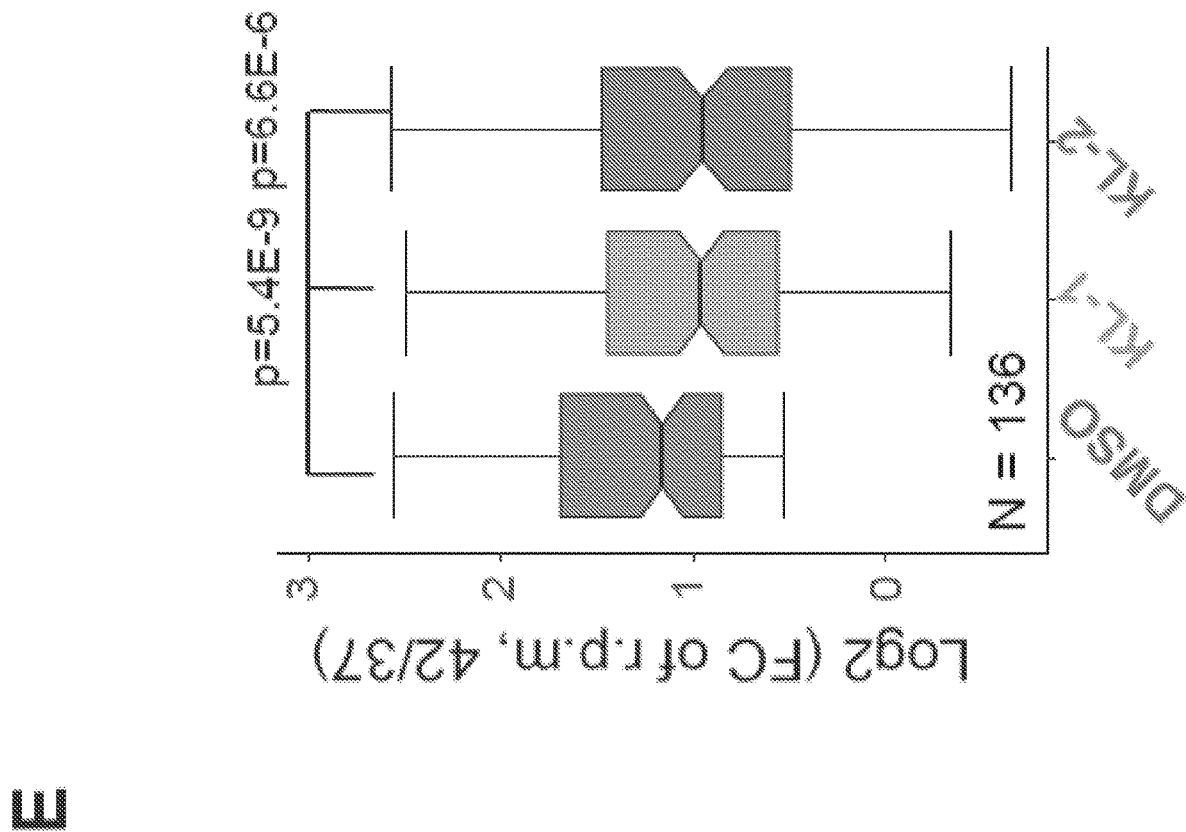
Figure 5:
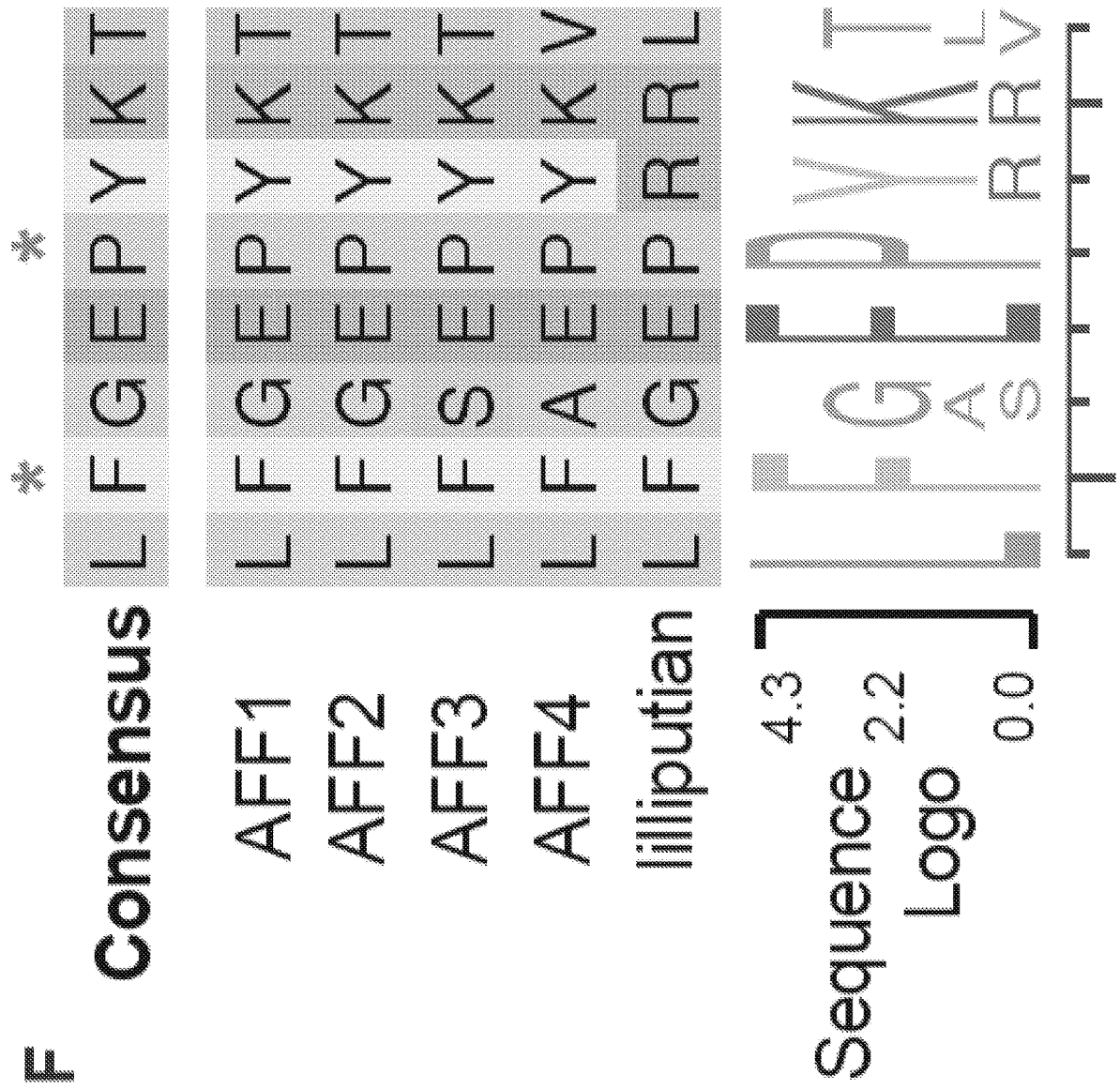
Figure 5:
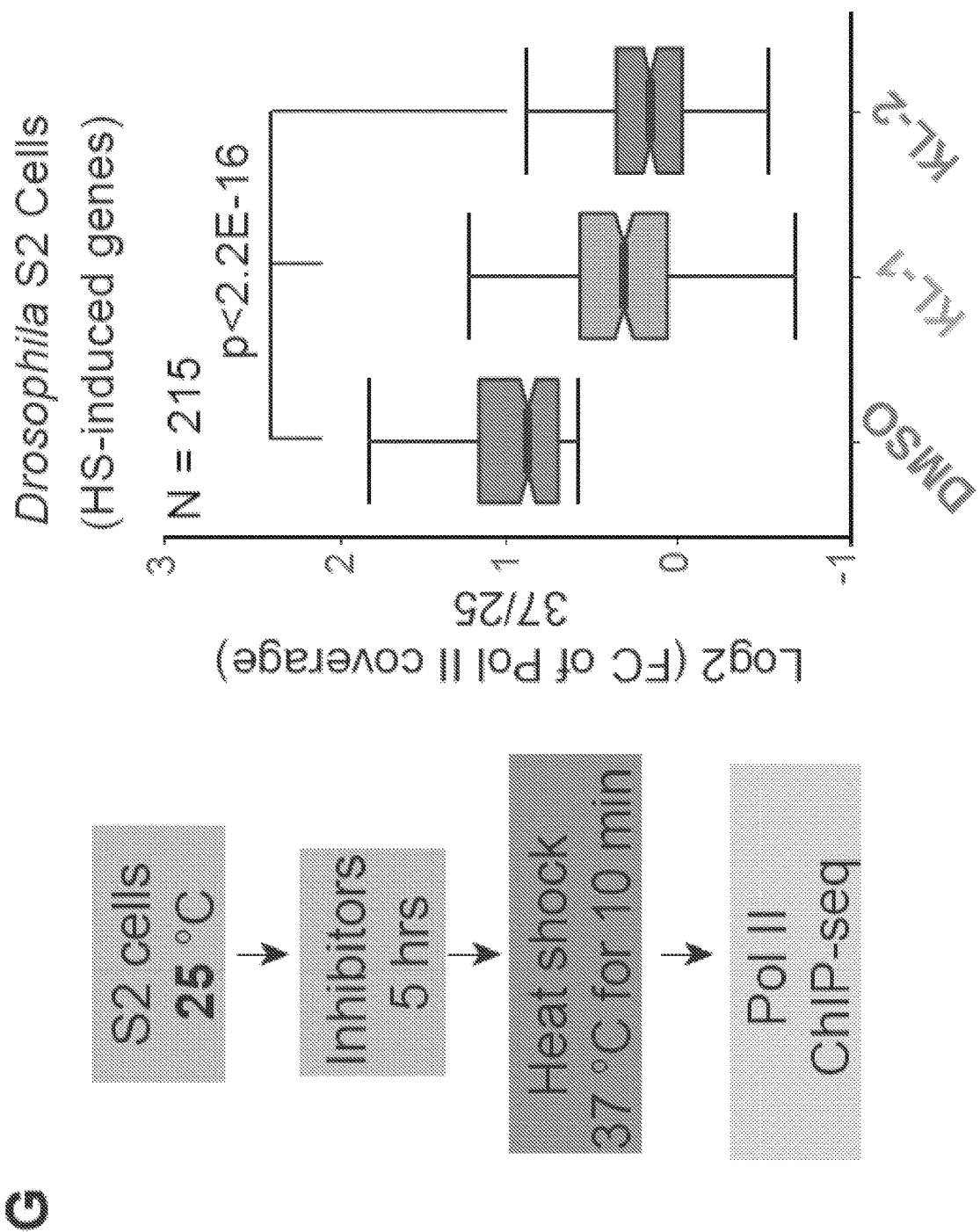
Figure 12:
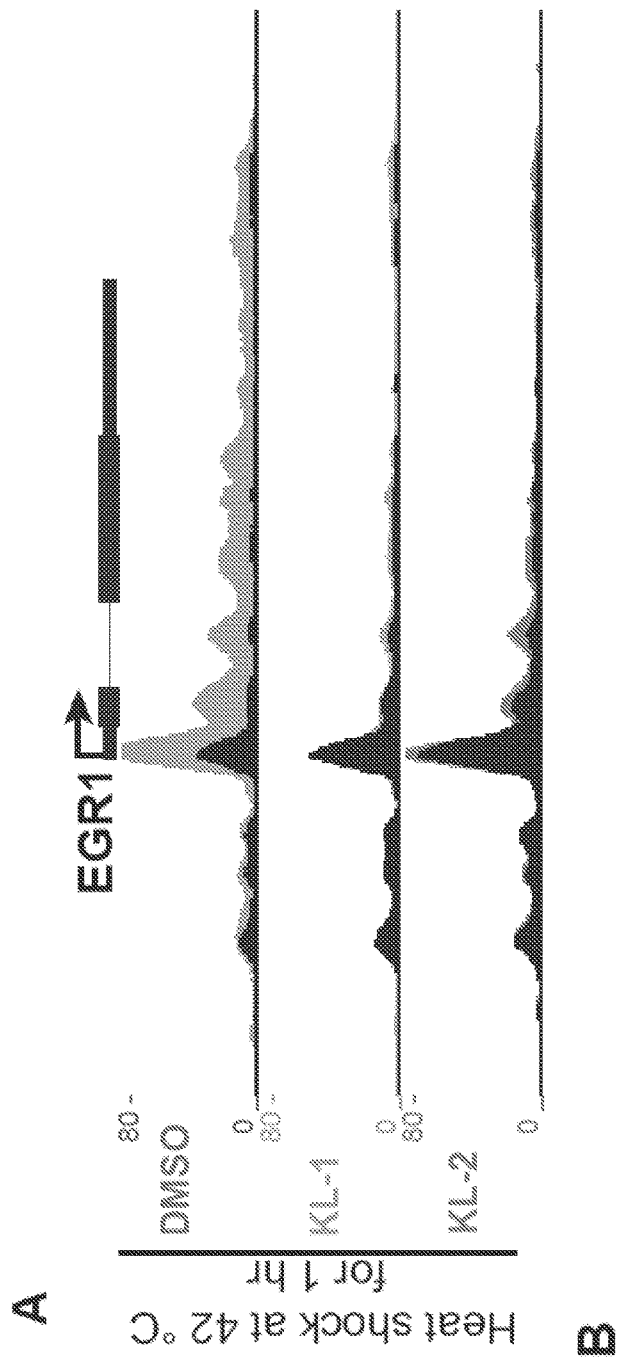
FIG. 12, related to FIG. 5. SEC inhibitors block transcription elongation in SEC-dependent rapid response models. (A) Genome browser tracks of Pol II occupancy demonstrating that SEC inhibitors attenuate the induction of heat shock-induced gene EGR1. (B) Gene Ontology analysis of the 136 identified heat shock-induced genes in HCT-116 cells. (C) Workflow of Tat-induced HIV genome activation in J-Lat 6.3 cells. J-Lat 6.3 cells contain an integrated copy of the HIV genome that has GFP replacing HIV nef and could be activated by Phorbol-12-Myristate-13-Acetate (PMA). J-Lat 6.3 cells were treated with vehicle or 20 µM SEC inhibitor along with PMA to activate the HIV genome transcription, which could be monitored by flow cytometry analysis. (D-E) SEC inhibitors block Tat-induced HIV genome activation in J-Lat 6.3 cells. (D) FACS analysis of J-Lat 6.3 cells treated with 10 nM PMA and SEC inhibitors for 17 hr. Treatment with SEC inhibitors attenuates HIV genome activation in a dose-dependent manner (E) as revealed by flow cytometry analysis with GFP (n=3-5). Unpaired two-way ANOVA was used to compare the groups between DMSO and SEC inhibitors. ***, p<0.001. Data are represented as Mean+/−SD. (F) Genome browser views demonstrating that SEC inhibitors inhibit the Tat-dependent induction of the integrated HIV genome. J-Lat 6.3 cells were first induced with 10 nM PMA for 11 hr to induce the Tat expression and then treated with 20 µM SEC inhibitors for 6 hr prior to Pol II ChIP-seq.
Figure 12:
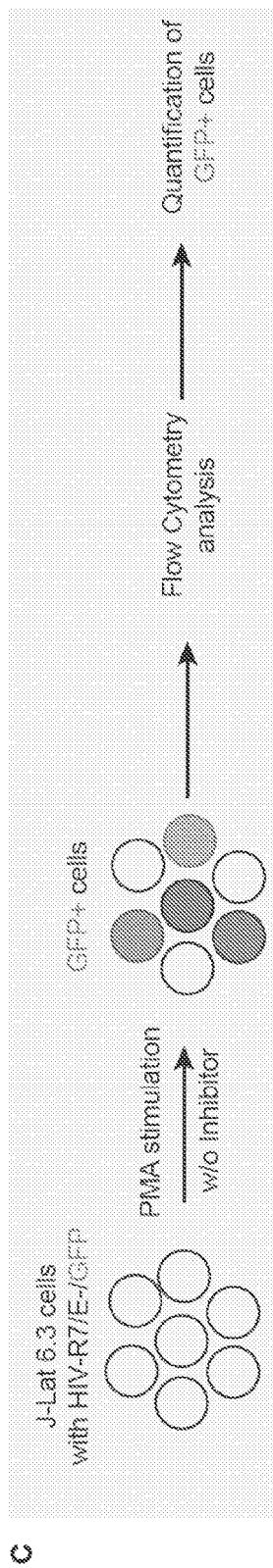
Figure 12:
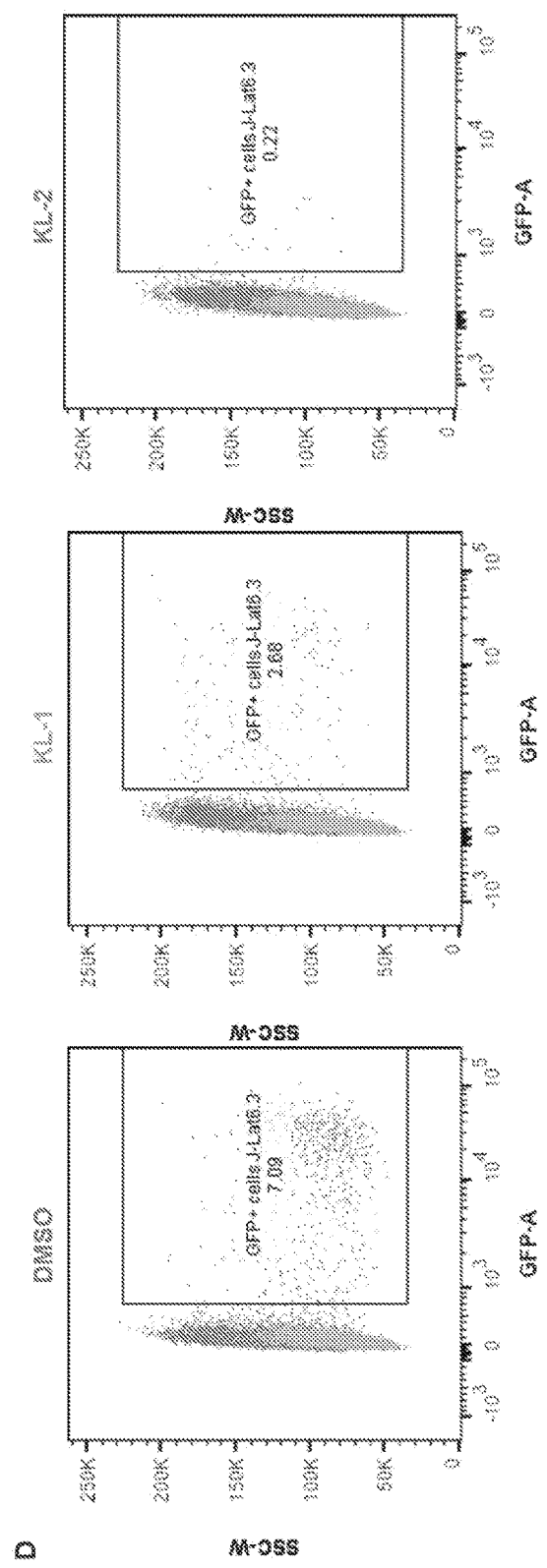
Figure 12:
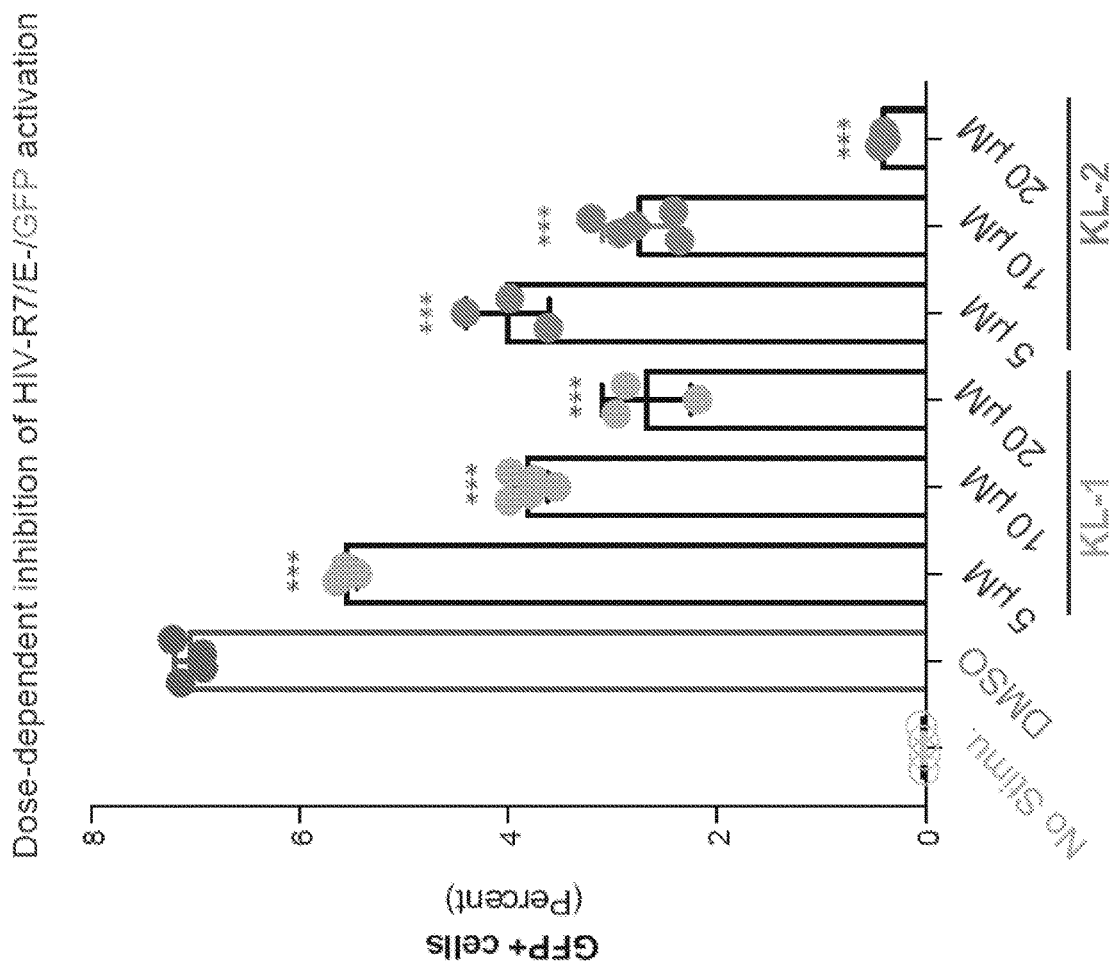
Figure 12:
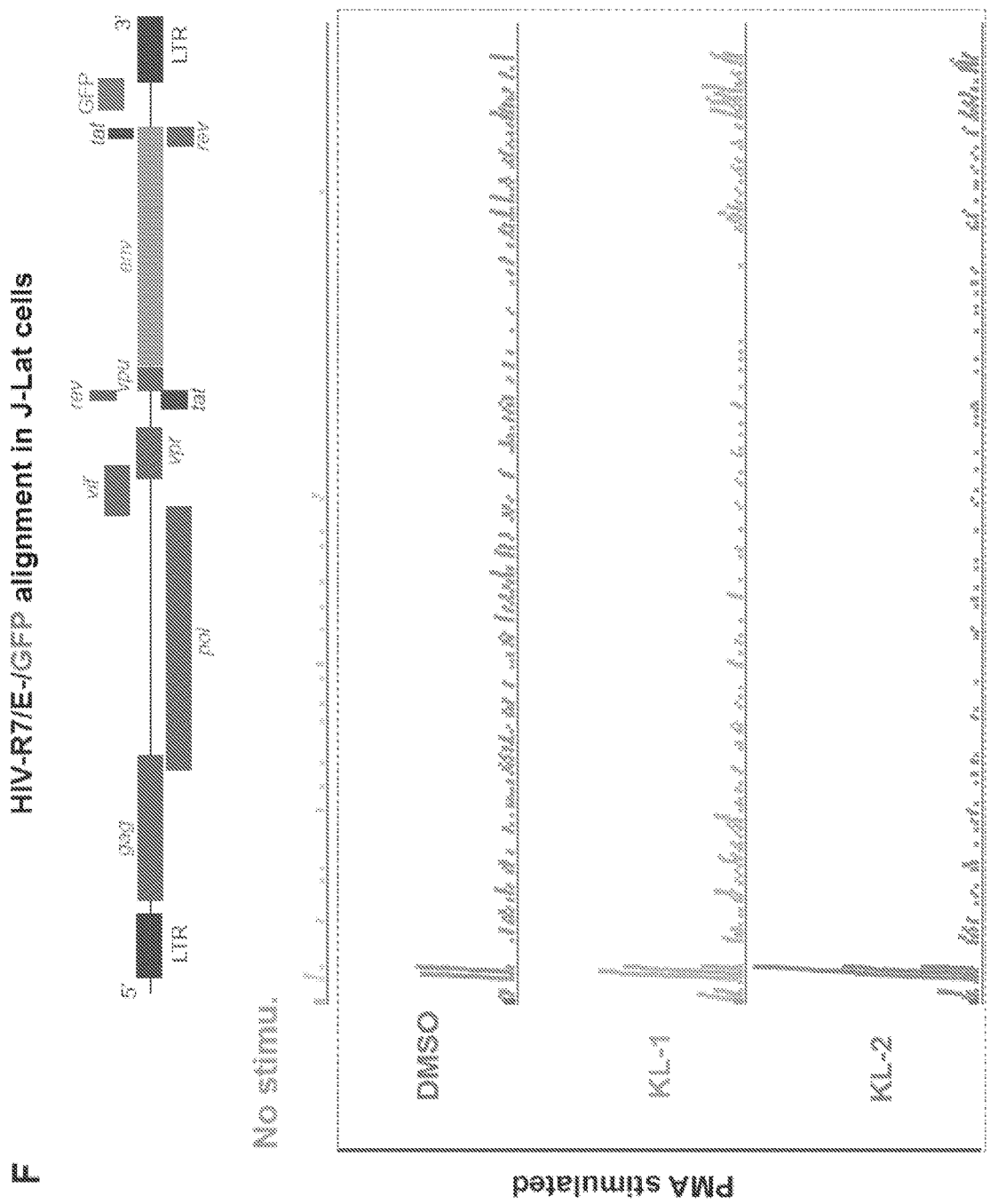

For heat shock induction, we pretreated HCT-116 cells with KL-1 or KL-2 for 5 hr to block SEC function and heat shocked the cells at 42° C. for 1 hr. ChIP-seq of Pol II demonstrates that SEC inhibitors KL-1 and KL-2 block induction of known heat shock inducible genes such as FOS, HSPD1, HSPE1 and EGR1 (FIGS. 5A, 5B and 12A). Analysis of Pol II occupancy at 136 genes induced by heat shock under vehicle conditions (FIGS. 5C and 12B) demonstrates that KL-1 and KL-2 treatments led to impaired heat shock response at those genes as shown by the fold change of Pol II reads at the gene bodies of heat shock responsive genes before and after heat shock (FIGS. 5D and 5E).

KL-1 and KL-2 structures mimic the AFF4 pentapeptide LFAEP (FIG. 1C), which is conserved across the AFF family in humans and is conserved in the sole Drosophila member of this family, Lilliputian (FIG. 5F). Therefore, we tested KL-1 and KL-2 with Drosophila S2 cells and determined their effects during heat shock induction. As shown in FIG. 5G, treatment of S2 cells with KL-1 and KL-2 attenuated heat shock induction of the 215 heat shock responsive genes in these Drosophila cells (FIG. 5G).

Since SEC interacts with, and is an essential coactivator for the HIV transactivator Tat (He et al., 2010; Sobhian et al., 2010), we examined the effect of KL-1 and KL-2 in this process using the J-Lat 6.3 clone, a derivative of Jurkat cells that has an integrated HIV genome in which GFP replaces the HIV nef gene (Jordan et al., 2003). In this system, the activation of the HIV genome can be achieved by treatment with 10 nM Phorbol 12-myristate 13-acetate (PMA) and the expression of the HIV genome can be monitored with GFP fluorescence (FIG. 12C). Treating cells with 20 µM KL-1 or KL-2 resulted in a strong inhibition of GFP expression in J-Lat 6.3 cells after PMA induction as revealed by FACS analysis (FIG. 12D), and this inhibition is dose-dependent (FIG. 12E). ChIP-seq of Pol II in the J-Lat 6.3 cell's confirmed that SEC inhibitors block transcription elongation of the Tat-dependent integrated HIV genome (FIG. 12F). Together, these studies demonstrate that KL-1 and KL-2 can inhibit SEC-mediated transcription elongation in both the heat-shock and the Tat-mediated rapid-transcriptional induction models.

Figure 6:
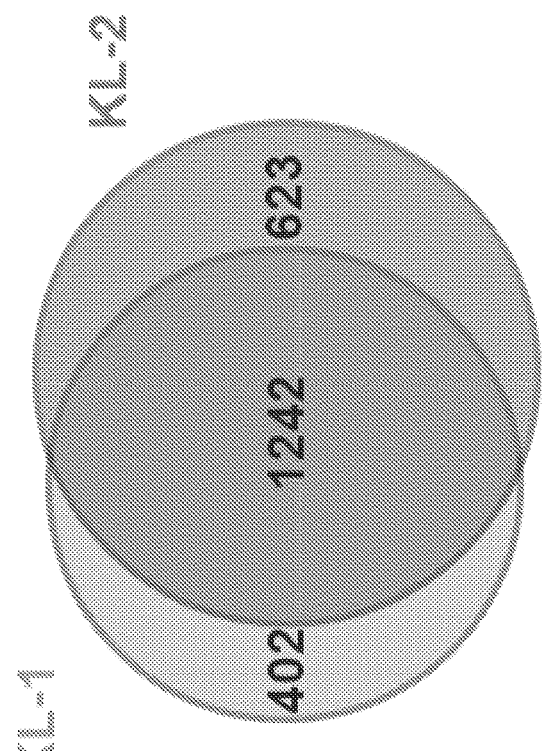
FIG. 6. SEC disruption targets MYC and MYC target genes. (A-B) Venn diagram of deregulated genes in 293T cells by KL-1 and KL-2. 1,911 genes were downregulated and 1,242 genes were upregulated by both inhibitors. (C) Heat map showing the expression changes in response to SEC inhibitors, with differentially expressed canonical MYC targets, RNA splicing factors, and core SNRP assembly genes highlighted. Z score-normalized values are displayed (n=3). (D) Network enrichment analysis determined by Metascape (Tripathi et al., 2015) of the 1,911 genes downregulated by both KL-1 and KL-2. RNA splicing terms, MYC targets, and cell proliferation related terms are highly enriched with the downregulated gene set. Each cluster is represented by different colors and a circle node denotes each enriched term. (E) MA plots of RNA splicing and Hallmark MYC target genes in KL-2 treated, AFF1 and AFF4 co-depletion, and ELL2-depleted cells. Circles mark the downregulated splicing and Hallmark MYC target genes. The MYC genes, the PRMT5 gene, and genes encoding SEC components are denoted as red squares. (F) Western analysis of MYC protein levels in the MYC lowly expressed small cell lung cancer cell line SW2171 and MYC-amplified small cell lung cancer cell line H2171. (G) Gained SEC occupancy at the MYC binding sites in MYC highly expressed H2171 cells. Genome browser tracks of MYC and SEC occupancy around the PRMT5 gene in SW1271 and H2171 cells are shown. (H) ChIP-seq analysis of MYC binding peaks in SW1271 and H2171 cells. Venn diagram of the MYC peaks showing that H2171 cells gain more MYC binding sites. (I) Venn diagram of the MYC and SEC peaks in SW1271 and H2171 cells. The SEC and MYC peaks were determined by MACS with a p-value cutoff at 1E-5. (J) Heatmap showing the SEC occupancy at the 50,819 gained MYC binding sites in H2171 cells. The heatmap is separated based on whether the gained SEC peaks could be called by MACS with a p-value cutoff of 1E-5. (K) MYC-amplified H2171 cells are more sensitive to KL-1 and KL-2 inhibition than MYC lowly expressed SW2171 cells. Both cell lines were treated with increasing concentrations of KL-1 and KL-2 for 3 days and the cell proliferation was measured with CellTiter-Glo luminescent cell viability assay (Promega) (n=3-6).
Figure 6:
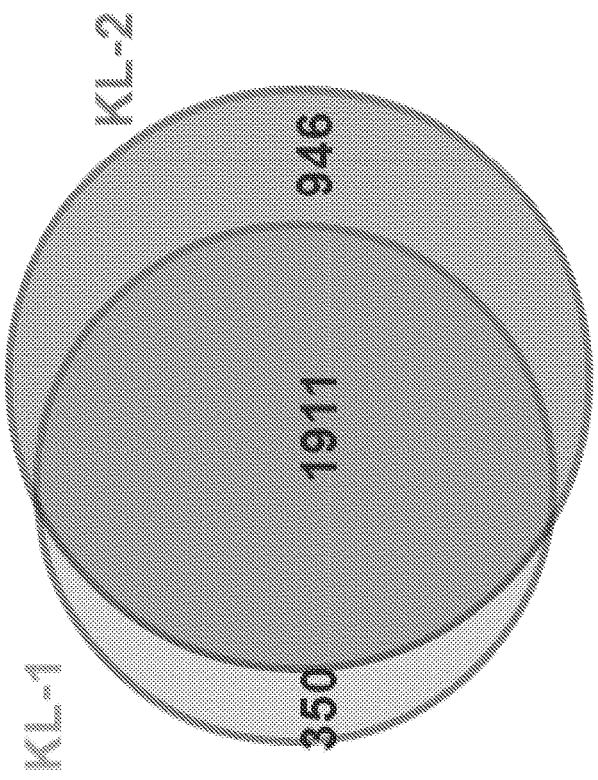
Figure 6:
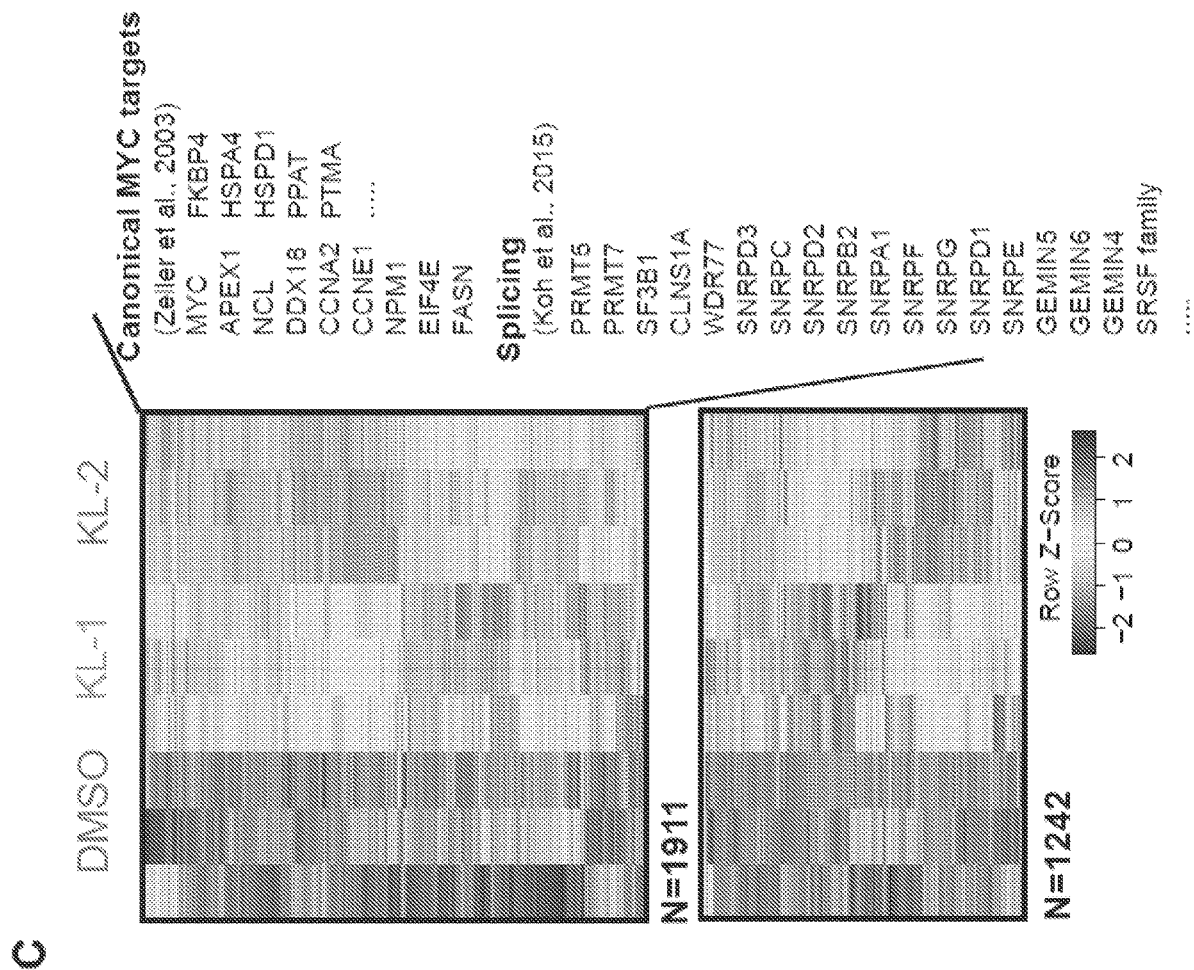
Figure 6:
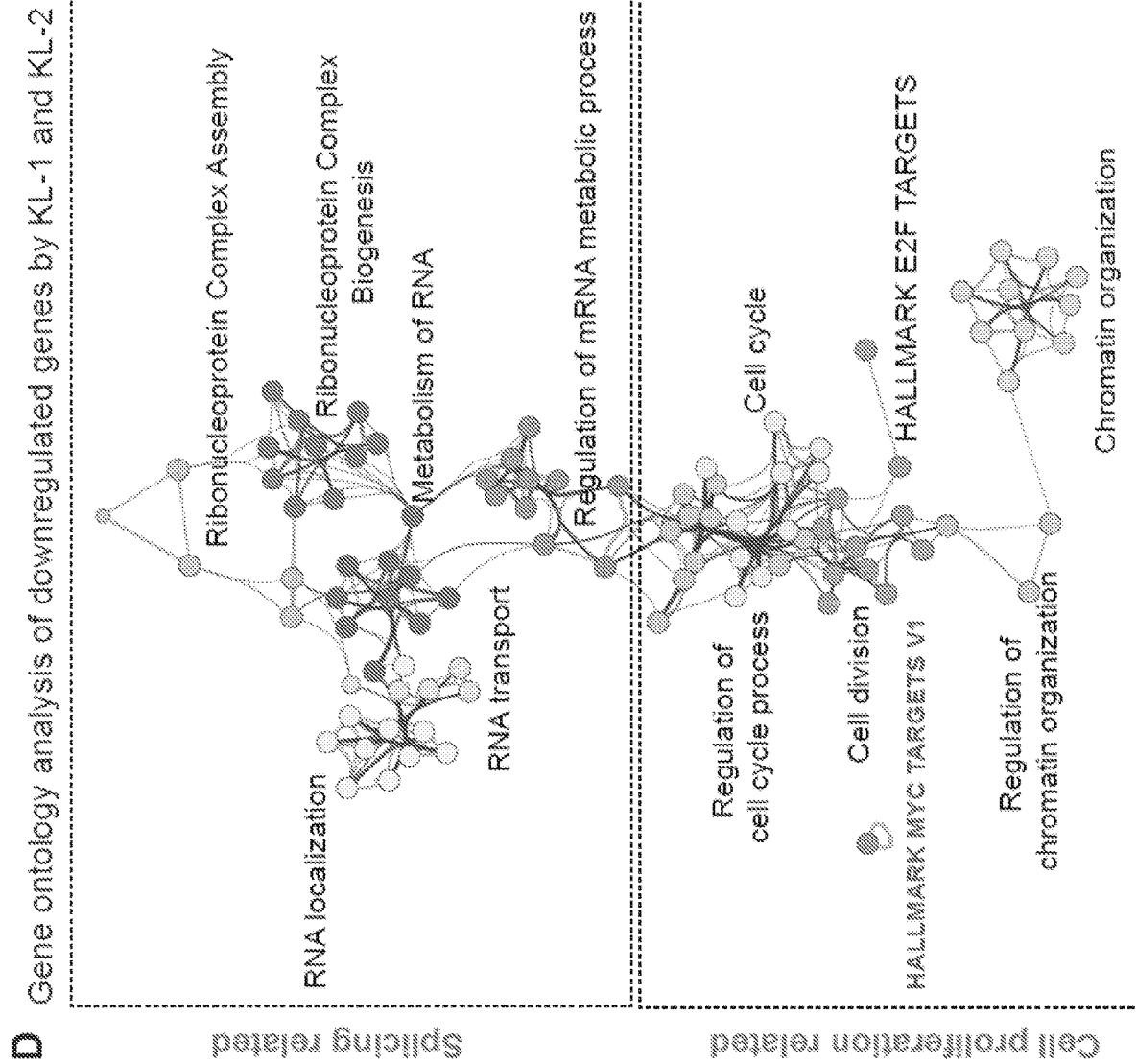
Figure 6:
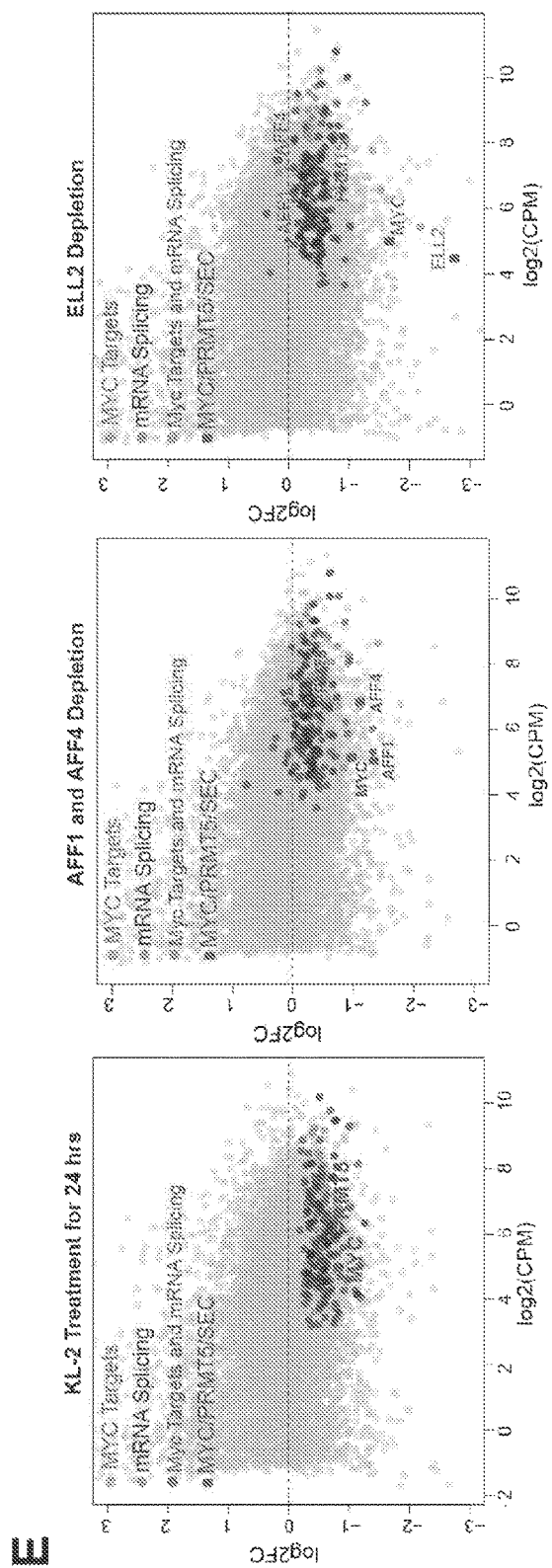
Figure 6:
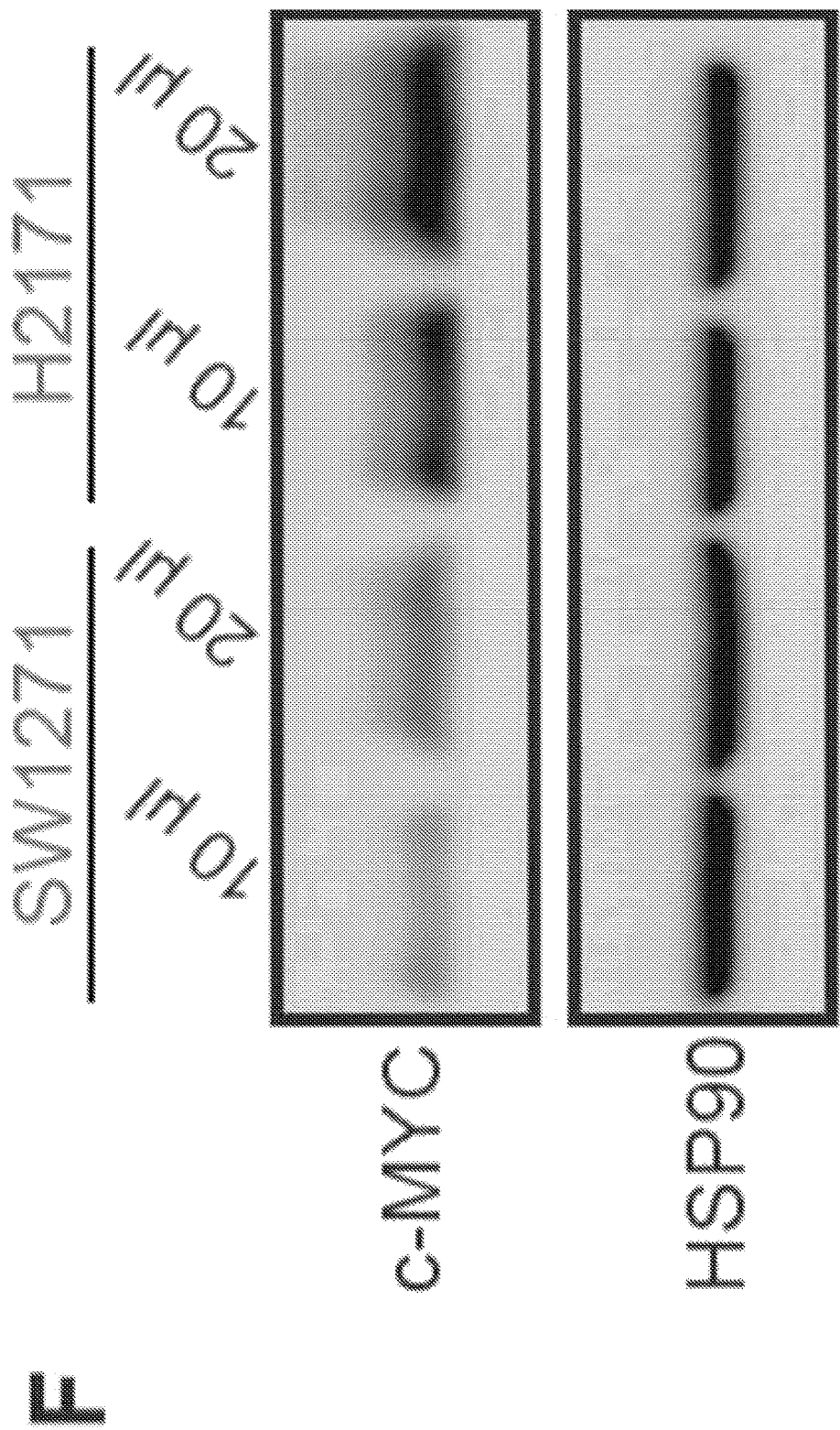
Figure 6:
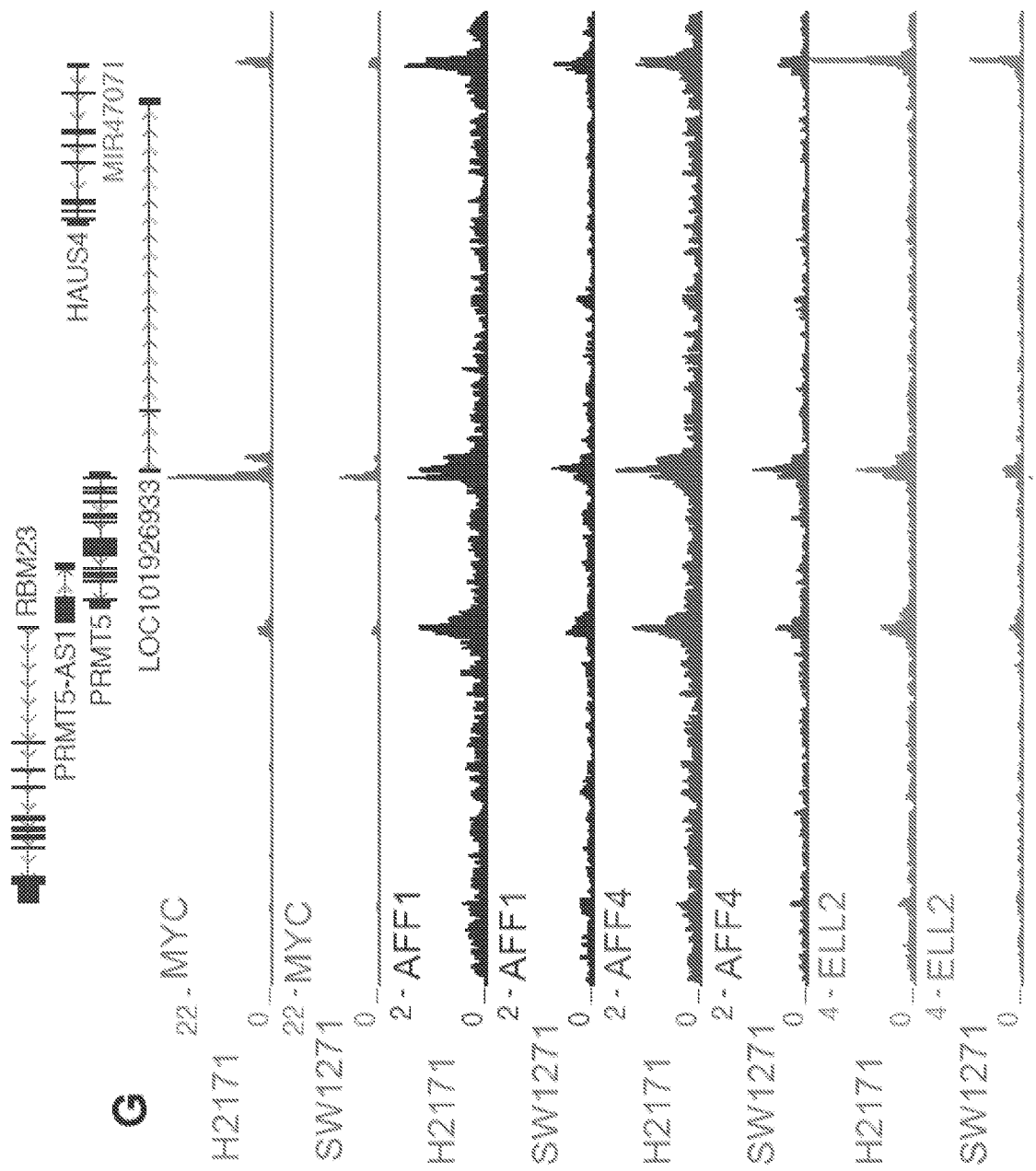
Figure 6:
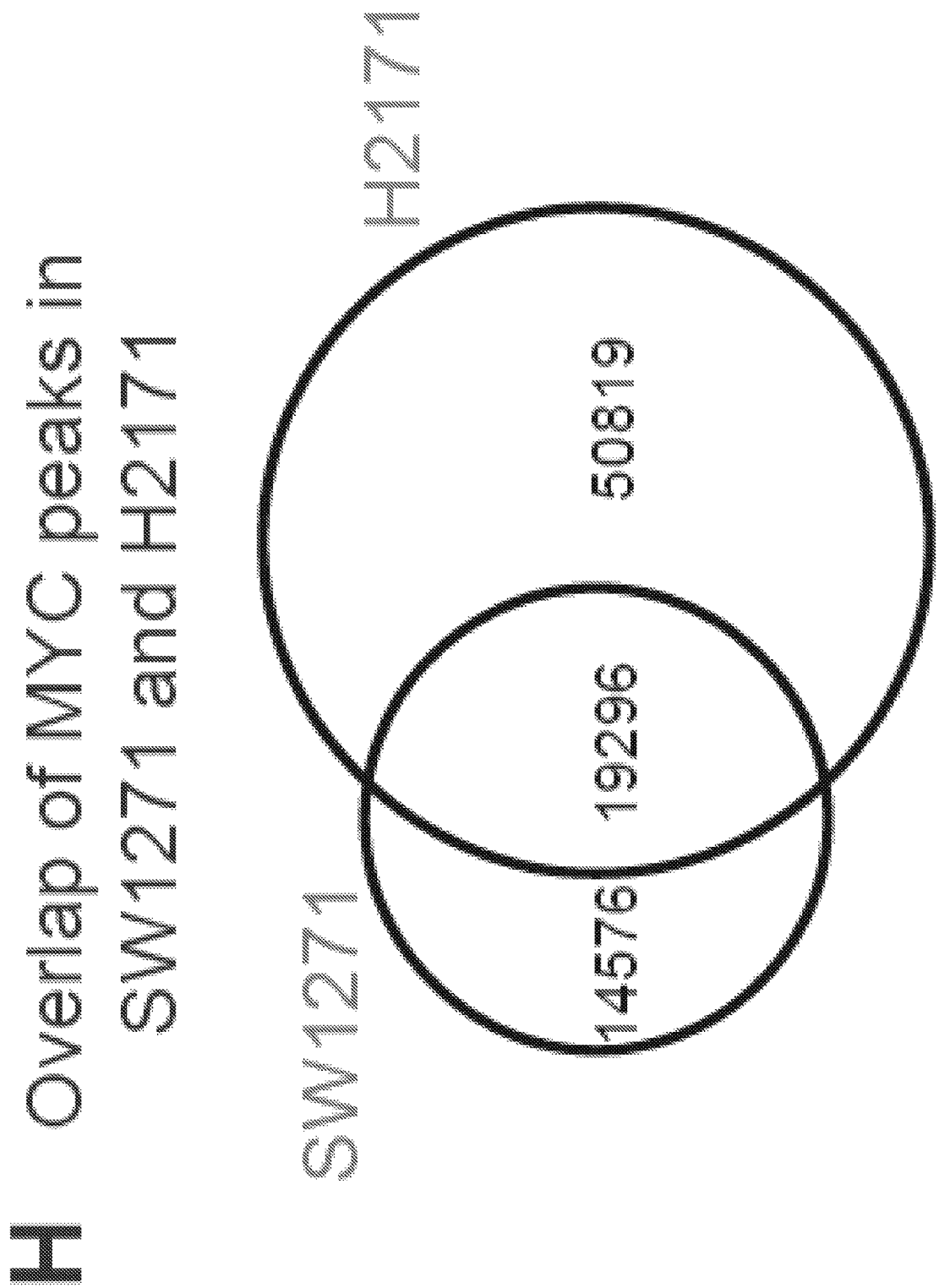
Figure 6:
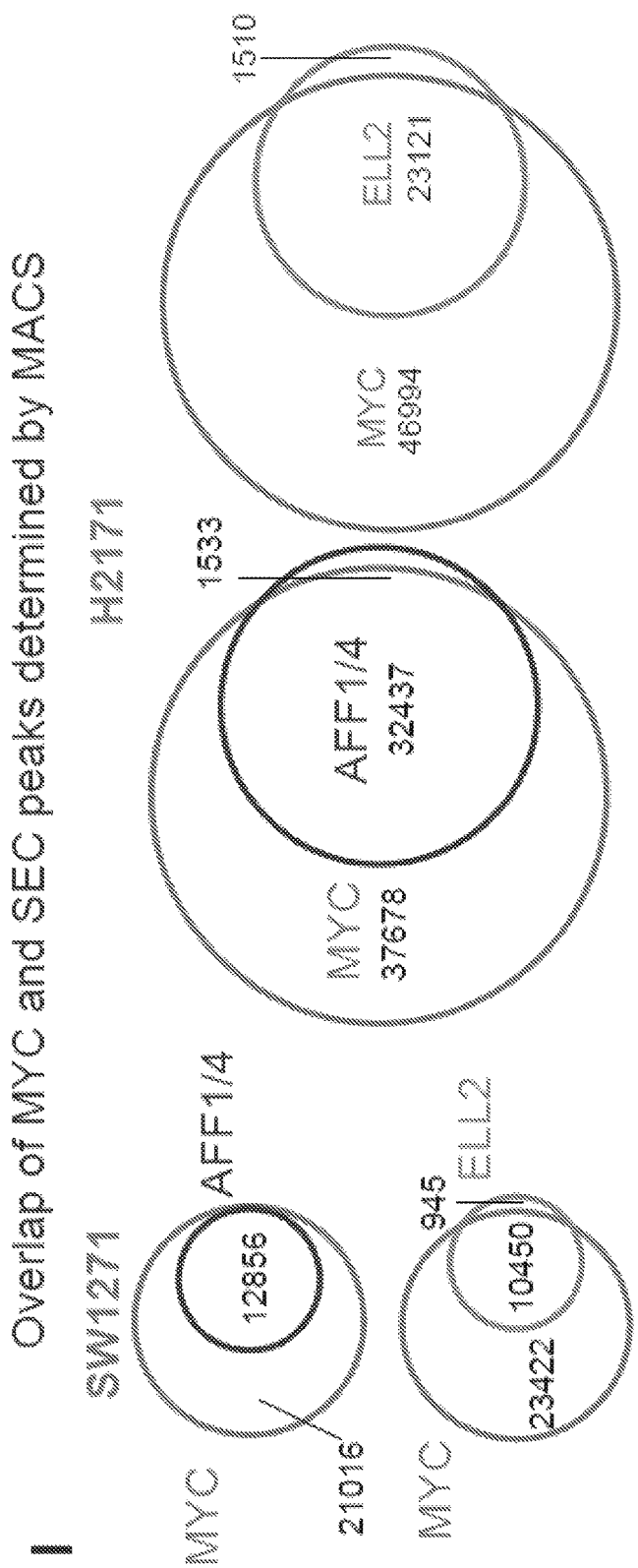
Figure 6:
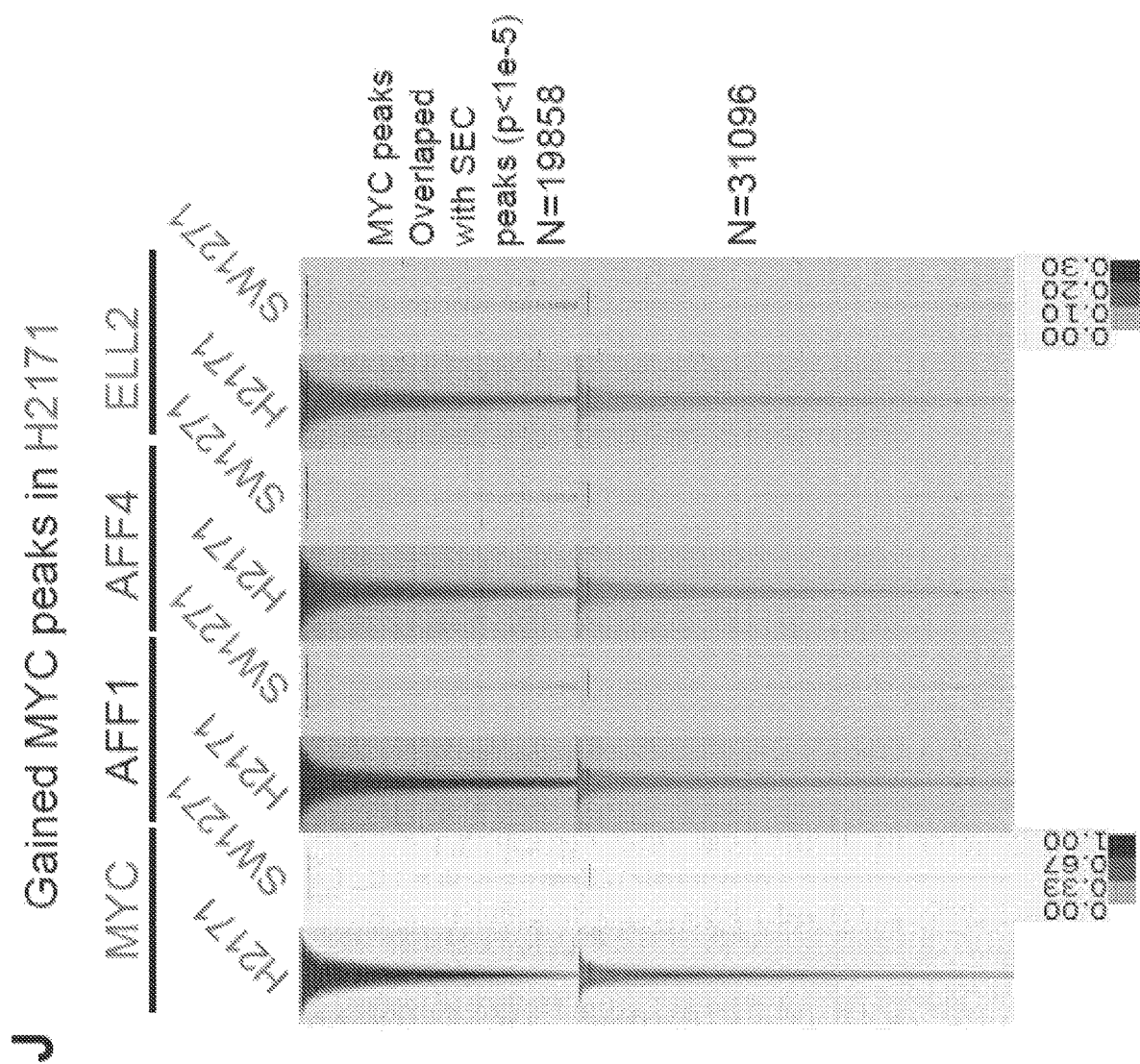
Figure 6:
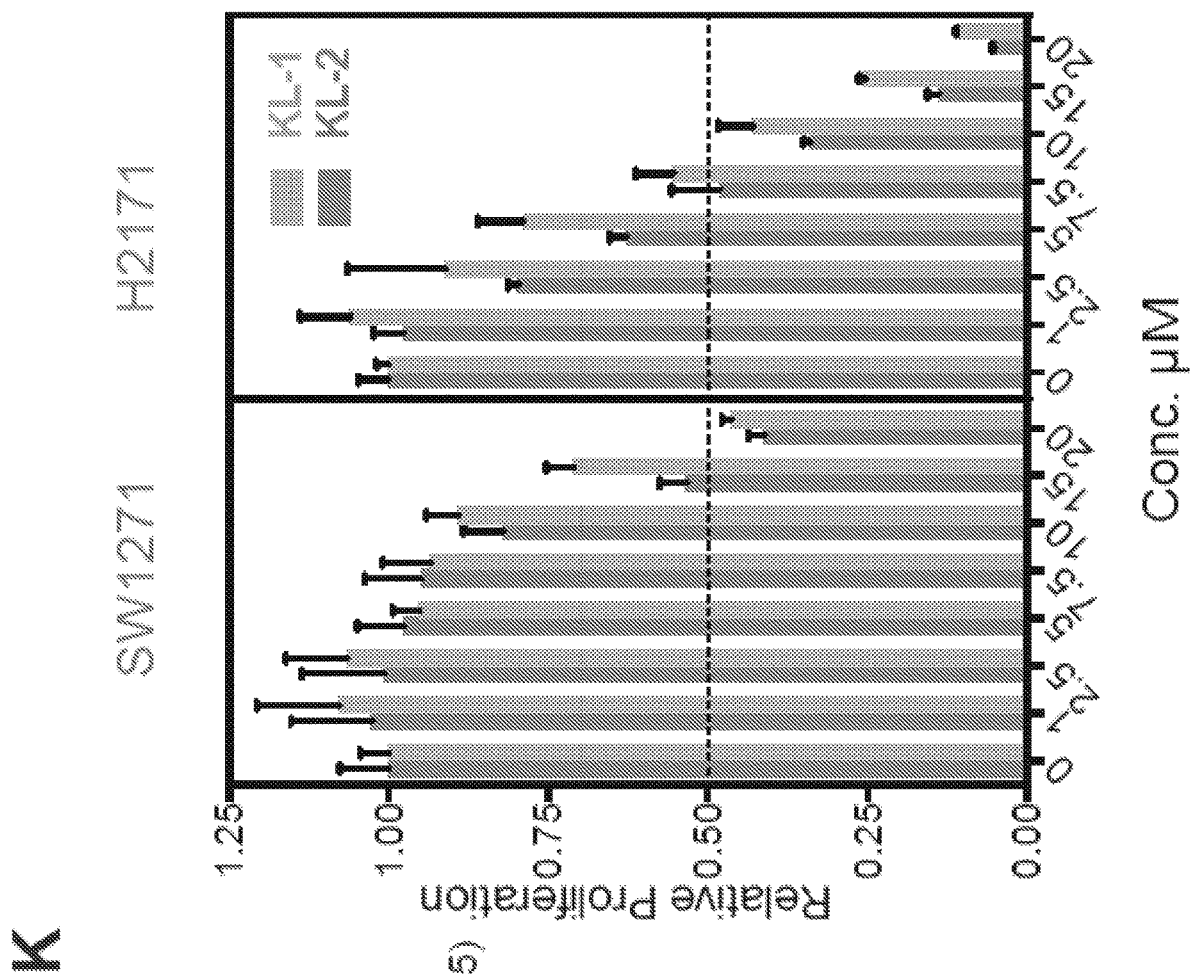
Figure 13:
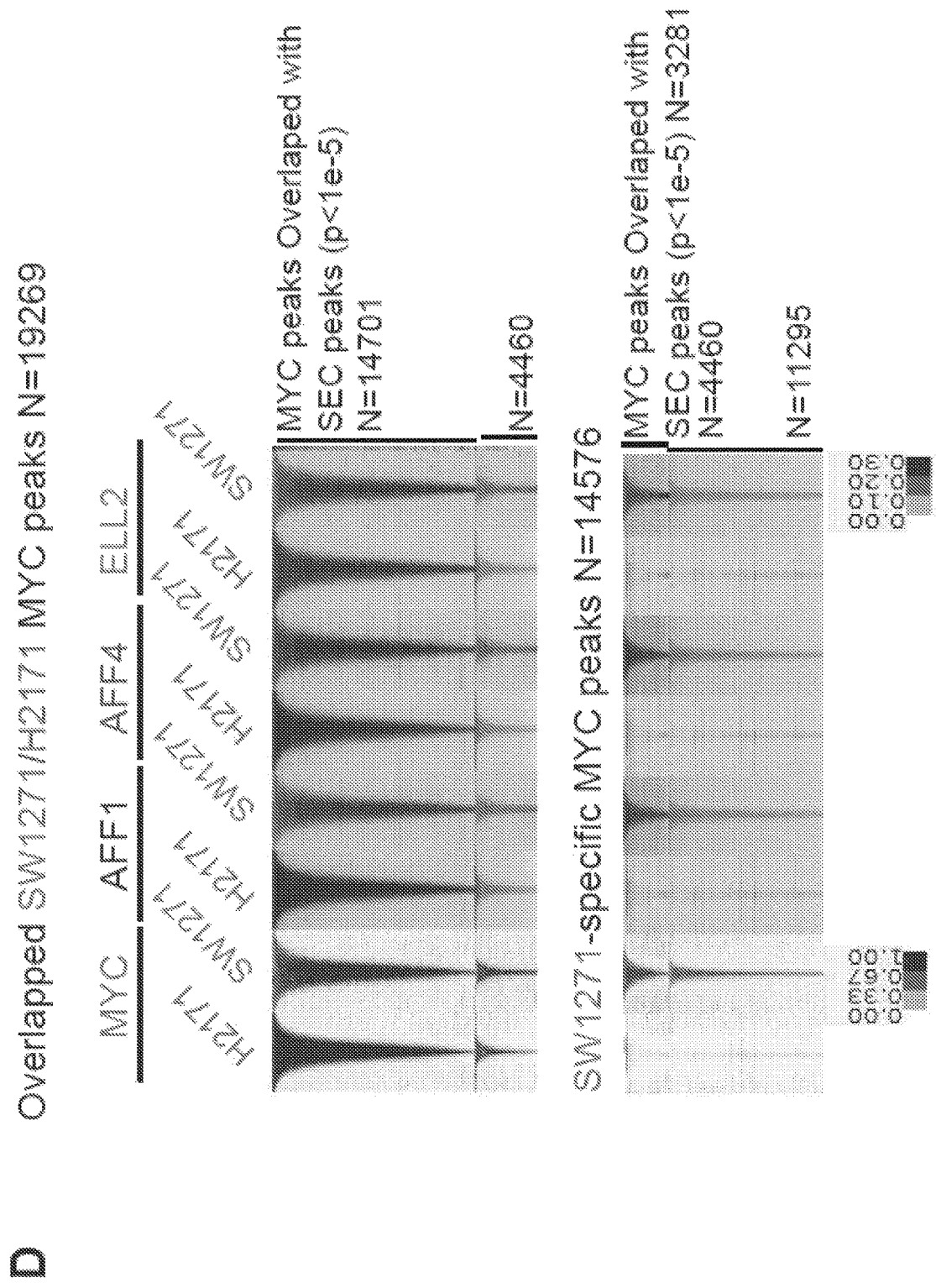
FIG. 13, related to FIG. 6. SEC disruption targets MYC and MYC target genes. (A-B) Gene ontology analysis of the deregulated genes performed with Metascape (Tripathi et al., 2015), showing that MYC target genes and RNA splicing terms are highly enriched, while the upregulated genes are related to stress response and apoptosis. The enriched terms are shown with FDR-adjusted q-values. (C) Gene ontology analysis of the 1,226 common genes downregulated by SEC inhibitors and SEC depletion. 1,226 out of the 1,911 genes downregulated by SEC inhibitor treatments are also downregulated by SEC depletion with either AFF1 and AFF4 co-knockdown or ELL2 knockdown. Analysis of these 1,226 genes shows that RNA splicing and MYC target genes are highly enriched terms with FDR-adjusted q-values indicated. (D) Heatmap showing the SEC occupancy at the shared MYC peaks (upper panel) and SW1271-unique MYC peaks (bottom panel). The heatmap is separated based on whether the SEC peaks could be called by MACS with a p-value cutoff of 1E-5. (E) SEC inhibition reduces the proliferative capacity of MYC highly expressed small cell lung cancer cells. H2171 cells with MYC amplification were subjected to either shGFP or MYC shRNA for 3 days, followed by seeding cells at 0.3 million cells/mL in the presence of the indicated doses of SEC inhibitors for 3 days. Viable cells were counted with a Vi-CELL XR (Beckman Coulter) (n=3). (F-G) Depletion of MYC reduces the SEC recruitment at the MYC binding sites in 293T cells. 293T cells were depleted with either shGFP (control) or shMYC shRNAs for 2 days, and then used for ChIP-seq and 4sU-FP-seq for measurement of elongation rates (F). Heatmap of MYC, AFF1 and AFF4 occupancy showing that MYC knockdown decreases both MYC occupancy and the SEC occupancy at the overlapped MYC and SEC peaks (G). (H) Genome browser tracks of 4sU-FP-seq after shGFP and MYC knockdown in 293T cells at the MTR loci. Cells were paused with flavopiridol and release with fresh medium in plates. Knockdown of MYC reduces the distance Pol II travels following Pol II release, suggesting decreased elongation rates after MYC depletion. (I) Metaplot of strand-specific 4sU-FP-seq signals in shGFP and MYC depleted cells. (J) Boxplots showing the $\log_2$ fold change of elongation rates as determined by HIM after MYC depletion (N=1,021). Three replicates of MYC knockdown were plotted and showed that MYC depletion decreases the elongation rates in 293T cells.
Figure 13:
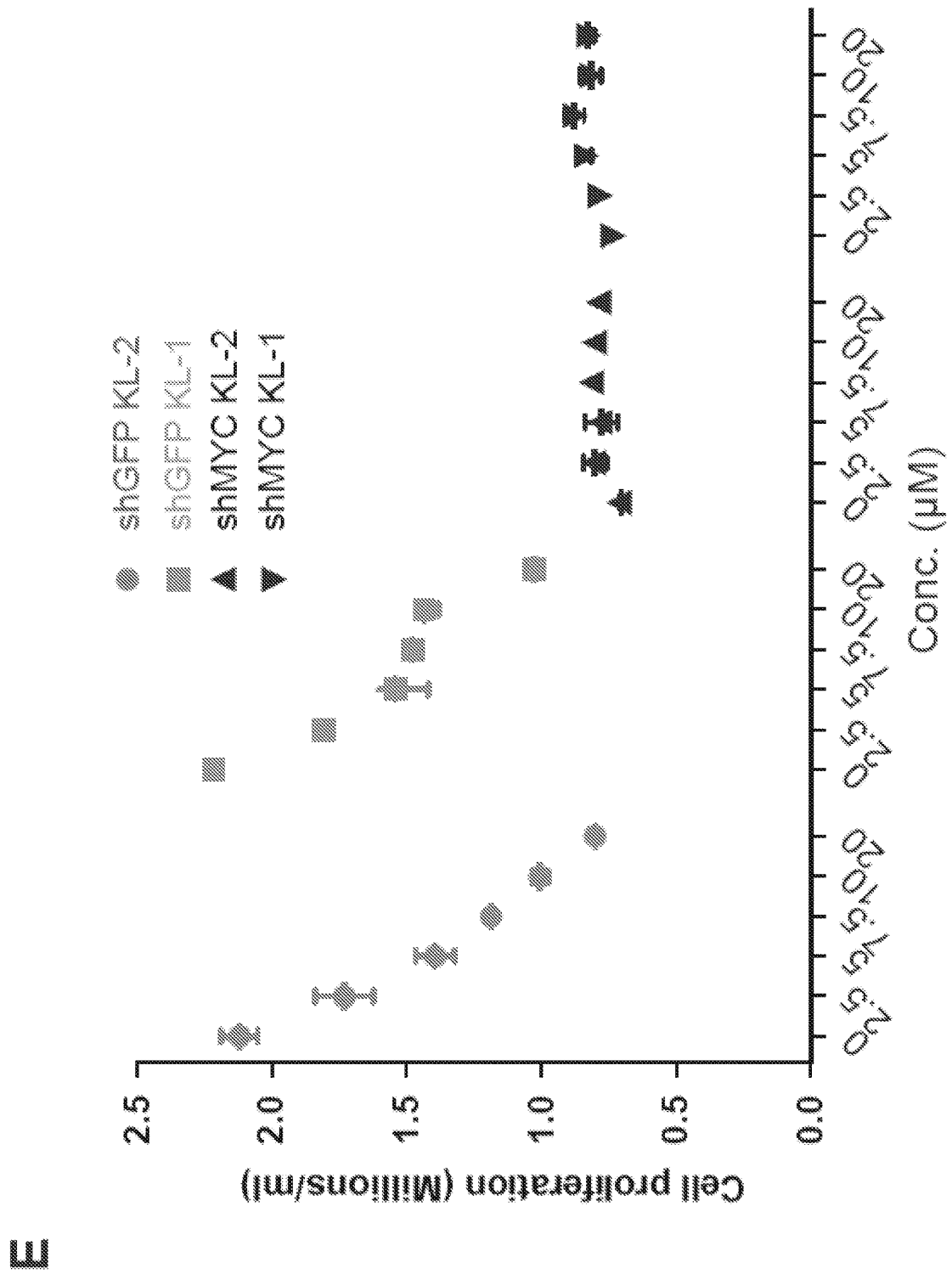
Figure 13:
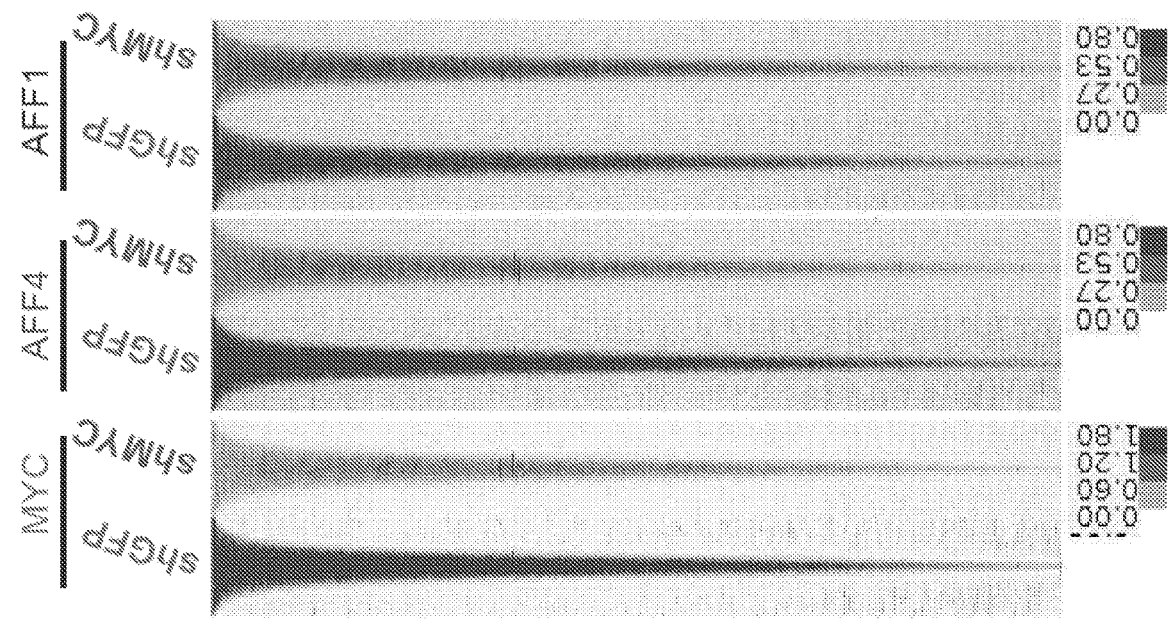
Figure 13:
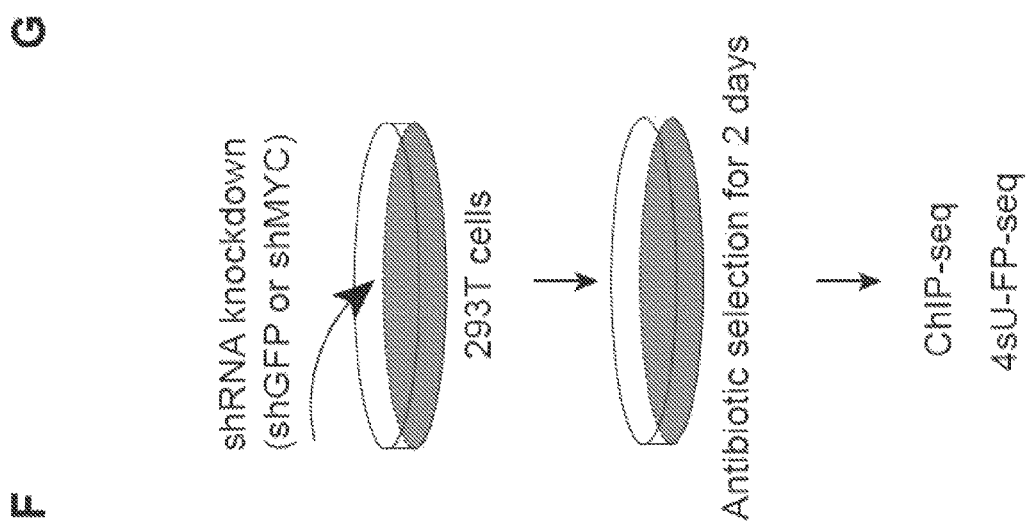
Figure 13:
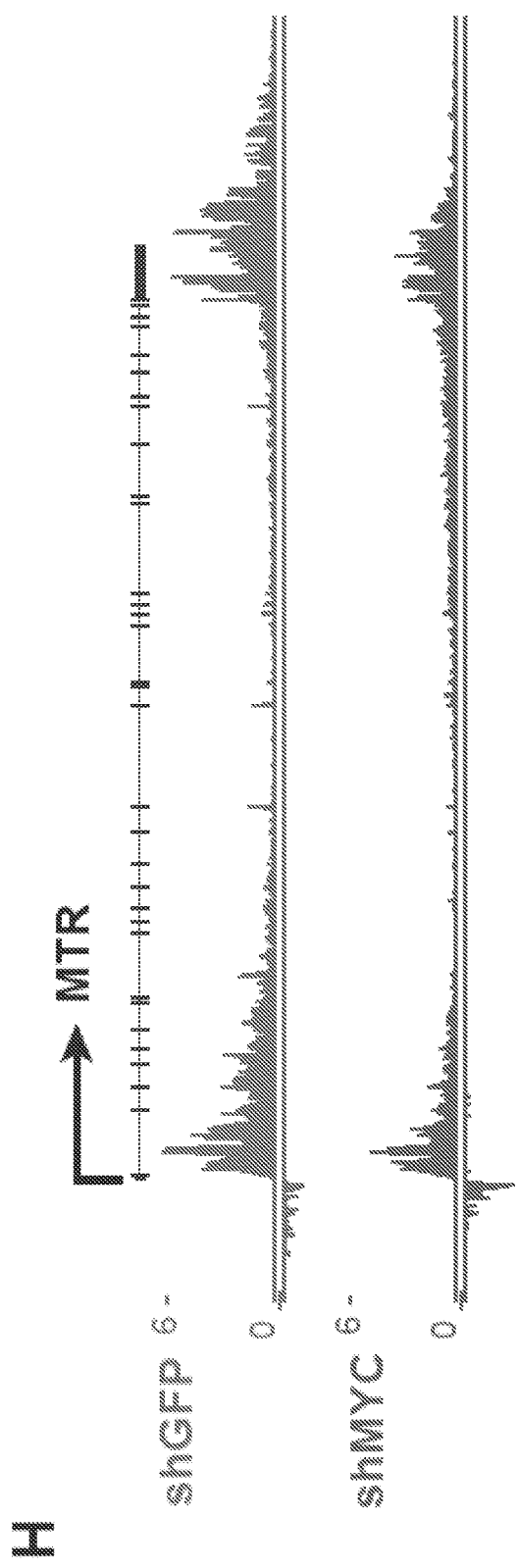
Figure 13:
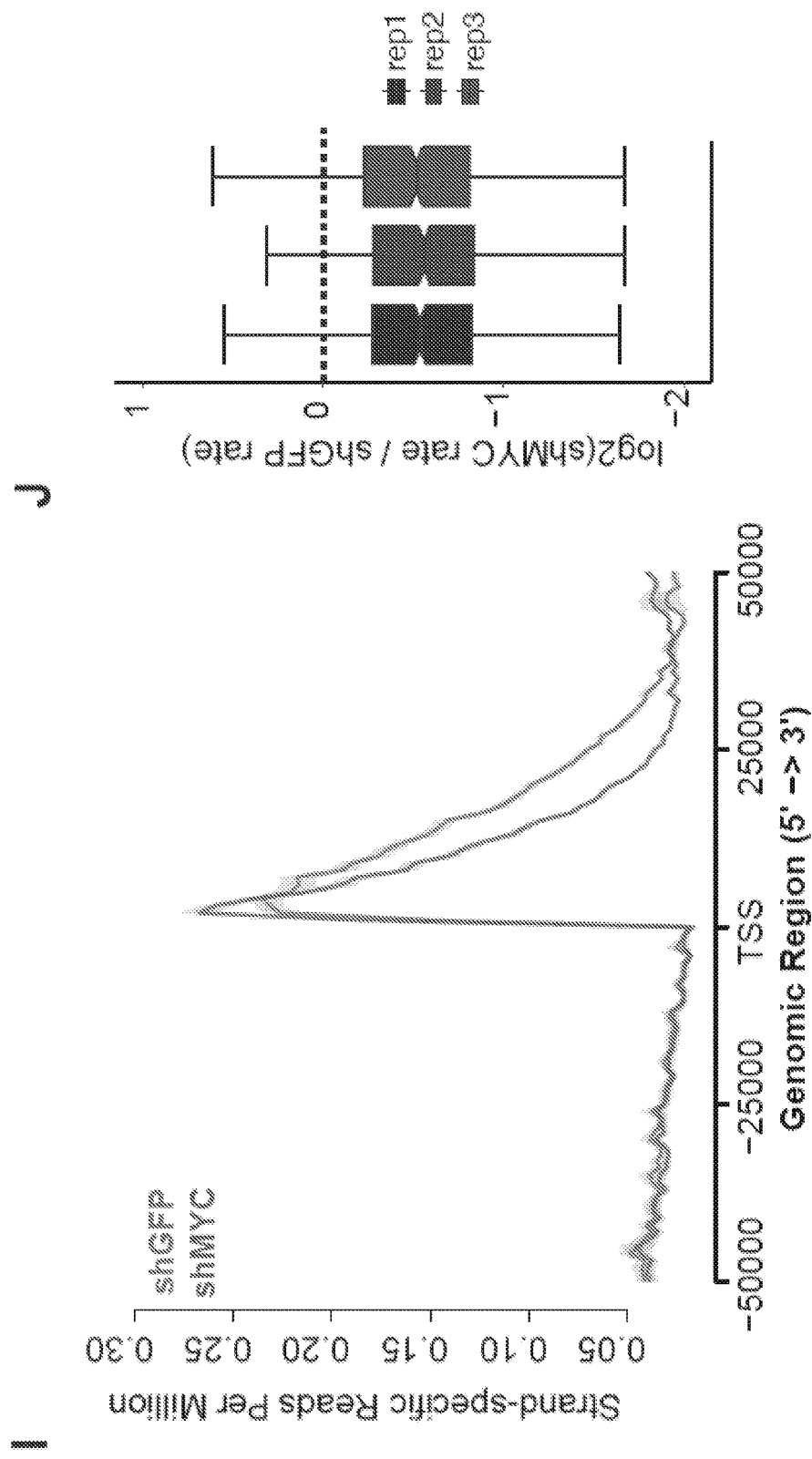

SEC inhibition downregulates MYC and MYC-dependent transcriptional programs. We performed mRNA-seq of 293T cells after KL-1 and KL-2 treatments for 24 hr and found a large overlap in gene expression changes, with 1,911 genes being downregulated and 1,242 genes being upregulated by both treatments (FIGS. 6A, 6B and 6C). Gene ontology analysis revealed that RNA splicing-related factors, MYC target gene sets, and cell proliferation-related terms are among the top enriched terms for the downregulated genes in response to SEC inhibitors (FIGS. 6D and 13A). DNA repair, apoptosis, and cellular response to unfolded protein were modestly enriched terms for the upregulated genes, suggesting a stress response of these cells after SEC inhibition (FIG. 13B).

KL-1 and KL-2 treatments led to decreased MYC expression, decreased expression of both canonical MYC targets (Zeller et al., 2003) and RNA splicing-related genes (FIG. 6C), which were recently identified as direct MYC targets important for MYC-driven cancers (Hsu et al., 2015; Koh et al., 2015). Interestingly, the PRMT5 gene, which encodes an enzyme responsible for methylation of splicing machinery proteins, is also among the downregulated genes, suggesting that SEC inhibitors perturb the MYC— PRMT5 axis (Koh et al., 2015), which could potentially be used to target splicing vulnerabilities in these cancers. We compared mRNA-seq after SEC depletion with either AFF1 and AFF4 co-knockdown or ELL2 knockdown with gene expression changes after SEC chemical inhibition. We found that 1,221 genes out of the 1,911 (63.8%) SEC inhibitors-downregulated genes were significantly downregulated by SEC depletion and, accordingly, gene ontology analysis showed enrichment for RNA splicing and MYC target gene terms (FIGS. 13C and 6E), which were also significantly downregulated after acute-degradation of SEC subunit ENL (Erb et al., 2017).

These findings led us to investigate the potential of using SEC inhibitors in cancer cells exhibiting transcriptional addiction (Bradner et al., 2017), such as those with high expression of MYC, which leads to increased transcription of downstream genes necessary for cancer cell proliferation (Lin et al., 2012; Sabo et al., 2014). We used the previously characterized MYC-amplified small cell lung carcinoma H2171 cells (Lin et al., 2012) and a corresponding low-MYC expressing small cell lung cell line, SW1271 (FIG. 6F). ChIP-seq of MYC protein in both H2171 and SW1271 cells demonstrates that the MYC-amplified H2171 has more MYC-occupied sites, consistent with a previous study (Lin et al., 2012) (FIGS. 6G and 6H).

To elucidate the role of SEC in MYC-mediated transcriptional regulation, we also performed ChIP-seq of SEC subunits in both H2171 and SW1271 cells and found that SEC is co-localized with MYC on chromatin (FIG. 6G). Genome-wide analysis of MYC and SEC occupancy shows that the high-expressing MYC H2171 cells have more MYC and SEC co-bound regions and increased occupancy of SEC (FIGS. 6H, 6I and 6J), suggesting that SEC is involved in MYC-mediated transcriptional regulation in these cancer cells. We further observed that the high MYC expressing H2171 cells (Lin et al., 2012) are more sensitive to KL-1 and KL-2 treatments than the low MYC expressing SW1271 cells (FIG. 6K), and knockdown of MYC in H2171 cells resulted in decreased sensitivity to SEC inhibition (FIG. 13E), indicating that SEC inhibitors could be useful for abrogating the growth advantage of high MYC expressing cancer cells.

Since MYC has been shown to recruit the P-TEFb complex (Rahl et al., 2010) and co-localizes with the P-TEFb containing SEC complex (FIG. 6I), we further examined the role of MYC in SEC recruitment and productive transcription elongation. We depleted MYC in 293T cells for 2 days and found that MYC depletion leads to reduced chromatin occupancy of SEC subunits AFF1 and AFF4 (FIGS. 13F and 13G). We also performed 4sU-FP-seq in MYC-knockdown cells and found that MYC depletion for 2 days results in reduced processivity at the MTR loci (FIG. 13H) and metagene analysis demonstrates a global defect in distance traveled after release from flavopiridol (FIG. 13I). Comparison of elongation rates measured by HMM analysis demonstrated that MYC knockdown leads to decreased elongation rates (FIG. 13J). Together, these data suggest that SEC acts as a MYC cofactor by enhancing transcription processivity.

Figure 14:
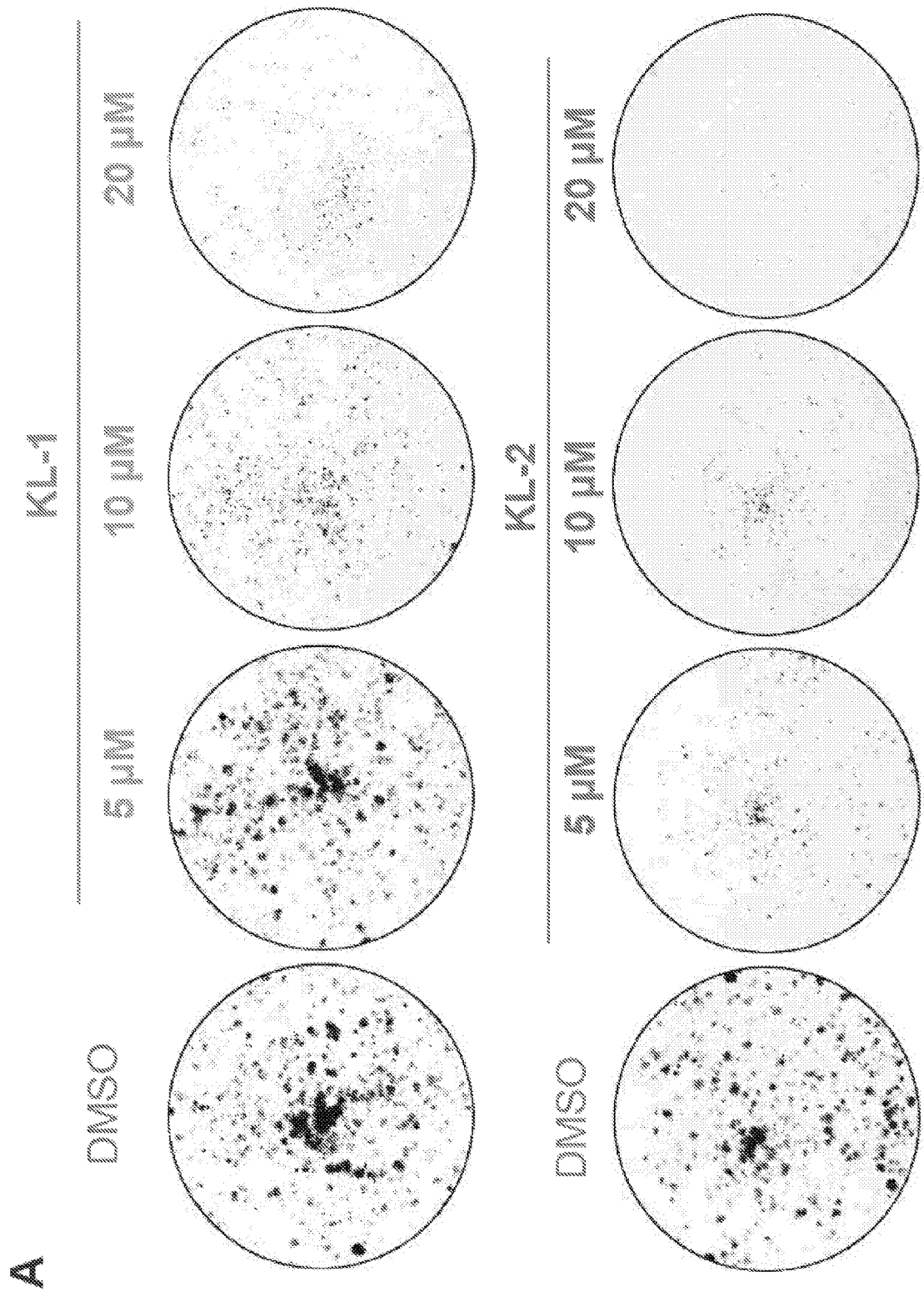
FIG. 14, related to FIG. 7. SEC disruptors delay tumor progression and improve survival of MDA231-LM2 tumor mice. (A) KL-1 and KL-2 inhibit the colony formation of MDA231-LM2 cells in vitro. $5 \times 10^3$ MDA231-LM2 cells were seeded in 6-well plates and treated with KL-1 or KL-2 at the indicated doses for 5 days. Crystal violet staining was performed to stain the colonies. (B) KL-1 and KL-2 induce apoptosis in MDA231-LM2 cells. Bar graph depiction of Annexin V positive MDA231-LM2 cells after 24 hr of KL-1 and KL-2 treatments at the indicated concentrations. Data are represented as Mean+/−SD. (C) and (D) Five intraperitoneal injections of 50 mg/kg of KL-1 (C) or 10 mg/kg of KL-2 (D) do not cause significant weight loss in mice after monitoring for 35 days. Each individual line indicates the weights of each mouse during toxicity test.
Figure 14:
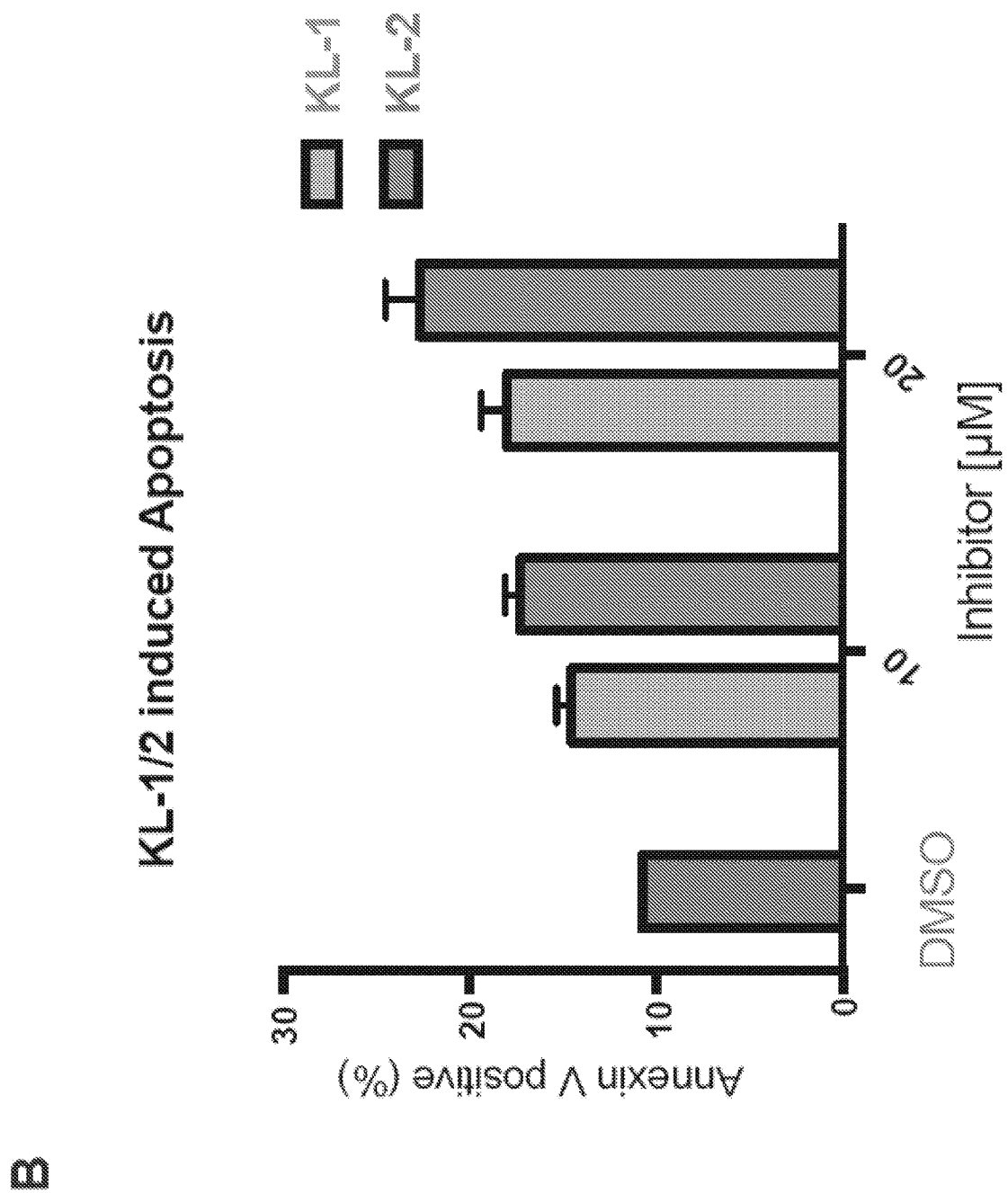
Figure 14:
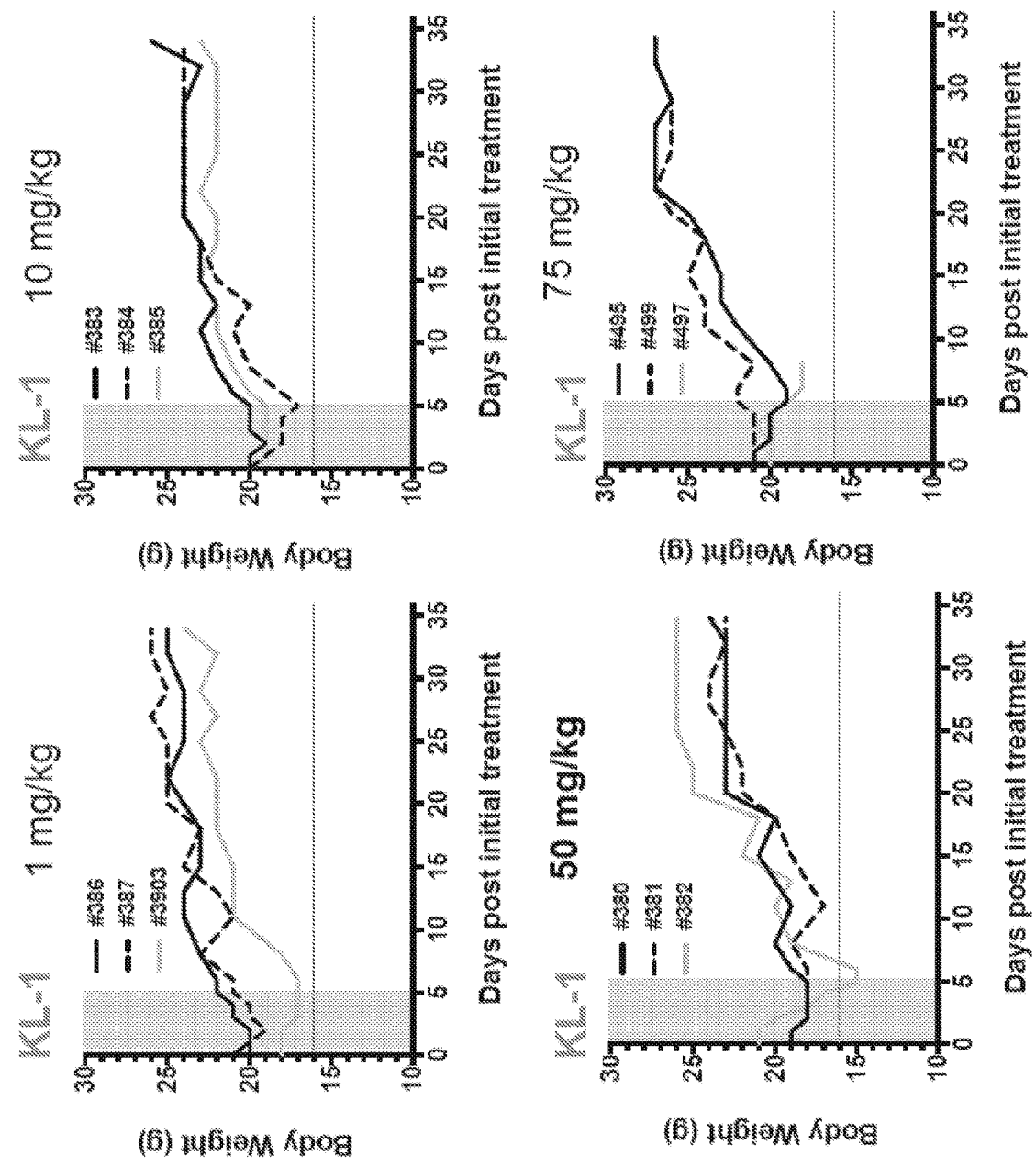
Figure 14:
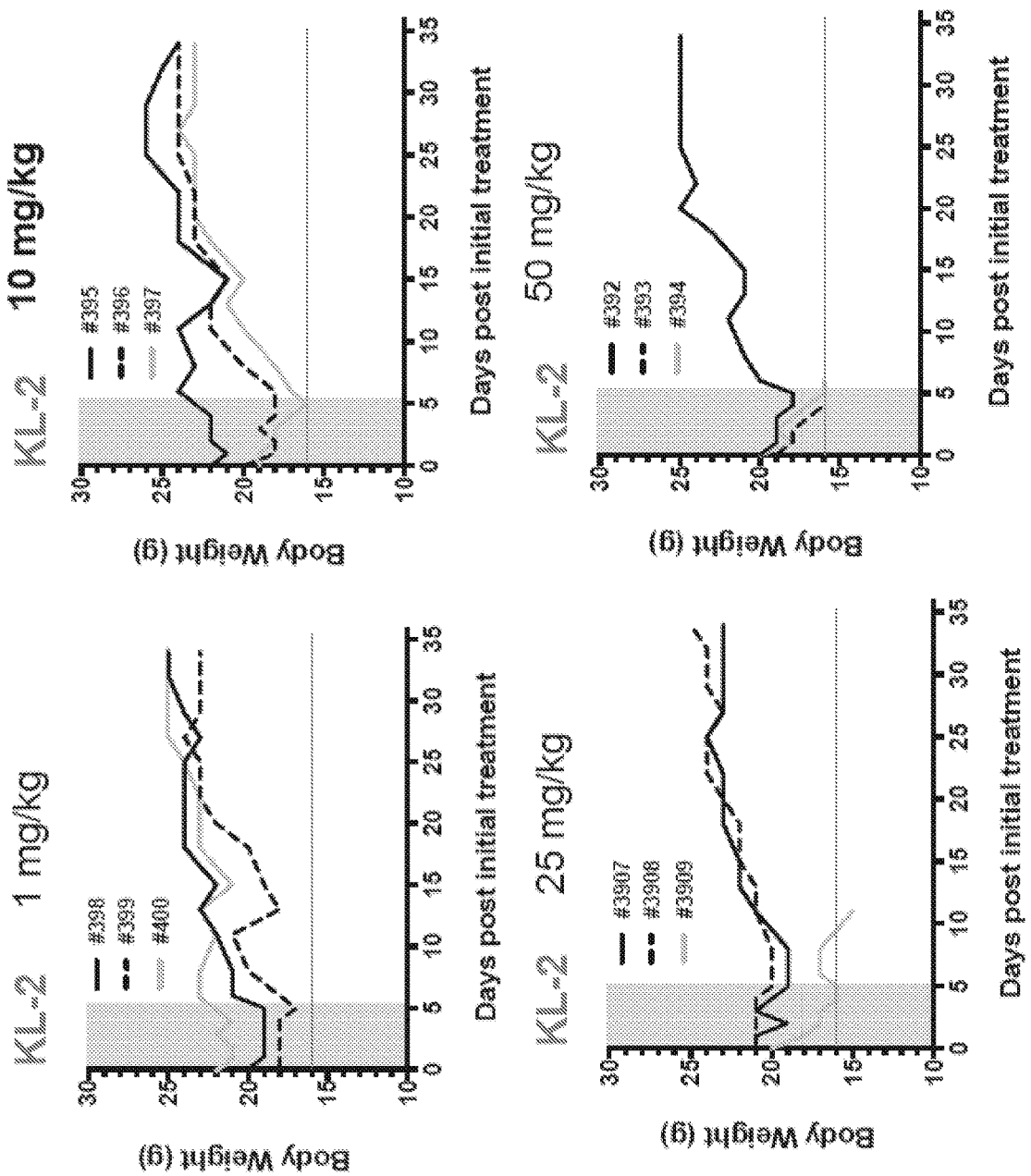

SEC disruptors delay tumor progression and improve survival of MDA231-LM2 tumor mice. To determine if the SEC disruptors KL-1 and KL-2 could be used in vivo as possible cancer therapeutics through the regulation of the rate of transcription elongation, we employed the murine MDA231-LM2 tumor model (FIG. 7A), which has been extensively characterized as a MYC-dependent tumor model (Hsu et al., 2015) and has been recently established in our lab (Wang et al., 2017). Both KL-1 and KL-2 could inhibit the colony formation capability of MDA231-LM2 cells in vitro (FIG. 14A) and both SEC disruptors increase apoptosis as shown by Annexin V staining (FIG. 14B). We first assessed the toxicity of KL-1 and KL-2 in mice with increasing doses and found that injection of 5 doses of 50 mg/kg KL-1 or 10 mg/kg KL-2 for 5 days does not result in significant weight loss in mice after monitoring for 35 days, and no obvious sign of sickness was observed during this period (FIGS. 14C and 14D).

To measure the potential of SEC inhibition in the MDA231-LM2 tumor model, we initiated the injection of the animals with SEC inhibitors on day 17 after inoculation, when the average tumor size reached 100 $mm^3$ (FIG. 7A). After once daily administration for 15 days, we further monitored tumor weights and mice were euthanized when the tumor size reached 1000 $mm^3$. Both KL-1 and KL-2 delayed tumor progression as monitored by tumor sizes (FIG. 7B-D). Our study demonstrated that both SEC inhibitors significantly extended survival of the recipient mice (FIG. 7E). Together, these data suggest that SEC disruptors could potentially be used to delay the progression and improve the survival of MYC-dependent cancer.

DISCUSSION

In this study, we found that the disruption of the Super Elongation Complex (SEC) by small molecules leads to defects in release from promoter-proximal pausing and reduced processivity of Pol II. We show that KL-1 and KL-2 disrupt SEC by competing with AFF4 for binding to CCNT1 within P-TEFb. AFF4 is a scaffolding protein for SEC, directly binding to both P-TEFb and ELL2, thus bringing together these distinct transcription elongation factors. The observed defect in release from pausing likely reflects the loss of the activity of the P-TEFb module of SEC, while reduced processivity of Pol II upon SEC inhibition is consistent with loss of the activity of ELL2, which had previously been demonstrated to increase the Vmax of the rate of Pol II transcription using an in vitro transcription assay with highly purified components (Shilatifard et al., 1997; Shilatifard et al., 1996).

Both KL-1 and KL-2 treatments result in reduced protein levels of SEC subunits AFF1, AFF4 and ELL2, proteins whose stability is highly regulated. Germline mutations that stabilize AFF4 cause the human developmental disorder CHOPS syndrome (Izumi et al., 2015). Both AFF4 and ELL2 are targeted by the SIAH1 E3 ligase (Liu et al., 2012). The SEC destabilizing property of KL-1 and KL-2 likely enhances the efficacy of our lead compounds in the transcription elongation assays and in vivo animal tumor model. Proteolysis-Targeting Chimera (PROTAC) methods that allow targeted degradation of proteins with small molecules have been shown to be much more efficacious than the small molecule inhibitor alone (Neklesa et al., 2017; Winter et al., 2015; Winter et al., 2017). For example, JQ1 and related compound IBET-151 bind to the bromodomains of BRD4 and block its interactions with acetylated histones on chromatin (Dawson et al., 2011; Filippakopoulos et al., 2010). When JQ1-like molecules are fused to phthalimides to target BRD4 degradation by the endogenous cellular ubiquitin ligase cereblon, the loss of BRD4 protein obviates the need for constant interaction of JQ1 with BRD4 (Lu et al., 2015; Winter et al., 2015; Winter et al., 2017).

Figure 7:
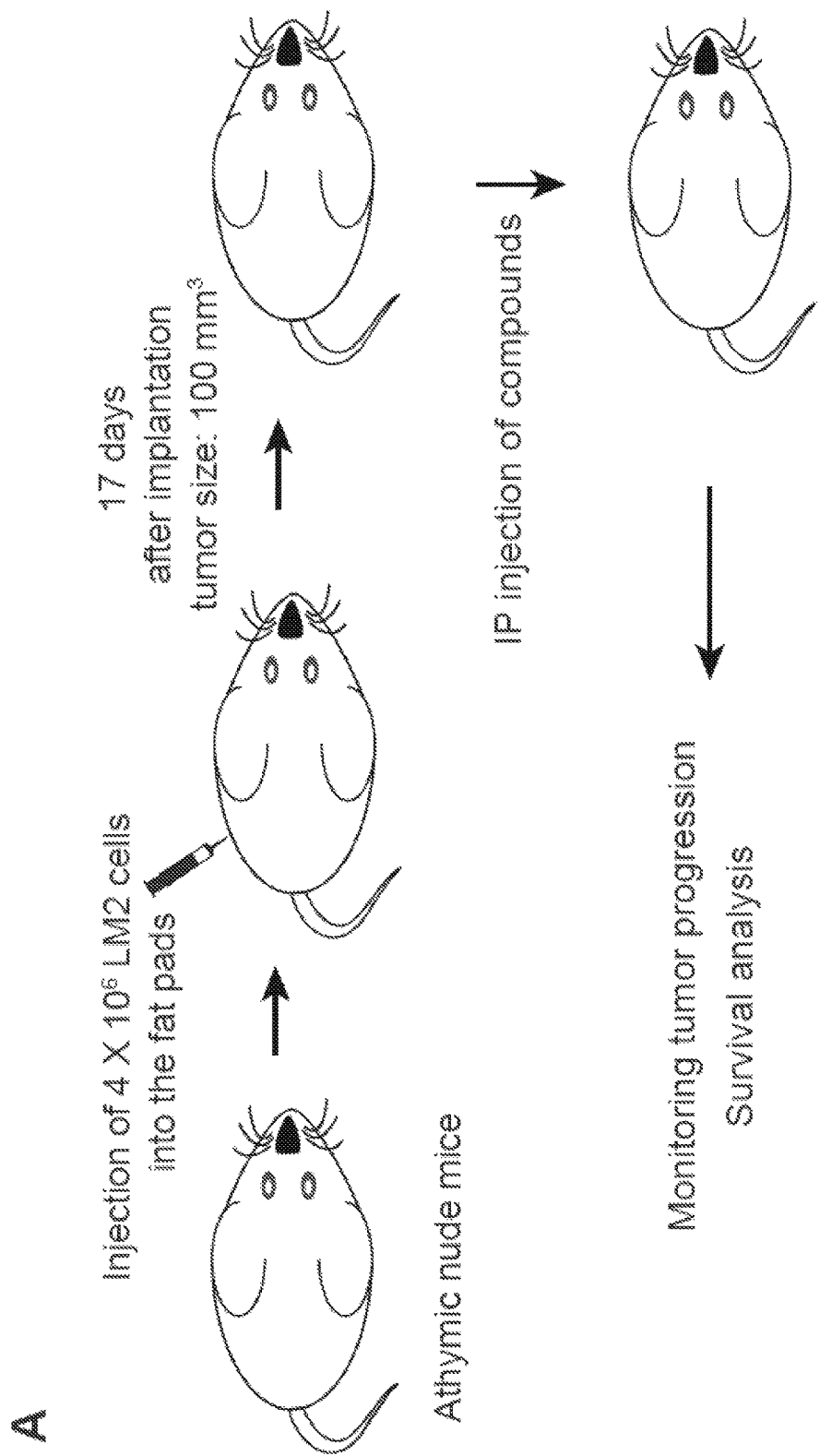
FIG. 7. SEC disruptors delay tumor progression and improve survival of MDA231-LM2 tumor mice. (A) Schematic of the development of MDA231-LM2 tumors in athymic nude mice (Wang et al., 2017). $4 \times 10^6$ MDA231-LM2 cells were inoculated into the fat pads of nude mice. 17 days after injection, when the tumor reached 100 mm$^3$, mice were divided randomly into three groups. Drug treatments were performed with once daily with 50 mg/kg KL-1, 10 mg/kg KL-2 or PBS (vehicle) for a total of 15 intraperitoneal injections. (B-C) KL-1 and KL-2 delay the tumor growth in the MDA231-LM2 tumor mouse model. The average tumor sizes of the vehicle (n=6), KL-1 (n=7), and KL-2 (n=5) treated groups were plotted from day 5 to day 36 after inoculation (B). Representative tumors sizes are shown (C). (D) Dot plots of tumor sizes at day 36 after inoculation and vehicle, KL-1, and KL-2 treatment, indicating that SEC disruptors KL-1 and KL-2 delay tumor progression in vivo. A 2-way unpaired student's t-test was used for statistical analysis. (E) Kaplan-Meier survival curves of vehicle, KL-1, and KL-2 treated nude mice transplanted with $4 \times 10^6$ MDA231-LM2 cells. 17 days after inoculation, vehicle (n=6), KL-1 (n=7), and KL-2 (n=5) were administered daily for 15 intraperitoneal injections. Mice were euthanized when the tumor size reached 1000 mm$^3$. The p values were calculated using the log-rank test.
Figure 7:
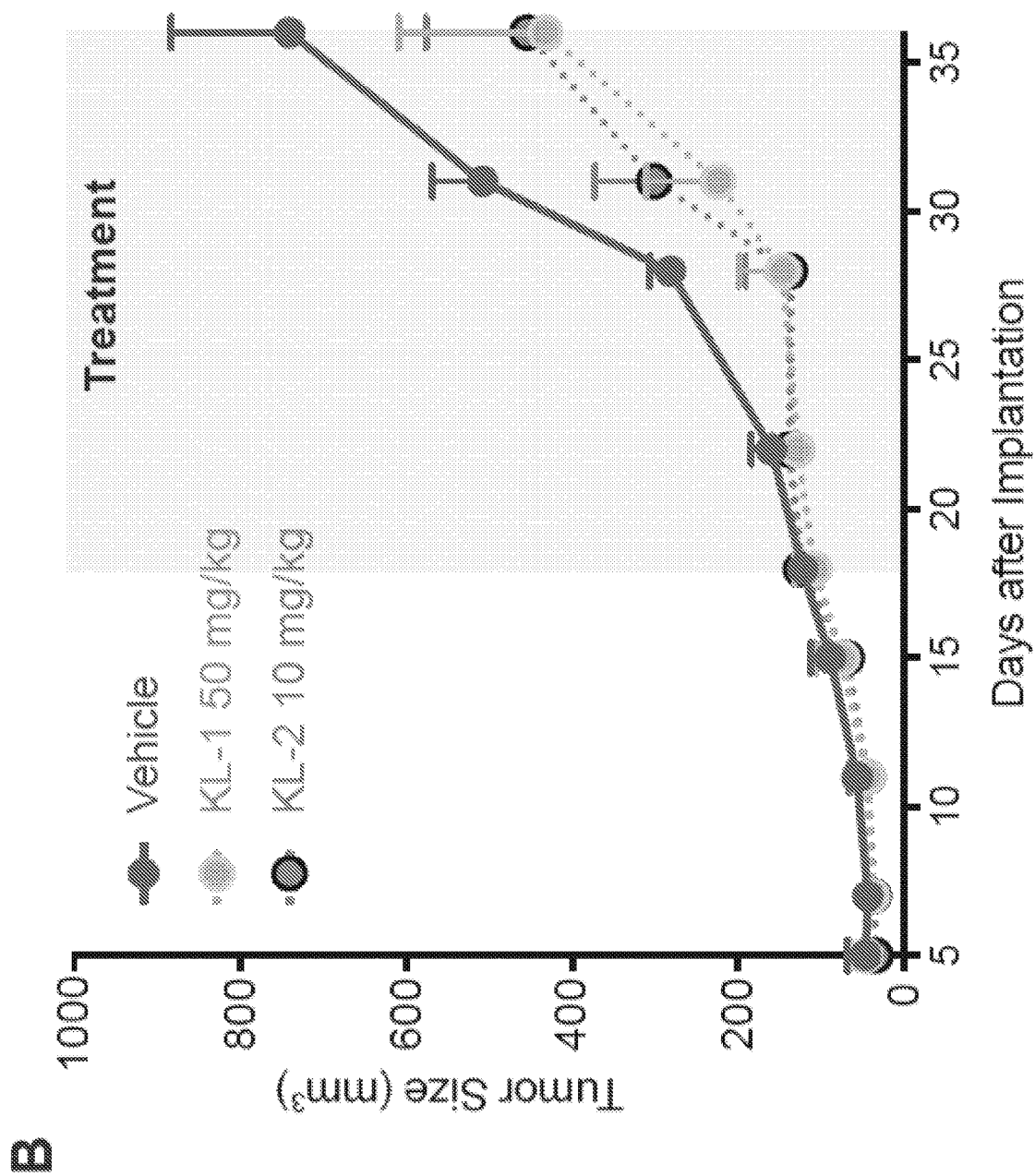
Figure 7:
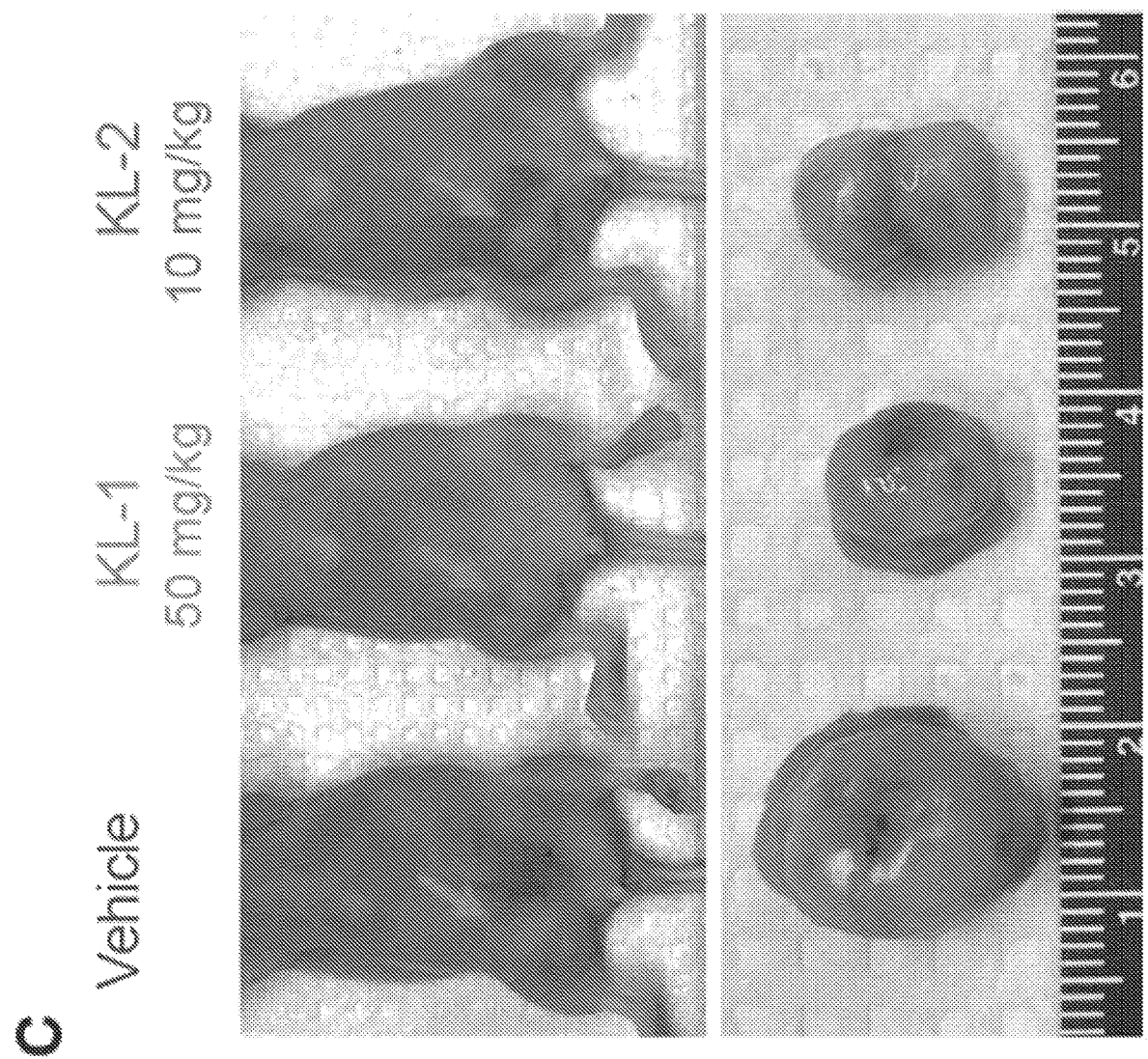
Figure 7:
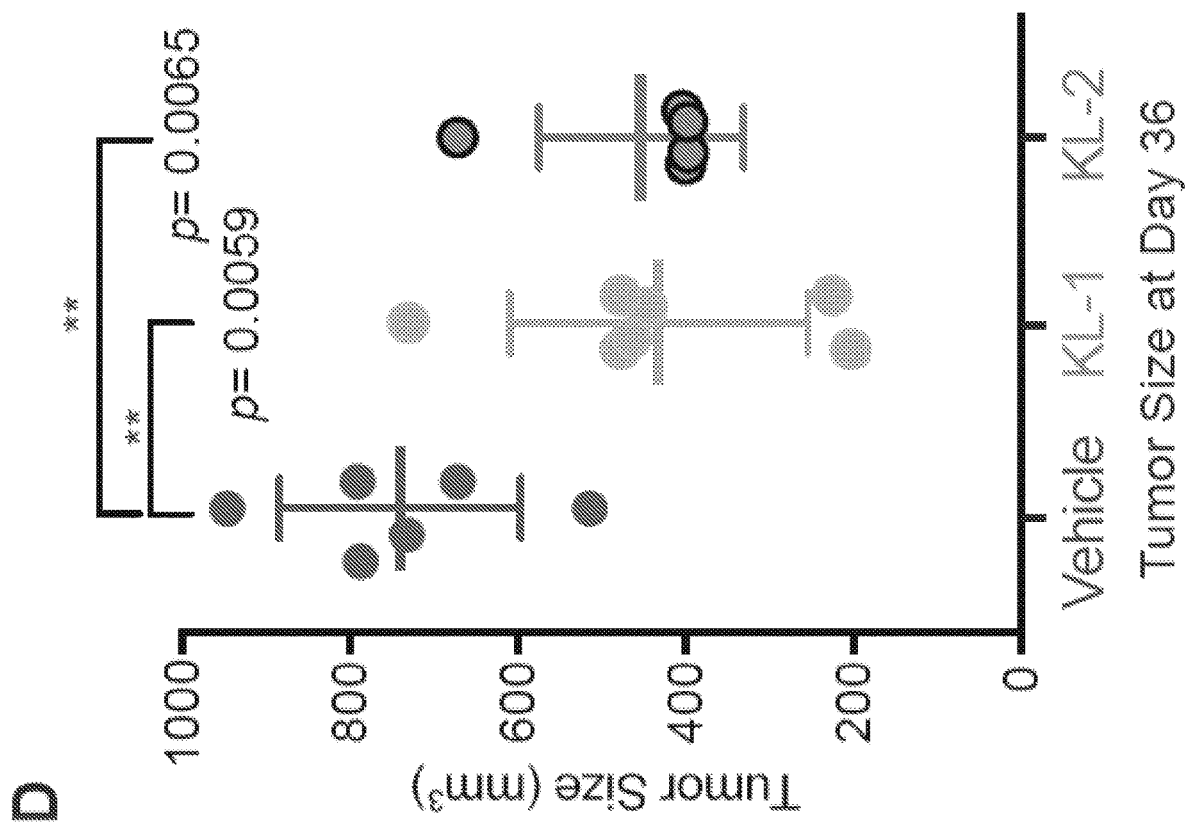
Figure 7:
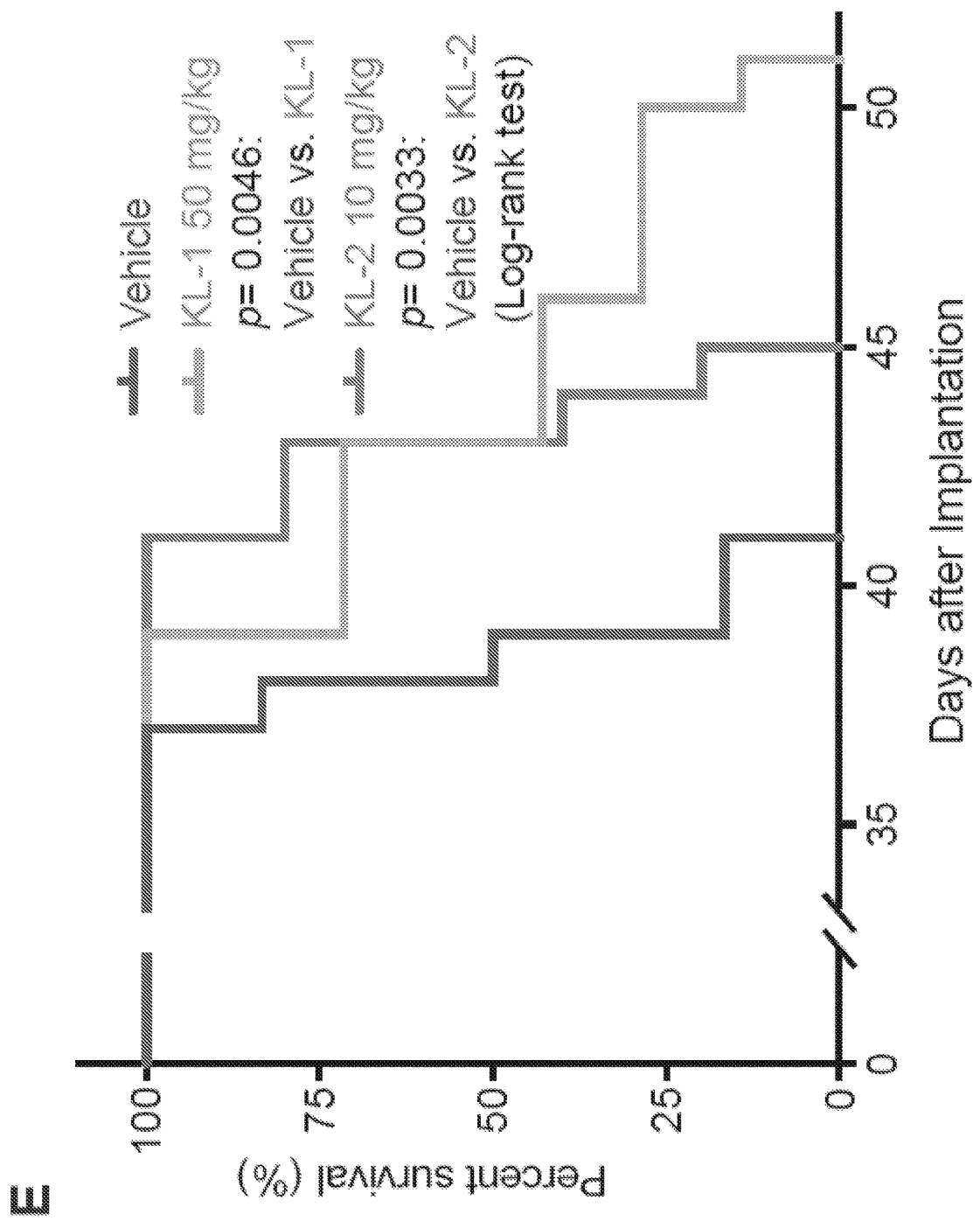

SEC acts as a transcriptional cofactor that is required for driving high rates of transcription for immediate-early genes, heat shock genes under stress, for production of the HIV provirus, and contributes to oncogenesis by driving high rates of coordinated transcriptional programs such as occurs in MYC amplified cancers (Luo et al., 2012b). Indeed, we found that these SEC disruptors could block transcription elongation in multiple SEC-dependent transcriptional models (FIGS. 5 and 12), demonstrating these compounds can be used a convenient chemical perturbation tool for the mechanistic and functional studies of SEC in other SEC-related cellular and developmental processes. Interestingly, we found that the MYC-dependent cancer cells are sensitive to the SEC inhibitors, providing the mechanistic finding that SEC is co-localized with MYC and exhibit increased occupancy in the MYC highly expressing cells, suggesting a dependency of transcription elongation for MYC-dependent cancers. Indeed, we also showed that SEC complex is involved in MYC-dependent transcription through promotion of transcription elongation rates (FIG. 13) and these SEC disruptors can be potentially used in vivo (FIG. 7).

MYC hyperactivation induces transcriptional amplification and increases messenger RNA synthesis, which leads to an increased burden on the core spliceosome to properly process mRNA, suggesting that RNA splicing is a therapeutic vulnerability in MYC-driven cancer (Hsu et al., 2015; Lee and Abdel-Wahab, 2016). RNA expression profiling analysis shows that KL-1 and KL-2 treatment leads to a significantly decreased output of the MYC transcriptional program, including RNA splicing-related genes including the PRMT5 gene, which is a key regulator among the MYC-upregulated genes (Bezzi et al., 2013; Koh et al., 2015), suggesting that KL-1 and KL-2 could directly target MYC to lead to an impaired downstream MYC-PRMT5 axis.

KL-1 and KL-2 share the same scaffold and have similar activities toward SEC disruption and Pol II processivity, suggesting that this scaffold could function as a lead for future optimization. These leads already exhibit efficacy in impairing SEC function in rapid response models and delaying the progression of a MYC-dependent tumor. Therefore, we anticipate that development of small molecule inhibitors targeting SEC or otherwise slowing RNA Pol II processivity will be useful both for understanding the regulation of transcription elongation in cells and as therapeutic tools for human disease.

Experimental Model and Subject Details

Cell Lines. HEK293T (ATCC CRL-3216), HCT-116 (ATCC CCL-247), MDA231-LM2, Flag-AFF1 and Flag-AFF4 stable cell lines were cultured in Dulbecco's Modified Eagle Medium (DMEM) supplemented with 10% fetal bovine serum (FBS, catalog No. F6178, Sigma). NCI-H2171 [H2171] (ATCC CRL-5929) and SW1271 (ATCC CRL-2177) small cell lung cancer cells were maintained in RPMI-1640 and DMEM/F12 medium supplemented with 20% FBS. The Jurkat J-Lat full-length cells (6.3) (NIH-ARP Cat#9846-446) were provided by the NIH AIDS Reagent Program and cultured in RPMI-1640 medium with 10% FBS. Drosophila S2 cells were maintained in Schneider's medium. The wild-type Pol II, slow Pol II (R749H) and fast Pol II (E1 126G) mutant HEK293T cell lines (Fong et al., 2014) were provided by Dr. David Bentley (University of Colorado School of Medicine) and cultured in DMEM with 10% FBS. After induction with doxycycline (2.0 µg/mL) for 16 hr, speed-mutant cells were treated with α-amanitin (2.5 µg/mL, Santa Cruz) for 42 hr prior to ChIP-seq analysis.

Plasmids, Peptides and Chemicals. pGEX-2TK cyclin T1 (1-300) (Addgene P#432) was purchased from Addgene and used to express recombinant GST-CCNT1(1-300) in Rosetta cells. GST-CCNT1 (AA1-300) recombinant protein was purified with glutathione superflow agarose (Thermo, Cat#25236). shRNAs for human AFF1 (TRCN0000021975 and TRCN0000330908), and AFF4 (TRCN0000426769 and TRCN0000015825) were obtained from Sigma. ELL2 was also depleted with shRNAs targeting the sequences AAC GCC AGA ATT ATA AGG ATG and AAA TGA TCC CCT CAA TGA AGT.

Biotin labeled AFF4 peptide (AA32-67) and mutant AFF4 peptide abolishing the binding with CCNT1 were synthesized and purified (purity >96%) by VCPBIO with further Trifluoroacetic acid removal. The sequence for wild-type AFF4 peptide is Biotin-GABA-SPL FAE PYK VTS KED KLS SRI QSM LGN YDE MKD FIG-amide and the mutant AFF4 peptide sequence is Biotin-GABA-SAA AAE PYK VTS KAA KLSS RIQ SAA GNY DEM KDF IG-amide where Biotin indicates N-terminal biotin labeling and GABA indicates γ-amino-butyric acid spacer. The candidate chemicals from the in silico screening were purchased from the vendors ChemDiv, ChemBridge and Enamine.

MDA231-LM2 Tumor Model. MDA231-LM2 tumor model was established as previously reported (Wang et al., 2017). Briefly, Six-week-old female athymic mice (nu./nu genotype, BALB/c background) were purchased from Envigo (Indianapolis, Ind.) and housed under aseptic conditions. All protocols, described below, were approved by the Northwestern University Institutional Animal Care and Use Committee. $4 \times 10^6$ MDA231-LM2 cells, in 0.4 ml of cell culture media with matrigel (BD Bioscience) were injected in the right mammary pad of mice under anesthetization by isoflurane. For the in vivo therapy-response study, mice were randomly assigned to vehicle (DMSO,) KL-1, and KL-2 treatment groups when the size of tumor reached 100 $mm^3$. Mice were treated with drug administration by intraperitoneal injection at 50 mg/kg of KL1 and 10 mg/kg of KL2, with once daily administration for 15 days for 3 weeks. The tumor sizes were measured twice a week and the mice were euthanized when the tumor size reached 1000 $mm^3$.

Method Details

Chemical Synthesis. All chemical reagents were obtained from commercial suppliers and used without further purification unless otherwise stated. Anhydrous solvents were purchased from Sigma-Aldrich and dried over 3 Å molecular sieves when necessary. Normal phase flash column chromatography was performed using Biotage KP-Sil 50 μm silica gel columns and ACS grade solvents on a Biotage Isolera flash purification system. Analytical thin layer chromatography (TLC) was performed on EM Reagent 0.25 mm silica gel 60 F254 plates and visualized by UV light. Proton ($^1H$), and carbon ($^{13}C$) NMR spectra were recorded on a 500 MHz Bruker Avance III with direct cryoprobe spectrometer. Chemical shifts were reported in ppm (δ) and were referenced using residual non-deuterated solvent as an internal standard. The chemical shifts for $^1H$ NMR and $^{13}C$ NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. Low resolution liquid chromatography/mass spectrometry (LCMS) was performed on a Waters Acquity-H UPLC/MS system with a 2.1 mm×50 mm, 1.7 μm, reversed phase BEH C18 column and LCMS grade solvents. A gradient elution from 95% water+ 0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). High-resolution mass spectra were obtained using an Agilent 6210 LC-TOF spectrometer in the positive ion mode using electrospray ionization with an Agilent G1312A HPLC pump and an Agilent G1367B autoinjector at the Integrated Molecular Structure Education and Research Center (IMSERC), Northwestern University.

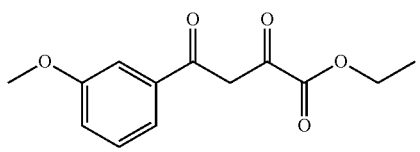 [SMILES: CCOC(=O)C(=O)CC(=O)c1cccc(OC)c1]

Ethyl 4-(3-methoxyphenyl)-2,4-dioxobutanoate (2a): To a solution of diisopropylamine (1.4 mL, 10 mmol) in THF (33 mL) at −78° C. was added n-BuLi (4.0 mL, 10 mmol). 3'-methoxyacetophenone (0.91 mL, 6.7 mmol) was added slowly, and the reaction was stirred at −78° C. for 15 min. Diethyl oxalate (1.4 mL, 10 mmol) was added slowly, and the reaction stirred at −78° C. for 1.5 hr. The reaction was slowly warmed to room temperature, then was quenched by the addition of 1M HCl (10 mL). The aqueous layer was extracted with EtOAc (3×75 mL) and then combined organic layers were washed with 1M HCl (10 mL), saturated aqueous $NaHCO_3$ (10 mL), water (10 mL), and brine (10 mL). The organic phase was dried over $Na_2SO_4$, decanted into a round bottom flask and concentrated by rotary evaporation. The crude material was recrystallized from EtOH to obtain 2a (0.764 g, 46% yield) as an off-white solid. $^1H$ NMR (500 MHz, $CDCl_3$) δ 15.47 (s, 1H), 7.78 (dt, J=7.7, 1.3 Hz, 1H), 7.73 (t, J=2.1 Hz, 1H), 7.62 (t, J=7.9 Hz, 1H), 7.47 (s, 1H), 7.36 (dd, J=8.3, 2.6 Hz, 1H), 4.61 (q, J=7.2 Hz, 2H), 4.09 (s, 3H), 1.63 (t, J=7.2 Hz, 3H). $^{13}C$ NMR (125 MHz, $CDCl_3$) δ 190.98, 169.47, 162.36, 160.17, 136.53, 130.03, 120.64, 120.38, 112.38, 98.38, 62.79, 55.67, 14.26.

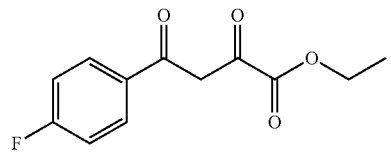 [SMILES: CCOC(=O)C(=O)CC(=O)c1ccc(F)cc1]

Ethyl 4-(4-fluorophenyl)-2,4-dioxobutanoate (2b): To a solution of diisopropyl amine (6.2 mL, 44 mmol) in THF (44 mL) at 0° C. was added n-BuLi (16.2 mL, 40.5 mmol). The cloudy yellow solution was stirred at 0° C. for 30 min., then cooled to −78° C. 4'-fluoroacetophenone (3.2 mL, 26 mmol) was added slowly along the sides of the flask and was stirred for 15 min. Diethyl oxalate (7.9 mL, 58 mmol) was added and the reaction stirred at −78° C. for 1 hour. The mixture was warmed to room temperature and stirred for 20 min and the reaction was quenched by the addition of 1M HCl. The organic solvent was removed by rotary evaporation. The aqueous phase was extracted with EtOAc (3×75 mL) and the combined organic layers were washed with 1M HCl (25 mL), saturated aqueous $NaHCO_3$(25 mL), and brine (25 mL). The organic phase was dried over $Na_2SO_4$, filtered, and concentrated. The crude material was purified by flash column chromatography and recrystallized from EtOH to obtain 2b (3.38 g, 54% yield) as a yellow solid. $^1$H NMR (500 MHz, CDCl$_3$) δ 15.83-15.03 (m, 1H), 8.42-8.09 (m, 2H), 7.50 (s, 1H), 7.42 (t, J=8.5 Hz, 2H), 4.64 (q, J=7.1 Hz, 2H), 1.65 (t, J=7.2 Hz, 3H). $^{13}$C NMR (125 MHz, CDCl$_3$) δ 189.86, 169.33, 166.36 (d, J=256.5 Hz), 162.27, 131.50 (d, J=2.5 Hz), 130.72 (d, J=9.5 Hz)*, 116.3 (d, J=22.0 Hz)*, 97.96, 62.83, 14.25.

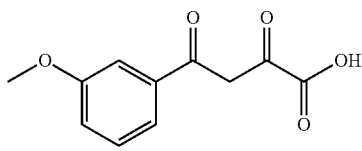 [SMILES: COc1cccc(C(=O)CC(=O)C(=O)O)c1]

4-(3-methoxyphenyl)-2,4-dioxobutanoic acid (3a): To a solution of 2a (0.764 g, 3.05 mmol) in THF (15 mL) was added a solution of NaOH (1.22 g, 30.5 mmol) in 15 mL of water. The reaction stirred at room temperature for 15 min. The organic solvent was removed by rotary evaporation. The aqueous phase was extracted with Et$_2$O (3×30 mL), then acidified with 1M HCl. The aqueous layer was extracted with EtOAc (3×50 mL), and the combined organic layers were washed with brine (50 mL), dried over Na$_2$SO$_4$, filtered, and concentrated by rotary evaporation to obtain 3a (0.450 g, 66% yield) as an off-white solid. NMR (500 MHz, CDCl$_3$) δ 15.32 (s, 1H), 7.74-7.66 (m, 1H), 7.66-7.59 (m, 1H), 7.54 (t, J=8.0 Hz, 1H), 7.37 (s, 1H), 7.29 (dd, J=8.7, 3.0 Hz, 2H), 4.00 (s, 3H). $^{13}$C NMR (125 MHz, CDCl$_3$) δ 186.77, 174.75, 161.49, 160.07, 134.35, 130.09, 120.69, 120.49, 112.27, 95.27, 55.56.

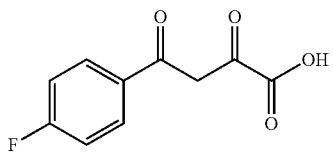 [SMILES: O=C(O)C(=O)CC(=O)c1ccc(F)cc1]

4-(4-fluorophenyl)-2,4-dioxobutanoic acid (3b): To a solution of 2b (3.38 g, 14.2 mmol) in THF (47 mL) was added a solution of NaOH (5.68 g, 142 mmol) in 45 mL of water. The reaction stirred at room temperature for 15 min., then the organic solvent was removed by rotary evaporation. The aqueous phase was extracted with Et$_2$O (3×50 mL), then acidified with conc. HCl. The aqueous layer was extracted with EtOAc (3×100 mL), and the combined organic layers were washed with brine (50 mL), dried over Na$_2$SO$_4$, filtered, and concentrated to obtain 3b (1.92 g, 64% yield) as an off-white solid. $^1$H NMR (500 MHz, CDCl$_3$) δ 15.21 (s, 1H), 8.25-8.01 (m, 2H), 7.27 (s, 1H), 7.22 (t, J=8.6 Hz, 2H), 7.14 (s, 1H). $^1$+1 NMR (500 MHz, DMSO-D6) δ 8.30-8.02 (m, 2H), 7.41 (t, J=8.8 Hz, 2H), 7.10 (s, 1H), (Carboxylic acid —OH and enol-OH not observed). $^{13}$C NMR (125 MHz, CDCl$_3$) δ 185.90, 174.19, 166.49 (d, J=257.7 Hz), 161.63, 130.62 (d, J=9.5 Hz)*, 129.42 (d, J=3.1 Hz), 116.44 (d, J=22.1 Hz)*, 95.08. * Indicates two equivalent carbons with the same chemical shift that couple with $^{19}$F.

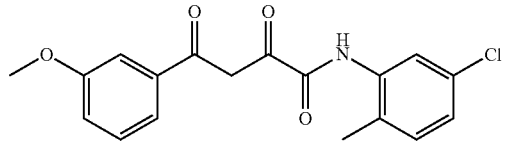 [SMILES: COc1cccc(C(=O)CC(=O)C(=O)Nc2cc(Cl)ccc2C)c1]

N-(5-chloro-2-methylphenyl)-4-(3-methoxyphenyl)-2,4-dioxobutanamide (4a): Acid 3a (0.400 g, 1.80 mmol) was dissolved in THF (9.00 mL) and 5-chloro-2-methylaniline (0.33 mL, 2.7 mmol) was added, followed by EEDQ (0.467 g, 1.89 mmol). The reaction stirred at room temperature for 18 hr then was diluted with EtOAc. The organic phase was washed with 1M HCl (2×20 mL), saturated aqueous NaHCO$_3$ (2×20 mL), water (20 mL) and brine (20 mL). The organic phase was dried over Na$_2$SO$_4$, filtered, and concentrated. The crude material was recrystallized from MeOH to obtain 4a (0.412 g, 66% yield) as a yellow powder. $^1$H NMR (500 MHz, CDCl$_3$) δ 15.65 (s, 1H), 9.02 (s, 1H), 8.28 (d, J=2.2 Hz, 1H), 7.63 (d, J=7.7 Hz, 1H), 7.59-7.49 (m, 1H), 7.43 (t, J=8.0 Hz, 1H), 7.31 (s, 1H), 7.25-7.15 (m, 2H), 7.10 (dd, J=8.1, 2.2 Hz, 1H), 3.90 (s, 3H), 2.35 (s, 3H). $^{13}$C NMR (125 MHz, CDCl$_3$) δ 185.77, 179.73, 160.15, 159.08, 135.81, 134.96, 132.59, 131.55, 130.12, 126.23, 125.43, 121.28, 120.48, 120.38, 112.19, 94.18, 55.68, 17.20.

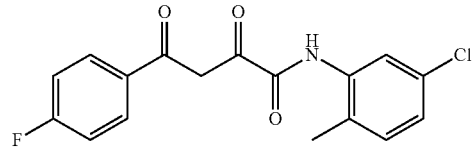 [SMILES: Cc1ccc(Cl)cc1NC(=O)C(=O)CC(=O)c1ccc(F)cc1]

N-(5-chloro-2-methylphenyl)-4-(4-fluorophenyl)-2,4-dioxobutanamide (4b): To a solution of 3b (0.208 g, 0.990 mmol) in THF (5 mL) was added 5-chloro-2-methylaniline (0.18 mL, 1.5 mmol), followed by EEDQ (0.257 g, 1.04 mmol). The reaction stirred at room temperature for 18 hr, then was diluted with EtOAc. The organic phase was washed with 1M HCl (3×10 mL), saturated aqueous NaHCO$_3$ (3×10 mL), water (10 mL), and brine (10 mL). The organic layer was dried over Na$_2$SO$_4$, filtered, and concentrated by rotary evaporation. The crude material was recrystallized from MeOH to obtain 4b (0.061 g, 59% yield) as a yellow powder. NMR (500 MHz, CDCl$_3$): δ 15.65 (s, 1H), 9.00 (s, 1H), 8.27 (d, J=2.3 Hz, 1H), 8.07 (dd, J=8.5, 5.3 Hz, 2H), 7.21 (t, J=8.4 Hz, 2H), 7.16 (d, J=8.1 Hz, 1H), 7.10 (dd, J=8.3, 2.2 Hz, 1H), 2.35 (s, 3H). $^1$H NMR (500 MHz, DMSO-D6) δ 10.24 (s, 1H), 8.17 (dd, J=8.5, 5.3 Hz, 2H), 7.58 (d, J=2.5 Hz, 1H), 7.46-7.35 (m, 3H), 7.31 (d, J=8.3 Hz, 1H), 7.24 (dd, J=8.3, 2.3 Hz, 1H), 7.17 (s, 1H), 2.22 (s, 3H). 13C NMR (125 MHz, CDCl$_3$) δ 184.81, 179.44, 166.34 (d, J=256.6 Hz), 158.98, 135.76, 132.60, 131.57, 130.50 (d, J=9.4 Hz)*, 129.91 (d, J=2.85 Hz), 126.26, 125.48, 121.30, 116.42 (d, J=22.2 Hz)*, 93.80, 17.19. * Indicates two equivalent carbons with the same chemical shift that couple with $^{19}$F.

In Silico High-throughput Screening

In Silico Filtering of The Small Molecule Database for Ligand Preparation. The ZINC database (Irwin et al., 2012), which contains approximately 41 million commercially available compounds, was used for virtual high-throughput screening (vHTS). All compounds in the ZINC library were subjected to a panel of PAINS substructures filters with Smiles ARbitrary Target Specifications (SMARTS) strings (Baell and Holloway, 2010) to eliminate promiscuous and non-drug-like molecules that interfere with functionality of the target proteins. Filtering generated a list of approximately 10 million commercially available compounds for further screening. The 10 million compound dataset was then subjected to the LigPrep module of Schrodinger (Small-Molecule Drug Discovery Suite 2017-2, Schrodinger, LLC, New York) in OPLS2005 force field at pH 7.4±1 (physiological pH) retaining the specific chirality. A low energetic 3D structure for each molecule was generated in this ligand preparation panel.

Protein Preparation for Small Molecule Screening and Grid Generation. The protein preparation (prot-prep) engine implemented in the SchrOdinger software suite was utilized to prepare the protein for small molecule docking simulations. Analysis of the tripartite complex crystal structure (4IMY.pdb) having a resolution 2.94 Å reveals the binding of the AFF4 protein to CCNT1, a subunit of P-TEFb. We observed that five terminal residues of AFF4 (L34, F35, A36, E37 and P38) are having good interactions with the binding groove of CCNT1containing the residues W221, Y224, L163, V164, R165, Y175, F176, D169, W207, W210 and E211. Furthermore, the mutation data of Y175, E211, D169, F176, R165, W210 and W207 of CCNT1 reported in the literature (Schulze-Gahmen et al., 2013) guided us to select the small molecule ligand-binding site. A 12 Å$^3$ grid was generated considering the centroid of the above mention critical residues in the CCNT1 groove.

Virtual Screening Workflow. For vHTS, we began with the curated library of approximately 10 million drug-like compounds described above and the OPLS 2005 force field was set. The ligand van der Waals radii was scaled to 0.80 Å with partial atomic charges <0.15 esu. A three-tier Glide docking algorithm (Small-Molecule Drug Discovery Suite 2017-2, Schrodinger, LLC) was employed that incorporates vHTS followed by Standard Precision (SP) and Extra Precision (XP) docking protocols. The output of this three-tier docking engine was analyzed using the XP-visualization tools by considering the interactions of the compounds with the critical residues reported above. Based on the docking scores, a list of 122 compounds was selected for cross validation using a 5-point structure focus pharmacophore generated by the pharmacophore module implemented in BIOVIA software considering the interactions of residues of AFF4 and Cyclin T1. Using the 5-point pharmacophore as the query, the glide hits were scored. Based on fitting scores and low energetics conformers, 67 hits were selected. We selected 40 available compounds having a Glide docking score <−6.0. The Glide score is a function of the binding energy (Small-Molecule Drug Discovery Suite 2017-2, Schrodinger, LLC)

AlphaLISA Assay. The interaction of CCNT1-AFF4 was measured by Perkin Elmer's bead-based AlphaLISA assays. Recombinant GST-CCNT1 (1-300), which was purified by Glutathione Superflow Agarose from Rosetta cells, and AFF4 peptides were diluted in incubation buffer (25 mM HEPES, PH 7.4, 100 mM NaCl, 0.1% NP-40). GST-CCNT1 (AA1-300) and AFF4 peptides at indicated concentrations were mixed together with 0.5 µg of AlphaScreen Streptavidin Donor beads, and 0.5 µg of Glutathione AlphaLISA Acceptor Beads. For inhibition assays, inhibitors were added right after the mixture of CCNT1 and AFF4 peptide. Reactions were subsequently incubated for 2 hr with agitation in the dark. Plates were read with a Tecan INFINITE M1000 PRO. The dissociation constant Kd of CCNT1-AFF4 interaction was calculated based on the hyperbolic binding equation in Prism 7 (Graphpad). The IC$_{50}$ values of the KL-1 and KL-2 were calculated with a four-parameter sigmoid fitting equation in Prism 7 and converted to the inhibitory Constants (K$_i$) with the Cheng and Prusoff equation.

Heat Shock Induction. Heat shock of mammalian cells was performed using ~70-80% confluent HCT-116 cells by adding pre-heated (42° C.) conditioned media collected from identically growing cells (Mahat et al., 2016b). The heat shock cells were incubated at 42° C. for 1 hour. After washing with PBS, the heat shock and non-heat shock HCT-116 cells were fixed with 1% formaldehyde in PBS for downstream ChIP-seq analysis. For heat shock induction of *Drosophila* S2 cells, the S2 cells were mixed with pre-heated medium to instantly increase the medium temperature from 24° C. to 37° C. and maintained in a water bath at 37° C. for 10 min before fixation for ChIP-seq.

Induction of J-Lat 6.3 Cells. The J-Lat 6.3 cell line was derived from human Jurkat cells with the integration of a full-length green fluorescent protein (GFP)-encoding HIV-1 vector (HIV-R7/E⁻/GFP) under the control of the viral 5'-LTR (Jordan et al., 2003). To measure the effects on Tat-mediated HIV inducibility with flow cytometry, J-Lat 6.3 cells were incubated with 10 nM PMA (Phorbol 12-myristate 13-acetate) in the presence of vehicle or SEC inhibitors at the indicated concentrations for 17 hr. Cells were washed in PBS and GFP fluorescence was measured with a FACSVantage instrument (Becton Dickinson, San Jose, Calif.). Analysis was gated on live cells according to forward and side scatter. A two-parameter analysis to distinguish GFP-derived fluorescence from background fluorescence was used: GFP was measured in FL1 and cellular autofluorescence was monitored in FL2. The percentage of GFP-positive cells was calculated based on live cells (Jordan et al., 2003). The J-Lat 6.3 cells were also induced with 10 nM PMA for 11 hr and then treated with Vehicle or SEC inhibitors for 6 hr prior to ChIP-seq analysis.

Chromatin Immunoprecipitation Sequencing. Chromatin Immunoprecipitation Sequencing (ChIP-seq) was performed according to a previously published protocol (Liang et al., 2015). Briefly, cells were crosslinked with 1% paraformaldehyde for 10 min and were quenched with glycine for 5 min at room temperature. Fixed chromatin was sonicated with a Covaris Focused-ultrasonicator for 6 min and immunoprecipitated with the indicated antibody and Dynabeads Protein G. Libraries were prepared with the HTP Library Preparation Kit for Illumina (KAPA Biosystems) and sequenced on a NextSeq 500. ChIP-seq reads were aligned to the *Drosophila* genome (UCSC dm3) or human genome (UCSC hg19). Alignments were processed with Bowtie version 1.1.2, allowing only uniquely mapping reads with up to two mismatches within the 50 bp read. The resulting reads were extended to 150 bp toward the interior of the sequenced fragment and normalized to total reads aligned (reads per million, r.p.m.). Peaks were called using MACS (model based analysis of ChIP-Seq) (Zhang et al., 2008) version 1.4.2 using default parameters. Ensembl version 75 transcripts were chosen with the highest total coverage from the annotated TSS to 200 nt downstream for protein coding genes that also have a RefSeq identifier, were at least 2 kb long, and 2 kb away from the nearest gene. The genes with SEC and Pol II occupancy were defined by the overlapping of peaks with Pol II and SEC peaks by MACS 1.4.2 using default parameters. For pausing indexes, the promoter region was defined as −200 bp upstream to 400 bp downstream, and the body region was the remainder of the entire gene body. The ratio of the average coverage (r.p.m.) of the promoter over the average coverage of the gene body was then taken to be the pausing index. ECDF plots were made in R version 3.3.3 using the ecdf function. P-values were calculated with a two-sided Kolmogorov-Smirnov test. Heatmap tables were made for the indicated windows around the TSS or TES using the average coverage (r.p.m.) in 25 bp & 50 bp bins (50 bp bins for 50 kb downstream of the TSS). Metagene tables were made by approximating the coverage across all genes to the same length. All ChIP-seq heatmaps were sorted by the decreasing coverage in indicated windows by the control samples and visualized using JavaTreeView version 1.6.4 (Saldanha, 2004). Average profile plots were made by averaging the coverage for all genes using colMeans in R.

Precision Nuclear Run-on and Sequencing. Precision Nuclear Run-on and Sequencing (PRO-seq) was performed according to the previously published protocol (Mahat et al., 2016a) with minor modifications. All 4 biotinylated nucleotides were used at 25 μM each final concentration for the run-on reaction. RPPH (NEB) was used to remove the 5' RNA cap. Libraries were size selected using a 2% agarose gel on a Pippin HT programmed to elute 140-350 bp. After sequencing, adaptors were removed with cutadapt version 1.14 (Martin, 2011). Reads were trimmed from the 3'-end to 36 bp with removing low quality bases using Trimmomatic version 0.33 (Bolger et al., 2014) requiring a minimal read length of 16nt. Reads were then mapped to the human genome (UCSC hg19) using Bowtie version 1.1.2 (Langmead et al., 2009). Only uniquely mapped reads with up to 2 mismatches in the entire read were used for further analysis. Read where then converted to single nucleotide 3' BigWig strand specific tracks by taking 5' positions of the read (using bedtools genomecov version 2.17 (Quinlan and Hall, 2010) with options —strand—bg—5. Strands were then swapped to give the correct orientation with the 5'-end now becoming the 3'-end of the read (Mahat et al., 2016a). PRO-seq genome browser track examples show coverage of the entire length of the read for easier visualization. The single nucleotide 3' BigWig strand specific tracks were used to generate all other figures. For the Pol II-selected genes described above, we found the site of maximum coverage, in the region from the annotated TSS to 500 bp downstream, to which we assign the pausing site. Heatmap tables were made as described above but instead centering at this calculated pausing site.

4sU-FP-Seq

Cell Labeling with 4sU, RNA Extraction and Fragmentation. 20-50 million cells were treated with flavopiridol for 1-2 hr to pause the Pol II at the TSS sites. For the release of Pol II and measurement of elongation rates, the cells were labeled with 4-thiouridine (4sU, Sigma-Aldrich, St. Louis, Mo., USA) either in water bath or in plates. For water bath labeling, the cells were harvested through centrifugation for 3 min at 350 g and washed with PBS twice. Then, the cells were released with prewarmed medium containing 500 μM 4-thiouridine for 15 min, and harvested by centrifuge at 1800 g for 3 min. For labeling in plates, the cells were washed with PBS twice after flavopiridol treatment and released with prewarmed medium containing 500 μM 4-thiouridine in $CO_2$ incubator at 37° C. for 15 min. RNA was extracted with 4 mL Trizol (Invitrogen) and 5 μL 20 mg/mL glycogen. The extracted RNA was further fragmented by base hydrolysis in 0.2 M NaOH on ice for 18 min, neutralized by adding 1× volume of 1 M Tris-HCl pH 6.8 and precipitated with isopropanol.

Biotinylation of RNA. Biotinylation of 4sU-labeled RNA was performed using EZ-Link Biotin-HPDP (Pierce) dissolved in dimethylformamide (DMF, Sigma) at a concentration of 1 mg/mL and stored at 4° C. Biotinylation was carried out in 10 mM Tris (pH 7.4), 1 mM EDTA, and 0.2 mg/mL Biotin-HPDP at a final RNA concentration of 200 ng/μL, for 1.5 hrs. at room temperature. After biotinylation, unbound Biotin-HPDP was removed by extracting twice with chloroform and phase lock gel. Afterward, a 1/10 volume of 5 M NaCl and an equal volume of isopropanol was added to precipitate RNA. RNA was collected by centrifugation at 20,000 g for 20 min and the pellet was washed with an equal volume of 80% ethanol. The pellet was resuspended in 200 μL RNAse-free water.

Purification of 4sU-Labeled RNA, Library Preparation and Alignment. After denaturation of RNA samples at 65° C. for 5 min followed by rapid cooling on ice for 5 min, biotinylated RNA was captured using streptavidin beads. Up to 200 μg of biotinylated RNA were incubated with 50 μL of Dynabeads® MyOne™ Streptavidin C1 with rotation for 15 min at room temperature. Beads were washed two times with 65° C. wash buffer (10 mM Tris-HCl, pH 7.4, 1 mM EDTA, 1 M NaCl, 0.1% Tween20) followed by four washes with room temperature wash buffer. Labeled RNA was eluted twice for 5 min with 100 μL of freshly prepared 100 mM dithiothreitol (DTT). RNA was recovered from the elute fractions and purified using the RNeasy MinElute Spin columns (Qiagen). Libraries were made with the TruSeq RNA Sample Prep kit (Illumina) and subjected to Illumina sequencing. 4sU-FP-seq reads were aligned to the human genome (UCSC hg19). Alignments were processed with Bowtie version 1.1.2, allowing only uniquely mapping reads with up to two mismatches within the 50 bp read. The resulting reads were extended to 150 bp toward the interior of the sequenced fragment and normalized to total reads aligned (reads per million, r.p.m) for each strand.

Elongation Rate Analysis. Genes used for calculating elongation rates were required to have an observed transcription start site with 4sU RNA signals, a minimum gene length of 50 kb and must be at least 2 kb away from the transcription start site of another gene. Genes were further filtered for activity/coverage by filtering on the reads-per-million count within each gene body (+400 to TES) in our untreated, wild-type data. Thus, the read coverage must be present at levels above background (r.p.m. >1).

We first used the Hidden Markov Model (HMM) to calculate elongation rates. Advancing waves were identified using a three state Hidden Markov Model (HMM) that was previously developed and implemented on GRO-seq data from a human cell line (Danko et al., 2013). We also used SICER peak calling to determine elongation rates. Peaks were called with SICER version 1.1 (Zang et al., 2009) with the following options—windowSize 150—fragSize 150—gapSize 3 with strand separated reads over input. These strand-specific peaks were filtered for an FDR <0.01. Peaks were merged if there was a gap less than 2 kb. Peaks were then overlapped with TSS's of genes on the same strand that were greater than 50 kb. The distance traveled was calculated from the TSS to the 3'-end of the merged peak and the elongation rate in kb/min was calculated using the time after release.

RNA-seq Analysis. Total RNA-seq reads were trimmed from the 3' end until the final base had a quality score >30, using Trimmomatic version 0.33 (Bolger et al., 2014) and then aligned to the human genome (UCSC hg19, using Tophat version 2.1.0 (Kim et al., 2013)) with the following options-no-novel-juncs—read-mismatches 2—read-edit-dist 2—num-threads 10—max-multihits 20 then post filtering for uniquely mapped reads using the NH flag. Protein coding genes from Ensembl version 75 that also had a RefSeq identifier were only considered for analysis. Raw read counts were normalized to r.p.m. per sample and then displayed in the UCSC genome browser as bigWig-formatted coverage tracks. Exonic reads were assigned to specific genes from Ensembl release 75 using Bioconductor package GenomicRanges countOverlaps. The R Bioconductor package edgeR (Robinson et al., 2010), version 3.12.0 was used to fit the data to a negative binomial generalized log-linear model and estimate a dispersion parameter. To filter out lowly expressed genes, genes had to have at least 1 count per million (c.p.m) in at least 2 samples in each comparison. The total number of uniquely mapped reads was provided to edgeR for the calcNormFactors normalization rather than the default column sums. An adjusted-p value threshold of 0.01 and a $\log_2$ r.p.m cut off of 3 was used to identify genes significantly differentially expressed in one experimental condition relative to another. GO term analysis was done using Metascape (Tripathi et al., 2015).

Quantification and Statistical Analyses

Data are presented as Mean+SD. The sample sizes (n) in the figure legends indicate the number of replicates in each experiment and is provided in the corresponding figure legends. The peak or gene size (N) in the heatmaps indicates the number of peaks or genes included. For FIGS. 8I and 12E, One-Way ANOVA tests were performed with Prism 7 (GraphPad Software, La Jolla, Calif.) to determine the statistical significance. P value <0.005 (**) was considered as highly significantly different, p value <0.05 was considered as significantly different, n.s, not significantly different, p >0.05. For FIGS. 2F, 2H, 9G and 9H, the two-sided Kolmogorov-Smirnov test was performed for the ECDF curves and the p values were provided in each figure. For FIGS. 9E, 9F, 4G, 11E, 5E and 5G, the statistical significance was determined by a two-sided Wilcoxon signed-rank test using R 3.3.3 package with the p values provided in each figure. For FIG. 7D, a 2-tailed unpaired t-test was used for comparison the tumor size between each treatment group. For FIG. 7E, the Kaplan-Meier survival curves were plotted with GraphPad Prism 7 and the p values were calculated using the log-rank test.

Data and Software Availability

The accession number for the raw and processed ChIP-seq, RNA-seq, PRO-seq and 4sU-FP-seq data reported herein is GEO: GSE112608.

REFERENCES

Baell, J. B., and Holloway, G. A. (2010). New substructure filters for removal of pan assay interference compounds (PAINS) from screening libraries and for their exclusion in bioassays. J Med Chem 53, 2719-2740.

Bezzi, M., Teo, S. X., Muller, J., Mok, W. C., Sahu, S. K., Vardy, L. A., Bonday, Z. Q., and Guccione, E. (2013). Regulation of constitutive and alternative splicing by PRMT5 reveals a role for Mdm4 pre-mRNA in sensing defects in the spliceosomal machinery. Genes Dev 27, 1903-1916.

Bolger, A. M., Lohse, M., and Usadel, B. (2014). Trimmomatic: a flexible trimmer for Illumina sequence data. Bioinformatics 30, 2114-2120.

Bradner, J. E., Hnisz, D., and Young, R. A. (2017). Transcriptional Addiction in Cancer. Cell 168, 629-643.

Chao, S. H., and Price, D. H. (2001). Flavopiridol inactivates P-TEFb and blocks most RNA polymerase II transcription in vivo. J Biol Chem 276, 31793-31799.

Chen, F. X., Smith, E. R., and Shilatifard, A. (2018). Born to run: control of transcription elongation by RNA polymerase II. Nat Rev Mol Cell Biol 19, 464-478.

Danko, C. G., Hah, N., Luo, X., Martins, A. L., Core, L., Lis, J. T., Siepel, A., and Kraus, W. L. (2013). Signaling pathways differentially affect RNA polymerase II initiation, pausing, and elongation rate in cells. Mol Cell 50, 212-222.

Dawson, M. A., Prinjha, R. K., Dittmann, A., Giotopoulos, G., Bantscheff, M., Chan, W. I., Robson, S. C., Chung, C. W., Hopf, C., Savitski, M. M., et al. (2011). Inhibition of BET recruitment to chromatin as an effective treatment for MLL-fusion leukaemia. Nature 478, 529-533.

Delmore, J. E., Issa, G. C., Lemieux, M. E., Rahl, P. B., Shi, J., Jacobs, H. M., Kastritis, E., Gilpatrick, T., Paranal, R. M., Qi, J., et al. (2011). BET bromodomain inhibition as a therapeutic strategy to target c-Myc. Cell 146, 904-917.

Erb, M. A., Scott, T. G., Li, B. E., Xie, H., Paulk, J., Seo, H. S., Souza, A., Roberts, J. M., Dastjerdi, S., Buckley, D. L., et al. (2017). Transcription control by the ENL YEATS domain in acute leukaemia. Nature 543, 270-274.

Filippakopoulos, P., Qi, J., Picaud, S., Shen, Y., Smith, W. B., Fedorov, O., Morse, E. M., Keates, T., Hickman, T. T., Felletar, I., et al. (2010). Selective inhibition of BET bromodomains. Nature 468, 1067-1073.

Fong, N., Brannan, K., Erickson, B., Kim, H., Cortazar, M. A., Sheridan, R. M., Nguyen, T., Karp, S., and Bentley, D. L. (2015). Effects of Transcription Elongation Rate and Xrn2 Exonuclease Activity on RNA Polymerase II Termination Suggest Widespread Kinetic Competition. Mol Cell 60, 256-267.

Fong, N., Kim, H., Zhou, Y., Ji, X., Qiu, J., Saldi, T., Diener, K., Jones, K., Fu, X D., and Bentley, D. L. (2014). Pre-mRNA splicing is facilitated by an optimal RNA polymerase II elongation rate. Genes Dev 28, 2663-2676.

Fong, N., Saldi, T., Sheridan, R. M., Cortazar, M. A., and Bentley, D. L. (2017). RNA Pol II Dynamics Modulate Co-transcriptional Chromatin Modification, CTD Phosphorylation, and Transcriptional Direction. Mol Cell 66, 546-557 e543.

Fuchs, G., Voichek, Y., Benjamin, S., Gilad, S., Amit, I., and Oren, M. (2014). 4sUDRB-seq: measuring genom-ewide transcriptional elongation rates and initiation frequencies within cells. Genome Biol 15, R69.

Galbraith, M. D., Allen, M. A., Bensard, C. L., Wang, X., Schwinn, M. K., Qin, B., Long, H. W., Daniels, D. L., Hahn, W. C., Dowell, R. D., et al. (2013). HIF1 Å employs CDK8-mediator to stimulate RNAPII elongation in response to hypoxia. Cell 153, 1327-1339.

Gu, J., Babayeva, N. D., Suwa, Y., Baranovskiy, A. G., Price, D. H., and Tahirov, T. H. (2014). Crystal structure of HIV-1 Tat complexed with human P-TEFb and AFF4. Cell Cycle 13, 1788-1797.

He, N., Liu, M., Hsu, J., Xue, Y., Chou, S., Burlingame, A., Krogan, N. J., Alber, T., and Zhou, Q. (2010). HIV-1 Tat and host AFF4 recruit two transcription elongation factors into a bifunctional complex for coordinated activation of HIV-1 transcription. Mol Cell 38, 428-438.

Hsu, T. Y., Simon, L. M., Neill, N. J., Marcotte, R., Sayad, A., Bland, C. S., Echeverria, G. V., Sun, T., Kurley, S. J., Tyagi, S., et al. (2015). The spliceosome is a therapeutic vulnerability in MYC-driven cancer. Nature 525, 384-388.

Hu, D., Smith, E. R., Garruss, A. S., Mohaghegh, N., Varberg, J. M., Lin, C., Jackson, J., Gao, X., Saraf, A., Florens, L., et al. (2013). The little elongation complex functions at initiation and elongation phases of snRNA gene transcription. Mol Cell 51, 493-505.

Irwin, J. J., Sterling, T., Mysinger, M. M., Bolstad, E. S., and Coleman, R. G. (2012). ZINC: a free tool to discover chemistry for biology. J Chem Inf Model 52, 1757-1768.

Izumi, K., Nakato, R., Zhang, Z., Edmondson, A. C., Noon, S., Dulik, M. C., Rajagopalan, R., Venditti, C. P., Gripp, K., Samanich, J., et al. (2015). Germline gain-of-function mutations in AFF4 cause a developmental syndrome functionally linking the super elongation complex and cohesin. Nat Genet 47, 338-344.

Ji, X., Zhou, Y., Pandit, S., Huang, J., Li, H., Lin, C. Y., Xiao, R., Burge, C. B., and Fu, X. D. (2013). SR proteins collaborate with 7SK and promoter-associated nascent RNA to release paused polymerase. Cell 153, 855-868.

Jonkers, I., and Lis, J. T. (2015). Getting up to speed with transcription elongation by RNA polymerase II. Nat Rev Mol Cell Biol 16, 167-177.

Jordan, A., Bisgrove, D., and Verdin, E. (2003). HIV reproducibly establishes a latent infection after acute infection of T cells in vitro. EMBO J 22, 1868-1877.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol 14, R36.

Koh, C. M., Bezzi, M., Low, D. H., Ang, W. X., Teo, S. X., Gay, F. P., Al-Haddawi, M., Tan, S. Y., Osato, M., Sabo, A., et al. (2015). MYC regulates the core pre-mRNA splicing machinery as an essential step in lymphomagenesis. Nature 523, 96-100.

Kwak, H., Fuda, N. J., Core, L. J., and Lis, J. T. (2013). Precise maps of RNA polymerase reveal how promoters direct initiation and pausing. Science 339, 950-953.

Langmead, B., Trapnell, C., Pop, M., and Salzberg, S. L. (2009). Ultrafast and memory-efficient alignment of short DNA sequences to the human genome. Genome Biol 10, R25.

Lee, S. C., and Abdel-Wahab, O. (2016). Therapeutic targeting of splicing in cancer. Nat Med 22, 976-986.

Liang, K., Volk, A. G., Haug, J. S., Marshall, S. A., Woodfin, A. R., Bartom, E. T., Gilmore, J. M., Florens, L., Washburn, M. P., Sullivan, K. D., et al. (2017). Therapeutic Targeting of MLL Degradation Pathways in MLL-Rearranged Leukemia. Cell 168, 59-72 e13.

Liang, K., Woodfin, A. R., Slaughter, B. D., Unruh, J. R., Box, A. C., Rickels, R. A., Gao, X., Haug, J. S., Jaspersen, S. L., and Shilatifard, A. (2015). Mitotic Transcriptional Activation: Clearance of Actively Engaged Pol II via Transcriptional Elongation Control in Mitosis. Mol Cell 60, 435-445.

Lin, C., Garrett, A. S., De Kumar, B., Smith, E. R., Gogol, M., Seidel, C., Krumlauf, R., and Shilatifard, A. (2011). Dynamic transcriptional events in embryonic stem cells mediated by the super elongation complex (SEC). Genes Dev 25, 1486-1498.

Lin, C., Smith, E. R., Takahashi, H., Lai, K. C., Martin-Brown, S., Florens, L., Washburn, M. P., Conaway, J. W., Conaway, R. C., and Shilatifard, A. (2010). AFF4, a component of the ELL/P-TEFb elongation complex and a shared subunit of MLL chimeras, can link transcription elongation to leukemia. Mol Cell 37, 429-437.

Lin, C. Y., Loven, J., Rahl, P. B., Paranal, R. M., Burge, C. B., Bradner, J. E., Lee, T. I., and Young, R. A. (2012). Transcriptional amplification in tumor cells with elevated c-Myc. Cell 151, 56-67.

Lu, J., Qian, Y., Altieri, M., Dong, H., Wang, J., Raina, K., Hines, J., Winkler, J. D., Crew, A. P., Coleman, K., et al. (2015). Hijacking the E3 Ubiquitin Ligase Cereblon to Efficiently Target BRD4. Chem Biol 22, 755-763.

Luo, Z., Lin, C., Guest, E., Garrett, A. S., Mohaghegh, N., Swanson, S., Marshall, S., Florens, L., Washburn, M. P., and Shilatifard, A. (2012a). The super elongation complex family of RNA polymerase II elongation factors: gene target specificity and transcriptional output. Mol Cell Biol 32, 2608-2617.

Luo, Z., Lin, C., and Shilatifard, A. (2012b). The super elongation complex (SEC) family in transcriptional control. Nat Rev Mol Cell Biol 13, 543-547.

Mahat, D. B., Kwak, H., Booth, G. T., Jonkers, I. H., Danko, C. G., Patel, R. K., Waters, C. T., Munson, K., Core, L. J., and Lis, J. T. (2016a). Base-pair-resolution genome-wide mapping of active RNA polymerases using precision nuclear run-on (PRO-seq). Nat Protoc 11, 1455-1476.

Mahat, D. B., Salamanca, H. H., Duarte, F. M., Danko, C. G., and Lis, J. T. (2016b). Mammalian Heat Shock Response and Mechanisms Underlying Its Genome-wide Transcriptional Regulation. Mol Cell 62, 63-78.

Martin, M. (2011). Cutadapt Removes Adapter Sequences From High-Throughput Sequencing Reads. EMBnetjournal 17, 10-12.

McNamara, R. P., Bacon, C. W., and D'Orso, I. (2016). Transcription elongation control by the 7SK snRNP complex: Releasing the pause. Cell Cycle 15, 2115-2123.

Mohan, M., Lin, C., Guest, E., and Shilatifard, A. (2010). Licensed to elongate: a molecular mechanism for MLL-based leukaemogenesis. Nat Rev Cancer 10, 721-728.

Neklesa, T. K., Winkler, J. D., and Crews, C. M. (2017). Targeted protein degradation by PROTACs. Pharmacol Ther 174, 138-144.

Nie, Z., Hu, G., Wei, G., Cui, K., Yamane, A., Resch, W., Wang, R., Green, D. R., Tessarollo, L., Casellas, R., et al. (2012). c-Myc is a universal amplifier of expressed genes in lymphocytes and embryonic stem cells. Cell 151, 68-79.

Peterlin, B. M., and Price, D. H. (2006). Controlling the elongation phase of transcription with P-TEFb. Mol Cell 23, 297-305.

Quinlan, A. R., and Hall, I. M. (2010). BEDTools: a flexible suite of utilities for comparing genomic features. Bioinformatics 26, 841-842.

Rahl, P. B., Lin, C. Y., Seila, A. C., Flynn, R. A., McCuine, S Burge, C. B., Sharp, P. A., and Young, R. A. (2010). c-Myc regulates transcriptional pause release. Cell 141, 432-445.

Robinson, M. D., McCarthy, D. J., and Smyth, G. K. (2010). edgeR: a Bioconductor package for differential expression analysis of digital gene expression data. Bioinformatics 26, 139-140.

Sabo, A., Kress, T. R., Pelizzola, M., de Pretis, S., Gorski, M. M., Tesi, A., Morelli, M. J., Bora, P., Doni, M., Verrecchia, A., et al. (2014). Selective transcriptional regulation by Myc in cellular growth control and lymphomagenesis. Nature 511, 488-492.

Saldanha, A. J. (2004). Java Treeview—extensible visualization of microarray data. Bioinformatics 20, 3246-3248.

Schulze-Gahmen, U., Upton, H., Birnberg, A., Bao, K., Chou, S., Krogan, N. J., Zhou, Q., and Alber, T. (2013). The AFF4 scaffold binds human P-TEFb adjacent to HIV Tat. Elife 2, e00327.

Shilatifard, A., Duan, D. R., Hague, D., Florence, C., Schubach, W. H., Conaway, J. W., and Conaway, R. C. (1997). ELL2, a new member of an ELL family of RNA polymerase II elongation factors. Proc Natl Acad Sci USA 94, 3639-3643.

Shilatifard, A., Lane, W. S., Jackson, K. W., Conaway, R. C., and Conaway, J. W. (1996). An RNA polymerase II elongation factor encoded by the human ELL gene. Science 271, 1873-1876.

Smith, E., Lin, C., and Shilatifard, A. (2011). The super elongation complex (SEC) and MLL in development and disease. Genes Dev 25, 661-672.

Sobhian, B., Laguette, N., Yatim, A., Nakamura, M., Levy, Y., Kiernan, R., and Benkirane, M. (2010). HIV-1 Tat assembles a multifunctional transcription elongation complex and stably associates with the 7SK snRNP. Mol Cell 38, 439-451.

Takahashi, H., Parmely, T. J., Sato, S., Tomomori-Sato, C., Banks, C. A., Kong, S. E., Szutorisz, H., Swanson, S. K., Martin-Brown, S., Washburn, M. P., et al. (2011). Human mediator subunit MED26 functions as a docking site for transcription elongation factors. Cell 146, 92-104.

Tripathi, S., Pohl, M. O., Zhou, Y., Rodriguez-Frandsen, A., Wang, G., Stein, D. A., Moulton, H. M., DeJesus, P., Che, J., Mulder, L. C., et al. (2015). Meta- and Orthogonal Integration of Influenza "OMICs" Data Defines a Role for UBR4 in Virus Budding. Cell Host Microbe 18, 723-735.

Walz, S., Lorenzin, F., Morton, J., Wiese, K. E., von Eyss, B., Herold, S., Rycak, L., Dumay-Odelot, H., Karim, S., Bartkuhn, M., et al. (2014). Activation and repression by oncogenic MYC shape tumour-specific gene expression profiles. Nature 511, 483-487.

Wan, L., Wen, H., Li, Y., Lyu, J., Xi, Y., Hoshii, T., Joseph, J. K., Wang, X., Loh, Y. E., Erb, M. A., et al. (2017). ENL links histone acetylation to oncogenic gene expression in acute myeloid leukaemia. Nature 543, 265-269.

Wang, L., Collings, C. K., Zhao, Z., Cozzolino, K. A., Ma, Q., Liang, K., Marshall, S. A., Sze, C. C., Hashizume, R., Savas, J. N., et al. (2017). A cytoplasmic COMPASS is necessary for cell survival and triple-negative breast cancer pathogenesis by regulating metabolism. Genes Dev 31, 2056-2066.

Winter, G. E., Buckley, D. L., Paulk, J., Roberts, J. M., Souza, A., Dhe-Paganon, S., and Bradner, J. E. (2015). DRUG DEVELOPMENT. Phthalimide conjugation as a strategy for in vivo target protein degradation. Science 348, 1376-1381.

Winter, G. E., Mayer, A., Buckley, D. L., Erb, M. A., Roderick, J. E., Vittori, S., Reyes, J. M., di Julio, J., Souza, A., Ott, C. J., et al. (2017). BET Bromodomain Proteins Function as Master Transcription Elongation Factors Independent of CDK9 Recruitment. Mol Cell 67, 5-18 e19.

Yang, Z., Yik, J. H., Chen, R., He, N., Jang, M K., Ozato, K., and Zhou, Q. (2005). Recruitment of P-TEFb for stimulation of transcriptional elongation by the bromodomain protein Brd4. Mol Cell 19, 535-545.

Yokoyama, A., Lin, M., Naresh, A., Kitabayashi, I., and Cleary, M. L. (2010). A higher-order complex containing AF4 and ENL family proteins with P-TEFb facilitates oncogenic and physiologic MLL-dependent transcription. Cancer Cell 17, 198-212.

Zeller, K. I., Jegga, A. G., Aronow, B. J., O'Donnell, K. A., and Dang, C. V. (2003). An integrated database of genes responsive to the Myc oncogenic transcription factor: identification of direct genomic targets. Genome Biol 4, R69.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome Biol 9, R137.

Zhou, Q., Li, T., and Price, D. H. (2012). RNA polymerase II elongation control. Annu Rev Biochem 81, 119-143.

Example 2

The following additional exemplary compounds were prepared using a similar synthesis pathway as the pathway utilized in Example 1 for synthesizing KL-1 and KL-2 with the following exceptions. Compounds NUCC-0202075, NUCC-0202089, and NUCC-0202090 were prepared by Suzuki coupling of the appropriate aryl chloride with 4-fluoro phenyl boronic acid, followed by hydrolysis of the ester to the carboxylic acid, then amide coupling using the same procedure as above to obtain the final compounds.

Compounds NUCC-0202071 and NUCC-0202072 were prepared by Claisen condensation of 4'-fluoroacetophenone with diethyl oxalate, condensation with either hydroxylamine or hydrazine, hydrolysis of the ester, and amide coupling using the same procedure as above to obtain the final compounds.

TABLE 1

Exemplary Compounds

| Molecule Name | Structure | $IC_{50}$ (µM) Alpha Screen |
|---|---|---|
| NUCC-0102301 | 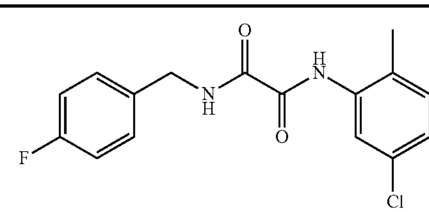 | n.d. |

TABLE 1-continued

Exemplary Compounds

| Molecule Name | Structure | IC$_{50}$ (µM) Alpha Screen |
|---|---|---|
| NUCC-0201231 | 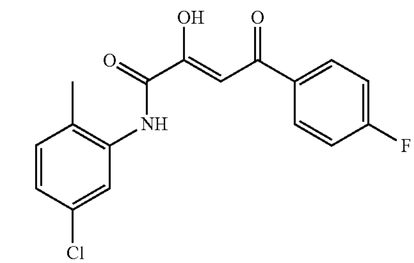 [SMILES: Cc1ccc(Cl)cc1NC(=O)/C(O)=C/C(=O)c1ccc(F)cc1] | n.t. |
| NUCC-0201256 | 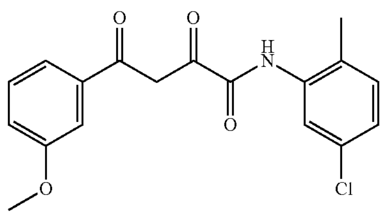 [SMILES: COc1cccc(C(=O)CC(=O)C(=O)Nc2cc(Cl)ccc2C)c1] | n.t. |
| NUCC-0201596 | 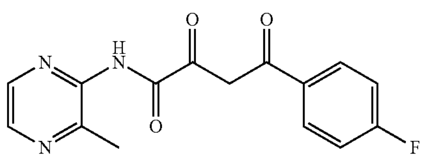 [SMILES: Cc1nccnc1NC(=O)C(=O)CC(=O)c1ccc(F)cc1] | ≥30 |
| NUCC-0201688 | 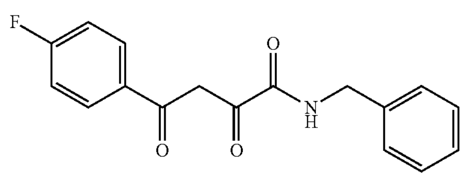 [SMILES: O=C(CC(=O)c1ccc(F)cc1)C(=O)NCc1ccccc1] | ≥30 |
| NUCC-0201689 | 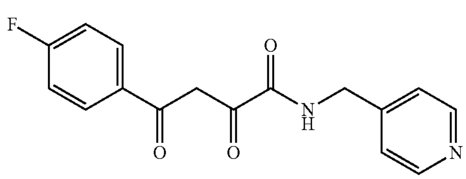 [SMILES: O=C(CC(=O)c1ccc(F)cc1)C(=O)NCc1ccncc1] | ≥30 |
| NUCC-0201690 | 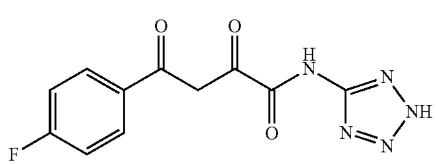 [SMILES: O=C(CC(=O)c1ccc(F)cc1)C(=O)Nc1nn[nH]n1] | 9.88 ± 0.60 |
| NUCC-0201691 | 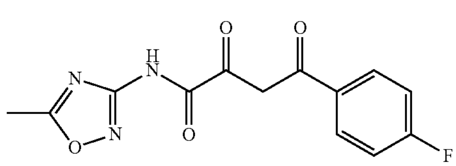 [SMILES: Cc1nc(NC(=O)C(=O)CC(=O)c2ccc(F)cc2)no1] | ≥60 |
| NUCC-0201692 | 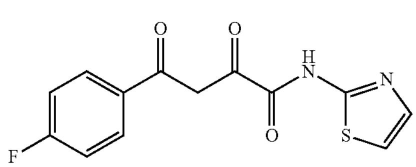 [SMILES: O=C(CC(=O)c1ccc(F)cc1)C(=O)Nc1nccs1] | 20.8 ± 4.2 |

TABLE 1-continued

Exemplary Compounds

| Molecule Name | Structure | IC$_{50}$ (μM) Alpha Screen |
|---|---|---|
| NUCC-0201693 | 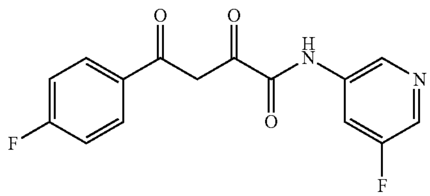 [SMILES: O=C(CC(=O)c1ccc(F)cc1)C(=O)Nc1cncc(F)c1] | 7.42 ± 0.26 |
| NUCC-0201921 | 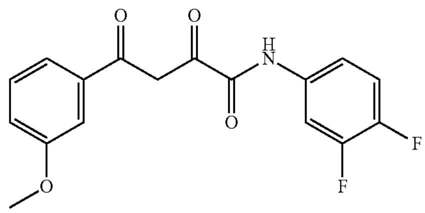 [SMILES: COc1cccc(C(=O)CC(=O)C(=O)Nc2ccc(F)c(F)c2)c1] | 17.37 |
| NUCC-0201922 | 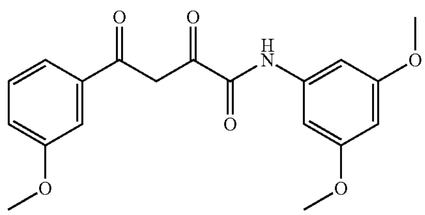 [SMILES: COc1cc(NC(=O)C(=O)CC(=O)c2cccc(OC)c2)cc(OC)c1] | 14.26 |
| NUCC-0201923 | 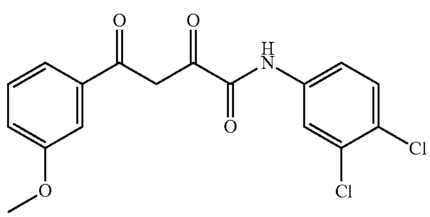 [SMILES: COc1cccc(C(=O)CC(=O)C(=O)Nc2ccc(Cl)c(Cl)c2)c1] | 12.83 |
| NUCC-0201924 | 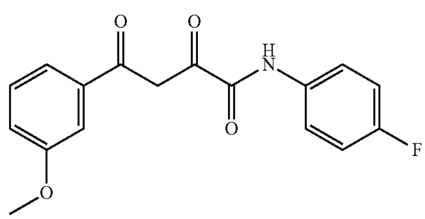 [SMILES: COc1cccc(C(=O)CC(=O)C(=O)Nc2ccc(F)cc2)c1] | 20 |
| NUCC-0201925 | 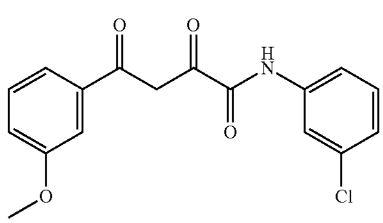 [SMILES: COc1cccc(C(=O)CC(=O)C(=O)Nc2cccc(Cl)c2)c1] | 14.44 |
| NUCC-0201926 | 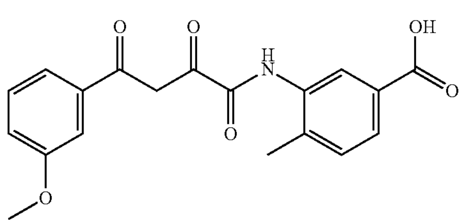 [SMILES: COc1cccc(C(=O)CC(=O)C(=O)Nc2cc(C(=O)O)ccc2C)c1] | 15.2 ± 8.0 |

TABLE 1-continued

Exemplary Compounds

| Molecule Name | Structure | IC$_{50}$ (μM) Alpha Screen |
|---|---|---|
| NUCC-0201927 | 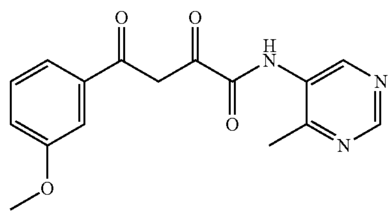 [SMILES: COc1cccc(C(=O)CC(=O)C(=O)Nc2cncnc2C)c1] | 17.9 ± 2.4 |
| NUCC-0201928 | 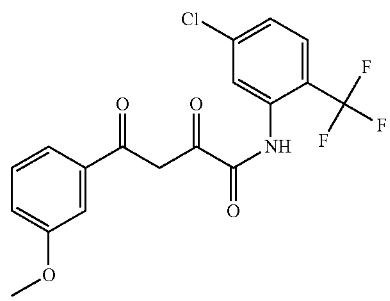 [SMILES: COc1cccc(C(=O)CC(=O)C(=O)Nc2cc(Cl)ccc2C(F)(F)F)c1] | n.t. |
| NUCC-0201929 | 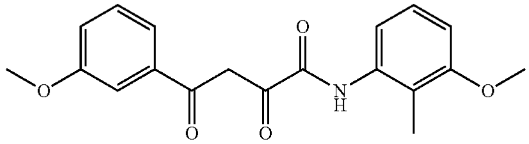 | 15.67 |
| NUCC-0201930 | 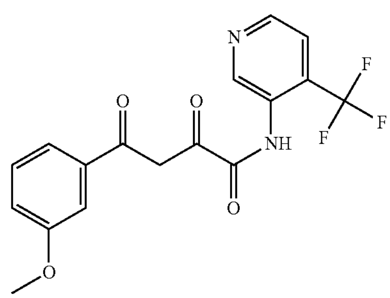 [SMILES: COc1cccc(C(=O)CC(=O)C(=O)Nc2cnccc2C(F)(F)F)c1] | n.t. |
| NUCC-0202066 | 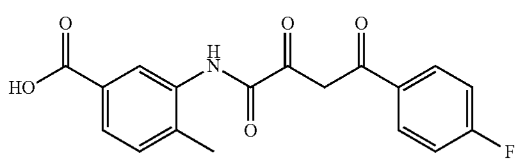 [SMILES: Cc1ccc(C(=O)O)cc1NC(=O)C(=O)CC(=O)c1ccc(F)cc1] | n.t. |
| NUCC-0202067 | 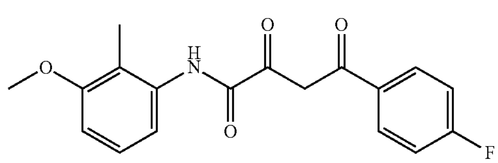 [SMILES: COc1cccc(NC(=O)C(=O)CC(=O)c2ccc(F)cc2)c1C] | 21.3 ± 3.1 |
| NUCC-0202068 | 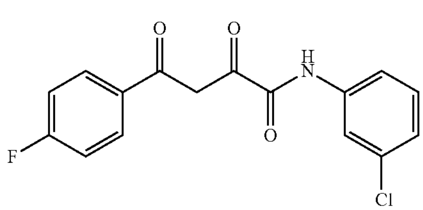 [SMILES: O=C(CC(=O)c1ccc(F)cc1)C(=O)Nc1cccc(Cl)c1] | 11.4 ± 0.9 |

TABLE 1-continued
Exemplary Compounds
| Molecule Name | Structure | IC$_{50}$ (μM) Alpha Screen |
|---|---|---|
| NUCC-0202069 | 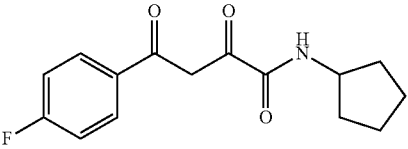 [SMILES: O=C(CC(=O)c1ccc(F)cc1)C(=O)NC1CCCC1] | ≥60 |
| NUCC-0202070 | 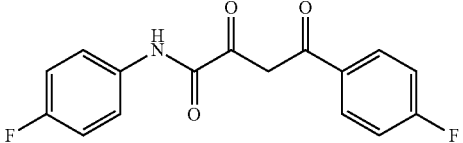 [SMILES: O=C(CC(=O)c1ccc(F)cc1)C(=O)Nc1ccc(F)cc1] | n.d. |
| NUCC-0202071 | 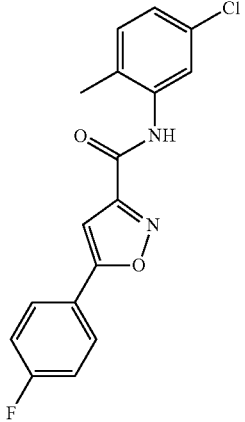 [SMILES: Cc1ccc(Cl)cc1NC(=O)c1cc(-c2ccc(F)cc2)on1] | n.d. |
| NUCC-0202072 | 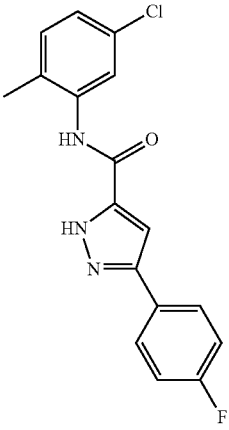 [SMILES: Cc1ccc(Cl)cc1NC(=O)c1cc(-c2ccc(F)cc2)n[nH]1] | n.d. |
| NUCC-0202073 | 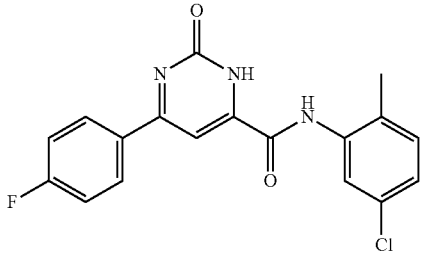 [SMILES: Cc1ccc(Cl)cc1NC(=O)c1cc(-c2ccc(F)cc2)nc(=O)[nH]1] | n.d. |

TABLE 1-continued
| Exemplary Compounds | | |
|---|---|---|
| Molecule Name | Structure | IC$_{50}$ (μM) Alpha Screen |
| NUCC-0202074 | 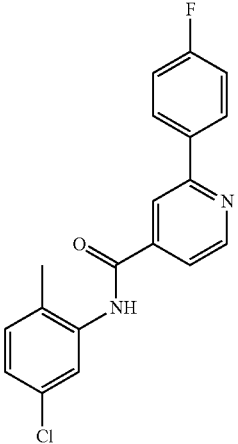 [SMILES: Cc1ccc(Cl)cc1NC(=O)c1ccnc(-c2ccc(F)cc2)c1] | n.d. |
| NUCC-0202075 | 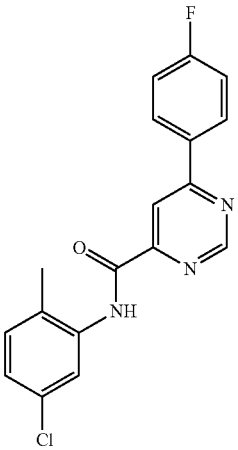 [SMILES: Cc1ccc(Cl)cc1NC(=O)c1cc(-c2ccc(F)cc2)ncn1] | n.d. |
| NUCC-0202089 | 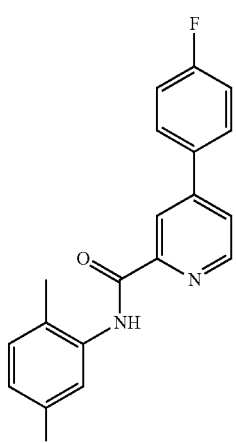 | n.d. |

TABLE 1-continued

Exemplary Compounds

| Molecule Name | Structure | IC$_{50}$ (μM) Alpha Screen |
|---|---|---|
| NUCC-0202090 | 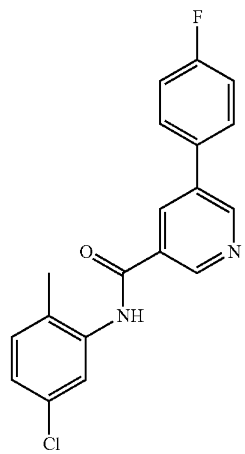 [SMILES: Cc1ccc(Cl)cc1NC(=O)c1cncc(-c2ccc(F)cc2)c1] | n.d. |
| NUCC-0202092 | 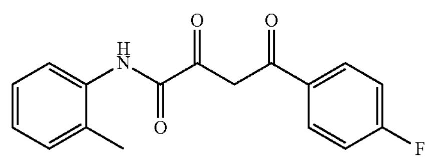 [SMILES: Cc1ccccc1NC(=O)C(=O)CC(=O)c1ccc(F)cc1] | 14.8 ± 2.0 |
| NUCC-0202161 | 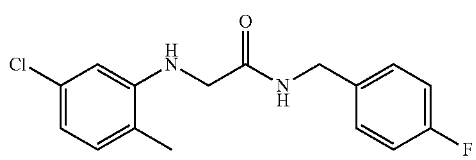 [SMILES: Cc1ccc(Cl)cc1NCC(=O)NCc1ccc(F)cc1] | n.d. |
| NUCC-0202162 | 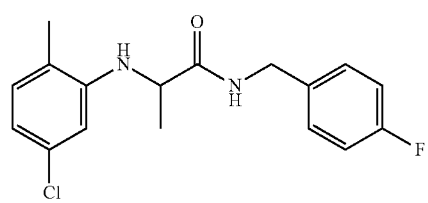 [SMILES: Cc1ccc(Cl)cc1NC(C)C(=O)NCc1ccc(F)cc1] | n.d. |
| NUCC-0202167 | 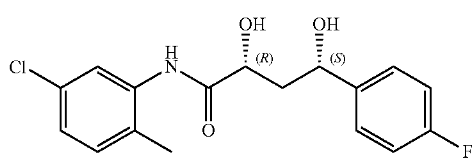 | n.d. |
| NUCC-0202169 | 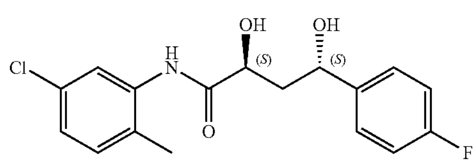 | n.d. |
| NUCC-0202170 | 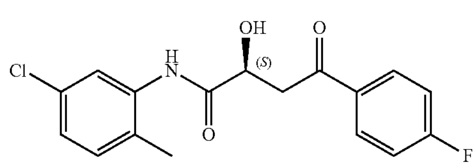 | 30.6 ± 1.4 |

TABLE 1-continued

| Exemplary Compounds | | |
|---|---|---|
| Molecule Name | Structure | IC$_{50}$ (μM) Alpha Screen |
| NUCC-0202548 | | n.t. |
| NUCC-0202549 | | n.t. |
| NUCC-0202550 | | n.t. |

*n.d. = not determined.
**n.t. = not tested.

TABLE 2

Exemplary Compounds

| Molecule Name | Structure | IC$_{50}$ (μM) Alpha Screen |
|---|---|---|
| NUCC-0202402 | 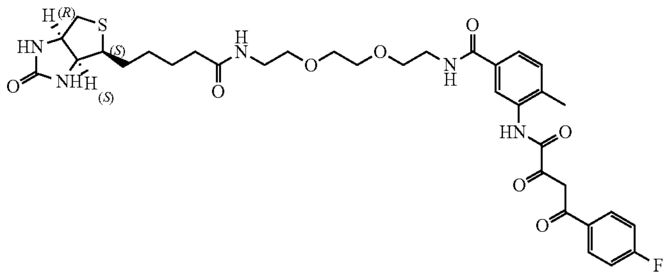 | n.t. |
| NUCC-0202403 | 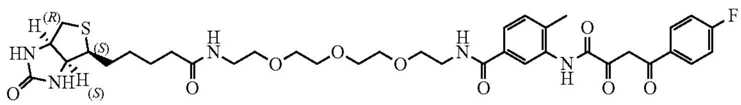 | n.t. |
| NUCC-0202404 | 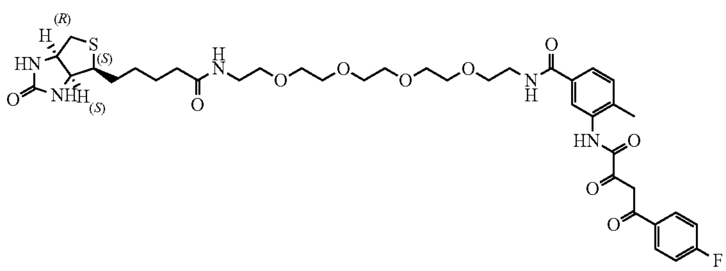 | n.t. |
| NUCC-0202405 | 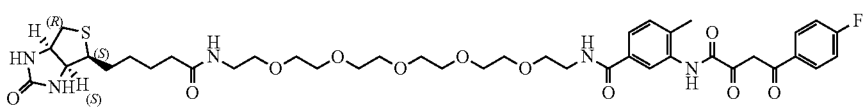 | n.t. |

**n.t. = not tested.

NUCC-0202550. Major tautomer: 1H NMR (500 MHz, Chloroform-d) δ 8.26 (s, 1H), 7.84 (dd, J=8.0, 1.8 Hz, 1H), 7.39 (d, J=7.9 Hz, 1H), 7.32-7.26 (m, 3H), 7.24 (s, 1H), 6.87 (dt, J=7.4, 2.0 Hz, 1H), 2.83 (s, 3H), 2.38 (s, 3H). Minor tautomer: 1H NMR (500 MHz, Chloroform-d) δ 8.33 (s, 1H), 7.84 (dd, J=8.0, 1.8 Hz, 1H), 7.39 (d, J=7.9 Hz, 1H), 7.34-7.22 (m, 3H), 7.20 (s, 1H), 6.87 (dt, J=7.4, 2.0 Hz, 1H), 2.83 (s, 3H), 2.38 (s, 3H). LCMS (M+H$^+$) calcd. 355.36, found 355.25.

NUCC-0202549. Major tautomer: 1H NMR (500 MHz, DMSO-d6)δ 12.93 (s, 1H), 10.17 (s, 1H), 8.66 (s, 1H), 8.17 (s, 1H), 8.04-8.01 (m, 1H), 7.74 (dd, J=7.9, 1.8 Hz, 1H), 7.40 (d, J=7.9 Hz, 1H), 6.89 (s, 1H), 3.91 (s, 3H), 2.29 (s, 3H). (—OH not observed.) Minor tautomer: 1H NMR (500 MHz, DMSO-d6) δ 12.93 (s, 1H), 10.17 (s, 1H), 8.46 (s, 1H), 7.99 (s, 1H), 7.95-7.89 (m, 1H), 7.73 (s, 2H), 7.38 (d, J=8.2 Hz, 1H), 3.89 (s,3), 2.26 (s, 3H). (—OH not observed.) LCMS (M+H$^+$) calcd. 330.31, found 330.29.

NUCC-0202548. Major tautomer: 1H NMR (500 MHz, Methanol-d4)8.25 (d, J=1.7 Hz, 1H), 7.91-7.84 (m, 2H), 7.80 (d, J=7.3 Hz, 1H), 7.75 (s, 1H), 7.42 (d, J=8.0 Hz, 1H), 7.03 (d, J=8.4 Hz, 1H), 4.03 (s, 3H), 2.39 (s, 3H). Minor tautomer: 1H NMR (500 MHz, Methanol-d4) δ 8.25 (d, J=1.7 Hz, 1H), 7.91-7.84 (m, 2H), 7.80 (d, J=7.3 Hz, 1H), 7.75 (s, 1H), 7.42 (d, J=8.0 Hz, 1H), 7.03 (d, J=8.4 Hz, 1H), 4.03 (s, 3H), 2.39 (s, 3H). LCMS (M+H$^-$) calcd. 357.33, found 357.39.

Compounds NUCCO$_{202170}$, NUCCO$_{202169}$, and NUCC-0202168 were prepared by reduction of KL-2 in the presence of 1 equivalent of NaBH4 in MeOH for 15 minutes. The compounds were separated by flash column chromatography on silica gel to obtain pure samples of each compound.

NUCC-0202170. 1H NMR (500 MHz, Chloroform-d) δ 8.81 (s, 1H), 8.23 (d, J=2.2 Hz, 1H), 8.13-8.04 (m, 2H), 7.24 (t, J=8.5 Hz, 2H), 7.18 (d, J=8.2 Hz, 1H), 7.12 (dd, J=8.1, 2.2 Hz, 1H), 4.87 (d, J=7.9 Hz, 1H), 4.35 (d, J=4.9 Hz, 1H), 3.81 (dd, J=18.2, 3.3 Hz, 1H), 3.51 (dd, J=18.2, 8.1 Hz, 1H), 2.35 (s, 3H).

NUCC-0202169. 1H NMR (500 MHz, Chloroform-d) δ 8.89 (s, 1H), 8.31 (d, J=2.2 Hz, 1H), 7.58-7.50 (m, 2H), 7.30 (d, J=8.1 Hz, 1H), 7.24 (t, J=8.6 Hz, 3H), 5.28 (dd, J=10.6, 2.5 Hz, 1H), 5.05 (s, 1H), 4.74 (dd, J=10.2, 2.3 Hz, 1H), 3.02 (s, 1H), 2.59 (dd, J=14.9, 2.4 Hz, 1H), 2.45 (s, 3H), 2.19 (dt, J=14.7, 10.4 Hz, 1H), 1.83 (s, 1H).

NUCC-0202167. 1H NMR (500 MHz, Chloroform-d) δ 8.85 (s, 1H), 8.17 (d, J=2.2 Hz, 1H), 7.38-7.30 (m, 2H), 7.09 (d, J=8.1 Hz, 1H), 7.07-7.01 (m, 3H), 5.10 (dt, J=8.4, 2.9 Hz, 1H), 4.56 (d, J=5.7 Hz, 1H), 4.43 (td, J=5.8, 4.1 Hz, 1H), 2.62-2.50 (m, 1H), 2.38-2.26 (m, 2H), 2.25 (s, 3H). LCMS (M+H$^+$) calcd. 338.78, found 338.35.

NUCC-0202162. 1H NMR (500 MHz, Chloroform-d) δ 7.18-7.07 (m, 2H), 6.99-6.91 (m, 3H), 6.89-6.81 (m, 1H), 6.69 (dd, J=7.9, 2.0 Hz, 1H), 6.45 (d, J=2.0 Hz, 1H), 4.44 (dd, J=15.0, 6.3 Hz, 1H), 4.35 (dd, J=14.9, 5.9 Hz, 1H), 3.84 (qd, J=7.0, 3.3 Hz, 1H), 3.77 (d, J=3.6 Hz, 1H), 2.12 (s, 3H), 1.56 (d, J=6.9 Hz, 3H). LCMS (M+H$^+$) calcd. 321.79, found 321.27.

NUCC-0202161. 1H NMR (400 MHz, Chloroform-d) δ 7.23-7.14 (m, 2H), 7.07-6.91 (m, 4H), 6.70 (dd, J=7.9, 2.0 Hz, 1H), 6.46 (d, J=2.0 Hz, 1H), 4.43 (d, J=6.1 Hz, 2H), 4.40-4.32 (m, 1H), 3.85 (s, 2H), 2.15 (s, 3H). LCMS (M+H$^+$) calcd. 307.77, found 307.25.

NUCC-0202092. 1H NMR (400 MHz, Chloroform-d) δ 9.01 (s, 1H), 8.15 (d, J=8.0 Hz, 1H), 8.12-8.01 (m, 2H), 7.33-7.26 (m, 3H), 7.26-7.23 (m, 1H), 7.21 (d, J=8.6 Hz, 1H), 7.18-7.12 (m, 1H), 2.40 (s, 3H). LCMS (M+H$^+$) calcd. 300.30, found 300.25.

NUCC-0202090. 1H NMR (500 MHz, Chloroform-d) δ 9.22 (s, 1H), 8.95 (d, J=2.1 Hz, 1H), 8.50 (t, J=2.1 Hz, 1H), 8.14 (s, 1H), 7.96 (d, J=2.2 Hz, 1H), 7.65-7.56 (m, 2H), 7.23-7.19 (m, 2H), 7.17 (d, J=8.2 Hz, 1H), 7.12 (dd, J=8.2, 2.1 Hz, 1H), 2.32 (s, 3H). LCMS (M+H$^+$) calcd. 341.78, found 341.24.

NUCC-0202089. 1H NMR (500 MHz, Chloroform-d) δ 10.14 (s, 1H), 8.63 (dd, J=5.2, 0.8 Hz, 1H), 8.48 (dd, J=2.0, 0.8 Hz, 1H), 8.42 (d, J=2.2 Hz, 1H), 7.81-7.67 (m, 2H), 7.64 (dd, J=5.1, 1.9 Hz, 1H), 7.22-7.16 (m, 2H), 7.13 (d, J=8.1 Hz, 1H), 7.04 (dd, J=8.1, 2.2 Hz, 1H), 2.38 (s, 3H). LCMS (M+H$^+$) calcd. 341.78, found 341.24.

NUCC-0202075. 1H NMR (500 MHz, Chloroform-d) δ 10.00 (s, 1H), 9.28 (d, J=1.3 Hz, 1H), 8.57 (d, J=1.4 Hz, 1H), 8.39 (d, J=2.2 Hz, 1H), 8.28-8.16 (m, 2H), 7.22 (m, 2H), 7.16 (d, J=8.1 Hz, 1H), 7.08 (dd, J=8.1, 2.2 Hz, 1H), 2.40 (s, 3H). LCMS (M+H$^+$) calcd. 342.77, found 342.26.

NUCC-0202074. 1H NMR (500 MHz, Chloroform-d) δ 8.83 (dd, J=5.0, 0.9 Hz, 1H), 8.15-8.09 (m, 1H), 8.08-7.98 (m, 3H), 7.71 (s, 1H), 7.54 (dd, J=5.0, 1.7 Hz, 1H), 7.21-7.14 (m, 2H), 7.12 (dd, J=8.2, 2.1 Hz, 1H), 2.31 (s, 3H). LCMS (M+H$^-$) calcd. 341.78, found 341.24.

NUCC-0202072. 1H NMR (500 MHz, DMSO-d6) δ 13.86 (s, 1H), 9.59 (s, 1H), 7.90 (dd, J=8.5, 5.3 Hz, 2H), 7.82-7.75 (m, 1H), 7.33 (dt, J=32.2, 8.8 Hz, 3H), 7.22 (d, J=1.8 Hz, 1H), 7.19 (dd, J=8.2, 2.3 Hz, 1H), 2.28 (s, 3H). LCMS (M+H$^+$) calcd. 330.76, found 330.24

NUCC-0202071. 1H NMR (500 MHz, DMSO-d6) δ 10.37 (s, 1H), 8.11-7.98 (m, 2H), 7.56-7.49 (m, 2H), 7.44 (t, J=8.8 Hz, 2H), 7.34 (d, J=8.2 Hz, 1H), 7.28 (dd, J=8.2, 2.2 Hz, 1H), 2.25 (s, 3H). LCMS (M+H$^+$) calcd. 331.74, found 331.28.

NUCC-0202070. LCMS (M+H$^+$) calcd. 304.27, found 304.31.

NUCC-0202069. 1H NMR (500 MHz, Chloroform-d) δ 15.68 (s, 1H), 8.10 (dd, J=8.6, 5.4 Hz, 2H), 7.29-7.22 (m, 3H), 7.20 (d, J=7.2 Hz, 1H), 4.37 (h, J—7.0 Hz, 1H), 2.13 (ddd, J=12.7, 7.5, 5.0 Hz, 2H), 1.82 (qd, J=10.5, 9.2, 5.3 Hz, 2H), 1.74 (qd, J=8.8, 7.3, 4.9 Hz, 2H), 1.64-1.53 (m, 2H). LCMS (M+H$^+$) calcd. 278.30, found 278.24.

NUCC-0202068. 1H NMR (500 MHz, Chloroform-d) δ 15.61 (s, 1H), 8.96 (s, 1H), 8.14-7.95 (m, 2H), 7.81 (t, J=2.0 Hz, 1H), 7.51 (ddd, J=8.3, 2.1, 1.0 Hz, 1H), 7.30 (t, J=8.1 Hz, 1H), 7.23 (s, 1H), 7.21-7.13 (m, 3H).). LCMS (M+H$^+$) calcd. 320.72, found 320.14.

NUCC-0202067. 1H NMR (500 MHz, Chloroform-d) δ 15.66 (s, 1H), 8.98 (s, 1H), 8.10-7.97 (m, 2H), 7.70 (d, J=8.1 Hz, 1H), 7.26 (s, 1H), 7.23-7.14 (m, 3H), 6.74 (d, J=8.3 Hz, 1H), 3.83 (s, 3H), 2.21 (s, 3H). LCMS (M+H$^+$) calcd. 330.33, found 330.31.

NUCC-0202066. Major tautomer: 1H NMR (500 MHz, DMSO-d6) δ 12.94 (s, 1H), 10.31 (s, 1H), 8.24-8.16 (m, 2H), 8.03 (d, J=1.8 Hz, 1H), 7.76 (dd, J=7.8, 1.8 Hz, 1H), 7.49-7.40 (m, 3H), 7.22 (s, 1H), 2.31 (s, 3H). (—OH not observed). Minor tautomer: 1H NMR (500 MHz, DMSO-d6) δ 12.94 (s, 1H), 10.21 (s, 1H), 8.13-8.07 (m, 2H), 7.93 (d, J=1.8 Hz, 1H), 7.73 (dd, J=8.0, 1.7 Hz, 1H), 7.43-7.37 (m, 3H), 7.10 (s, 1H), 2.28 (d, J=1.5 Hz, 3H). (—OH not observed.) LCMS (M+H$^+$) calcd. 344.31, found 344.21.

NUCC-0201929. 1H NMR (500 MHz, Chloroform-d) δ 15.66 (s, 1H), 9.00 (s, 1H), 7.72-7.68 (m, 1H), 7.60 (dt, J=7.9, 1.2 Hz, 1H), 7.51 (dd, J=2.7, 1.6 Hz, 1H), 7.39 (t, J=8.0 Hz, 1H), 7.29 (s, 1H), 7.21 (t, J=8.3 Hz, 1H), 7.13 (ddd, J=8.3, 2.6, 1.0 Hz, 1H), 6.74 (d, J=8.2 Hz, 1H), 3.87 (s, 3H), 3.83 (s, 3H), 2.21 (s, 3H). LCMS (M+H$^+$) calcd. 342.36, found 342.42.

NUCC-0201928. LCMS (M+W) calcd. 342.36, found 342.37.

NUCC-0201927. 1H NMR (500 MHz, Chloroform-d) δ 15.60 (s, 1H), 9.40 (s, 1H), 8.93 (d, J=3.5 Hz, 2H), 7.60 (dt, J=7.9, 1.2 Hz, 1H), 7.51 (dd, J=2.6, 1.6 Hz, 1H), 7.41 (t, J=8.0 Hz, 1H), 7.26 (s, 1H), 7.15 (ddd, J=8.2, 2.7, 1.0 Hz, 1H), 3.87 (s, 3H), 2.59 (s, 3H).). LCMS (M+H$^+$) calcd. 314.31, found 314.36.

NUCC-0201926. LCMS (M+H$^+$) calcd. 356.35, found 356.34.

NUCC-0201925. 1H NMR (500 MHz, DMSO-d6) δ 10.85 (s, 1H), 8.01 (t, J=2.0 Hz, 1H), 7.80 (ddd, J=7.5, 4.7, 2.0 Hz, 2H), 7.68 (d, J=7.7 Hz, 1H), 7.57-7.51 (m, 2H), 7.28 (dd, J=8.3, 2.5 Hz, 1H), 7.25-7.17 (m, 2H), 6.91 (s, 1H), 3.86 (s, 3H). LCMS (M+H$^+$) calcd. 332.75, found 332.23.

NUCC-0201924. 1H NMR (500 MHz, Chloroform-d) δ 15.63 (s, 1H), 8.95 (s, 1H), 7.69-7.61 (m, 2H), 7.60 (dt, J=7.8, 1.2 Hz, 1H), 7.52-7.48 (m, 1H), 7.40 (t, J=8.0 Hz, 1H), 7.27 (s, 1H), 7.13 (dd, J=8.2, 2.6 Hz, 1H), 7.10-7.01 (m, 2H), 3.87 (s, 3H). LCMS (M+H$^+$) calcd. 316.30, found 316.11.

NUCC-0201923. 1H NMR (500 MHz, Chloroform-d) δ 15.59 (s, 1H), 8.98 (s, 1H), 7.93 (d, J=2.5 Hz, 1H), 7.59 (d, J=7.7 Hz, 1H), 7.52-7.45 (m, 2H), 7.41 (dd, J=15.7, 8.2 Hz, 2H), 7.25 (s, 1H), 7.14 (dd, J=8.2, 2.6 Hz, 1H), 3.87 (s, 3H).). LCMS (M$^+$) calcd. 366.19, found 366.26.

NUCC-0201922. 1H NMR (500 MHz, Chloroform-d) δ 15.63 (s, 1H), 8.94 (s, 1H), 7.61 (dd, J=7.7, 1.5 Hz, 1H), 7.52 (t, J=2.1 Hz, 1H), 7.41 (t, J=8.0 Hz, 1H), 7.29 (s, 1H), 7.14 (dd, J=8.2, 2.6 Hz, 1H), 6.93 (d, J=2.2 Hz, 2H), 6.31 (t, J=2.2 Hz, 1H), 3.88 (s, 3H), 3.81 (s, 6H).). LCMS (M+H$^+$) calcd. 358.36, found 358.24.

NUCC-0201921. 1H NMR (500 MHz, Chloroform-d) δ 15.60 (s, 1H), 8.97 (s, 1H), 7.78 (ddd, J=11.8, 7.1, 2.6 Hz, 1H), 7.59 (d, J=7.6 Hz, 1H), 7.55-7.48 (m, 1H), 7.40 (t, J=8.0 Hz, 1H), 7.25 (d, J=6.8 Hz, 2H), 7.20-7.10 (m, 2H), 3.87 (s, 3H). LCMS (M+H$^+$) calcd. 334.29, found 334.2

NUCC-0201693. 1H NMR (500 MHz, Chloroform-d) δ 15.59 (s, 1H), 9.14 (s, 1H), 8.51 (t, J=1.5 Hz, 1H), 8.30 (d, J=2.6 Hz, 1H), 8.24 (dt, J=10.2, 2.4 Hz, 1H), 8.12-7.88 (m, 2H), 7.22 (s, 1H), 7.21-7.16 (m, 2H). LCMS (M+H$^+$) calcd. 305.25, found 305.18.

NUCC-0201692. 1H NMR (500 MHz, Chloroform-d) δ 8.22-7.82 (m, 2H), 7.59 (d, J=3.6 Hz, 1H), 7.24 (s, 1H), 7.19 (t, J=8.6 Hz, 2H), 7.10 (d, J=3.5 Hz, 1H). LCMS (M+H$^+$) calcd. 293.28, found 293.18.

NUCC-0201691. LCMS (M+H$^+$) calcd. 292.24, found 292.12.

NUCC-0201690. 1H NMR (500 MHz, DMSO-d6) δ 12.62 (s, 1H), 8.21 (dd, J=8.6, 5.3 Hz, 2H), 7.45 (t, J=8.7 Hz, 2H), 7.26 (s, 1H). (2 hydrogens not observed due to large water peak). LCMS (M+H$^+$) calcd. 278.22, found 278.16.

NUCC-0201689. 1H NMR (500 MHz, Chloroform-d) δ 8.79-8.56 (m, 2H), 8.17-7.93 (m, 2H), 7.76 (p, J=6.4, 5.1 Hz, 1H), 7.31-7.27 (m, 2H), 7.26-7.20 (m, 3H), 4.65 (d, J=6.4 Hz, 2H). LCMS (M+H$^+$) calcd. 301.29, found 301.19.

NUCC-0201688. 1H NMR (500 MHz, Chloroform-d) δ 15.62 (s, 1H), 8.15-8.01 (m, 2H), 7.61-7.48 (m, 1H), 7.43-7.32 (m, 5H), 7.26-7.17 (m, 3H), 4.62 (d, J=6.0 Hz, 2H). LCMS (M+H$^+$) calcd. 300.30, found 300.18.

NUCC-0201596. Major tautomer: 1H NMR (500 MHz, DMSO-d6) δ 11.05 (s, 1H), 8.52 (d, J=2.6 Hz, 1H), 8.44 (d, J=2.5 Hz, 1H), 8.27-8.17 (m, 2H), 7.48-7.38 (m, 2H), 7.21 (s, 1H), 2.47 (s, 3H). (—OH not observed.) Minor tautomer: 1H NMR (500 MHz, DMSO-d6) δ 10.97 (s, 1H), 8.52 (d, J=2.6 Hz, 1H), 8.46 (d, 1H), 8.13-8.07 (m, 2H), 7.41 (d, J=2.1 Hz, 2H), 7.21 (s, 1H), 2.43 (s, 3H). (—OH not observed.) LCMS (M+H$^+$) calcd. 302.28, found 302.21.

NUCC-201596. 1H NMR (500 MHz, Chloroform-d) δ 15.59 (s, 1H), 9.18 (s, 1H), 8.40 (d, J=2.6 Hz, 1H), 8.31 (d, J=2.5 Hz, 1H), 8.05 (dd, J=8.6, 5.3 Hz, 2H), 7.18 (t, J=8.4 Hz, 2H), 2.59 (s, 3H). (—OH not observed).

NUCC-0201256 (KL-1). 1H NMR (500 MHz, Chloroform-d) δ 15.61 (s, 1H), 8.99 (s, 1H), 8.25 (d, J=2.1 Hz, 1H), 7.60 (dt, J=7.9, 1.2 Hz, 1H), 7.51 (t, J=2.1 Hz, 1H), 7.40 (t, J=8.0 Hz, 1H), 7.27 (s, 1H), 7.17-7.11 (m, 2H), 7.07 (dd, J=8.2, 2.2 Hz, 1H), 3.87 (s, 3H), 2.32 (s, 3H). LCMS (M+H$^+$) calcd. 346.8, found 346.2.

NUCC-0201231 (KL-2). 1H NMR (500 MHz, Chloroform-d) δ 15.62 (s, 1H), 8.97 (s, 1H), 8.24 (d, J=2.3 Hz, 1H), 8.11-7.94 (m, 2H), 7.24 (s, 1H), 7.18 (t, J=8.6 Hz, 2H), 7.13 (d, J=8.1 Hz, 1H), 7.07 (dd, J=8.2, 2.2 Hz, 1H), 2.32 (s, 3H). LCMS (M+H$^+$) calcd. 334.7, found 334.2.

NUCC-0102301. 1H NMR (500 MHz, Chloroform-d) δ 9.47 (s, 1H), 8.33 (d, J=2.2 Hz, 1H), 8.17-7.92 (m, 1H), 7.53-7.47 (m, 2H), 7.33 (d, J=8.2 Hz, 1H), 7.28 (dd, J=8.2, 2.2 Hz, 1H), 7.24 (t, J=8.6 Hz, 2H), 4.72 (d, J=6.2 Hz, 2H), 2.51 (s, 3H). LCMS (M+H$^+$) calcd. 321.75, found 321.27.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

Zhou, Q., Li, T., and Price, D. H. (2012). RNA polymerase II elongation control. Annu Rev Biochem 81, 119-143.

Example 2

The following additional exemplary compounds were prepared using a similar synthesis pathway as the pathway utilized in Example 1 for synthesizing KL-1 and KL-2 with the following exceptions. Compounds NUCC-0202075, NUCC-0202089, and NUCC-0202090 were prepared by Suzuki coupling of the appropriate aryl chloride with 4-fluoro phenyl boronic acid, followed by hydrolysis of the ester to the carboxylic acid, then amide coupling using the same procedure as above to obtain the final compounds.

Compounds NUCC-0202071 and NUCC-0202072 were prepared by Claisen condensation of 4'-fluoroacetophenone with diethyl oxalate, condensation with either hydroxylamine or hydrazine, hydrolysis of the ester, and amide coupling using the same procedure as above to obtain the final compounds.

We claim:
1. The pharmaceutical composition comprising a compound of formula

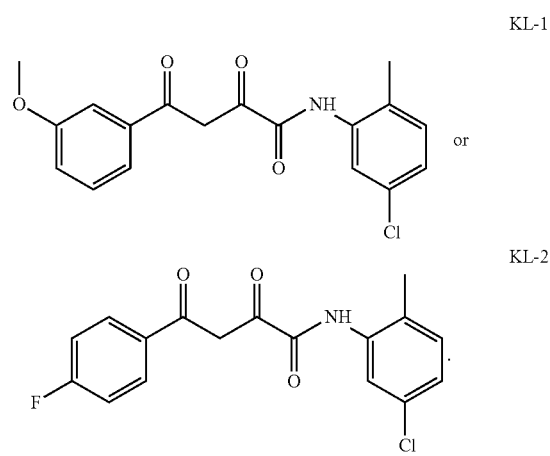

or a tautomer or pharmaceutical salt thereof and a pharmaceutically acceptable carrier.

2. A method for treating a disease or disorder associated with Super Elongation Complex (SEC) activity in a subject in need thereof, the method comprising administering to the subject the pharmaceutical composition according to claim 1, wherein the pharmaceutical composition comprises an effective amount of the compound for treating the disease or disorder and wherein the disease or disorder is a cell proliferative disease or disorder associated with relatively high levels of Myc expression.

3. A method for treating a disease or disorder associated with Super Elongation Complex (SEC) activity in a subject in need thereof, the method comprising administering to the subject the pharmaceutical composition according to claim 1, wherein the pharmaceutical composition comprises an effective amount of the compound for treating the disease or disorder and wherein the disease or disorder is associated with expression of a mixed lineage leukemia (MLL) chimera.

4. A method for treating a disease or disorder associated with Super Elongation Complex (SEC) activity in a subject in need thereof, the method comprising administering to the subject the pharmaceutical composition according to claim 1, wherein the pharmaceutical composition comprises an effective amount of the compound for treating the disease or disorder and wherein the disease or disorder is acute myeloid leukemia (AML) or acute lymphoid leukemia (ALL).

5. A method for treating a disease or disorder associated with Super Elongation Complex (SEC) activity in a subject in need thereof, the method comprising administering to the subject the pharmaceutical composition according to claim 1, wherein the pharmaceutical composition comprises an effective amount of the compound for treating the disease or disorder and wherein the disease or disorder is infection by human immunodeficiency virus (HIV).

\* \* \* \* \*